(12) United States Patent
Disis et al.

(10) Patent No.: US 10,759,836 B2
(45) Date of Patent: Sep. 1, 2020

(54) CANCER VACCINE COMPOSITIONS AND METHODS OF USE THEREOF

(71) Applicant: UNIVERSITY OF WASHINGTON, Seattle, WA (US)

(72) Inventors: Mary L. Disis, Seattle, WA (US); Elizabeth Broussard, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 511 days.

(21) Appl. No.: 15/327,225

(22) PCT Filed: Jul. 17, 2015

(86) PCT No.: PCT/US2015/040960
§ 371 (c)(1),
(2) Date: Jan. 18, 2017

(87) PCT Pub. No.: WO2016/011386
PCT Pub. Date: Jan. 21, 2016

(65) Prior Publication Data
US 2017/0283475 A1     Oct. 5, 2017

Related U.S. Application Data

(60) Provisional application No. 62/026,246, filed on Jul. 18, 2014.

(51) Int. Cl.
| | | |
|---|---|---|
| C07K 14/47 | (2006.01) |
| A61K 48/00 | (2006.01) |
| C07K 14/82 | (2006.01) |
| C12N 15/09 | (2006.01) |
| C12N 5/09 | (2010.01) |
| C07K 14/78 | (2006.01) |
| C12N 9/16 | (2006.01) |
| C07K 14/71 | (2006.01) |
| A61K 39/00 | (2006.01) |
| C07K 7/00 | (2006.01) |
| C07K 14/00 | (2006.01) |

(52) U.S. Cl.
CPC .......... *C07K 14/47* (2013.01); *A61K 39/0011* (2013.01); *A61K 48/00* (2013.01); *C07K 14/71* (2013.01); *C07K 14/78* (2013.01); *C07K 14/82* (2013.01); *C12N 5/0693* (2013.01); *C12N 9/16* (2013.01); *C12N 15/09* (2013.01); *A61K 39/00* (2013.01); *C07K 7/00* (2013.01); *C07K 14/00* (2013.01); *C07K 2319/00* (2013.01); *C07K 2319/03* (2013.01); *C07K 2319/40* (2013.01)

(58) Field of Classification Search
CPC ........ A61K 14/47; A61K 14/82; A61K 48/00; C12N 5/0693; C12N 15/09
See application file for complete search history.

(56) References Cited

U.S. PATENT DOCUMENTS

| | | |
|---|---|---|
| 3,625,214 A | 12/1971 | Higuchi |
| 4,270,537 A | 6/1981 | Romaine |
| 4,469,863 A | 9/1984 | Ts'o et al. |
| 4,596,556 A | 6/1986 | Morrow et al. |
| 4,789,734 A | 12/1988 | Pierschbacher |
| 4,790,824 A | 12/1988 | Morrow et al. |
| 4,886,499 A | 12/1989 | Cirelli et al. |
| 4,897,268 A | 1/1990 | Tice et al. |
| 4,906,474 A | 3/1990 | Langer et al. |
| 4,912,094 A | 3/1990 | Myers et al. |
| 4,925,673 A | 5/1990 | Steiner et al. |
| 4,940,460 A | 7/1990 | Casey et al. |
| 4,941,880 A | 7/1990 | Burns |
| 4,992,445 A | 2/1991 | Lawter et al. |
| 5,001,139 A | 3/1991 | Lawter et al. |
| 5,015,235 A | 5/1991 | Crossman |
| 5,023,252 A | 6/1991 | Hseih |
| 5,034,506 A | 7/1991 | Summerton et al. |
| 5,057,540 A | 10/1991 | Kensil et al. |
| 5,064,413 A | 11/1991 | McKinnon et al. |
| 5,075,109 A | 12/1991 | Tice et al. |
| 5,141,496 A | 8/1992 | Dalto et al. |
| 5,190,029 A | 3/1993 | Byron et al. |
| 5,190,521 A | 3/1993 | Hubbard et al. |
| 5,216,141 A | 6/1993 | Benner |
| 5,235,033 A | 8/1993 | Summerton et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,376,359 A | 12/1994 | Johnson |
| 5,383,851 A | 1/1995 | McKinnon, Jr. et al. |
| 5,386,023 A | 1/1995 | Sanghvi et al. |
| 5,417,662 A | 5/1995 | Hjertman et al. |
| 5,466,220 A | 11/1995 | Brenneman |
| 5,480,381 A | 1/1996 | Weston |

(Continued)

FOREIGN PATENT DOCUMENTS

| | | |
|---|---|---|
| EP | 0109942 B1 | 3/1991 |
| EP | 0362279 B1 | 1/1995 |

(Continued)

OTHER PUBLICATIONS

Sawai, H., Synthesis and properties of oligoadenylic acids containing 2-5- phosphoramide linkage. The chemical society of Japan. 1984.805-808 . . .

(Continued)

*Primary Examiner* — Antonio Galisteo Gonzalez
(74) *Attorney, Agent, or Firm* — Karen S. Canady; canady + lortz LLP

(57) ABSTRACT

The present application describes compositions that include an epitope of a peptide that elicits an immune response in a subject following administration. The compositions described herein include nucleic acids. The present application also describes compositions that include peptides. Also described herein are methods that include administering a composition comprising an epitope of a peptide to a subject in need thereof.

11 Claims, 85 Drawing Sheets
Specification includes a Sequence Listing.

(56) References Cited

U.S. PATENT DOCUMENTS

| | | | |
|---|---|---|---|
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,972 A | 1/1997 | Weiner et al. |
| 5,599,302 A | 2/1997 | Lilley et al. |
| 5,602,240 A | 2/1997 | De Mesmaeker et al. |
| 5,637,684 A | 6/1997 | Cook et al. |
| 5,644,048 A | 7/1997 | Yau |
| 5,649,912 A | 7/1997 | Peterson |
| 5,704,911 A | 1/1998 | Parsons |
| 5,776,434 A | 7/1998 | Purewal et al. |
| 5,811,128 A | 9/1998 | Tice et al. |
| 5,814,344 A | 9/1998 | Tice et al. |
| 5,820,883 A | 10/1998 | Tice et al. |
| 5,853,763 A | 12/1998 | Tice et al. |
| 5,893,397 A | 4/1999 | Peterson et al. |
| 5,928,647 A | 7/1999 | Rock |
| 5,942,252 A | 8/1999 | Tice et al. |
| 5,962,428 A | 10/1999 | Carrano et al. |
| 5,993,412 A | 11/1999 | Deily et al. |
| 2009/0148478 A1 | 6/2009 | Chiang et al. |
| 2010/0092523 A1 | 4/2010 | Disis et al. |

FOREIGN PATENT DOCUMENTS

| | | | |
|---|---|---|---|
| GB | 2122204 B | 12/1985 | |
| GB | 2220211 B | 11/1992 | |
| JP | 7-503131 | 4/1995 | |
| JP | 2007-511534 | 5/2007 | |
| JP | 2008-515928 | 5/2008 | |
| JP | 2008-527001 | 7/2008 | |
| WO | WO93/10242 | 5/1993 | |
| WO | WO-9400153 A1 | 1/1994 | |
| WO | WO-9416737 A1 | 8/1994 | |
| WO | WO-9421292 A1 | 9/1994 | |
| WO | WO-9517210 A1 | 6/1995 | |
| WO | WO-9602555 A1 | 2/1996 | |
| WO | WO-9611711 A1 | 4/1996 | |
| WO | WO-9633739 A1 | 10/1996 | |
| WO | WO-9713537 A1 | 4/1997 | |
| WO | WO-9737705 A1 | 10/1997 | |
| WO | WO-9843670 A2 | 10/1998 | |
| WO | WO-9843670 A3 | 12/1998 | |
| WO | WO-2004111636 A2 * | 12/2004 | ............ C07K 14/47 |
| WO | WO2005048943 A2 | 6/2005 | |
| WO | WO2006042254 | 4/2006 | |
| WO | WO2006076678 | 7/2006 | |
| WO | WO-2008073660 A1 | 6/2008 | |
| WO | WO-2013147509 A1 | 10/2013 | |
| WO | WO-2016011386 A1 | 1/2016 | |

OTHER PUBLICATIONS

Bangham et al. Diffusion of univalent ions across the lamellae of swollen phospholipids. J. Mol. Biol. 1965;13:238-252.
Beaucage, et al. The functionalization of oligonucleotides via phosphoramidite derivative. Tetrahedron. 1993;49(10):1925-63.
Bomford, et al. Adjuvanticity and ISCOM formation by structurally diverse saponins. Vaccine. 1992;10(9):572-7.
Brill et al. Synthesis of oligodeoxynucleoside phosphorodithioates via thioamidites. J. Am. Chem. Soc. 111:2321-2322 (1989).
Broussard, et al., Abstract 4774: Identification of Colon Cancer-associated Antigens Which Would be Key Therapeutic Targets in the Prevention of Disease Relapse or Progression, Immunology, DOI: 10.1158/1538-7445. AM10-4774, Published Apr. 2010.
Carlsson, et al., Screening for genetic mutations. Scientific correspondence. Nature. 1996; 380:207.
Cecil, et al., T-helper I immunity, specific for the breast cancer antigen insulin-like growth factor-I receptor (IGF-IR), is associated with increased adiposity, Breast Cancer Res Treat, 2013, 139:657-665.
Denpcy et al. Synthesis of a thymidyl pentamer of deoxyribonucleic guanidine and binding studies with DNA homopolynucleotides. Proc Natl Acad Sci U S A. Jun. 20, 1995;92(13):6097-101.
Disis, et al., A multi-antigen vaccine targeting neu, IGFBP-2 and IGF-IR prevents tumor progression in mice with pre-invasive breast disease, Cancer Prey Res (Phila). doi:10.1158/1940-6207, Dec. 2013, 6(12):19 pages.
Egholm et al. Peptide nucleic acids (PNA) oligonucleotide analogues with an achiral peptide backbone. J Am Chem Soc 114:1895-1897 (1992).
EP 15822502.9 Supplementary Partial European Search Report and Search Opinion dated Feb. 16, 2018.
Hilgers, et al. Synergistic effects of synthetic adjuvants on the humoral immune response. Int Arch Allergy Appl Immunol. 1986;79(4):392-6.
Hilgers, et al. Synthetic sulpholipopolysaccharides: novel adjuvants for humoral immune responses. Immunology. Jan. 1987;60(1):141-6.
Horn et al. Oligonucleotides with alternating anionic and cationic phosphoramidate linkages: Synthesis and hybridization of stereouniform isomers. Tetrahedron Lett 37:743-746 (1996).
International search report and written opinion dated Oct. 26, 2015 for PCT/US2015/040960.
Ishioka, et al., Multi-Epitope CTL Responses Induced by a Peptide Vaccine (EP-2101) in Colon and Non-Small Cell Lung Cancer Patients, Journal of Immunotherapy, Nov. 2004, 27(6):S23-S24.
Jeffs, et al., Unusual conformation of a 3'-thioformacetal linkage in a DNA duplex*. Journal of Biomolecular NMR. 1994. 17-34.
Jenkins, et al., The Biosynthesis of Carbocyclic Nucleosides. Chemical society reviews. 1995; 169-176.
Kensil, Saponins as vaccine adjuvants. Crit Rev Ther Drug Carrier Syst. 1996;13(1-2):1-55.
Kiedrowski, et al. Parabolic growth of a self-replicating hexadeoxynucleotide bearing a 3'-5'-phosphoamidate linkage. Angew. Chem. Intl. Ed. English 1991;30:423-426.
Koshkin, et al. LNA (Locked Nucleic Acid): An RNA Mimic Forming Exceedingly Stable LNA: LNA Duplexes. Journal American Chemical Society 1998: 120;13252-3.
Lacaille-Dubois, et al. A review of the biological and pharmacological activities of saponins. Phytomedicine. Mar. 1996;2(4):363-86. doi: 10.1016/S0944-7113(96)80081-X.
Letsinger et al., Cationic oligonucleotides. J. Am. Chem. Soc.1988; 110(3):4470-4471.
Letsinger et al., Effects of pendant groups at phosphorus on binding properties of d-ApA analogues. Nucleic Acids Res. Apr. 25, 1986;14(8):3487-99.
Letsinger et al., Hybridization of Alternating Cationic/Anionic Oligonucleotide to RNA Segments. Nucleosides & Nucleotides. 13:1597 (1994).
Letsinger, et al., Nucleotide chemistry. XVI. Phosporamidate analogs of oligonucleotides. J. Org. Chem.,1970,35(11),pp. 3800-3803.
Mag et al., Synthesis and selective cleavage of an oligodeoxynucleotide containing a bridged internucleotide 5'-phosphorothioate linkage. Nucleic Acids Res. 19:1437 (1991).
Medina-Echeverz, et al. Agonistic CD40 antibody induces immune-mediated liver damage and modulates tumor-induced myeloid suppressive cells. Journal for ImmunoTherapy of Cancer 2014, 2(Suppl 3):p. 174.
Meier, et al., Peptide nucleic acids (PNas)—Unusual properties nonionic oligonucleotide analogues. Angew. Chemical. Int. Ed. Engl. 1992; 31:8.
Pauwels et al., Biological activity of new 2-5A analogues. Chemica scripta. 1986. 26: 141-145.
Sprinzl, et al., Enzymatic Incorporation of ATP and CTP Analogues into the 3' End of tRNA. Eur. J. Biochem. 81, 579-589 (1977).
Szoka et al. Procedure for preparation of liposomes with large internal aqueous space and high capture by reverse-phase evaporation. PNAS. 1978;75:4194-4198.
Broussard, Elizabeth et al., Characterization of colon cancer-associated antigens that would be key therapeutic targets in the prevention of disease relapse or progression. Journal of Clinical Oncology 30, No. 4_suppl (Feb. 1, 2012) 594-594.

(56) References Cited

OTHER PUBLICATIONS

JP Office Action dated Aug. 27, 2019 in corresponding JP Application 2017502704.
Broussard, et al. Identification of Putative Immunologic Targets for Colon Cancer Prevention based on Conserved Gene Upregulation from Preinvasive to Malignant Lesions. Cancer Prev Res (Phila). Jul. 2013;6(7):666-74. doi: 10.1158/1940-6207.CAPR-12-0484. Epub May 16, 2013.
European search report with written opinion dated May 18, 2018 for EP Application No. 15822502.
Park, et al., Insulin-like growth factor binding protein 2 is a target for the immunomodulation of breast cancer, Cancer Res. Oct. 15, 2008, 68(20): 8400-09.
Ramduth, et al. Immunodominant HIV-1 Cd4+ T Cell Epitopes in Chronic Untreated Clade C HIV-1 Infection. PLoS One. 2009;4(4):e5013. doi: 10.1371/journal.pone.0005013. Epub Apr. 7, 2009.

\* cited by examiner

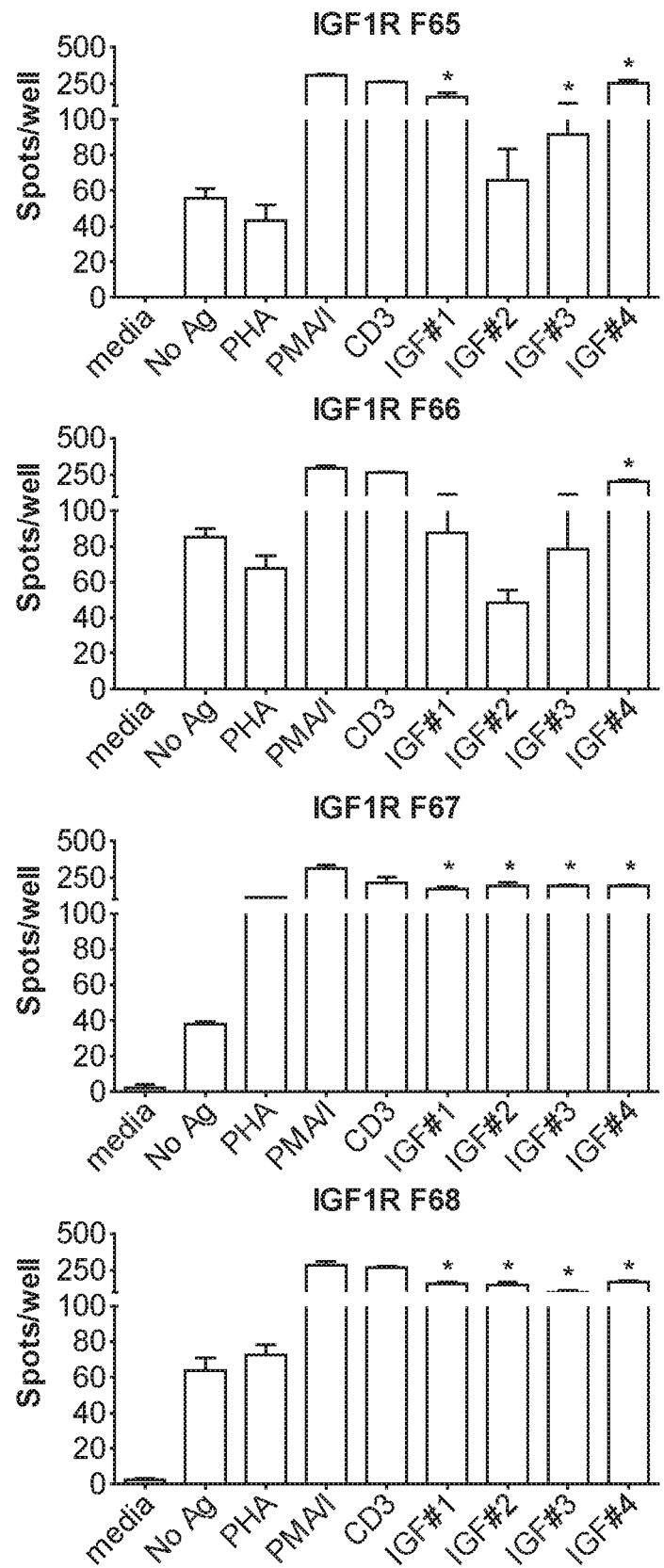
FIG. 52 (Cont.1)

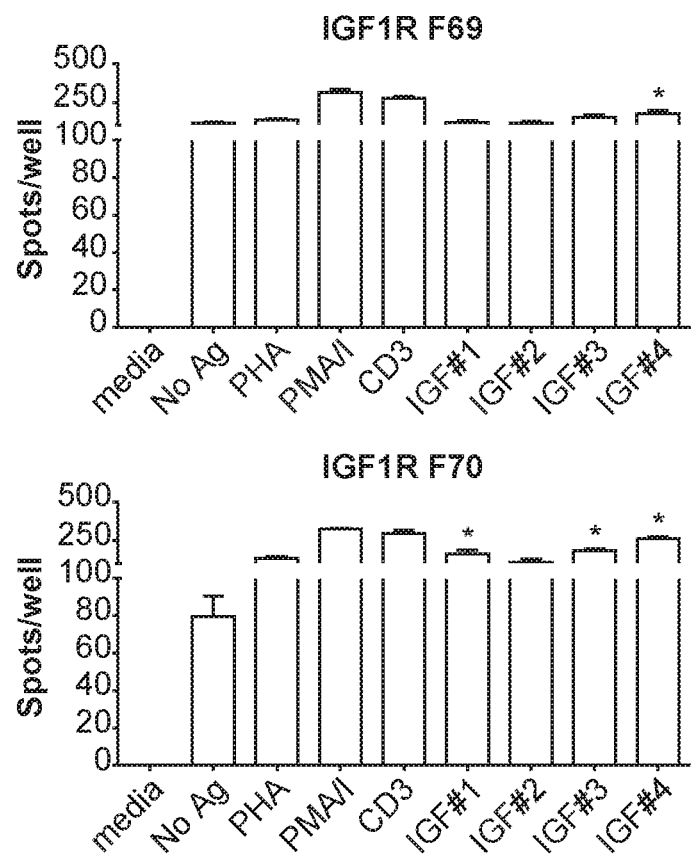
FIG. 52 (Cont.2)

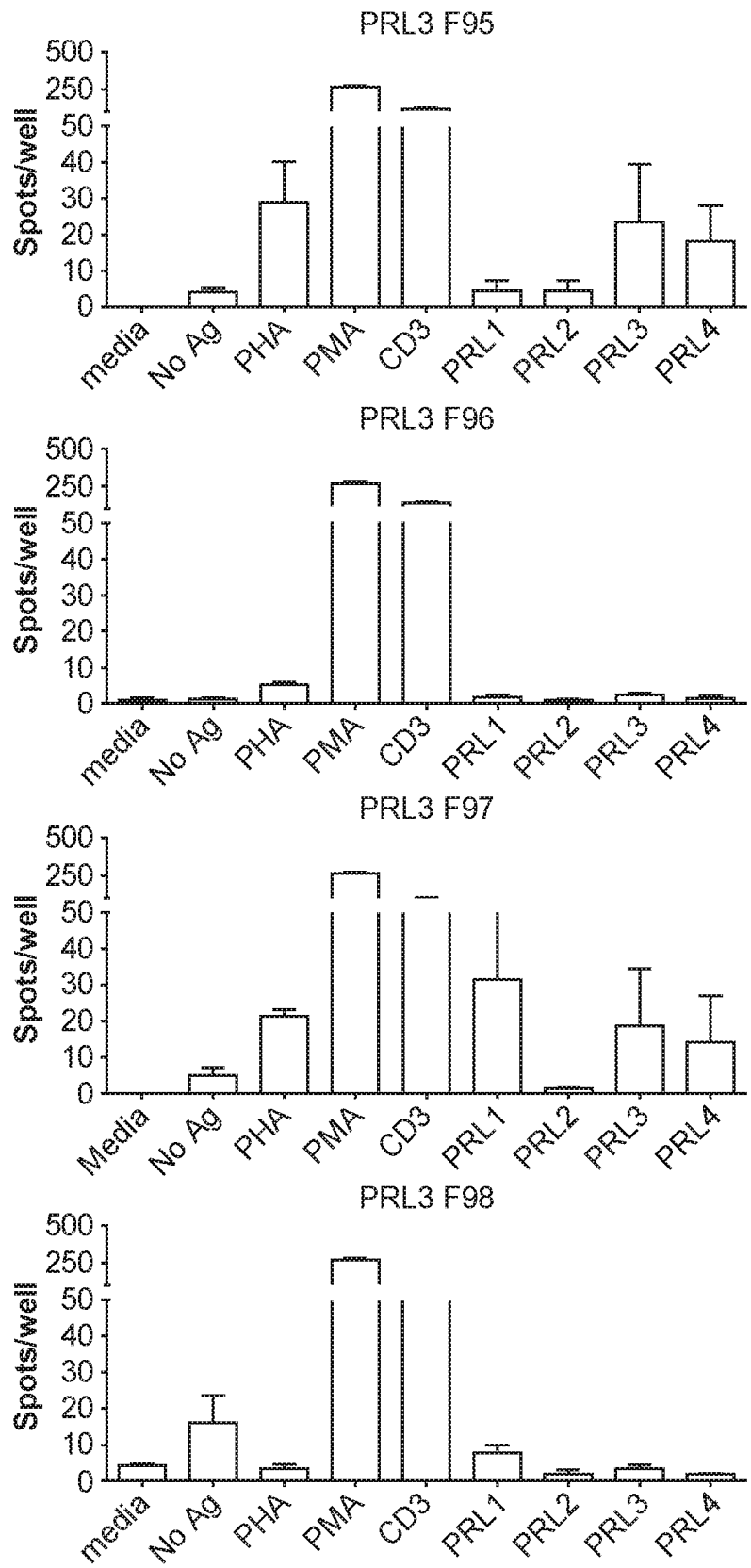
FIG. 53 (Cont.1)

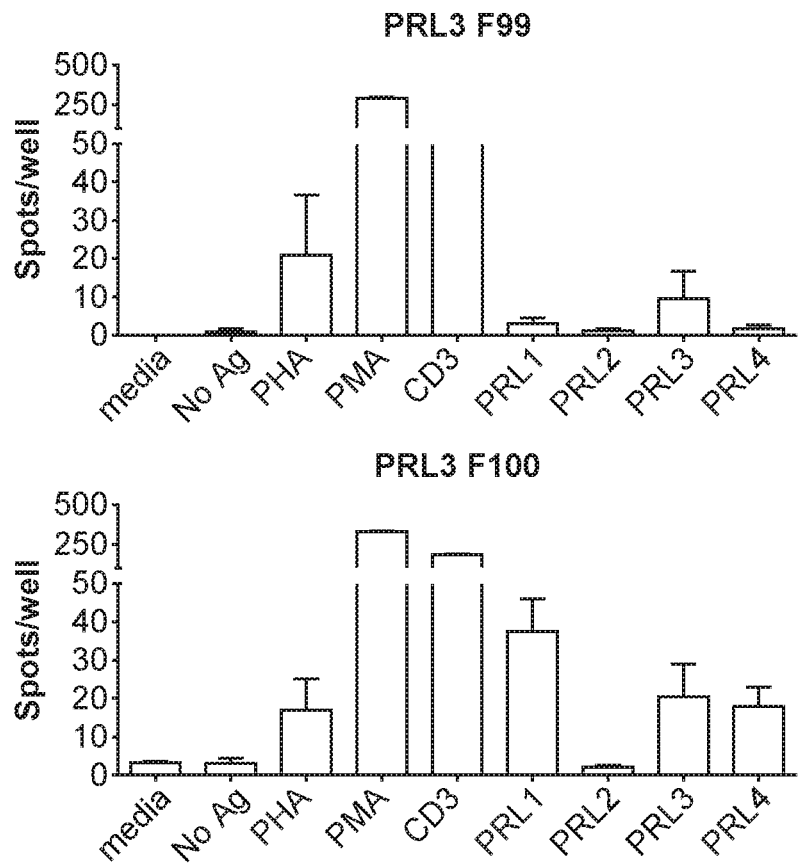
FIG. 53 (Cont.2)

```
SEQUENCE LISTING

<160> NUMBER OF SEQ ID NOS: 59

<210> SEQ ID NO 1
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 1

Gln Ala Ile Gln Ala Ala Ser Arg Ile Ile Arg Asn Glu Gln Phe Ala
1               5                   10                  15

Ile Arg Arg Phe Gln
            20

<210> SEQ ID NO 2
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 2

Val Asp Gly Lys His Gln Asp Leu Lys Tyr Ile Ser Pro Glu Thr Met
1               5                   10                  15

Val Ala Leu Leu Thr Gly Lys
            20

<210> SEQ ID NO 3
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 3

Phe Lys Gly Phe Trp Asn Val Val Asn Asn Ile Pro Phe Leu Arg Asn
1               5                   10                  15

<210> SEQ ID NO 4
<211> LENGTH: 17
<212> TYPE: PRT
<213> ORGANISM: Artificial Sequence
<220> FEATURE:
```

<223> OTHER INFORMATION: Synthetic polypeptide

<400> SEQUENCE: 4

Gly Leu Val Pro Gly Leu Met Met Tyr Ala Thr Ile Trp Leu Arg Glu
1               5                   10                  15

His

<210> SEQ ID NO 5
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 5

Gly Glu Val Gly Phe Gln Ile Ile Asn Thr Ala Ser Ile Gln Ser Leu
1               5                   10                  15

Ile Cys

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Asn Ala Ile Met Ser Tyr Val Leu Thr Ser Arg Ser His Leu Ile Asp
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 7

His Ile Tyr Gly Glu Thr Leu Ala Arg Gln Arg Lys Leu Arg Leu Phe
1               5                   10                  15

Lys Asp

<210> SEQ ID NO 8
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 8

Leu Phe Gln Thr Ser Arg Leu Ile Leu Ile Gly Glu Thr Ile Lys Ile
1               5                   10                  15

Val Ile

<210> SEQ ID NO 9
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 9

Gln Phe Gln Tyr Gln Asn Arg Ile Ala Ala Glu Phe Asn Thr Leu Tyr
1               5                   10                  15

<210> SEQ ID NO 10
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 10

Gln Gln Phe Ile Tyr Asn Asn Ser Ile Leu Leu Glu His Gly Ile Thr
1               5                   10                  15

Gln Phe Val

<210> SEQ ID NO 11
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 11

Ser Cys Val Arg Ala Cys Gly Ala Asp Ser Tyr Glu Met Glu Glu Asp
1               5                   10                  15

Gly Val Arg Lys
            20

<210> SEQ ID NO 12
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 12

Asn Asn Thr Leu Val Trp Lys Tyr Ala Asp Ala Gly His Val Cys His
1               5                   10                  15

Leu

<210> SEQ ID NO 13
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 13

Val Trp Ser Tyr Gly Val Thr Val Trp Glu Leu Met Thr Phe Gly Ser
1               5                   10                  15

Lys Pro Tyr

<210> SEQ ID NO 14
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 14

Ile Ala Met His Pro Gln Val Asn Ile Tyr Ser Val Thr Arg Lys Arg
1               5                   10                  15

Tyr Ala His

<210> SEQ ID NO 15

```
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 15

Thr Ala Asp His Arg Phe Leu Arg His Asp Gly Arg Leu Val Ala Arg
1               5                  10                  15

Pro Glu Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 16

Asn Lys Tyr Leu Thr Ala Glu Ala Phe Gly Phe Lys Val Asn Ala Ser
1               5                  10                  15

Ala Ser Ser Leu
            20

<210> SEQ ID NO 17
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 17

Glu Leu Phe Leu Met Lys Leu Ile Asn Arg Pro Ile Ile Val Phe Arg
1               5                  10                  15

Gly Glu His Gly Phe Ile Gly Cys Arg
            20                  25

<210> SEQ ID NO 18
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 18

Val Gln Ile Gln Phe Gly Leu Ile Asn Cys Gly Asn Lys Tyr Leu Thr
1               5                  10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 19

Ala Val Cys Leu Arg Ser His Leu Gly Arg Tyr Leu Ala Ala Asp Lys
1               5                  10                  15

Asp

<210> SEQ ID NO 20
<211> LENGTH: 16
<212> TYPE: PRT
<213> ORGANISM: Artificial Sequence
```

```
<220> FEATURE:
<223> OTHER INFORMATION: Synthetic polypeptide

<400> SEQUENCE: 20

Thr Gly Lys Tyr Trp Thr Leu Thr Ala Thr Gly Gly Val Gln Ser Thr
1               5                   10                  15

<210> SEQ ID NO 21
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 21

Leu Phe Ala Leu Glu Gln Ser Cys Ala Gln Val Val Leu Gln Ala Ala
1               5                   10                  15

Asn Glu Arg Asn
            20

<210> SEQ ID NO 22
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 22

Lys Asp Ser Thr Gly Lys Tyr Trp Thr Val Gly Ser Asp Ser Ala Val
1               5                   10                  15

Thr Ser

<210> SEQ ID NO 23
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 23

Val Val Thr Gly Tyr Val Lys Ile Arg His Ser His Ala Leu Val
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 24

Thr Gln Tyr Ala Val Tyr Val Lys Ala Val Thr Leu Thr Met Val
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 25

Leu Val Ile Met Leu Tyr Val Phe His Arg Lys Arg Asn Asn Ser
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 26

Gly Met Ala Tyr Leu Asn Ala Asn Lys Phe Val His Arg Asp Leu
1               5                   10                  15

<210> SEQ ID NO 27
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 27

Val Ser Tyr Lys His Met Arg Phe Leu Ile Thr His Asn Pro Thr Asn
1               5                   10                  15

Ala Thr Leu

<210> SEQ ID NO 28
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 28

Phe Ile Glu Asp Leu Lys Lys Tyr Gly Ala Thr Thr Val Val Arg Val
1               5                   10                  15

Cys Glu Val Thr Tyr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 29

Pro Cys Val Ala Gly Leu Gly Arg Ala Pro Val Leu Val Ala Leu Ala
1               5                   10                  15

Leu Ile Glu Ser
            20

<210> SEQ ID NO 30
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 30

Met Lys Tyr Glu Asp Ala Ile Gln Phe Ile Arg Gln Lys Arg Arg Gly
1               5                   10                  15

Ala Ile Asn

<210> SEQ ID NO 31
<211> LENGTH: 15
<212> TYPE: PRT
<213> ORGANISM: Artificial Sequence
```

-continued

```
<220> FEATURE:
<223> OTHER INFORMATION: Synthetic polypeptide

<400> SEQUENCE: 31

Val Glu Asp Trp Leu Ser Leu Val Lys Ala Lys Phe Cys Glu Ala
1               5                   10                  15

<210> SEQ ID NO 32
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 32

Glu Pro Asp Tyr Phe Lys Asp Met Thr Pro Thr Ile Arg Lys Thr Gln
1               5                   10                  15

Lys Ile Val Ile
            20

<210> SEQ ID NO 33
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 33

Asp Tyr Phe Lys Asp Met Thr Pro Thr Ile Arg Lys Thr Gln Lys Ile
1               5                   10                  15

Val Ile Lys Lys Arg
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 34

Leu Phe Lys Phe Cys Thr Cys Leu Ala Thr Val Phe Ser Phe Leu Lys
1               5                   10                  15

Arg Leu Ile Cys
            20

<210> SEQ ID NO 35
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 35

Gly Phe Ser Ser Arg Leu Ala Ala Thr Gln Asp Leu Pro Phe Ile His
1               5                   10                  15

Gln Ser Ser Glu Leu Gly Asp
            20

<210> SEQ ID NO 36
<211> LENGTH: 21
<212> TYPE: PRT
<213> ORGANISM: Artificial Sequence
<220> FEATURE:
<223> OTHER INFORMATION: Synthetic polypeptide
```

```
<400> SEQUENCE: 36

Glu Glu Glu Asp Ala Ala Trp Gln Ala Glu Glu Val Leu Arg Gln Gln
1               5                   10                  15

Lys Leu Ala Asp Arg
            20

<210> SEQ ID NO 37
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 37

Ile Arg Met Asn Arg Val Val Arg Asn Asn Leu Arg Val Arg Leu Gly
1               5                   10                  15

Asp Val Ile Ser Ile
            20

<210> SEQ ID NO 38
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 38

Leu Gln Leu Phe Arg Gly Asp Thr Val Leu Leu Lys Gly Lys Lys Arg
1               5                   10                  15

Arg

<210> SEQ ID NO 39
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 39

Tyr Phe Leu Glu Ala Tyr Arg Pro Ile Arg Lys Gly Asp Ile Phe Leu
1               5                   10                  15

Val Arg Gly

<210> SEQ ID NO 40
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 40

Val Glu Phe Lys Val Val Glu Thr Asp Pro Ser Pro Tyr Cys Ile Val
1               5                   10                  15

Ala Pro Asp Thr
            20

<210> SEQ ID NO 41
<211> LENGTH: 19
<212> TYPE: PRT
<213> ORGANISM: Artificial Sequence
<220> FEATURE:
<223> OTHER INFORMATION: Synthetic polypeptide
```

<400> SEQUENCE: 41

Leu Arg His Pro Ala Leu Phe Lys Ala Ile Gly Val Lys Pro Pro Arg
1               5                   10                  15

Gly Ile Leu

<210> SEQ ID NO 42
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 42

Glu Thr Gly Ala Phe Phe Phe Leu Ile Asn Gly Pro Glu Ile Met Ser
1               5                   10                  15

Lys

<210> SEQ ID NO 43
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 43

Ala Val Thr Met Asp Asp Phe Arg Trp Ala Leu Ser Gln Ser Asn Pro
1               5                   10                  15

Ser

<210> SEQ ID NO 44
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 44

Gln Arg Ala His Val Ile Val Met Ala Ala Thr Asn Arg Pro Asn Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 45

Lys Asn Val Phe Ile Ile Gly Ala Thr Asn Arg Pro Asp Ile Ile
1               5                   10                  15

<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
gccatccctt cacgttag                                              18

<210> SEQ ID NO 47
<211> LENGTH: 19
<212> TYPE: DNA

```
<213> ORGANISM: Artificial Sequence
<220> FEATURE:
<223> OTHER INFORMATION: Synthetic primer

<400> SEQUENCE: 47
ttccactttg gcataaggc                                                19

<210> SEQ ID NO 48
<211> LENGTH: 21
<212> TYPE: DNA
<213> ORGANISM: Artificial Sequence
<220> FEATURE:
<223> OTHER INFORMATION: Synthetic primer

<400> SEQUENCE: 48
tcctgagaaa gacagaagtt a                                             21

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
tgaacggatt tggccgtatt gggcg                                         25

<210> SEQ ID NO 50
<211> LENGTH: 25
<212> TYPE: DNA
<213> ORGANISM: Artificial Sequence
<220> FEATURE:
<223> OTHER INFORMATION: Synthetic primer

<400> SEQUENCE: 50
actgagctgc gttttacacc ctttc                                         25

<210> SEQ ID NO 51
<211> LENGTH: 25
<212> TYPE: DNA
<213> ORGANISM: Artificial Sequence
<220> FEATURE:
<223> OTHER INFORMATION: Synthetic primer

<400> SEQUENCE: 51
gcagagcgca cgtttgaaca ggcca                                         25

<210> SEQ ID NO 52
<211> LENGTH: 25
<212> TYPE: DNA
<213> ORGANISM: Artificial Sequence
<220> FEATURE:
<223> OTHER INFORMATION: Synthetic primer

<400> SEQUENCE: 52
gactgggcca tggagtggac ttaaa                                         25

<210> SEQ ID NO 53
<211> LENGTH: 25
<212> TYPE: DNA
<213> ORGANISM: Artificial Sequence
<220> FEATURE:
<223> OTHER INFORMATION: Synthetic primer

<400> SEQUENCE: 53
gcagttgccc caaatgtgat ccaag                                         25
```

```
<210> SEQ ID NO 54
<211> LENGTH: 25
<212> TYPE: DNA
<213> ORGANISM: Artificial Sequence
<220> FEATURE:
<223> OTHER INFORMATION: Synthetic primer

<400> SEQUENCE: 54
gaagtggagc agaataatct agtcc                                          25

<210> SEQ ID NO 55
<211> LENGTH: 25
<212> TYPE: DNA
<213> ORGANISM: Artificial Sequence
<220> FEATURE:
<223> OTHER INFORMATION: Synthetic primer

<400> SEQUENCE: 55
catcaaagac tccacgggca agtac                                          25

<210> SEQ ID NO 56
<211> LENGTH: 25
<212> TYPE: DNA
<213> ORGANISM: Artificial Sequence
<220> FEATURE:
<223> OTHER INFORMATION: Synthetic primer

<400> SEQUENCE: 56
gttcatccga cagaagcgcc gtggg                                          25

<210> SEQ ID NO 57
<211> LENGTH: 25
<212> TYPE: DNA
<213> ORGANISM: Artificial Sequence
<220> FEATURE:
<223> OTHER INFORMATION: Synthetic primer

<400> SEQUENCE: 57
aaactcagaa aattgtcatt aagaa                                          25

<210> SEQ ID NO 58
<211> LENGTH: 25
<212> TYPE: DNA
<213> ORGANISM: Artificial Sequence
<220> FEATURE:
<223> OTHER INFORMATION: Synthetic primer

<400> SEQUENCE: 58
ctgtcgtagt ttggggtggt gcagg                                          25

<210> SEQ ID NO 59
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 59

Phe Met Arg Arg Arg His Ile Val Arg Lys Arg Thr Leu Arg Arg Leu
 1               5                  10                  15

Leu Gln Glu Arg Glu Leu Val Glu Pro Leu Thr Pro Ser Gly Glu Ala
                20                  25                  30

Pro Asn Gln Ala Leu Leu Arg Ile Leu Lys Glu Thr Glu Phe Lys Lys
            35                  40                  45
```

```
Ile Lys Val Leu Gly Ser Gly Ala Phe Gly
    50                  55
```

CANCER VACCINE COMPOSITIONS AND METHODS OF USE THEREOF

STATEMENT OF GOVERNMENT LICENSE RIGHTS

This invention was made with government support under Grant Nos. RR025015 and CA053300 awarded by the National Institutes of Health. The government has certain rights in the invention.

CROSS-REFERENCE

This application is a U.S. National Phase Application under 35 U.S.C. § 371 of International Application No. PCT/US2015/040960, filed Jul. 17, 2015, which is related to U.S. provisional patent application No. 62/026,246, filed Jul. 18, 2014, which are herein incorporated by reference in their entirety.

REFERENCE TO A SEQUENCE LISTING SUBMITTED VIA EFS-WEB

The content of the ASCII text file of the sequence listing named "41299-781-601-seqlist_ST25.txt" which is 15.4 kb in size was created on Jun. 18, 2015, and electronically submitted via EFS-Web herewith the application is incorporated herein by reference in its entirety.

BACKGROUND

Cancer therapy has conventionally been accomplished by surgical reduction of a tumor mass and subsequent chemo- and/or radiotherapy. This strategy can reduce the tumor and, in less advanced stages, often results in complete remission. Unfortunately, the prognosis for more advanced tumors has changed little over the past 50 years and a significant proportion of cancer-related deaths are caused by subsequent metastases. New prophylactic and therapeutic treatments are needed to combat the increasing occurrence of cancer.

Over 1 million people are diagnosed with colorectal cancer each year worldwide and more than 700,000 people die of colorectal cancer each year. Preventing the development of colorectal cancer could have significant health and economic benefits for all individuals. Billions of dollars would be saved if people did not need to receive expensive cancer-related surveillance and therapeutic interventions. New approaches for the prevention and treatment of colorectal cancer are needed.

SUMMARY

The compositions described herein include, in some aspects, a composition comprising: a first plasmid comprising a first nucleotide sequence, the first nucleotide sequence encoding a first epitope of a first antigen expressed by cells associated with colorectal cancer; and a second nucleotide sequence, the second nucleotide sequence encoding a second epitope of a second antigen expressed by cells associated with colorectal cancer, wherein the first nucleotide sequence and the second nucleotide sequence are located in one or more plasmids.

The compositions described herein include, in some aspects, a composition comprising: a first plasmid comprising a first nucleotide sequence, the first nucleotide sequence encoding a first epitope of a first antigen, the first epitope is a portion of a peptide selected from: CDC25B, COX2, EGFR, FASCIN1, IGF1R, PRL3, RCAS1, and VCP, wherein the first nucleotide sequence is located in a plasmid.

In other aspects, the disclosure includes a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CDC25B, COX2, EGFR, FASCIN1, IGF1R, PRL3, RCAS1, and VCP, wherein the first nucleotide sequence and the second nucleotide sequence are located in one or more plasmids.

The compositions described herein include, in some aspects, a composition comprising: a first epitope of a first antigen expressed by cells associated with colorectal cancer; and a second epitope of a second antigen expressed by cells associated with colorectal cancer.

In other aspects, the disclosure includes a composition comprising: at least a first epitope of a first antigen, the first epitope is a portion of a peptide selected from: CDC25B, COX2, EGFR, FASCIN1, IGF1R, PRL3, RCAS1, and VCP.

In yet other aspects, the disclosure includes a composition comprising: at least a first epitope of a first antigen, at least a second epitope of a second antigen, the first and the second epitopes are independently selected from: CDC25B, COX2, EGFR, FASCIN1, IGF1R, PRL3, RCAS1, and VCP.

The compositions described herein include, in some aspects, a composition comprising an isolated and purified plasmid comprising a nucleotide sequence encoding a polypeptide, wherein the polypeptide comprises a plurality of epitopes selected from CDC25B, COX2, EGFR, FASCIN1, IGF1R, PRL3, RCAS1, and VCP; and an excipient.

The plurality of epitopes can comprise one or more epitopes comprising at least 90%, at least 95%, or at least 99% sequence identity to an amino acid sequence selected from SEQ ID NOs: 1-45. The plurality of epitopes can comprise one or more epitopes comprising at least 90%, at least 95%, or at least 99% sequence identity to at least 8 contiguous amino acids of SEQ ID NOs: 1-45. The plurality of epitopes can be a plurality of contiguous epitopes. The contiguous epitopes can further comprise a linker between one or more of the epitope sequences.

The composition can further comprise an additional isolated and purified plasmid comprising an additional nucleotide sequence encoding an additional polypeptide, wherein the additional polypeptide comprises a plurality of epitopes comprising one or more epitopes comprising at least 90%, at least 95%, or at least 99% sequence identity to an amino acid sequence selected from SEQ ID NOs: 1-45. The sequence of the polypeptide and the additional polypeptide can be different.

The composition can further comprise a first plasmid comprising a first nucleotide sequence, the first nucleotide sequence encoding a first epitope of a first antigen, the first epitope is a portion of a peptide selected from: CDC25B, COX2, EGFR, FASCIN1, IGF1R, PRL3, RCAS1, and VCP, wherein the first nucleotide sequence is located in a plasmid.

The composition can further comprise: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CDC25B, COX2, EGFR, FASCIN1, IGF1R, PRL3, RCAS1, and VCP, wherein the first nucleotide sequence and the second nucleotide sequence are located in one or more plasmids.

The composition can comprise a nucleic acid sequence encoding an epitope of the peptide CDC25B is selected from a nucleotide sequence encoding an amino acid sequence, wherein the amino acid sequence has at least 90% sequence identity to the amino acid sequence selected from SEQ ID NOs: 1-2.

The composition can comprise a nucleic acid sequence encoding an epitope of the peptide COX2 is selected from a nucleotide sequence encoding an amino acid sequence, wherein the amino acid sequence has at least 90% sequence identity to the amino acid sequence of SEQ ID NOs: 3-10.

The composition can comprise a nucleic acid sequence encoding an epitope of the peptide EGFR is selected from a nucleotide sequence encoding an amino acid sequence, wherein the amino acid sequence has at least 90% sequence identity to the amino acid sequence of SEQ ID NOs: 11-13.

The composition can comprise a nucleic acid sequence encoding an epitope of the peptide FASCIN1 is selected from a nucleotide sequence encoding an amino acid sequence, wherein the amino acid sequence has at least 90% sequence identity to the amino acid sequence of SEQ ID NOs: 14-22.

The composition can comprise a nucleic acid sequence encoding an epitope of the peptide IGF1R is selected from a nucleotide sequence encoding an amino acid sequence, wherein the amino acid sequence has at least 90% sequence identity to the amino acid sequence of SEQ ID NO: 23-26.

The composition can comprise a nucleic acid sequence encoding an epitope of the peptide PRL3 is selected from a nucleotide sequence encoding an amino acid sequence, wherein the amino acid sequence has at least 90% sequence identity to the amino acid sequence of SEQ ID NOs: 27-31.

The composition can comprise a nucleic acid sequence encoding an epitope of the peptide RCAS1 is selected from a nucleotide sequence encoding an amino acid sequence, wherein the amino acid sequence has at least 90% sequence identity to the amino acid sequence of SEQ ID NOs: 32-36.

The composition can comprise a nucleic acid sequence encoding an epitope of the peptide VCP is selected from a nucleotide sequence encoding an amino acid sequence, wherein the amino acid sequence has at least 90% sequence identity to the amino acid sequence of SEQ ID NO: 37-45.

The composition can comprise a first and a second epitope independently selected from: CDC25B, COX2, EGFR, FASCIN1, IGF1R, PRL3, RCAS1, and VCP.

The composition can further comprise at least an additional epitope, wherein the first and second epitopes and the at least an additional epitope are independently selected from: CDC25B, COX2, EGFR, FASCIN1, IGF1R, PRL3, RCAS1, and VCP.

The composition can further comprise a first plasmid comprising a first nucleotide sequence, the first nucleotide sequence encoding a first epitope of a first antigen, the first epitope is a portion of a peptide selected from: CDC25B, COX2, and PRL3, wherein the first nucleotide sequence is located in a plasmid.

The composition can further comprise: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CDC25B, COX2, and PRL3, wherein the first nucleotide sequence and the second nucleotide sequence are located in one or more plasmids.

The composition can comprise a nucleic acid sequence encoding an epitope of the peptide CDC25B is selected from a nucleotide sequence encoding an amino acid sequence, the amino acid sequence having at least 90% sequence identity to the amino acid sequence of SEQ ID NO: 1-2.

The composition can comprise a nucleic acid sequence encoding an epitope of the peptide COX2 is selected from a nucleotide sequence encoding an amino acid sequence, the amino acid sequence having at least 90% sequence identity to the amino acid sequence of SEQ ID NO: 3-10.

The composition can comprise a nucleic acid sequence encoding an epitope of the peptide PRL3 is selected from a nucleotide sequence encoding an amino acid sequence, the amino acid sequence having at least 90% sequence identity to the amino acid sequence of SEQ ID NOs: 27-31.

The composition can comprise a first and a second epitope independently selected from: CDC25B, COX2, EGFR, FASCIN1, IGF1R, PRL3, RCAS1, and VCP.

The composition can further comprise at least an additional epitope, wherein the first and second epitopes and the at least an additional epitope are independently selected from: CDC25B, COX2, EGFR, FASCIN1, IGF1R, PRL3, RCAS1, and VCP.

The first and the second nucleic acid sequences can be located on the first plasmid. The second nucleic acid sequence can be located on a second plasmid. The first and the second nucleic acid sequences can be purified to at least 70% purity. At least the first plasmid can be contained within a pharmaceutical composition.

The first and the second nucleic acid sequences can be located on the first plasmid and are separated by a sequence of linker nucleic acids.

The first nucleic acid sequence can be adjacent to the second nucleic acid sequence on the first plasmid.

The composition can further comprise at least a first epitope of a first antigen, the first epitope is a portion of a peptide selected from: CDC25B, COX2, EGFR, FASCIN1, IGF1R, PRL3, RCAS1, and VCP.

The composition can further comprise: at least a first epitope of a first antigen; and at least a second epitope of a second antigen, the first and the second epitopes are independently selected from: CDC25B, COX2, EGFR, FASCIN1, IGF1R, PRL3, RCAS1, and VCP.

At least a first epitope of the peptide CDC25B can be selected from an amino acid sequence, the amino acid sequence having at least 90% sequence identity to the amino acid sequence of SEQ ID NO: 1-2.

At least a first epitope of the peptide COX2 can be selected from an amino acid sequence, the amino acid sequence having at least 90% sequence identity to the amino acid sequence of SEQ ID NO: 3-10.

At least a first epitope of the peptide EGFR can be selected from an amino acid sequence, the amino acid sequence having at least 90% sequence identity to the amino acid sequence of SEQ ID NOs: 11-13.

At least a first epitope of the peptide FASCIN1 can be selected from an amino acid sequence, the amino acid sequence having at least 90% sequence identity to the amino acid sequence of SEQ ID NOs: 14-22.

At least a first epitope of the peptide IGF1R can be selected from an amino acid sequence, the amino acid sequence having at least 90% sequence identity to the amino acid sequence of SEQ ID NOs: 23-26.

At least a first epitope of the peptide PRL3 can be selected from an amino acid sequence, the amino acid sequence having at least 90% sequence identity to the amino acid sequence of SEQ ID NOs: 27-31.

At least a first epitope of the peptide RCAS1 can be selected from an amino acid sequence, the amino acid sequence having at least 90% sequence identity to the amino acid sequence of SEQ ID NOs: 32-36.

At least a first epitope of the peptide VCP can be selected from an amino acid sequence, the amino acid sequence having at least 90% sequence identity to the amino acid sequence of SEQ ID NOs: 37-45.

The composition can comprise a first and a second epitope independently selected from: CDC25B, COX2, EGFR, FASCIN1, IGF1R, PRL3, RCAS1, and VCP.

The composition can further comprise at least an additional epitope wherein the first and second epitopes and the at least an additional epitope are independently selected from: CDC25B, COX2, EGFR, FASCIN1, IGF1R, PRL3, RCAS1, and VCP.

The composition can comprise at least a first epitope of a first antigen, the first epitope is a portion of a peptide selected from: CDC25B, COX2, and PRL3.

The composition can comprise: at least a first epitope of a first antigen; and at least a second epitope of a second antigen, the first and the second epitopes are independently selected from: CDC25B, COX2, and PRL3.

At least a first epitope of the peptide CDC25B can be selected from an amino acid sequence, the amino acid sequence having at least 90% sequence identity to the amino acid sequence of SEQ ID NOs: 1-2.

At least a first epitope of the peptide COX2 can be selected from an amino acid sequence, the amino acid sequence having at least 90% sequence identity to the amino acid sequence of SEQ ID NOs: 3-10.

At least a first epitope of the peptide PRL3 can be selected from an amino acid sequence, the amino acid sequence having at least 90% sequence identity to the amino acid sequence of SEQ ID NOs: 27-31.

The composition can comprise a first and a second epitope independently selected from: CDC25B, COX2, and PRL3.

The composition can further comprise at least an additional epitope, wherein the first, and second epitopes and the at least an additional epitope are independently selected from: CDC25B, COX2, and PRL3.

The composition can be administered to a subject.

The cells associated with colorectal cancer can be selected from the group consisting of: colon cells expressing atypical features, rectal cells expressing atypical features, pre-neoplastic colon cells, pre-neoplastic rectal cells, colon cancer cells, rectal cancer cells, pre-invasive colon cancer cells, pre-invasive rectal cancer cells, colon cancer stem cells, rectal cancer stem cells, epithelial cells, mesenchymal cells, stromal cells, and combinations thereof.

The cells associated with non-small cell lung cancer can be selected from the group consisting of: lung cells expressing atypical features, pre-neoplastic lung cells, lung cancer cells, pre-invasive lung cancer cells, lung cancer stem cells, epithelial cells, mesenchymal cells, stromal cells, and combinations thereof.

The composition can be effective to elicit an immune response in a subject. The composition can be effective to eliminate a number of cells associated with colorectal cancer, non-small cell lung cancer, or ovarian cancer in a subject. The composition may be used to prevent the growth of cells associated with colorectal cancer, non-small cell lung cancer, or ovarian cancer in a subject. The immune response can be a Type 1 immune response.

At least the first epitope can be contained within a pharmaceutical composition. The composition can further comprise a pharmaceutical carrier and/or an adjuvant.

The amino acid sequences of the first and the second epitopes can be separated by a sequence of linker amino acids. The amino acid sequence of the first epitope can be adjacent to the amino acid sequence of the second epitope.

The immune response can be characterized by a ratio of Type I cytokine production to Type II cytokine production that is greater than 1. The immune response can be characterized by a ratio of Type I cytokine production to Type II cytokine production that is less than 1. The immune response can be characterized by a ratio of IFN-γ production to IL-10 production that is greater than 1. The immune response can be characterized by a ratio of IFN-γ production to IL-10 production that is less than 1.

The adjuvant can be GM-CSF.

Described herein can include a method of treating colorectal cancer or non-small cell lung cancer in a subject in need thereof, the method comprising administering the composition described herein to the subject. Also described herein can include a method of prolonging the remission duration of colorectal cancer or non-small cell lung cancer in a subject in need thereof, comprising administering to the subject a composition described herein. At least one dose of the composition can be administered. The composition can be administered by subcutaneous injection, intradermal injection, intramuscular injection, intravascular injection, topical application or inhalation. The method can further comprise administering to the subject an additional therapeutic agent.

Described herein also include an isolated and purified plasmid comprising at least one nucleotide sequence encoding a polypeptide comprising at least 70% sequence identity to an epitope sequence selected from SEQ ID NOs: 1-45. The at least one nucleotide sequence can encode a polypeptide comprising at least 80%, 85%, 90%, 95%, or 99% sequence identity to an epitope sequence selected from SEQ ID NOs: 1-45. The at least one nucleotide sequence can encode a polypeptide comprising at least 70%, 80%, 85%, 90%, 95%, or 99% sequence identity to at least 8 contiguous amino acids of SEQ ID NOs: 1-45. The plasmid can be about 50%, about 60%, about 70%, about 80%, about 90%, or about 100% pure.

Also described herein include a colorectal cancer vaccine comprising a composition disclosed herein. The vaccine can be administered by subcutaneous injection, intradermal injection, intramuscular injection, intravascular injection, topical application or inhalation. The vaccine can be administered to a subject prior to, after, or in combination with an additional therapeutic agent.

Further described herein include a non-small cell lung cancer vaccine comprising a composition disclosed herein. The vaccine can be administered by subcutaneous injection, intradermal injection, intramuscular injection, intravascular injection, topical application or inhalation. The vaccine can be administered to a subject prior to, after, or in combination with an additional therapeutic agent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
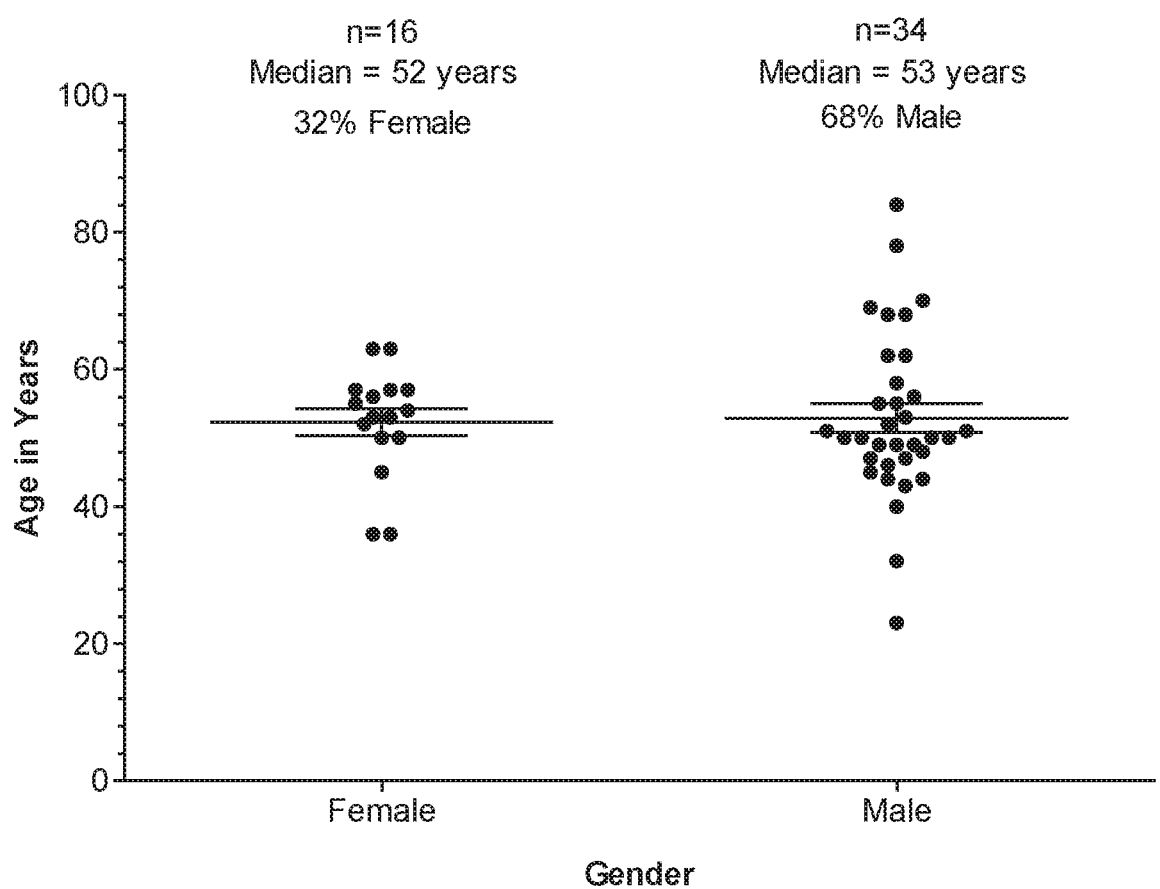
FIG. 1 shows colorectal cancer patient age and gender statistics.

This disclosure provides compositions of cancer vaccines (e.g., colorectal cancer, non-small cell lung cancer, or ovarian cancer vaccines) for the prevention or treatment of colorectal cancer, non-small cell lung cancer, or ovarian cancer. The disclosure further provides methods of administering cancer vaccines to a subject. In some aspects, the compositions provided herein are used in combination with the methods provided herein for the prevention or treatment of colorectal cancer, non-small cell lung cancer, or ovarian cancer.

In some cases, the compositions include: sequences of nucleic acids encoding epitopes of cancer antigens (e.g., colorectal cancer, non-small cell lung cancer, or ovarian cancer antigens), wherein the epitopes elicit an immunogenic response in a subject, plasmids containing the sequences described herein, an adjuvant, a pharmaceutical carrier, and inert chemicals suitable for use with pharmaceutical compositions. The cancer antigens (e.g., colorectal cancer, non-small cell lung cancer, or ovarian cancer antigens) are at least one of any antigen expressed in a subject that has or may develop colorectal cancer, non-small cell lung cancer, or ovarian cancer. Often, the cancer antigens are expressed by cancer cells and/or tissues such as cancer stem cells. For example, the colorectal cancer antigens are expressed by colorectal cancer cells and/or tissues such as colorectal cancer stem cells (CSC)s. Colorectal CSCs may exhibit self renewal, unregulated growth, and drug resistance. In some cases, colorectal CSCs express proteins (e.g., antigens) and in an aspect, the level of expression of proteins (e.g., antigens) by CSCs is upregulated (e.g., increased expression relative to a given amount) or downregulated (e.g., decreased expression relative to a given amount). In some cases, proteins that are upregulated by colorectal CSCs compared to normal tissue or cells are involved in the development and/or progression of colorectal cancer. In an aspect, the proteins are identified and epitopes of antigens targeted, using the compositions and methods described herein.

In some cases, one epitope of a cancer antigens (e.g., colorectal cancer, non-small cell lung cancer, or ovarian cancer antigens) is used in the composition. In other cases, more than one epitope of a cancer antigens (e.g., colorectal cancer, non-small cell lung cancer, or ovarian cancer antigens) is used in the composition. In other cases, more than two antigens, more than three, more than four, more than five, more than six, more than seven, more than eight, more than nine, more than ten, more than 15, more than 20, more than 25 or more than 30 cancer antigens (e.g., colorectal cancer, non-small cell lung cancer, or ovarian cancer antigens) are used in the composition. In some cases, the antigens are the same. In other cases, the antigens are different. In some aspects, the compositions of cancer vaccines (e.g., colorectal cancer, non-small cell lung cancer, or ovarian cancer vaccines) described herein are formulated for the prevention of colorectal cancer, non-small cell lung cancer, or ovarian cancer. In an aspect, prevention compositions eliminate cells (e.g., colorectal CSCs) with abnormal (e.g., upregulated) expression of proteins to prevent colorectal cancer.

In some cases, the epitope and/or epitopes are on the same cancer antigens (e.g., colorectal cancer, non-small cell lung cancer, or ovarian cancer antigens) or the epitope and/or epitopes are on a different cancer antigens (e.g., colorectal cancer, non-small cell lung cancer, or ovarian cancer antigens). In some cases, one epitope on a cancer antigen (e.g., colorectal cancer, non-small cell lung cancer, or ovarian cancer antigen) is used in the composition. In other cases, more than one epitope on a cancer antigen (e.g., colorectal cancer, non-small cell lung cancer, or ovarian cancer antigen), more than two antigens, more than three, more than four, more than five, more than six, more than seven, more than eight, more than nine, more than ten, more than 15, more than 20, more than 25 or more than 30 epitopes on cancer antigens (e.g., colorectal cancer, non-small cell lung cancer, or ovarian cancer antigens) are used in the composition.

In some aspects, the compositions and methods described herein elicit an immune response in a subject. In some aspects, the immune response is an immune response to the epitopes of the antigens in the composition (e.g., vaccine). Vaccines arm the immune system of the subject such that the immune system detects and destroys that which contains the antigens of the vaccines in the subject. In some aspects, the compositions and methods described herein elicit a Type 1 (Th1) immune response in the subject. In some cases, Th1 immune responses include secretion of inflammatory cytokines (e.g., IFN-γ, TNF-α) by a subset of immune cells (e.g., antigen specific T cells). In other cases, the inflammatory cytokines activate another subtype of immune cells (e.g., cytotoxic T cells) which destroy that which contains the antigen in the subject.

In some aspects, the screening methods described herein are used to identify epitopes and binding peptides from tumor antigens, epitopes of a plurality of antigens are screened for induction of a Th1 immune responses. In an aspect, the methods of screening identify epitopes from at least one tumor antigen that elicit a Th1 response (e.g., causing secretion of Th1 cytokines) to cancer antigens (e.g., colorectal cancer, non-small cell lung cancer, or ovarian cancer antigens), and can further include such as for example colorectal CSC antigens.

In some cases, the epitopes and/or antigens used in the compositions and methods described herein are recognized by the immune system of a subject to elicit a ThI immune response and release Type I cytokines. In some aspects, the Th1 response is initiated by the interaction between the epitope and the T cell, more specifically, the major histocompatibility complex (MHC) expressed by the T cell. In an aspect, high affinity binding of an epitope to an MHC receptor stimulates a Th1 response. MHC receptors are at least one of a plurality of types of MHC receptors. In some aspects, the MHC receptors engaged on a T cell vary across individuals in a population.

The epitopes and/or antigens used in the compositions and methods described herein can be used to generate a chimeric antigen receptor (CAR) T cell. The engineered T cell can express an antibody, such as a single chain variable fragment (scFv), and can recognize one or more of the epitopes described herein present on a colorectal tumor cell, a non small cell lung carcinoma (NSCLC) cell, or an ovarian cancer cell. The expressed antibody can further induce an engineered immune response by the tumor cell. Sometimes, the one or more of the epitopes are selected from CDC25B, COX2, EGFR, FASCIN1, IGF1R, PRL3, RCAS1, or VCP. The one or more of the epitopes can comprise at least 90%, at least 95%, or at least 99% sequence identity to at least 8 contiguous amino acids of SEQ ID NOs: 1-45. In some instances, the engineered T cell can express an antibody and can recognize one or more of the epitopes selected from CDC25B, COX2, EGFR, FASCIN1, IGF1R, PRL3, RCAS1, or VCP present on a colorectal tumor cell or a NSCLC cell. In additional instances, the engineered T cell can express an antibody and can recognize one or more of the epitopes comprising at least 90%, at least 95%, or at least 99% sequence identity to at least 8 contiguous amino acids of SEQ ID NOs: 1-45 present on a colorectal tumor cell or a NSCLC cell.

The epitopes and/or antigens used in the compositions and methods described herein can be used as suitable targets for engineered T cell receptors (TCRs). In some instances, the gene encoding the engineered T cell receptor is introduce into a T cell such as for example by a viral delivery method and subsequently expresses the engineered TCR. The engineered TCRs which can recognize one or more of the epitopes described herein can be used for engineered T Cell Receptor-based therapies including autologous and heterologous cell therapies. As disclosed above, the one or more of the epitopes are selected from CDC25B, COX2, EGFR, FASCIN1, IGF1R, PRL3, RCAS1, or VCP. The one or more of the epitopes can comprise at least 90%, at least 95%, or at least 99% sequence identity to at least 8 contiguous amino acids of SEQ ID NOs: 1-45. In some instances, the engineered TCR can recognize one or more of the epitopes selected from CDC25B, COX2, EGFR, FASCIN1, IGF1R, PRL3, RCAS1, or VCP. In additional instances, the engineered TCR can recognize one or more of the epitopes comprising at least 90%, at least 95%, or at least 99% sequence identity to at least 8 contiguous amino acids of SEQ ID NOs: 1-45.

In some aspects, the compositions described herein include components in addition to nucleic acids encoding epitopes of antigens. In some cases, the compositions include at least one adjuvant. In some cases, the compositions include at least one pharmaceutical carrier. In some cases, the compositions include at least one inert chemical suitable for use with pharmaceutical compositions. In some cases, the compositions include at least one adjuvant and at least one pharmaceutical carrier. In some cases, the compositions include at least one adjuvant and at least one inert chemical suitable for use with pharmaceutical compositions. In some cases, the compositions include at least one inert chemical suitable for use with pharmaceutical compositions and a pharmaceutical carrier. In some cases, the compositions contain a plurality of adjuvants, a plurality of pharmaceutical carriers and a plurality of inert chemicals suitable for use with pharmaceutical compositions.

In some cases, one adjuvant is used in the composition. In other cases, more than one adjuvant, more than two adjuvants, more than three adjuvants, more than four adjuvants, more than five adjuvants, more than six adjuvants, more than seven adjuvants, more than eight adjuvants, more than nine adjuvants or more than ten adjuvants are used in the composition. In some cases, one pharmaceutical carrier is used in the composition. In other cases, more than one pharmaceutical carrier, more than two pharmaceutical carriers, more than three pharmaceutical carriers, more than four pharmaceutical carriers, more than five pharmaceutical carriers, more than six pharmaceutical carriers, more than seven pharmaceutical carriers, more than eight pharmaceutical carriers, more than nine pharmaceutical carriers or more than ten pharmaceutical carriers are used in the composition. In some cases, one chemical is used in the composition. In other cases, more than one chemical, more than two chemicals, more than three chemicals, more than four chemicals, more than five chemicals, more than six chemicals, more than seven chemicals, more than eight chemicals, more than nine chemicals or more than ten chemicals are used in the composition.

The disclosure further describes methods of administering cancer vaccines (e.g., colorectal cancer, non-small cell lung cancer, or ovarian cancer vaccines) to a subject. In some cases, the methods include constructing a plasmid based vaccine that targets those antigens and determining whether administration of the vaccine is safe, immunogenic, and effective to prevent the development of colorectal cancer, NSCLC, or ovarian cancer. In an aspect, the composition is a multi-antigen Th1 polyepitope plasmid based vaccine. In some cases, the methods include conducting at least one clinical trial to determine the safety and immunogenicity of the plasmid based vaccine in subjects with colorectal cancer, NSCLC, or ovarian cancer. In an aspect, antigens are expressed by or associated with colorectal CSCs and/or the transition of a cell from an epithelial cell to a mesenchymal cell (EMT). In some cases, epitopes of the compositions are derived from antigens wherein the epitopes may elicit a Th1 immune response in the subject. In an aspect, the Th1 immune response includes immune cells, often $CD4^+$ T cells. In some cases, the composition is a nucleic acid (e.g., plasmid based vaccine) that includes nucleic acids encoding more than one antigen or more than one epitope of an antigen. In some cases, the methods are used to determine if the compositions described herein prevent the development of cancer (e.g., colorectal cancer, small cell lung cancer, or ovarian cancer) in a plurality of organisms, and in an aspect, in models of cancer (e.g., colorectal cancer, small cell lung cancer, or ovarian cancer) using genetically similar rodents (e.g., mice), using genetically diverse rodents (e.g., mice), and in subjects which do or do not have cancer (e.g., colorectal cancer, small cell lung cancer, or ovarian cancer).

Identification of Antigens

The compositions and methods described herein include the identification and engineering of cancer antigens (e.g., colorectal cancer, non-small cell lung cancer, or ovarian cancer antigens) in a pharmaceutical composition (e.g., a vaccine). While any techniques known to one of ordinary skill in the art may be used to identify antigens expressed by a subject with colorectal cancer, in an aspect, suitable antigens are identified using the methods described herein. In some cases, the methods include screening sera from subjects. In some cases, the screening is antibody screening. In an aspect, the antibodies screened are IgG antibodies. In some cases, the sera is from a subject with cancer (e.g., colorectal cancer, NSCLC, or ovarian cancer). In other cases, the sera is from a subject that does not have cancer.

In some aspects, cancer antigens (e.g., colorectal cancer, non-small cell lung cancer, or ovarian cancer antigens) are a portion of a protein, a portion of a peptide or a portion of a polyamino acid. In some cases, the portion is a percentage of a protein, a percentage of a peptide or a percentage of a polyamino acid. In some cases, the percentage is less than 1%, 5%, 10%, 15%, 20%, 25%, 30%, 35%, 40%, 45%, 50%, 55%, 60%, 65%, 70%, 75%, 80%, 85%, 90%, 95% or 100% of a protein, a peptide or a polyamino acid. In some cases, the portion is located at the C terminus of a protein, a peptide or a polyamino acid. In other cases, the portion is located near the C terminus of a protein, a peptide or a polyamino acid. In some aspects, the portion located near the C terminus is within 1%, 5%, 10%, 15%, 20%, 25%, 30%, 35%, 40%, 45%, 50% of the length of the total protein, peptide or polyamino acid from the median. In some cases, the portion is located at the N terminus of a protein, a peptide or a polyamino acid. In other cases, the portion is located near the N terminus of a protein, a peptide or a polyamino acid. In some aspects, the portion located near the N terminus may be within 1%, 5%, 10%, 15%, 20%, 25%, 30%, 35%, 40%, 45%, 50% of the length of the total protein, peptide or polyamino acid from the median. In some cases, the portion is located near the middle of a protein, a peptide or a polyamino acid. In other cases, the portion is located near the middle of a protein, a peptide or a polyamino acid. In some aspects, the portion located near the middle may be within 1%, 5%, 10%, 15%, 20%, 25%, 30%, 35%, 40%, 45%, 50% of the length of the total protein, peptide or polyamino acid from the termini.

In some aspects, at least one antigen is identified and screened for suitability as an antigen in a composition described herein (e.g., a vaccine). In some cases, one antigen is identified and screened. In other cases, more than one antigen is identified and screened, more than two antigens are identified and screened, more than three antigens are identified and screened, more than four antigens are identified and screened, more than five antigens are identified and screened, more than six antigens are identified and screened, more than seven antigens are identified and screened, more than eight antigens are identified and screened, more than nine antigens are identified and screened, more than ten antigens are identified and screened, more than 11 antigens are identified and screened, more than 12 antigens are identified and screened, more than 13 antigens are identified and screened, more than 14 antigens are identified and screened, more than 15 antigens are identified and screened, more than 20 antigens are identified and screened, more than 25 antigens are identified and screened, more than 30 antigens are identified and screened, more than 35 antigens are identified and screened, more than 40 antigens are identified and screened, more than 45 antigens are identified and screened or more than 50 antigens are identified and screened for suitability in a vaccine.

In some aspects, the antigens screened for suitability in a vaccine are derived from any protein to which an immune response is detected in the sera from a subject with colorectal cancer, NSCLC, or ovarian cancer using the screening techniques known to one of ordinary skill in the art. In some cases, the screening is antibody screening. While the proteins are any protein detected in the sera from a subject with colorectal cancer, NSCLC, or ovarian cancer, in an aspect, the proteins from which antigens are derived are classified as stem cell proteins and/or EMT proteins. In an aspect, stem cell/EMT proteins include CDC25B, COX2, EGFR, FAS-CIN1, IGF1R, PRL3, RCAS1, and VCP. In some aspects, the antigens are immunogenic in both colorectal cancer, NSCLC, or ovarian cancer subjects and subjects without colorectal cancer, NSCLC, or ovarian cancer.

Mapping Epitopes of Antigens

The compositions and methods provided herein include mapping of at least one epitope within antigens, such that the epitopes result in a Th1 immune response when administered to a subject. In some cases, the epitope is administered as a cancer vaccines (e.g., colorectal cancer, non-small cell lung cancer, or ovarian cancer vaccines). While any technique known to one of ordinary skill in the art may be used to identify epitopes which elicit a Th1 immune response by a subject, the methods described herein are preferably used. In some cases, the epitope is a portion of an antigen (e.g., identified above). In an aspect, the epitope is a peptide of an antigenic protein and/or a portion of an antigenic protein.

In some cases, the epitopes are human leukocyte antigen (HLA) class I epitopes derived from cancer antigens (e.g., colorectal cancer, non-small cell lung cancer, or ovarian cancer antigens). In an aspect, HLA class I epitopes include epitopes which bind to HLA-A, -B, and -C molecules. In some cases, the epitopes are class II epitopes derived from cancer antigens for cancer vaccines (e.g., colorectal cancer, non-small cell lung cancer, or ovarian cancer vaccines) development. In an aspect, HLA class II epitopes include epitopes which bind to HLA-DP, -DM, -DOA, -DOB, -DQ and -DR molecules. In some cases, in addition to the methods described herein, epitopes are mapped using the steps of, (1) determining if the epitopes bind MHC (e.g., with high affinity) by at least one HLA allele (e.g., HLA-DR, i.e., are universal epitopes), (2) determining if the epitopes stimulate IFN-g and/or IL-10 secretion (e.g., from antigen specific T cells), and (3) determining whether T cells may recognize peptides (e.g., epitopes) processed by antigen presenting cells (APC)s, i.e., are native epitopes. In some cases, T cell lines are used. In an aspect, T cell lines are epitope-derived T cell lines. In some cases, the epitopes are derived from proteins (e.g., recombinant proteins). In other cases, the proteins are native proteins. In some cases, the proteins are processed endogenously. In other cases, the proteins are processed exogenously. In some cases, the proteins are processed endogenously by autologous APCs. In other cases, the proteins are processed exogenously by autologous APCs.

In some cases, the peptides are epitopes mapped from antigens and are identified using the methods described herein for the selection of peptide epitopes. In some cases, the epitopes are derived from human proteins that are used directly in a peptide based vaccine. In other cases, the epitopes are derived from human proteins and the encoding nucleic acid sequences are incorporated into a nucleic acid construct designed to induce expression of the epitope in the subject following administration. In an aspect, the nucleic acid construct allows for the immune response to at least one epitope to be entrained, amplified, attenuated, suppressed, or eliminated to specific sets of self-proteins. In some cases, the peptide or the nucleic acid construct is optimized into a protein or plasmid-based vaccination to induce, amplify or entrain a Th1 immune response. In some cases, the epitopes are extended Th1 epitopes. In other cases, the peptide or the nucleic acid construct is optimized into a protein or plasmid-based vaccination to suppress, attenuate or eliminate a pathological response, in a subject (e.g., human or animal) in need thereof.

In some cases, the peptides are located within portions of a protein, peptide or polyamino acid such that the protein, peptide or polyamino acid stimulates secretion of IFN-g. In some cases, the peptides are located within portions of a protein, peptide or polyamino acid such that the protein, peptide or polyamino acid stimulates secretion of IL-10. In some cases, the peptide stimulates secretion of IFN-g and stimulates secretion of IL-10.

In some cases, the amino acids comprising the peptide are tuned such that the desired effect of the peptide on IFN-g secretion and/or the desired effect of the peptide on IL-10 secretion is achieved. In an aspect, a peptide which stimulates secretion of both IFN-g and IL-10 is tuned such that the length of the peptide is shortened to eliminate amino acids which stimulate IL-10 secretion such that the peptide only stimulates secretion of IFN-g.

In some cases, identified epitopes are included in vaccine compositions of extended epitope vaccines. In some cases, extended epitopes are 40-80-mer peptides. In an aspect, either the nucleic acid sequences or the peptide sequences are juxtaposed for construction of extended epitope sequences. In some aspects, juxtaposition (e.g., within 10 amino acids of each other) of selected peptides within the parent protein allows for the construction of in-tandem extended epitopes that contain tolerizing and/or suppressive epitopes. In an aspect, the in-tandem extended epitopes contain short intervening, <10 amino acid sequences. In some aspects, any of these peptides and/or extended epitopes (embodied either as the peptide itself, or as the corresponding nucleic acid construct) singularly, or in any combination, are optimized into a protein or plasmid-based vaccination that will specifically induce, amplify or entrain a protective immune response, or alternatively, will suppress, attenuate or eliminate a pathological one, in a subject (human or animal) in need thereof.

In some cases, the epitopes are a length of amino acids. In some cases, the epitopes are less than five amino acids, less than 10 amino acids, less than 15 amino acids, less than 20 amino acids, less than 25 amino acids, less than 30 amino acids, less than 35 amino acids, less than 40 amino acids, less than 45 amino acids, less than 50 amino acids, less than 55 amino acids, less than 60 amino acids, less than 70 amino acids, less than 75 amino acids, less than 80 amino acids, less than 85 amino acids, less than 90 amino acids, less than 95 amino acids, less than 100 amino acids, less than 110 amino acids, less than 120 amino acids, less than 130 amino acids, less than 140 amino acids, less than 150 amino acids, less than 160 amino acids, less than 170 amino acids, less than 180 amino acids, less than 190 amino acids, less than 200 amino acids, less than 210 amino acids, less than 220 amino acids, less than 230 amino acids, less than 240 amino acids, less than 250 amino acids, less than 260 amino acids, less than 270 amino acids, less than 280 amino acids, less than 290 amino acids, less than 300 amino acids, less than 350 amino acids, less than 400 amino acids, less than 450 amino acids or less than 500 amino acids.

The compositions described herein can include a composition comprising: a first plasmid comprising a first nucleotide sequence, the first nucleotide sequence encoding a first epitope of a first antigen expressed by cells associated with colorectal cancer, NSCLC, or ovarian cancer; and a second nucleotide sequence, the second nucleotide sequence encoding a second epitope of a second antigen expressed by cells associated with colorectal cancer, NSCLC, or ovarian cancer; wherein the first nucleotide sequence and the second nucleotide sequence are located in one or more plasmids. In some cases, the compositions include nucleic acids which encode epitopes from the following proteins, CDC25B, COX2, EGFR, FASCIN1, IGF1R, PRL3, RCAS1, and VCP.

In some cases, the compositions include a composition comprising: a first plasmid comprising a first nucleotide sequence, the first nucleotide sequence encoding a first epitope of a first antigen, the first epitope is a portion of a peptide selected from: CDC25B, COX2, EGFR, FASCIN1, IGF1R, PRL3, RCAS1, and VCP, wherein the first nucleotide sequence is located in a plasmid. In other cases, the composition may include a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CDC25B, COX2, EGFR, FASCIN1, IGF1R, PRL3, RCAS1, and VCP, wherein the first nucleotide sequence and the second nucleotide sequence are located in one or more plasmids.

In some cases, the compositions include nucleic acids which encode epitopes from the following proteins: CDC25B, COX2, EGFR, FASCIN1, IGF1R, PRL3, RCAS1, and VCP. In some cases, the compositions include a nucleic acid sequence encoding an epitope of the peptide CDC25B selected from the group consisting of: a nucleotide sequence encoding an amino acid sequence, the amino acid sequence having at least 90% sequence identity to the amino acid sequence of QAIQAASRIIRNEQFAIRRFQ (SEQ ID NO: 1); and a nucleotide sequence encoding an amino acid sequence, the amino acid sequence having at least 90% sequence identity to the amino acid sequence of VDG-KHQDLKYISPETMVALLTGK (SEQ ID NO: 2). In some cases, the compositions include a nucleic acid sequence encoding an epitope of the peptide COX2 selected from the group consisting of: a nucleotide sequence encoding an amino acid sequence, the amino acid sequence having at least 90% sequence identity to the amino acid sequence of FKGFWNVVNNIPFLRN (SEQ ID NO: 3); a nucleotide sequence encoding an amino acid sequence, the amino acid sequence having at least 90% sequence identity to the amino acid sequence of GLVPGLMMYATIWLREH (SEQ ID NO: 4); a nucleotide sequence encoding an amino acid sequence, the amino acid sequence having at least 90% sequence identity to the amino acid sequence of GEVGFQIINTASIQSLIC (SEQ ID NO: 5); a nucleotide sequence encoding an amino acid sequence, the amino acid sequence having at least 90% sequence identity to the amino acid sequence of NAIMSYVLTSRSHLID (SEQ ID NO: 6); a nucleotide sequence encoding an amino acid sequence, the amino acid sequence having at least 90% sequence identity to the amino acid sequence of HIYGETLARQRKLRLFKD (SEQ ID NO: 7); a nucleotide sequence encoding an amino acid sequence, the amino acid sequence having at least 90% sequence identity to the amino acid sequence of LFQTSR-LILIGETIKIVI (SEQ ID NO: 8); a nucleotide sequence encoding an amino acid sequence, the amino acid sequence having at least 90% sequence identity to the amino acid sequence of QFQYQNRIAAEFNTLY (SEQ ID NO: 9); and a nucleotide sequence encoding an amino acid sequence, the amino acid sequence having at least 90% sequence identity to the amino acid sequence of QQFIYNNSILLEHGITQFV (SEQ ID NO: 10). In some cases, the compositions include a nucleic acid sequence encoding an epitope of the peptide EGFR selected from the group consisting of: a nucleotide sequence encoding an amino acid sequence, the amino acid sequence having at least 90% sequence identity to the amino acid sequence of SCVRACGADSYEMEEDGVRK (SEQ ID NO: 11); a nucleotide sequence encoding an amino acid sequence, the amino acid sequence having at least 90% sequence identity to the amino acid sequence of NNTLVWKYADAGHVCHL (SEQ ID NO: 12); and a nucleotide sequence encoding an amino acid sequence, the amino acid sequence having at least 90% sequence identity to the amino acid sequence of VWSYGVTVWELMTFG-SKPY (SEQ ID NO: 13). In some cases, the compositions include a nucleic acid sequence encoding an epitope of the peptide FASCIN1 selected from the group consisting of: a nucleotide sequence encoding an amino acid sequence, the amino acid sequence having at least 90% sequence identity to the amino acid sequence of IAMHPQVNIYS-VTRKRYAH (SEQ ID NO: 14); a nucleotide sequence encoding an amino acid sequence, the amino acid sequence having at least 90% sequence identity to the amino acid sequence of TADHRFLRHDGRLVARPEPA (SEQ ID NO: 15); a nucleotide sequence encoding an amino acid sequence, the amino acid sequence having at least 90% sequence identity to the amino acid sequence of NKYL-TAEAFGFKVNASASSL (SEQ ID NO: 16); a nucleotide sequence encoding an amino acid sequence, the amino acid sequence having at least 90% sequence identity to the amino acid sequence of ELFLMKLINRPIIVFRGEHGFIGCR (SEQ ID NO: 17); a nucleotide sequence encoding an amino acid sequence, the amino acid sequence having at least 90% sequence identity to the amino acid sequence of VQIQF-GLINCGNKYLT (SEQ ID NO: 18); a nucleotide sequence encoding an amino acid sequence, the amino acid sequence having at least 90% sequence identity to the amino acid sequence of AVCLRSHLGRYLAADKD (SEQ ID NO: 19); a nucleotide sequence encoding an amino acid sequence, the amino acid sequence having at least 90% sequence identity to the amino acid sequence of TGKYWTLTATGGVQST (SEQ ID NO: 20); a nucleotide sequence encoding an amino acid sequence, the amino acid sequence having at least 90% sequence identity to the amino acid sequence of LFALEQS-CAQVVLQAANERN (SEQ ID NO: 21); and a nucleotide sequence encoding an amino acid sequence, the amino acid sequence having at least 90% sequence identity to the amino acid sequence of KDSTGKYWTVGSDSAVTS (SEQ ID NO: 22). In some cases, the compositions include a nucleic acid sequence encoding an epitope of the peptide IGF1R selected from the group consisting of: a nucleotide sequence encoding an amino acid sequence, the amino acid sequence having at least 90% sequence identity to the amino acid sequence of VVTGYVKIRHSHALV (SEQ ID NO: 23); a nucleotide sequence encoding an amino acid sequence, the amino acid sequence having at least 90% sequence identity to the amino acid sequence of TQYAVYVKAVTLTMV (SEQ ID NO: 24); a nucleotide sequence encoding an amino acid sequence, the amino acid sequence having at least 90% sequence identity to the amino acid sequence of LVIMLY-VFHRKRNNS (SEQ ID NO: 25); and a nucleotide sequence encoding an amino acid sequence, the amino acid sequence having at least 90% sequence identity to the amino acid sequence of GMAYLNANKFVHRDL (SEQ ID NO: 26). In some cases, the compositions include a nucleic acid sequence encoding an epitope of the peptide PRL3 selected from the group consisting of: a nucleotide sequence encoding an amino acid sequence, the amino acid sequence having at least 90% sequence identity to the amino acid sequence of VSYKHMRFLITHNPTNATL (SEQ ID NO: 27); a nucleotide sequence encoding an amino acid sequence, the amino acid sequence having at least 90% sequence identity to the amino acid sequence of FIEDLKKYGATTVVRVCEVTY (SEQ ID NO: 28); a nucleotide sequence encoding an amino acid sequence, the amino acid sequence having at least 90% sequence identity to the amino acid sequence of PCVAGL-GRAPVLVALALIES (SEQ ID NO: 29); a nucleotide sequence encoding an amino acid sequence, the amino acid sequence having at least 90% sequence identity to the amino acid sequence of MKYEDAIQFIRQKRRGAIN (SEQ ID NO: 30); and a nucleotide sequence encoding an amino acid sequence, the amino acid sequence having at least 90% sequence identity to the amino acid sequence of VED-WLSLVKAKFCEA (SEQ ID NO: 31). In some cases, the compositions include a nucleic acid sequence encoding an epitope of the peptide RCAS1 selected from the group consisting of: a nucleotide sequence encoding an amino acid sequence, the amino acid sequence having at least 90% sequence identity to the amino acid sequence of EPDYFKD-MTPTIRKTQKIVI (SEQ ID NO: 32); a nucleotide sequence encoding an amino acid sequence, the amino acid sequence having at least 90% sequence identity to the amino acid sequence of DYFKDMTPTIRKTQKIVIKKR (SEQ ID NO: 33); a nucleotide sequence encoding an amino acid sequence, the amino acid sequence having at least 90% sequence identity to the amino acid sequence of LFKFCT-CLATVFSFLKRLIC (SEQ ID NO: 34); a nucleotide sequence encoding an amino acid sequence, the amino acid sequence having at least 90% sequence identity to the amino acid sequence of GFSSRLAATQDLPFIHQSSELGD (SEQ ID NO: 35); and a nucleotide sequence encoding an amino acid sequence, the amino acid sequence having at least 90% sequence identity to the amino acid sequence of EEEDAAWQAEEVLRQQKLADR (SEQ ID NO: 36). In some cases, the compositions include a nucleic acid sequence encoding an epitope of the peptide VCP selected from the group consisting of: a nucleotide sequence encoding an amino acid sequence, the amino acid sequence having at least 90% sequence identity to the amino acid sequence of IRMNRVVRNNLRVRLGDVISI (SEQ ID NO: 37); a nucleotide sequence encoding an amino acid sequence, the amino acid sequence having at least 90% sequence identity to the amino acid sequence of LQLFRGDTVLLKGKKRR (SEQ ID NO: 38); a nucleotide sequence encoding an amino acid sequence, the amino acid sequence having at least 90% sequence identity to the amino acid sequence of YFLEAY-RPIRKGDIFLVRG (SEQ ID NO: 39); a nucleotide sequence encoding an amino acid sequence, the amino acid sequence having at least 90% sequence identity to the amino acid sequence of VEFKVVETDPSPYCIVAPDT (SEQ ID NO: 40); a nucleotide sequence encoding an amino acid sequence, the amino acid sequence having at least 90% sequence identity to the amino acid sequence of LRH-PALFKAIGVKPPRGIL (SEQ ID NO: 41); a nucleotide sequence encoding an amino acid sequence, the amino acid sequence having at least 90% sequence identity to the amino acid sequence of ETGAFFFLINGPEIMSK (SEQ ID NO: 42); a nucleotide sequence encoding an amino acid sequence, the amino acid sequence having at least 90% sequence identity to the amino acid sequence of AVTMDD-FRWALSQSNPS (SEQ ID NO: 43); a nucleotide sequence encoding an amino acid sequence, the amino acid sequence having at least 90% sequence identity to the amino acid sequence of QRAHVIVMAATNRPNS (SEQ ID NO: 44); and a nucleotide sequence encoding an amino acid sequence, the amino acid sequence having at least 90% sequence identity to the amino acid sequence of KNVFII-GATNRPDII (SEQ ID NO: 45).

In some cases, the compositions comprise a first and a second epitope independently selected from: CDC25B, COX2, EGFR, FASCIN1, IGF1R, PRL3, RCAS1, and VCP. In some cases, the compositions comprise a first, a second and a third epitope, the first, second and third epitopes independently selected from: CDC25B, COX2, EGFR, FASCIN1, IGF1R, PRL3, RCAS1, and VCP. In some cases, the compositions comprise a first, a second, a third and a fourth epitope, the first, second, third and fourth epitopes independently selected from: CDC25B, COX2, EGFR, FASCIN1, IGF1R, PRL3, RCAS1, and VCP. In some cases, the compositions comprise a first, a second, a third, a fourth and a fifth epitope, the first, second, third, fourth and fifth epitopes independently selected from: CDC25B, COX2, EGFR, FASCIN1, IGF1R, PRL3, RCAS1, and VCP. In some cases, the compositions comprise a first, a second, a third, a fourth, a fifth and a sixth epitope, the first, second, third, fourth, fifth and sixth epitopes independently selected from: CDC25B, COX2, EGFR, FASCIN1, IGF1R, PRL3, RCAS1, and VCP. In some cases, the compositions comprise a first, a second, a third, a fourth, a fifth, a sixth and a seventh epitope, the first, second, third, fourth, fifth, sixth and seventh epitopes independently selected from: CDC25B, COX2, EGFR, FASCIN1, IGF1R, PRL3, RCAS1, and VCP. In some cases, the compositions comprise a first, a second, a third, a fourth, a fifth, a sixth, a seventh and an eighth epitope, the first, second, third, fourth, fifth, sixth, seventh and eighth epitopes independently selected from: CDC25B, COX2, EGFR, FASCIN1, IGF1R, PRL3, RCAS1, and VCP.

The compositions described herein can include a composition comprising: a first plasmid comprising a first nucleotide sequence, the first nucleotide sequence encoding a first epitope of a first antigen expressed by cells associated with cancer (e.g., colorectal cancer, NSCLC, or ovarian cancer); and a second nucleotide sequence, the second nucleotide sequence encoding a second epitope of a second antigen expressed by cells associated with cancer (e.g., colorectal cancer, NSCLC, or ovarian cancer), wherein the first nucleotide sequence and the second nucleotide sequence are located in one or more plasmids. In some cases, the compositions include nucleic acids which encode epitopes from the following proteins, CDC25B, COX2, and PRL3.

In some cases, the compositions include a composition comprising: a first plasmid comprising a first nucleotide sequence, the first nucleotide sequence encoding a first epitope of a first antigen, the first epitope is a portion of a peptide selected from: CDC25B, COX2, and PRL3, wherein the first nucleotide sequence is located in a plasmid. In other cases, the composition includes a composition comprising: a first plasmid comprising a first nucleotide sequence, the first nucleotide sequence encoding a first epitope of a first antigen; and a second nucleotide sequence, the second nucleotide sequence encoding a second epitope of a second antigen, wherein the first and the second epitopes are independently selected from: CDC25B, COX2, and PRL3, wherein the first nucleotide sequence and the second nucleotide sequence are located in one or more plasmids.

In some cases, the compositions include nucleic acids which encode epitopes from the following proteins, CDC25B, COX2, and PRL3. In some cases, the compositions include a nucleic acid sequence encoding an epitope of the peptide CDC25B selected from the group consisting of: a nucleotide sequence encoding an amino acid sequence, the amino acid sequence having at least 90% sequence identity to the amino acid sequence of QAIQAASRIIRNEQFAIR-RFQ (SEQ ID NO: 1); and a nucleotide sequence encoding an amino acid sequence, the amino acid sequence having at least 90% sequence identity to the amino acid sequence of VDGKHQDLKYISPETMVALLTGK (SEQ ID NO: 2). In some cases, the compositions include a nucleic acid sequence encoding an epitope of the peptide COX2 selected from the group consisting of: a nucleotide sequence encoding an amino acid sequence, the amino acid sequence having at least 90% sequence identity to the amino acid sequence of FKGFWNVVNNIPFLRN (SEQ ID NO: 3); a nucleotide sequence encoding an amino acid sequence, the amino acid sequence having at least 90% sequence identity to the amino acid sequence of GLVPGLMMYATIWLREH (SEQ ID NO: 4); a nucleotide sequence encoding an amino acid sequence, the amino acid sequence having at least 90% sequence identity to the amino acid sequence of GEVGFQIINTA-SIQSLIC (SEQ ID NO: 5); a nucleotide sequence encoding an amino acid sequence, the amino acid sequence having at least 90% sequence identity to the amino acid sequence of NAIMSYVLTSRSHLID (SEQ ID NO: 6); a nucleotide sequence encoding an amino acid sequence, the amino acid sequence having at least 90% sequence identity to the amino acid sequence of HIYGETLARQRKLRLFKD (SEQ ID NO: 7); a nucleotide sequence encoding an amino acid sequence, the amino acid sequence having at least 90% sequence identity to the amino acid sequence of LFQTSR-LILIGETIKIVI (SEQ ID NO: 8); a nucleotide sequence encoding an amino acid sequence, the amino acid sequence having at least 90% sequence identity to the amino acid sequence of QFQYQNRIAAEFNTLY (SEQ ID NO: 9); and a nucleotide sequence encoding an amino acid sequence, the amino acid sequence having at least 90% sequence identity to the amino acid sequence of QQFIYNNSILLEHGITQFV (SEQ ID NO: 10). In some cases, the compositions include a nucleic acid sequence encoding an epitope of the peptide PRL3 selected from the group consisting of: a nucleotide sequence encoding an amino acid sequence, the amino acid sequence having at least 90% sequence identity to the amino acid sequence of VSYKHMRFLITHNPTNATL (SEQ ID NO: 27); a nucleotide sequence encoding an amino acid sequence, the amino acid sequence having at least 90% sequence identity to the amino acid sequence of FIEDLK-KYGATTVVRVCEVTY (SEQ ID NO: 28); a nucleotide sequence encoding an amino acid sequence, the amino acid sequence having at least 90% sequence identity to the amino acid sequence of PCVAGLGRAPVLVALALIES (SEQ ID NO: 29); a nucleotide sequence encoding an amino acid sequence, the amino acid sequence having at least 90% sequence identity to the amino acid sequence of MKYE-DAIQFIRQKRRGAIN (SEQ ID NO: 30); and a nucleotide sequence encoding an amino acid sequence, the amino acid sequence having at least 90% sequence identity to the amino acid sequence of VEDWLSLVKAKFCEA (SEQ ID NO: 31).

In some cases, the compositions comprise a first and a second epitope independently selected from: CDC25B, COX2, and PRL3. In some cases, the compositions comprise a first, a second and a third epitope, the first, second and third epitopes independently selected from: CDC25B, COX2, and PRL3.

In some cases, the compositions can be capable of being administered to a subject. In some cases, the subject is in need of administration of the composition. In some cases, the composition is effective to elicit an immune response in a subject. In some cases, the composition is effective to eliminate a number of cells associated with colorectal cancer, NSCLC, or ovarian cancer in a subject. In some cases, the composition is used to prevent the growth of cells associated with colorectal cancer, NSCLC, or ovarian cancer in a subject.

In some cases, the first and the second nucleic acid sequences are located on the first plasmid. In some cases, the second nucleic acid sequence is located on a second plasmid.

Colorectal cancer describes cancers including colon cancer and rectal cancer. In some cases, the cells associated with colorectal cancer are selected from: colon cells expressing atypical features, rectal cells expressing atypical features, pre-neoplastic colon cells, pre-neoplastic rectal cells, colon cancer cells, rectal cancer cells, pre-invasive colon cancer cells, pre-invasive rectal cancer cells, colon cancer stem cells, rectal cancer stem cells, epithelial cells, mesenchymal cells, stromal cells, or a combination thereof.

Non-small cell lung cancer described herein include cells selected from the group consisting of: lung cells expressing atypical features, pre-neoplastic lung cells, lung cancer cells, pre-invasive lung cancer cells, lung cancer stem cells, epithelial cells, mesenchymal cells, stromal cells, and combinations thereof.

In some cases, the first and the second nucleic acid sequences are purified to at least 70% purity. The first and the second nucleic acid sequences can be purified to at least 80%, 90%, 95%, 99%, 99.5%, or more in purity. In some cases, the first and the second nucleic acid sequences are located on the first plasmid and are separated by a sequence of linker nucleic acids. In some cases, the first nucleic acid sequence is adjacent to the second nucleic acid sequence on the first plasmid.

In some cases, at least the first plasmid is contained within a pharmaceutical composition. In some cases, at least the first plasmid is contained within a pharmaceutical composition further comprising a pharmaceutical carrier. In some cases, at least the first plasmid is contained within a pharmaceutical composition further comprising a pharmaceutical carrier and an adjuvant. In some cases, at least the first plasmid is contained within a pharmaceutical composition further comprising an adjuvant. In some cases, the composition further comprises an adjuvant and a pharmaceutically acceptable carrier. In some cases, the adjuvant is GM-CSF.

In some cases, a subject is selected from: a human with colorectal cancer, NSCLC, or ovarian cancer; a mouse with colorectal cancer, NSCLC, or ovarian cancer; or a rat with colorectal cancer, NSCLC, or ovarian cancer. In some cases, a subject is selected from: a human without colorectal cancer, NSCLC, or ovarian cancer; a mouse without colorectal cancer, NSCLC, or ovarian cancer; or a rat without colorectal cancer, NSCLC, or ovarian cancer.

In some cases, the immune response is a Type 1 immune response. In some cases, the first nucleic acid sequence is a species selected from: human, mouse or rat. In some cases, the second nucleic acid sequence is a species selected from: human, mouse or rat. In some cases, the immune response is characterized by a ratio of Type I cytokine production to Type II cytokine production that is greater than 1. In some cases, the immune response is characterized by a ratio of Type I cytokine production to Type II cytokine production that is less than 1. In some cases, the immune response is characterized by a ratio of IFN-γ production to IL-10 production that is greater than 1. In some cases, the immune response is characterized by a ratio of IFN-γ production to IL-10 production that is less than 1.

In some aspects, the nucleic acid sequences which encode epitopes from the following proteins, CD105, HIF-1a, MDM2, Yb1, SOX-2, HER-2, IGFBP2, IGF-R1 and CDH3 differ from those listed herein. In some cases, nucleic acid sequences which are greater than 95%, 90%, 85%, 80%, 75%, 70%, 65%, 60%, 55% or greater than 50% homologous to those disclosed herein are used in the compositions described herein.

The compositions described herein, in some cases, include a composition comprising: a first epitope of a first antigen expressed by cells associated with colorectal cancer, NSCLC, or ovarian cancer; and a second epitope of a second antigen expressed by cells associated with colorectal cancer, NSCLC, or ovarian cancer.

In some cases, the compositions comprise: at least a first epitope of a first antigen, the first epitope is a portion of a peptide selected from: CDC25B, COX2, EGFR, FASCIN1, IGF1R, PRL3, RCAS1, and VCP. In some cases, the compositions comprise: at least a first epitope of a first antigen, at least a second epitope of a second antigen, the first and the second epitopes are independently selected from: CDC25B, COX2, EGFR, FASCIN1, IGF1R, PRL3, RCAS1, and VCP. In some cases, the epitope of the peptide CDC25B is selected from the group consisting of: an amino acid sequence, the amino acid sequence having at least 90% sequence identity to the amino acid sequence of QAIQAAS-RIIRNEQFAIRRFQ (SEQ ID NO: 1); and an amino acid sequence, the amino acid sequence having at least 90% sequence identity to the amino acid sequence of VDG-KHQDLKYISPETMVALLTGK (SEQ ID NO: 2). In some cases, the epitope of the peptide COX2 is selected from the group consisting of: an amino acid sequence, the amino acid sequence having at least 90% sequence identity to the amino acid sequence of FKGFWNVVNNIPFLRN (SEQ ID NO: 3); an amino acid sequence, the amino acid sequence having at least 90% sequence identity to the amino acid sequence of GLVPGLMMYATIWLREH (SEQ ID NO: 4); an amino acid sequence, the amino acid sequence having at least 90% sequence identity to the amino acid sequence of GEVGFQI-INTASIQSLIC (SEQ ID NO: 5); an amino acid sequence, the amino acid sequence having at least 90% sequence identity to the amino acid sequence of NAIMSYVLTSR-SHLID (SEQ ID NO: 6); an amino acid sequence, the amino acid sequence having at least 90% sequence identity to the amino acid sequence of HIYGETLARQRKLRLFKD (SEQ ID NO: 7); an amino acid sequence, the amino acid sequence having at least 90% sequence identity to the amino acid sequence of LFQTSRLILIGETIKIVI (SEQ ID NO: 8); an amino acid sequence, the amino acid sequence having at least 90% sequence identity to the amino acid sequence of QFQYQNRIAAEFNTLY (SEQ ID NO: 9); and an amino acid sequence, the amino acid sequence having at least 90% sequence identity to the amino acid sequence of QQFI-YNNSILLEHGITQFV (SEQ ID NO: 10). In some cases, the epitope of the peptide EGFR is selected from the group consisting of: an amino acid sequence, the amino acid sequence having at least 90% sequence identity to the amino acid sequence of SCVRACGADSYEMEEDGVRK (SEQ ID NO: 11); an amino acid sequence, the amino acid sequence having at least 90% sequence identity to the amino acid sequence of NNTLVWKYADAGHVCHL (SEQ ID NO: 12); and an amino acid sequence, the amino acid sequence having at least 90% sequence identity to the amino acid sequence of VWSYGVTVWELMTFGSKPY (SEQ ID NO: 13). In some cases, the epitope of the peptide FASCIN1 is selected from the group consisting of: an amino acid sequence, the amino acid sequence having at least 90% sequence identity to the amino acid sequence of IAMH-PQVNIYSVTRKRYAH (SEQ ID NO: 14); an amino acid sequence, the amino acid sequence having at least 90% sequence identity to the amino acid sequence of TADHRFL-RHDGRLVARPEPA (SEQ ID NO: 15); an amino acid sequence, the amino acid sequence having at least 90% sequence identity to the amino acid sequence of NKYL-TAEAFGFKVNASASSL (SEQ ID NO: 16); an amino acid sequence, the amino acid sequence having at least 90% sequence identity to the amino acid sequence of ELFLM- KLINRPIIVFRGEHGFIGCR (SEQ ID NO: 17); an amino acid sequence, the amino acid sequence having at least 90% sequence identity to the amino acid sequence of VQIQF-GLINCGNKYLT (SEQ ID NO: 18); an amino acid sequence, the amino acid sequence having at least 90% sequence identity to the amino acid sequence of AVCLR-SHLGRYLAADKD (SEQ ID NO: 19); an amino acid sequence, the amino acid sequence having at least 90% sequence identity to the amino acid sequence of TGKY-WTLTATGGVQST (SEQ ID NO: 20); an amino acid sequence, the amino acid sequence having at least 90% sequence identity to the amino acid sequence of LFALEQS-CAQVVLQAANERN (SEQ ID NO: 21); and an amino acid sequence, the amino acid sequence having at least 90% sequence identity to the amino acid sequence of KDSTG-KYWTVGSDSAVTS (SEQ ID NO: 22). In some cases, the epitope of the peptide IGF1R is selected from the group consisting of: an amino acid sequence, the amino acid sequence having at least 90% sequence identity to the amino acid sequence of VVTGYVKIRHSHALV (SEQ ID NO: 23); an amino acid sequence, the amino acid sequence having at least 90% sequence identity to the amino acid sequence of TQYAVYVKAVTLTMV (SEQ ID NO: 24); an amino acid sequence, the amino acid sequence having at least 90% sequence identity to the amino acid sequence of LVIMLYVFHRKRNNS (SEQ ID NO: 25); and an amino acid sequence, the amino acid sequence having at least 90% sequence identity to the amino acid sequence of GMAYL-NANKFVHRDL (SEQ ID NO: 26). In some cases, the epitope of the peptide PRL3 is selected from the group consisting of: an amino acid sequence, the amino acid sequence having at least 90% sequence identity to the amino acid sequence of VSYKHMRFLITHNPTNATL (SEQ ID NO: 27); an amino acid sequence, the amino acid sequence having at least 90% sequence identity to the amino acid sequence of FIEDLKKYGATTVVRVCEVTY (SEQ ID NO: 28); an amino acid sequence, the amino acid sequence having at least 90% sequence identity to the amino acid sequence of PCVAGLGRAPVLVALALIES (SEQ ID NO: 29); an amino acid sequence, the amino acid sequence having at least 90% sequence identity to the amino acid sequence of MKYEDAIQFIRQKRRGAIN (SEQ ID NO: 30); and an amino acid sequence, the amino acid sequence having at least 90% sequence identity to the amino acid sequence of VEDWLSLVKAKFCEA (SEQ ID NO: 31). In some cases, the epitope of the peptide RCAS1 is selected from the group consisting of: an amino acid sequence, the amino acid sequence having at least 90% sequence identity to the amino acid sequence of EPDYFKDMTPTIRK-TQKIVI (SEQ ID NO: 32); an amino acid sequence, the amino acid sequence having at least 90% sequence identity to the amino acid sequence of DYFKDMTPTIRKTQKI-VIKKR (SEQ ID NO: 33); an amino acid sequence, the amino acid sequence having at least 90% sequence identity to the amino acid sequence of LFKFCTCLAT-VFSFLKRLIC (SEQ ID NO: 34); an amino acid sequence, the amino acid sequence having at least 90% sequence identity to the amino acid sequence of GFSSRLAATQDLP-FIHQSSELGD (SEQ ID NO: 35); and an amino acid sequence, the amino acid sequence having at least 90% sequence identity to the amino acid sequence of EEEDAAWQAEEVLRQQKLADR (SEQ ID NO: 36). In some cases, the epitope of the peptide VCP is selected from the group consisting of: an amino acid sequence, the amino acid sequence having at least 90% sequence identity to the amino acid sequence of EIRMNRVVRNNLRVRLGDVISI (SEQ ID NO: 37); an amino acid sequence, the amino acid sequence having at least 90% sequence identity to the amino acid sequence of LQLFRGDTVLLKGKKRR (SEQ ID NO: 38); an amino acid sequence, the amino acid sequence having at least 90% sequence identity to the amino acid sequence of YFLEAYRPIRKGDIFLVRG (SEQ ID NO: 39); an amino acid sequence, the amino acid sequence having at least 90% sequence identity to the amino acid sequence of VEFKVVETDPSPYCIVAPDT (SEQ ID NO: 40); an amino acid sequence, the amino acid sequence having at least 90% sequence identity to the amino acid sequence of LRHPALFKAIGVKPPRGIL (SEQ ID NO: 41); an amino acid sequence, the amino acid sequence having at least 90% sequence identity to the amino acid sequence of ETGAFFFLINGPEIMSK (SEQ ID NO: 42); an amino acid sequence, the amino acid sequence having at least 90% sequence identity to the amino acid sequence of AVTMDDFRWALSQSNPS (SEQ ID NO: 43); an amino acid sequence, the amino acid sequence having at least 90% sequence identity to the amino acid sequence of QRAHVIV-MAATNRPNS (SEQ ID NO: 44); and an amino acid sequence, the amino acid sequence having at least 90% sequence identity to the amino acid sequence of KNVFII-GATNRPDII (SEQ ID NO: 45).

In some cases, the compositions comprise a first and a second epitope independently selected from: CDC25B, COX2, EGFR, FASCIN1, IGF1R, PRL3, RCAS1, and VCP. In some cases, the compositions comprise a first, a second and a third epitope, the first, second and third epitopes independently selected from: CDC25B, COX2, EGFR, FASCIN1, IGF1R, PRL3, RCAS1, and VCP. In some cases, the compositions comprise a first, a second, a third and a fourth epitope, the first, second, third and fourth epitopes independently selected from: CDC25B, COX2, EGFR, FASCIN1, IGF1R, PRL3, RCAS1, and VCP. In some cases, the compositions comprise a first, a second, a third, a fourth and a fifth epitope, the first, second, third, fourth and fifth epitopes independently selected from: CDC25B, COX2, EGFR, FASCIN1, IGF1R, PRL3, RCAS1, and VCP. In some cases, the compositions comprise a first, a second, a third, a fourth, a fifth and a sixth epitope, the first, second, third, fourth, fifth and sixth epitopes independently selected from: CDC25B, COX2, EGFR, FASCIN1, IGF1R, PRL3, RCAS1, and VCP. In some cases, the compositions comprise a first, a second, a third, a fourth, a fifth, a sixth and a seventh epitope, the first, second, third, fourth, fifth, sixth and seventh epitopes independently selected from: CDC25B, COX2, EGFR, FASCIN1, IGF1R, PRL3, RCAS1, and VCP. In some cases, the compositions comprise a first, a second, a third, a fourth, a fifth, a sixth, a seventh and an eighth epitope, the first, second, third, fourth, fifth, sixth, seventh and eighth epitopes independently selected from: CDC25B, COX2, EGFR, FASCIN1, IGF1R, PRL3, RCAS1, and VCP.

In some cases, the compositions comprise: at least a first epitope of a first antigen, the first epitope is a portion of a peptide selected from: CDC25B, COX2, and PRL3. In some cases, the compositions comprise: at least a first epitope of a first antigen, at least a second epitope of a second antigen, the first and the second epitopes are independently selected from: CDC25B, COX2, and PRL3. In some cases, the epitope of the peptide CDC25B is selected from the group consisting of: an amino acid sequence, the amino acid sequence having at least 90% sequence identity to the amino acid sequence of QAIQAASRIIRNEQFAIRRFQ (SEQ ID NO: 1); and an amino acid sequence, the amino acid sequence having at least 90% sequence identity to the amino acid sequence of VDGKHQDLKYISPETMVALLTGK (SEQ ID NO: 2). In some cases, the epitope of the peptide COX2 is selected from the group consisting of: an amino acid sequence, the amino acid sequence having at least 90% sequence identity to the amino acid sequence of FKGFWNVVNNIPFLRN (SEQ ID NO: 3); an amino acid sequence, the amino acid sequence having at least 90% sequence identity to the amino acid sequence of GLVPGLMMYATIWLREH (SEQ ID NO: 4); an amino acid sequence, the amino acid sequence having at least 90% sequence identity to the amino acid sequence of GEVGFQIINTASIQSLIC (SEQ ID NO: 5); an amino acid sequence, the amino acid sequence having at least 90% sequence identity to the amino acid sequence of NAIMSYVLTSRSHLID (SEQ ID NO: 6); an amino acid sequence, the amino acid sequence having at least 90% sequence identity to the amino acid sequence of HIYGETLARQRKLRLFKD (SEQ ID NO: 7); an amino acid sequence, the amino acid sequence having at least 90% sequence identity to the amino acid sequence of LFQTSRLILIGETIKIVI (SEQ ID NO: 8); an amino acid sequence, the amino acid sequence having at least 90% sequence identity to the amino acid sequence of QFQYQNRIAAEFNTLY (SEQ ID NO: 9); and an amino acid sequence, the amino acid sequence having at least 90% sequence identity to the amino acid sequence of QQFIYNNSILLEHGITQFV (SEQ ID NO: 10). In some cases, the epitope of the peptide PRL3 is selected from the group consisting of: an amino acid sequence, the amino acid sequence having at least 90% sequence identity to the amino acid sequence of VSYKHMRFLITHNPTNATL (SEQ ID NO: 27); an amino acid sequence, the amino acid sequence having at least 90% sequence identity to the amino acid sequence of FIEDLKKYGATTVVRVCEVTY (SEQ ID NO: 28); an amino acid sequence, the amino acid sequence having at least 90% sequence identity to the amino acid sequence of PCVAGLGRAPVLVALALIES (SEQ ID NO: 29); an amino acid sequence, the amino acid sequence having at least 90% sequence identity to the amino acid sequence of MKYEDAIQFIRQKRRGAIN (SEQ ID NO: 30); and an amino acid sequence, the amino acid sequence having at least 90% sequence identity to the amino acid sequence of VEDWLSLVKAKFCEA (SEQ ID NO: 31).

In some cases, the compositions comprise a first and a second epitope independently selected from: CDC25B, COX2, and PRL3. In some cases, the compositions comprise a first, a second and a third epitope, the first, second and third epitopes independently selected from: CDC25B, COX2, and PRL3.

The amino acid sequences of the epitopes from the following proteins, CDC25B, COX2, EGFR, FASCIN1, IGF1R, PRL3, RCAS1, and VCP may differ from those listed herein. In some cases, amino acid sequences which are greater than 95%, 90%, 85%, 80%, 75%, 70%, 65%, 60%, 55% or greater than 50% homologous to those disclosed herein may be used in the compositions described herein.

In some cases, the first amino acid sequences are selected from a group of species consisting of human, mouse and rat. In some cases, the second amino acid sequences are selected from a group of species consisting of human, mouse and rat.

In some cases, the first and the second nucleic acid sequences are located on the first plasmid. In some cases, the second nucleic acid sequence is located on a second plasmid. In some cases, the amino acid sequences of the first and the second epitopes are separated by a sequence of linker amino acids. In some cases, the amino acid sequence of the first epitope is adjacent to the amino acid sequence of the second epitope.

In some cases, the immune response is a Type 1 immune response. In some cases, the immune response is characterized by a ratio of Type I cytokine production to Type II cytokine production that is greater than 1. In some cases, the immune response is characterized by a ratio of Type I cytokine production to Type II cytokine production that is less than 1. In some cases, the immune response is characterized by a ratio of IFN-γ production to IL-10 production that is greater than 1. In some cases, the immune response is characterized by a ratio of IFN-γ production to IL-10 production that is less than 1.

In some cases, the composition is administered to a subject. In some cases, the subject is in need of administration of the composition. In some cases, the composition is effective to elicit an immune response in a subject. In some cases, the composition is effective to eliminate a number of cells associated with colorectal cancer, NSCLC, or ovarian cancer in a subject. In some cases, the composition is used to prevent the growth of cells associated with colorectal cancer, NSCLC, or ovarian cancer in a subject.

In some cases, a subject is selected from the group consisting of a human with colorectal cancer, NSCLC, or ovarian cancer; a mouse with colorectal cancer, NSCLC, or ovarian cancer; and a rat with colorectal cancer, NSCLC, or ovarian cancer. In some cases, a subject is selected from the group consisting of a human without colorectal cancer, NSCLC, or ovarian cancer; a mouse without colorectal cancer, NSCLC, or ovarian cancer; and a rat without colorectal cancer, NSCLC, or ovarian cancer.

Colorectal cancer describes cancers including colon cancer and rectal cancer. In some cases, the cells associated with colorectal cancer are selected from: colon cells expressing atypical features, rectal cells expressing atypical features, pre-neoplastic colon cells, pre-neoplastic rectal cells, colon cancer cells, rectal cancer cells, pre-invasive colon cancer cells, pre-invasive rectal cancer cells, colon cancer stem cells, rectal cancer stem cells, epithelial cells, mesenchymal cells, stromal cells, or a combination thereof.

The cells associated with non-small cell lung cancer are selected from the group consisting of: lung cells expressing atypical features, pre-neoplastic lung cells, lung cancer cells, pre-invasive lung cancer cells, lung cancer stem cells, epithelial cells, mesenchymal cells, stromal cells, and combinations thereof.

In some cases, at least the first epitope is contained within a pharmaceutical composition. In some cases, at least the first epitope is contained within a pharmaceutical composition further comprising a pharmaceutical carrier. In some cases, at least the first epitope is contained within a pharmaceutical composition further comprising a pharmaceutical carrier and an adjuvant. In some cases, at least the first epitope is contained within a pharmaceutical composition further comprising an adjuvant. In some cases, the composition further comprises an adjuvant and a pharmaceutical carrier. In some cases, the adjuvant is GM-CSF.

In some cases, the composition is administered to a subject. In some cases, the subject is in need thereof. In some cases, methods for preventing cancer (e.g., colorectal cancer, NSCLC, or ovarian cancer) in a subject are provided herein such that the method comprises administering the compositions described herein to a subject. In some cases, methods for treating cancer (e.g., colorectal cancer, NSCLC, or ovarian cancer) in a subject are provided herein such that the method comprises administering the compositions described herein to a subject. In some cases, administering further comprises delivery of at least one dose of the composition described herein to the subject. In some cases, the administering further comprises delivery of the compositions described herein to the subject by subcutaneous injection, intradermal injection, intramuscular injection, intravascular injection, topical application or inhalation. In some cases, the subject is selected from the group consisting of a human with cancer (e.g., colorectal cancer, NSCLC, or ovarian cancer), a mouse with cancer (e.g., colorectal cancer, NSCLC, or ovarian cancer) and a rat with cancer (e.g., colorectal cancer, NSCLC, or ovarian cancer). In some cases, the subject is selected from the group consisting of a human without cancer (e.g., colorectal cancer, NSCLC, or ovarian cancer), a mouse without cancer (e.g., colorectal cancer, NSCLC, or ovarian cancer) and a rat without cancer (e.g., colorectal cancer, NSCLC, or ovarian cancer).

The disclosure also provides for a kit for preparing the compositions described herein, the kit comprising instructions for preparing the compositions. The disclosure also provides for a kit for administering the compositions described herein, the kit comprising instructions for administering the compositions.

Plasmids for Pharmaceutical Compositions

In some cases, the epitopes are derived from human proteins that are used directly in a peptide based vaccine. In other cases, the epitopes are derived from human proteins and the nucleic acid sequences encoding the epitopes are incorporated into a nucleic acid construct designed to induce expression of the epitope in a subject following administration. In an aspect, epitopes encoded from the nucleic acid construct allow for the immune response to at least one epitope to be entrained, amplified, attenuated, suppressed, or eliminated to specific sets of proteins (e.g., self-proteins). In some cases, the peptide or the nucleic acid construct is optimized into a protein or plasmid-based vaccination to induce, amplify or entrain a Th1 immune response. In some cases, the epitopes are extended Th1 epitopes. In other cases, the peptide or the nucleic acid construct is optimized into a protein or plasmid-based vaccination to suppress, attenuate or eliminate a pathological response, in a subject (e.g., human or animal) in need thereof.

In some aspects, the compositions described herein include plasmids which contain nucleic acid sequences to express at least one epitope in a subject following administration of the composition (e.g., vaccine). Any plasmid backbones (e.g., vectors) known to one of ordinary skill in the art suitable for pharmaceutical use for expression of a nucleic acid sequence may be used in the compositions described herein. In some cases, commercially available plasmid backbones are used. In an aspect, the plasmid pUMVC3 is used. In some cases, commercially available plasmid backbones are modified, mutated, engineered or cloned prior to use. In other cases, non-commercially available plasmid backbones are used.

In some aspects, prior to inserting the nucleic acid sequence of at least one epitope, the plasmid backbone is less than about 500 bp, about 1.0 kB, about 1.2 kB, about 1.4 kB, about 1.6 kB, about 1.8 kB, about 2.0 kB, about 2.2 kB, about 2.4 kB, about 2.6 kB, about 2.8 kB, about 3.0 kB, about 3.2 kB, about 3.4 kB, about 3.6 kB, about 3.8 kB, about 4.0 kB, about 4.2 kB, about 4.4 kB, about 4.6 kB, about 4.8 kB, about 5.0 kB, about 5.2 kB, about 5.4 kB, about 5.6 kB, about 5.8 kB, about 6.0 kB, about 6.2 kB, about 6.4 kB, about 6.6 kB, about 6.8 kB, about 7.0 kB, about 7.2 kB, about 7.4 kB, about 7.6 kB, about 7.8 kB, about 8.0 kB, about 8.2 kB, about 8.4 kB, about 8.6 kB, about 8.8 kB, about 9.0 kB, about 9.2 kB, about 9.4 kB, about 9.6 kB, about 9.8 kB, about 10.0 kB, about 10.2 kB, about 10.4 kB, about 10.6 kB, about 10.8 kB, about 11.0 kB, about 11.2 kB, about 11.4 kB, about 11.6 kB, about 11.8 kB, about 12.0 kB, about 12.2 kB, about 12.4 kB, about 12.6 kB, about 12.8 kB, about 13.0 kB, about 13.2 kB, about 13.4 kB, about 13.6 kB, about 13.8 kB, about 14 kB, about 14.5 kB, about 15 kB, about 15.5 kB, about 16 kB, about 16.5 kB, about 17 kB, about 17.5 kB, about 18 kB, about 18.5 kB, about 19 kB, about 19.5 kB, about 20 kB, about 30 kB, about 40 kB, about 50 kB, about 60 kB, about 70 kB, about 80 kB, about 90 kB, about 100 kB, about 110 kB, about 120 kB, about 130 kB, about 140 kB, about 150 kB, about 160 kB, about 170 kB, about 180 kB, about 190 kB or about 200 kB in length. In an aspect, the plasmid is about 4 kB in length prior to addition of the nucleic acid sequence encoding at least one epitope.

In some cases, the compositions described herein include one plasmid. In other cases, the compositions described herein include more than one plasmid. In an aspect, the compositions described herein include two plasmids, three plasmids, four plasmids, five plasmids, six plasmids, seven plasmids, eight plasmids, nine plasmids, ten plasmids, 11 plasmids, 12 plasmids, 13 plasmids, 14 plasmids, 15 plasmids, 16 plasmids, 17 plasmids, 18 plasmids 19 plasmids, 20 plasmids or more than 20 plasmids.

In some cases, the nucleic acids which encode at least one epitope of a plasmid are deoxyribonucleic acids. In an aspect, the deoxyribonucleic acids are single stranded, double stranded or complementary. In some cases, the deoxyribonucleic acids are derived from genomic, mitochondrial or plasmid deoxyribonucleic acids. In other cases, the nucleic acids of a plasmid are ribonucleic acids. In an aspect, the ribonucleic acids are single stranded or double stranded. In some cases, the ribonucleic acids are micro, antisense, short hairpin, small interfering, messenger, transfer, ribosomal, or the like. In some cases, the nucleic acids of the plasmids are a portion of deoxyribonucleic acids and a portion of ribonucleic acids.

The nucleic acids which encode at least one epitope of a plasmid are derived from any species such that the epitope expressed from the nucleic acids results in an immune response in a subject. In some cases, the subject is a rodent, a non-human primate or a human. The nucleic acids encoding the epitope of the plasmid are isolated from any source of nucleic acids using methods and techniques known to one of ordinary skill in the art. The nucleic acids encoding the epitope of the plasmid may be cloned into the plasmid backbone using methods and techniques known to one of ordinary skill in the art.

In some cases, the nucleic acid sequence encoding the epitope is an endogenous nucleic acid sequence to the subject. In an aspect, the nucleic acid sequence for CDC25B from a human is used to express CDC25B in a human. In other cases, the nucleic acid sequence for the antigenic epitope is an exogenous nucleic acid sequence to the subject. In an aspect, the nucleic acid sequence for CDC25B from a non-human is used to express CDC25B in a human.

In some cases, the nucleic acid sequences used to express the antigenic epitope are wild-type nucleic acid sequences. In an aspect, the naturally occurring nucleic acid sequence for CDC25B in the genome of a species is used to express CDC25B in a subject. In other cases, the nucleic acid sequences encoding the epitope are synthetic nucleic acid sequences. In an aspect, the naturally occurring nucleic acid sequence for CDC25B in the genome of a species is modified using molecular techniques known to one of ordinary skill in the art and used to express CDC25B in a subject.

Sometimes, the nucleic acid sequence used to express the CDC25B epitope may encode a polypeptide in which the sequence of the polypeptide is at least 70%, 75%, 80%, 85%, 90%, 95%, 99%, or 100% identical to a sequence selected from SEQ ID NOs: 1-2. The nucleic acid sequence used to express the CDC25B epitope may further encode a polypeptide in which the sequence of the polypeptide is at least 70%, 75%, 80%, 85%, 90%, 95%, 99%, or 100% identical to at least 8 amino acids of SEQ ID NOs: 1-2.

In some cases, the nucleic acid sequence encoding the epitope is an endogenous nucleic acid sequence to the subject. In an aspect, the nucleic acid sequence for COX2 from a human is used to express COX2 in a human. In other cases, the nucleic acid sequence for the antigenic epitope is an exogenous nucleic acid sequence to the subject. In an aspect, the nucleic acid sequence for COX2 from a non-human is used to express COX2 in a human.

In some cases, the nucleic acid sequences used to express the antigenic epitope are wild-type nucleic acid sequences. In an aspect, the naturally occurring nucleic acid sequence for COX2 in the genome of a species is used to express COX2 in a subject. In other cases, the nucleic acid sequences encoding the epitope are synthetic nucleic acid sequences. In an aspect, the naturally occurring nucleic acid sequence for COX2 in the genome of a species is modified using molecular techniques known to one of ordinary skill in the art and used to express COX2 in a subject.

The nucleic acid sequence used to express the COX2 epitope may encode a polypeptide in which the sequence of the polypeptide is at least 70%, 75%, 80%, 85%, 90%, 95%, 99%, or 100% identical to a sequence selected from SEQ ID NOs: 3-10. The nucleic acid sequence used to express the COX2 epitope may further encode a polypeptide in which the sequence of the polypeptide is at least 70%, 75%, 80%, 85%, 90%, 95%, 99%, or 100% identical to at least 8 amino acids of SEQ ID NOs: 3-10.

In some cases, the nucleic acid sequence encoding the epitope is an endogenous nucleic acid sequence to the subject. In an aspect, the nucleic acid sequence for EGFR from a human is used to express EGFR in a human. In other cases, the nucleic acid sequence for the antigenic epitope is an exogenous nucleic acid sequence to the subject. In an aspect, the nucleic acid sequence for EGFR from a non-human is used to express EGFR in a human.

In some cases, the nucleic acid sequences used to express the antigenic epitope are wild-type nucleic acid sequences. In an aspect, the naturally occurring nucleic acid sequence for EGFR in the genome of a species is used to express EGFR in a subject. In other cases, the nucleic acid sequences encoding the epitope are synthetic nucleic acid sequences. In an aspect, the naturally occurring nucleic acid sequence for EGFR in the genome of a species is modified using molecular techniques known to one of ordinary skill in the art and used to express EGFR in a subject.

The nucleic acid sequence used to express the EGFR epitope may encode a polypeptide in which the sequence of the polypeptide is at least 70%, 75%, 80%, 85%, 90%, 95%, 99%, or 100% identical to a sequence selected from SEQ ID NOs: 11-13. The nucleic acid sequence used to express the EGFR epitope may further encode a polypeptide in which the sequence of the polypeptide is at least 70%, 75%, 80%, 85%, 90%, 95%, 99%, or 100% identical to at least 8 amino acids of SEQ ID NOs: 11-13.

In some cases, the nucleic acid sequence encoding the epitope is an endogenous nucleic acid sequence to the subject. In an embodiment, the nucleic acid sequence for FASCIN1 from a human is used to express FASCIN1 in a human. In other cases, the nucleic acid sequence for the antigenic epitope is an exogenous nucleic acid sequence to the subject. In an aspect, the nucleic acid sequence for FASCIN1 from a non-human is used to express FASCIN1 in a human.

In some cases, the nucleic acid sequences used to express the antigenic epitope are wild-type nucleic acid sequences. In an aspect, the naturally occurring nucleic acid sequence for FASCIN1 in the genome of a species is used to express FASCIN1 in a subject. In other cases, the nucleic acid sequences encoding the epitope are synthetic nucleic acid sequences. In an aspect, the naturally occurring nucleic acid sequence for FASCIN1 in the genome of a species is modified using molecular techniques known to one of ordinary skill in the art and used to express FASCIN1 in a subject.

The nucleic acid sequence used to express the FASCIN1 epitope may encode a polypeptide in which the sequence of the polypeptide is at least 70%, 75%, 80%, 85%, 90%, 95%, 99%, or 100% identical to a sequence selected from SEQ ID NOs: 14-22. The nucleic acid sequence used to express the FASCIN1 epitope may further encode a polypeptide in which the sequence of the polypeptide is at least 70%, 75%, 80%, 85%, 90%, 95%, 99%, or 100% identical to at least 8 amino acids of SEQ ID NOs: 14-22.

In some cases, the nucleic acid sequence encoding the epitope is an endogenous nucleic acid sequence to the subject. In an aspect, the nucleic acid sequence for IGF1R from a human is used to express IGF1R in a human. In other cases, the nucleic acid sequence for the antigenic epitope is an exogenous nucleic acid sequence to the subject. In an aspect, the nucleic acid sequence for IGF1R from a non-human is used to express IGF1R in a human.

In some cases, the nucleic acid sequences used to express the antigenic epitope are wild-type nucleic acid sequences. In an aspect, the naturally occurring nucleic acid sequence for IGF1R in the genome of a species is used to express IGF1R in a subject. In other cases, the nucleic acid sequences encoding the epitope are synthetic nucleic acid sequences. In an aspect, the naturally occurring nucleic acid sequence for IGF1R in the genome of a species are modified using molecular techniques known to one of ordinary skill in the art and used to express IGF1R in a subject.

The nucleic acid sequence used to express the IGF1R epitope may encode a polypeptide in which the sequence of the polypeptide is at least 70%, 75%, 80%, 85%, 90%, 95%, 99%, or 100% identical to a sequence selected from SEQ ID NOs: 23-26. The nucleic acid sequence used to express the IGF1R epitope may further encode a polypeptide in which the sequence of the polypeptide is at least 70%, 75%, 80%, 85%, 90%, 95%, 99%, or 100% identical to at least 8 amino acids of SEQ ID NOs: 23-26.

In some cases, the nucleic acid sequence encoding the epitope is an endogenous nucleic acid sequence to the subject. In an aspect, the nucleic acid sequence for PRL3 from a human is used to express PRL3 in a human. In other cases, the nucleic acid sequence for the antigenic epitope is an exogenous nucleic acid sequence to the subject. In an aspect, the nucleic acid sequence for PRL3 from a non-human is used to express PRL3 in a human.

In some cases, the nucleic acid sequences used to express the antigenic epitope are wild-type nucleic acid sequences. In an aspect, the naturally occurring nucleic acid sequence for PRL3 in the genome of a species is used to express PRL3 in a subject. In other cases, the nucleic acid sequences encoding the epitope are synthetic nucleic acid sequences. In an aspect, the naturally occurring nucleic acid sequence for PRL3 in the genome of a species is modified using molecular techniques known to one of ordinary skill in the art and used to express PRL3 in a subject.

The nucleic acid sequence used to express the PRL3 epitope may encode a polypeptide in which the sequence of the polypeptide is at least 70%, 75%, 80%, 85%, 90%, 95%, 99%, or 100% identical to a sequence selected from SEQ ID NOs: 27-31. The nucleic acid sequence used to express the PRL3 epitope may further encode a polypeptide in which the sequence of the polypeptide is at least 70%, 75%, 80%, 85%, 90%, 95%, 99%, or 100% identical to at least 8 amino acids of SEQ ID NOs: 27-31.

In some cases, the nucleic acid sequence encoding the epitope is an endogenous nucleic acid sequence to the subject. In an aspect, the nucleic acid sequence for RCAS1 from a human is used to express RCAS12 in a human. In other cases, the nucleic acid sequence for the antigenic epitope is an exogenous nucleic acid sequence to the subject. In an aspect, the nucleic acid sequence for RCAS1 from a non-human is used to express RCAS1 in a human.

In some cases, the nucleic acid sequences used to express the antigenic epitope are wild-type nucleic acid sequences. In an aspect, the naturally occurring nucleic acid sequence for RCAS1 in the genome of a species is used to express RCAS1 in a subject. In other cases, the nucleic acid sequences encoding the epitope are synthetic nucleic acid sequences. In an aspect, the naturally occurring nucleic acid sequence for RCAS1 in the genome of a species is modified using molecular techniques known to one of ordinary skill in the art and used to express RCAS1 in a subject.

The nucleic acid sequence used to express the RCAS1 epitope may encode a polypeptide in which the sequence of the polypeptide is at least 70%, 75%, 80%, 85%, 90%, 95%, 99%, or 100% identical to a sequence selected from SEQ ID NOs: 32-36. The nucleic acid sequence used to express the RCAS1 epitope may further encode a polypeptide in which the sequence of the polypeptide is at least 70%, 75%, 80%, 85%, 90%, 95%, 99%, or 100% identical to at least 8 amino acids of SEQ ID NOs: 32-36.

In some cases, the nucleic acid sequence encoding the epitope is an endogenous nucleic acid sequence to the subject. In an aspect, the nucleic acid sequence for VCP from a human is used to express VCP in a human. In other cases, the nucleic acid sequence for the antigenic epitope is an exogenous nucleic acid sequence to the subject. In an aspect, the nucleic acid sequence for VCP from a non-human is used to express VCP in a human.

In some cases, the nucleic acid sequences used to express the antigenic epitope are wild-type nucleic acid sequences. In an aspect, the naturally occurring nucleic acid sequence for VCP in the genome of a species is used to express VCP in a subject. In other cases, the nucleic acid sequences encoding the epitope are synthetic nucleic acid sequences. In an aspect, the naturally occurring nucleic acid sequence for VCP in the genome of a species is modified using molecular techniques known to one of ordinary skill in the art and used to express VCP in a subject.

The nucleic acid sequence used to express the VCP epitope may encode a polypeptide in which the sequence of the polypeptide is at least 70%, 75%, 80%, 85%, 90%, 95%, 99%, or 100% identical to a sequence selected from SEQ ID NOs: 37-45. The nucleic acid sequence used to express the VCP epitope may further encode a polypeptide in which the sequence of the polypeptide is at least 70%, 75%, 80%, 85%, 90%, 95%, 99%, or 100% identical to at least 8 amino acids of SEQ ID NOs: 37-45.

The compositions described herein may contain short epitopes encoded on a single plasmid backbone. In some aspects, short epitopes may comprise <40 amino acids. In some cases, the plasmid backbone encodes one short epitope. In other cases, the plasmids described herein encode more than one short epitope. In an aspect, the compositions described herein encode two short epitopes, three short epitopes, four short epitopes, five short epitopes, six short epitopes, seven short epitopes, eight short epitopes, nine short epitopes, ten short epitopes, 11 short epitopes, 12 short epitopes, 13 short epitopes, 14 short epitopes, 15 short epitopes, 16 short epitopes, 17 short epitopes, 18 short epitopes 19 short epitopes, 20 short epitopes or more than 20 short epitopes. In an aspect, the plasmid encodes no more than six short epitopes.

In some aspects, the compositions described herein contain extended epitopes encoded on a single plasmid backbone. In some aspects, extended epitopes may comprise 40 to 80 amino acids. In some cases, the plasmid encodes one extended epitope. In other cases, the compositions encode more than one extended epitope. In an aspect, the plasmids encode two extended epitopes, three extended epitopes, four extended epitopes, five extended epitopes, six extended epitopes, seven extended epitopes, eight extended epitopes, nine extended epitopes, ten extended epitopes, 11 extended epitopes, 12 extended epitopes, 13 extended epitopes, 14 extended epitopes, 15 extended epitopes, 16 extended epitopes, 17 extended epitopes, 18 extended epitopes 19 extended epitopes, 20 extended epitopes or more than 20 extended epitopes. In an aspect, the plasmid encodes no more than four extended epitopes.

The compositions of colorectal cancer, NSCLC, or ovarian cancer vaccines described herein can contain short epitopes and extended epitopes on a single plasmid backbone. In some cases, the plasmid includes one short epitope. In other cases, the compositions of plasmids described herein include more than one short epitope. In an aspect, the compositions of plasmids described herein include two short epitopes, three short epitopes, four short epitopes, five short epitopes, six short epitopes, seven short epitopes, eight short epitopes, nine short epitopes, ten short epitopes, 11 short epitopes, 12 short epitopes, 13 short epitopes, 14 short epitopes, 15 short epitopes, 16 short epitopes, 17 short epitopes, 18 short epitopes 19 short epitopes, 20 short epitopes or more than 20 short epitopes.

The plasmid can encode one extended epitope. The compositions described herein can encode more than one extended epitope. In an aspect, the compositions described herein encode two extended epitopes, three extended epitopes, four extended epitopes, five extended epitopes, six extended epitopes, seven extended epitopes, eight extended epitopes, nine extended epitopes, ten extended epitopes, 11 extended epitopes, 12 extended epitopes, 13 extended epitopes, 14 extended epitopes, 15 extended epitopes, 16 extended epitopes, 17 extended epitopes, 18 extended epitopes 19 extended epitopes, 20 extended epitopes or more than 20 extended epitopes.

In some aspects, plasmids for the compositions containing more than one sequence encoding an epitope contain spacers between each epitope sequence. In some aspects, spacers include intervening amino acids sequences comprising <10 amino acids. In some cases, sequences of short epitopes are encoded in tandem without the use of spacers. In some cases, sequences of extended epitopes are encoded in tandem without the use of spacers. In some cases, sequences of short epitopes are encoded in tandem with the use of spacers. In some cases, sequences of extended epitopes are encoded in tandem with the use of spacers.

Any plasmid backbones (e.g., vectors) known to one of ordinary skill in the art suitable for pharmaceutical use for expression of a nucleic sequence may be used in the compositions described herein.

The vector can be a circular plasmid or a linear nucleic acid. The circular plasmid or linear nucleic acid can be capable of directing expression of a particular nucleotide sequence in an appropriate subject cell. The vector can have a promoter operably linked to the polypeptide-encoding nucleotide sequence, which can be operably linked to termination signals. The vector can also contain sequences required for proper translation of the nucleotide sequence. The vector comprising the nucleotide sequence of interest can be chimeric, meaning that at least one of its components is heterologous with respect to at least one of its other components. The expression of the nucleotide sequence in the expression cassette can be under the control of a constitutive promoter or of an inducible promoter, which can initiate transcription only when the host cell is exposed to some particular external stimulus.

The vector can be a plasmid. The plasmid can be useful for transfecting cells with nucleic acid encoding the polypeptide, which the transformed host cells can be cultured and maintained under conditions wherein expression of the polypeptide takes place.

The plasmid can comprise a nucleic acid sequence that encodes one or more of the various polypeptide disclosed herein. A single plasmid can contain coding sequence for a single polypeptide, or coding sequence for more than one polypeptide. Sometimes, the plasmid can further comprise coding sequence that encodes an adjuvant, such as an immune stimulating molecule, such as a cytokine.

The plasmid can further comprise an initiation codon, which can be upstream of the coding sequence, and a stop codon, which can be downstream of the coding sequence. The initiation and termination codon can be in frame with the coding sequence. The plasmid can also comprise a promoter that is operably linked to the coding sequence, and an enhancer upstream of the coding sequence. The enhancer can be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737.

The plasmid can be suitable for either eukaryotic or prokaryotic expression. Plasmids can be from bacteria (e.g., *E. coli*), insects, yeast, or mammalian source. The plasmid can also be for a cell-free expression system.

Suitable bacterial plasmids can include pSE420, pcDNA I, pcDNA 3, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect plasmids can include MAXBAC™, pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

Yeast plasmids can include pYES2, Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pTEF1/Zeo, pYES2 yeast vector, pYES2/CT yeast vector, pYES2/NT A, B, & C yeast vector, or pYES3/CT yeast vector.

Exemplary mammalian plasmids can include pUMVC3, pVAXI, pCEP4, pREP4, pMCP-tag(m), pTARGET™, FreeStyle™ 293 system, pFLAG-CMV 3, pFLAG-Myc-CMV 21, p3xFLAG-Myc-CMV 25, pBICEP-CMV 1, pBICEP-CMV 2, or Expi293™ system.

Exemplary plasmids for a cell free system can include pF25K ICE T7 Flexi® vector, pF3A WG (BYDV) Flexi® vector, pTNT™, or pCMVTNT™ vector.

The plasmid can also comprise a regulatory sequence, which may be well suited for gene expression in a cell into which the plasmid is administered. The coding sequence can comprise a codon that can allow more efficient transcription of the coding sequence in the host cell.

In some instances, the vector is a circular plasmid, which can transform a target cell by integration into the cellular genome or exist extrachromosomally (e.g., autonomous replicating plasmid with an origin of replication). Exemplary vectors include pVAX, pcDNA3.0, or provax, or any other expression vector capable of expressing DNA encoding the antigen and enabling a cell to translate the sequence to an antigen that is recognized by the immune system.

The nucleic acid based vaccine can also be a linear nucleic acid vaccine, or linear expression cassette ("LEC"), that is capable of being efficiently delivered to a subject via electroporation and expressing one or more polypeptides disclosed herein. The LEC can be any linear DNA devoid of any phosphate backbone. The DNA can encode one or more polypeptides disclosed herein. The LEC can contain a promoter, an intron, a stop codon, and/or a polyadenylation signal. The expression of the polypeptide may be controlled by the promoter. The LEC can not contain any antibiotic resistance genes and/or a phosphate backbone. The LEC can not contain other nucleic acid sequences unrelated to the polypeptide expression.

The LEC can be derived from any plasmid capable of being linearized. The plasmid can express the polypeptide. Exemplary plasmids include: pNP (Puerto Rico/34), pM2 (New Caledonia/99), WLV009, pVAX, pcDNA3.0, provax, or any other expression vector capable of expressing DNA encoding the antigen and enabling a cell to translate the sequence to an antigen that is recognized by the immune system.

A composition can be a plasmid-based vaccine containing short and extended antigenic epitopes. In an aspect, the plasmid, or plasmids, of the vaccine are constructed using a 4 kB plasmid backbone (e.g., pUMVC3 or pNGVL3). In some aspects, the plasmid contains one or more antibiotic resistance genes. In other aspects, the plasmid contains kanamycin resistance gene, carbenicillin resistance gene, ampicillin resistance gene, Actinomycin D resistance gene, Streptomycin resistance gene, Neomycin resistance gene, Polymyxin resistance gene, or Zeocin resistance gene, or a combination thereof. In an aspect, pUMVC3 contains the kanamycin resistance gene in addition to an origin of replication for selection and propagation in bacteria. In some cases, the multiple cloning site in pUMVC3 is flanked by eukaryotic transcriptional control elements to promote the expression of inserted sequences (e.g., gene cassettes) in eukaryotic cells. In an aspect, the inserted sequences are epitopes.

In an aspect, the nucleic acid coding sequence of the antigenic epitope peptides is assembled with the Kozak consensus translation initiation sequence, a termination codon, and cloning sites in the plasmid backbone. Standard molecular techniques known to one of ordinary skill in the art which include synthetic oligonucleotides, polymerase chain reaction amplification, restriction endonucleases, and nucleic acid ligase (e.g., DNA ligase) may be used to generate nucleic acid (e.g., DNA fragments) and insert the nucleic acid fragments into the plasmid vector backbone.

In some cases, the plasmid contains a nucleic acid sequence coding for at least one tag. In some cases, the tag is translated into a peptide. Any nucleic acid sequence for a tag known to one of ordinary skill in the art may be used with the plasmids described herein. In an aspect, the tag is a histidine tag with three histidine residues, a histidine tag with four histidine residues, a histidine tag with five histidine residues, or a histidine tag with six histidine residues, or the like. In some aspects, expression of the tag in a subject is determined, using any suitable technique known to one of ordinary skill in the art.

In some cases, plasmids are sequenced using any sequencing technique known to one of ordinary skill in the art such that the results of the sequencing technique provides nucleotide level resolution of the entire plasmid.

In some aspects, the composition is a multiantigen cancer vaccines (e.g., colorectal cancer, non-small cell lung cancer, or ovarian cancer vaccines). In an aspect, the multiantigen cancer vaccines (e.g., colorectal cancer, non-small cell lung cancer, or ovarian cancer vaccines) contains a plurality of antigens. In some cases, expression of one antigen impacts expression of a different antigen. In some cases, expression of more than one antigen impacts expression of a different antigen. In some cases, expression of one antigen impacts expression of more than one different antigen. In some cases, expression of one antigen does not impact expression of a different antigen. In some cases, expression of more than one antigen does not impact expression of a different antigen. In some cases, expression of one antigen does not impact expression of more than one different antigen. In an aspect, antigenic competition limits the immunogenicity of multiantigen vaccines. In some aspects, any techniques known to one of ordinary skill in the art are used to determine if an immune response elicited following administration of a multiple antigen vaccine is of comparable magnitude to each antigen as a single antigen vaccine. In an aspect, ELISPOT (e.g., for secretion of IFN-γ) determines the magnitude of the immune response. In some cases, the ELISPOT detects rodent, non-human primate or human peptides.

Nucleic Acids

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Isolated nucleic acid molecule can include DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Nucleic acid molecules may refer to at least two nucleotides covalently linked together. A nucleic acid described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica. Scripta 26:141 (1986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989)), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995)); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In some aspects, a recombinant molecule includes nucleic acid molecules operatively linked to expression vectors containing regulatory sequences such as transcription control sequences, translation control sequences, origins of replication, and other regulatory sequences that are compatible with the host cell and that control the expression of nucleic acid molecules of the present invention. In an aspect, recombinant molecules of the include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

Pharmaceutical Compositions

In some aspects, the immunogenic compositions of the disclosure are preferably formulated as a vaccine for in vivo administration to the subject, such that they confer an antibody titer superior to the criterion for seroprotection for each antigenic component for an acceptable percentage of subjects. Antigens with an associated antibody titer above which a subject is considered to be seroconverted against the antigen are well known, and such titers are published by organizations such as WHO. In some aspects, preferably more than 80% of a statistically significant sample of subjects is seroconverted, more preferably more than 90%, still more preferably more than 93% and most preferably 96-100%.

In some aspects, the immunogenic compositions of the disclosure are preferably adjuvanted. Suitable adjuvants include an aluminum salt such as aluminum hydroxide gel (alum) or aluminum phosphate, a salt of calcium, iron or zinc, or an insoluble suspension of acylated tyrosine, or acylated sugars, cationically or anionically derivatized polysaccharides, or polyphosphazenes.

Sometimes, the adjuvants can elicit a TH1-type response. Other times, adjuvants can elicit a TH2-type response. A TH1-type response can be characterized by the production of cytokines such as IFN-γ as opposed to a TH2-type response which can be characterized by the production of cytokines such as IL-4, IL-5 and IL-10.

In some aspects, the adjuvant is selected to be a preferential inducer of a TH1 type of response to aid the cell mediated branch of the immune response.

Suitable adjuvants can include stimulatory molecules such as cytokines. Non-limiting examples of cytokines include: CCL20, a-interferon (IFN-a), β-interferon (IFN-β), γ-interferon, platelet derived growth factor (PDGF), TNFa, TNFp, granulocyte macrophage colony-stimulating factor (GM-CSF), epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2. In some instances, the adjuvant is granulocyte macrophage colony-stimulating factor (GM-CSF).

Additional adjuvants include: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

In some aspects, an adjuvant can be a modulator of a toll like receptor. Examples of modulators of toll-like receptors include TLR-9 agonists and are not limited to small molecule modulators of toll-like receptors such as Imiquimod. Other examples of adjuvants that are used in combination with a vaccine described herein can include and are not limited to saponin, CpG ODN and the like.

Sometimes, adjuvants may include an aluminum salt such as aluminum hydroxide gel (alum), aluminum phosphate, a salt of calcium, iron or zinc, or may be an insoluble suspension of acylated tyrosine, or acylated sugars, cationically or anionically derivatized polysaccharides, or polyphosphazenes.

Sometimes, the adjuvant can be Complete Freund's adjuvant (CFA). Complete Freund's adjuvant can contain heat-killed mycobacteria, which can be responsible for stimulating antibody production.

The adjuvant can also include Incomplete Freund's adjuvant (IFA). Incomplete Freund's adjuvant, water-in-oil (w/o) emulsion, can elicit a Th2-biased response through the formation of depot at the injection site and stimulation of antibody producing plasma cells.

In some aspects, suitable adjuvant systems which promote a predominantly Th1 response include, Monophosphoryl lipid A or a derivative thereof, particularly 3-de-O-acylated monophosphoryl lipid A, and a combination of monophosphoryl lipid A, preferably 3-de-O-acylated monophosphoryl lipid A (3D-MPL) together with an aluminum salt. In some aspects, an enhanced system involves the combination of a monophosphoryl lipid A and a saponin derivative, particularly the combination of QS21 and 3D-MPL as disclosed in WO 94/00153, or a less reactogenic composition where the QS21 is quenched with cholesterol as disclosed in WO 96/33739. In some aspects, a particularly potent adjuvant formulation involves QS21, 3D-MPL and tocopherol in an oil in water emulsion as described in WO 95/17210. In some aspects, the vaccine additionally comprises a saponin, more preferably QS21. In some aspects, the formulation also comprises an oil in water emulsion and tocopherol (WO 95/17210). In some aspects, unmethylated CpG containing oligonucleotides (WO 96/02555) are also preferential inducers of a TH1 response and are suitable for use in the present disclosure.

In some aspects, aluminum salts are preferred adjuvants in the above immunogenic compositions. In some aspects, in order to minimize the levels of adjuvant (particularly aluminum salts) in the compositions of the disclosure, the polysaccharide conjugates are unadjuvanted.

In some aspects, the vaccine according to the disclosure further comprises an adjuvant or immunostimulant such as but not limited to detoxified lipid A from any source and non-toxic derivatives of lipid A, saponins and other reagents capable of stimulating a TH1 type response. It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p40'7-419).

A further detoxified version of MPL results from the removal of the acyl chain from the 3-position of the disaccharide backbone, and is called 3-O-Deacylated monophosphoryl lipid A (3D-MPL). In some aspects, it is purified and prepared by the methods taught in GB 2122204B, a reference also disclosing the preparation of diphosphoryl lipid A, and 3-O-deacylated variants thereof.

A preferred form of 3D-MPL is in the form of an emulsion having a small particle size less than 0.2 µm in diameter, and its method of manufacture is disclosed in WO 94/21292. Aqueous formulations comprising monophosphoryl lipid A and a surfactant have been described in WO9843670A2. In some aspects, the bacterial lipopolysaccharide derived adjuvants to be formulated in the compositions of the present disclosure are purified and processed from bacterial sources, or alternatively they are synthetic. In an aspect, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al, 1986, Int. ArchAllergy. Immunol, 79(4):392-6; Hilgers et al, 1987, Immunology, 60(1):141-6; and EP 0 549 074 B1). In some aspects, a particularly preferred bacterial lipopolysaccharide adjuvant is 3D-MPL.

Accordingly, in some aspects, the LPS derivatives used in the present disclosure are those immuno stimulants that are similar in structure to that of LPS or MPL or 3D-MPL. In another aspect of the present disclosure, the LPS derivative is an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja *Saponaria* Molina), and fractions thereof, are described in U.S. Pat. No. 5,057,540 and "Saponins as vaccine adjuvants", Kensil, C. R., CritRev TherDrug Carrier Syst, 1996, 12 (1-2):1-55; and EP 0362 279 B1.

Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0362279 B1. Other saponins which have been used in systemic vaccination studies include those derived from other plant species such as *Gypsophila* and *Saponaria* (Bomford et al., Vaccine, 10(9):572-577, 1992).

In some aspects, an enhanced system involves the combination of a non-toxic lipid A derivative and a saponin derivative, particularly the combination of QS21 and 3D-MPL as disclosed in WO 94/00153, or a less reactogenic composition where the QS21 is quenched with cholesterol as disclosed in WO 96/33739.

In some aspects, a particularly potent adjuvant formulation involves QS21 and 3D-MPL in an oil in water emulsion as described in WO 95/17210 and is a preferred formulation.

Accordingly, in an aspect of the present disclosure, there is provided a vaccine comprising an antigen preparation of the present disclosure adjuvanted with detoxified lipid A or a non-toxic derivative of lipid A, more preferably adjuvanted with a monophosphoryl lipid A or derivative thereof.

In some aspects, preferably the vaccine additionally comprises a saponin, more preferably QS21. In some aspects, preferably the formulation additionally comprises an oil in water emulsion. The present disclosure also provides a method for producing a vaccine formulation comprising mixing an antigen preparation of the present disclosure together with a pharmaceutically acceptable excipient, such as 3D-MPL.

In some aspects, additional components that are preferably present in an adjuvanted vaccine formulation according to the disclosure, include non-ionic detergents such as the octoxynols and polyoxyethylene esters as described herein, particularly t-octylphenoxy polyethoxyethanol (Triton X-100) and polyoxyethylene sorbitan monooleate (Tween 80); and bile salts or cholic acid derivatives as described herein, in particular sodium deoxycholate or taurodeoxycholate. Thus, in some aspects, a particularly preferred formulation comprises 3D-MPL, Triton X-100, Tween 80 and sodium deoxycholate, which may be combined with an antigen preparation to provide a vaccine suitable for intradermal application.

In some aspects, in one preferred case of the present disclosure, the intradermal vaccines comprise a vesicular adjuvant formulation. In this regard, in some aspects, the preferred adjuvant formulation comprises a unilamellar vesicle comprising cholesterol, having a lipid bilayer preferably comprising dioleoyl phosphatidyl choline, wherein the saponin and the LPS derivative are associated with, or embedded within, the lipid bilayer. In some aspects, more preferably, these adjuvant formulations comprise QS21 as the saponin, and 3D-MPL as the LPS derivative, wherein the ratio of QS21:cholesterol is from 1:1 to 1:100 mass/mass, and most preferably 1:5 mass/mass. Such adjuvant formulations are described in EP 0 822 831 B, the disclosure of which is incorporated herein by reference.

Sometimes, a vaccine described herein can further comprise an adjuvant selected from bacteria toxoids, non-toxin proteins, proteosomes, polyoxypropylene-polyoxyethylene block polymers, liposomes, CpG polymers, oil-in-water emulsions, or a combination thereof. Exemplary bacterai toxoids can include toxins of *Vibrio cholerae* (CT), *E. coli* (HLT), toxin from *Pertussigen pertussis* (PT), toxin A and toxin B of *Clostridium difficile*, Shiga toxin (STx) from *Shiga dysenteriae*, or enterotoxins from *Staphylococcal aureus*.

Non-toxin proteins can include muramyl dipeptide (MDP) (N-aceylyl muramyl-L-alanyl-D-isoglutamine). In some instances, MDP is derived from the cell wall of mycobacteria, and is an inducer of IL-1, which can activate macrophages and T cells.

Proteosomes can include the meningococcal outer membrane protein, which can elicit an anti-toxin IgA response. Additional proteosome-based adjuvant can include Protollin.

Liposomes can include lipid A (LA), monophsophoryl lipid A (MPL), cationic liposomes such as dimethyl dioctadecyl-ammonium bromide (DDA), 1,2-diacyl-sn-glycero-3-ethylphosphocholine (eDPPC), or 3β-[N—(N',N'-dimethylaminoethane)-carbamoyl] cholesterol (DC-Chol), or neutral phospholipid such as 1,2-Dipalmitoyl-sn-glycero-3-phosphocholine (DPPC).

CpG polymers can include oligodeoxynucleotide polymers that include unmethylated CpG dinucleotide which can exert a strong stimulatory influence on the immune system.

Sometimes, an adjuvant is an oil-in-water emulsion. The oil-in-water emulsion can include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

The oils used can include such as those from an animal (such as fish) or vegetable source. Sources for vegetable oils can include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil, etc. The grain group can include: corn oil and oils of other cereal grains such as wheat, oats, rye, rice, teff, triticale, and the like. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk can be metabolizable and can therefore be used in with the vaccines described herein. The procedures for separation, purification, saponification and other means necessary for obtaining pure oils from animal sources are well known in the art. Fish can contain metabolizable oils which can be readily recovered. For example, cod liver oil, shark liver oils, and whale oil such as spermaceti can exemplify several of the fish oils which can be used herein. A number of branched chain oils can be synthesized biochemically in 5-carbon isoprene units and can be generally referred to as terpenoids. Shark liver oil contains a branched, unsaturated terpenoid known as squalene, 2,6,10,15,19,23-hexamethyl-2,6,10,14,18,22-tetracosahexaene. Squalane, the saturated analog to squalene, can also be used. Fish oils, including squalene and squalane, can be readily available from commercial sources or can be obtained by methods known in the art.

Other useful oils include tocopherols, can included in vaccines for use in elderly patients (e.g. aged 60 years or older) due to vitamin E been reported to have a positive effect on the immune response in this patient group. Further, tocopherols have antioxidant properties that can help to stabilize the emulsions. Various tocopherols exist (α, β, γ, δ, ε or ξ) but α is usually used. An example of α-tocopherol is DL-α-tocopherol. α-tocopherol succinate can be compatible with cancer vaccines and can be a useful preservative as an alternative to mercurial compounds.

Mixtures of oils can be used e.g. squalene and α-tocopherol. An oil content in the range of 2-20% (by volume) can be used.

Surfactants can be classified by their 'HLB' (hydrophile/lipophile balance). In some cases, surfactants have a HLB of at least 10, at least 15, and/or at least 16. Surfactants can include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxy-polyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants can be used herein.

Mixtures of surfactants can be used e.g. Tween 80/Span 85 mixtures. A combination of a polyoxyethylene sorbitan ester and an octoxynol can also be suitable. Another combination can comprise laureth 9 plus a polyoxyethylene sorbitan ester and/or an octoxynol.

The amounts of surfactants (% by weight) can be: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Exemplary oil-in-water emulsion adjuvants can include, but are not limited to:

A submicron emulsion of squalene, polysorbate 80, and sorbitan trioleate. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59'. The MF59 emulsion advantageously includes citrate ions e.g. 10 mM sodium citrate buffer.

A submicron emulsion of squalene, a tocopherol, and polysorbate 80. These emulsions can have from 2 to 10% squalene, from 2 to 10% tocopherol and from 0.3 to 3% polysorbate 80, and the weight ratio of squalene:tocopherol is preferably ≤1 (e.g. 0.90) as this can provide a more stable emulsion. Squalene and polysorbate 80 may be present at a volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion has submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80.

An emulsion of squalene, a tocopherol, and a Triton detergent (e.g. Triton X-100). The emulsion can also include a 3d-MPL (see below). The emulsion can contain a phosphate buffer.

An emulsion comprising a polysorbate (e.g. polysorbate 80), a Triton detergent (e.g. Triton X-100) and a tocopherol (e.g. an α-tocopherol succinate). The emulsion can include these three components at a mass ratio of about 75:11:10 (e.g. 750 μml polysorbate 80, 110 μml Triton X-100 and 100 μ/ml α-tocopherol succinate), and these concentrations should include any contribution of these components from antigens. The emulsion can also include squalene. The emulsion may also include a 3d-MPL. The aqueous phase can contain a phosphate buffer.

An emulsion of squalane, polysorbate 80 and poloxamer 401 ("Pluronic™ L121"). The emulsion can be formulated in phosphate buffered saline, pH 7.4. This emulsion can be a useful delivery vehicle for muramyl dipeptides, and can be used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2% polysorbate 80).

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion can be thermoreversible and/or has at least 90% of the oil droplets (by volume) with a size less than 200 nm. The emulsion can also include one or more of: alditol; a cryoprotective agent (e.g. a sugar, such as dodecylmaltoside and/or sucrose); and/or an alkylpolyglycoside. The emulsion can include a TLR4 agonist. Such emulsions can be lyophilized.

An emulsion of squalene, poloxamer 105 and Abil-Care. The final concentration (weight) of these components in adjuvanted vaccines can be 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. Phospholipid components can include phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives can include, QuilA saponin, cholesterol, a saponin-lipophile conjugate (such as GPI-0100, produced by addition of aliphatic amine to desacylsaponin via the carboxyl group of glucuronic acid), dimethyldioctadecylammonium bromide and/or N,N-dioctadecyl-N,N-bis (2-hydroxyethyl)propanediamine.

Carriers and Excipients

The present disclosure also provides a method for producing a vaccine formulation comprising the step of mixing the components of the vaccine together with a pharmaceutically acceptable excipient.

In some aspects, preferred surfactants include octylphenoxy polyoxyethanols and polyoxyethylene sorbitan esters as described in "Surfactant systems" Eds: Attwood and Florence (1983, Chapman and Hall). Octylphenoxy polyoxyethanols (the octoxynols), including t-octylphenoxypolyethoxyethanol (Triton X-100 ™) are also described in Merck Index Entry 6858 (Page 1162, 12th Edition, Merck & Co. Inc., Whitehouse Station, N.J., USA; ISBN 0911910-12-3). The polyoxyethylene sorbitan esters, including polyoxyethylene sorbitan monooleate (Tween 80™) are described in Merck Index Entry 7742 (Page 1308, 12th Edition, Merck & Co. Inc., Whitehouse Station, N.J., USA; ISBN 0911910-12-3). Both may be manufactured using methods described therein, or purchased from commercial sources such as Sigma Inc.

In some aspects, particularly preferred non-ionic surfactants include Triton X-45, t-octylphenoxy polyethoxyethanol (Triton X-100), Triton X-102, Triton X-114, Triton X-165, Triton X-205, Triton X-305, Triton-57, Triton-101, Triton-128, Breij 35, polyoxyethylene-9-lauryl ether (laureth 9) and polyoxyethylene-9-stearyl ether (steareth 9). In some aspects, Triton X-100 and laureth 9 are particularly preferred. In some aspects, also particularly preferred is the polyoxyethylene sorbitan ester, polyoxyethylene sorbitan monooleate (Tween 80™). In some aspects, further suitable polyoxyethylene ethers of general formula are selected from the following group: polyoxyethylene-8-stearyl ether, polyoxyethylene-4-lauryl ether, polyoxyethylene-35-lauryl ether, and polyoxyethylene-23-lauryl ether.

Alternative terms or names for polyoxyethylene lauryl ether are disclosed in the CAS registry. The CAS registry number of polyoxyethylene-9 lauryl ether is: 9002-92-0. Polyoxyethylene ethers such as polyoxyethylene lauryl ether are described in the Merck index (12th ed: entry 7717, Merck & Co. Inc., Whitehouse Station, N.J., USA; ISBN 0911910-12-3). Laureth 9 is formed by reacting ethylene oxide with dodecyl alcohol, and has an average of nine ethylene oxide units.

The ratio of the length of the polyoxyethylene section to the length of the alkyl chain in the surfactant (i.e., the ratio of n:alkyl chain length), affects the solubility of this class of surfactant in an aqueous medium. Thus, in some aspects, the surfactants of the present disclosure are in solution or form particulate structures such as micelles or vesicles. As a solution, the surfactants of the present disclosure are safe, easily sterilisable, simple to administer, and may be manufactured in a simple fashion without the GMP and QC issues associated with the formation of uniform particulate structures. Some polyoxyethylene ethers, such as laureth 9, are capable of forming non-vesicular solutions. However, polyoxyethylene-8 palmitoyl ether (C18E8) is capable of forming vesicles. Accordingly, in some aspects, vesicles of polyoxyethylene-8 palmitoyl ether in combination with at least one additional non-ionic surfactant, are employed in the formulations of the present disclosure.

Within the inherent experimental variability of such a biological assay, the polyoxyethylene ethers, or surfactants of general formula (I), of the present disclosure, in some aspects, preferably have a haemolytic activity, of approximately between 0.5-0.0001%, more preferably between 0.05-0.0001%, even more preferably between 0.005-0.0001%, and most preferably between 0.003-0.0004%. In some aspects, ideally, said polyoxyethylene ethers or esters should have a haemolytic activity similar (i.e., within a ten-fold difference) to that of either polyoxyethylene-9 lauryl ether or polyoxyethylene-8 stearyl ether.

In some aspects, two or more non-ionic surfactants from the different groups of surfactants described are present in the vaccine formulation described herein. In particular, in some aspects, a combination of a polyoxyethylene sorbitan ester such as polyoxyethylene sorbitan monooleate (Tween 80™) and an octoxynol such as t-octylphenoxypolyethoxyethanol (Triton) X-100™ is preferred. In other aspects, another particularly preferred combination of non-ionic surfactants comprises laureth 9 plus a polyoxyethylene sorbitan ester or an octoxynol or both.

In some aspects, preferably each non-ionic surfactant is present in the final vaccine formulation at a concentration of between 0.001 to 20%, more preferably 0.01 to 10%, and most preferably up to about 2% (w/v). In some aspects, where one or two surfactants are present, these are generally present in the final formulation at a concentration of up to about 2% each, typically at a concentration of up to about 0.6% each. In some aspects, one or more additional surfactants are present, generally up to a concentration of about 1% each and typically in traces up to about 0.2% or 0.1% each. In some aspects, any mixture of surfactants are present in the vaccine formulations according to the disclosure. In some aspects, non-ionic surfactants such as those discussed above have preferred concentrations in the final vaccine composition as follows: polyoxyethylene sorbitan esters such as Tween80™: 0.01 to 1%, most preferably about 0.1% (w/v); octyl- or nonylphenoxy polyoxyethanols such as Triton X-100™ or other detergents in the Triton series: 0.001 to 0.1%, most preferably 0.005 to 0.02% (w/v); polyoxyethylene ethers of general formula (I) such as laureth 9:0.1 to 20%, preferably 0.1 to 10% and most preferably 0.1 to 1% or about 0.5% (w/v).

In some aspects, other reagents are also present in the formulation. As such, in some aspects, the formulations of the present disclosure also comprise a bile acid or a derivative thereof, in particular in the form of a salt. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic-, derivatives of the aforementioned bile acids, or N,N-bis (3Dgluconoamidopropyl) deoxycholamide. In some aspects, a particularly preferred example is sodium deoxycholate (NaDOC) which is present in the final vaccine dose.

A composition may be encapsulated within liposomes using well-known technology. Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The composition may be administered in liposomes or microspheres (or microparticles). Methods for preparing liposomes and microspheres for administration to a patient are well known to those of skill in the art, U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

A composition may include preservatives such as thiomersal or 2-phenoxyethanol. In some instances, the vaccine is substantially free from (e.g. <10 µg/ml) mercurial material e.g. thiomersal-free. α-Tocopherol succinate may be used as an alternative to mercurial compounds.

For controlling the tonicity, a physiological salt such as sodium salt can be included in the vaccine. Other salts can include potassium chloride, potassium dihydrogen phosphate, disodium phosphate, and/or magnesium chloride, or the like.

A composition may have an osmolality of between 200 mOsm/kg and 400 mOsm/kg, between 240-360 mOsm/kg, or within the range of 290-310 mOsm/kg.

A composition may comprise one or more buffers, such as a Tris buffer; a borate buffer; a succinate buffer; a histidine buffer (particularly with an aluminum hydroxide adjuvant); or a citrate buffer. Buffers, in some cases, are included in the 5-20 mM range.

The pH of the composition may be between about 5.0 and about 8.5, between about 6.0 and about 8.0, between about 6.5 and about 7.5, or between about 7.0 and about 7.8.

A composition may be sterile. The vaccine can be non-pyrogenic e.g. containing <1 EU (endotoxin unit, a standard measure) per dose, and can be <0.1 EU per dose. The composition can be gluten free.

A composition may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent can be present only at trace amounts. Thus the vaccine can include less than 1 mg/ml of each of octoxynol-10 and polysorbate 80. Other residual components in trace amounts can be antibiotics (e.g. neomycin, kanamycin, polymyxin B).

A composition may be formulated as a sterile solution or suspension, in suitable vehicles, well known in the art. The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

A composition may be formulated with one or more pharmaceutically acceptable salts. Pharmaceutically acceptable salts can include those of the inorganic ions, such as, for example, sodium, potassium, calcium, magnesium ions, and the like. Such salts can include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

Additional salts may comprise a bile acid or a derivative thereof. These include derivatives of cholic acid and salts thereof, in particular sodium salts of cholic acid or cholic acid derivatives. Examples of bile acids and derivatives thereof include cholic acid, deoxycholic acid, chenodeoxycholic acid, lithocholic acid, ursodeoxycholic acid, hyodeoxycholic acid and derivatives such as glyco-, tauro-, amidopropyl-1-propanesulfonic-, amidopropyl-2-hydroxy-1-propanesulfonic derivatives of the aforementioned bile acids, or N,N-bis (3Dgluconoamidopropyl) deoxycholamide. A particularly preferred example is sodium deoxycholate (NaDOC) which may be present in the final vaccine dose.

A composition comprising an active agent such as a peptide or a nucleic acid described herein, in combination with one or more adjuvants may be formulated in conventional manner using one or more physiologically acceptable carriers, comprising excipients, diluents, and/or auxiliaries, e.g., which facilitate processing of the active agents into preparations that can be administered. Proper formulation may depend at least in part upon the route of administration chosen. The agent(s) described herein may be delivered to a patient using a number of routes or modes of administration, including oral, buccal, topical, rectal, transdermal, transmucosal, subcutaneous, intravenous, and intramuscular applications, as well as by inhalation.

The active agents may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol.

For injectable formulations, the vehicle may be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation may also comprise polymer compositions which are biocompatible, biodegradable, such as poly(lactic-co-glycolic)acid. These materials may be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular intraocular injection are well known in the art.

In some instances, a composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it may be dispensed with an infusion bottle containing sterile pharmaceutical grade water or saline. Where the composition is administered by injection, an ampoule of sterile water for injection or saline can be provided so that the ingredients may be mixed prior to administration.

When administration is by injection, the active agent may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the active compound may be in powder form for constitution with a suitable vehicle, e.g., sterile pyrogen-free water, before use. In another embodiment, the pharmaceutical composition does not comprise an adjuvant or any other substance added to enhance the immune response stimulated by the peptide. In another embodiment, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In addition to the formulations described above, the active agents may also be formulated as a depot preparation. Such long acting formulations may be administered by implantation or transcutaneous delivery (for example subcutaneously or intramuscularly), intramuscular injection or use of a transdermal patch. Thus, for example, the agents may be formulated with suitable polymeric or hydrophobic materials (for example as an emulsion in an acceptable oil) or ion exchange resins, or as sparingly soluble derivatives for example, as a sparingly soluble salt.

In some cases, compositions comprising one or more agents exert local and regional effects when administered topically or injected at or near particular sites of infection. Direct topical application, e.g., of a viscous liquid, solution, suspension, dimethylsulfoxide (DMSO)-based solutions, liposomal formulations, gel, jelly, cream, lotion, ointment, suppository, foam, or aerosol spray, can be used for local administration, to produce for example local and/or regional effects. Pharmaceutically appropriate vehicles for such formulation include, for example, lower aliphatic: alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983. In another embodiment, local/topical formulations comprising a transporter, carrier, or ion channel inhibitor are used to treat epidermal or mucosal viral infections.

Compositions may contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents can be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Lubricants which may be used to form pharmaceutical compositions and dosage forms can include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

The compositions may be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions may be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions can also consist of solid preparations constituting soaps or cleansing bars.

Compositions may contain adjuvants such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

For oral administration, the active agent(s) may be formulated readily by combining the active agent(s) with pharmaceutically acceptable carriers well known in the art. Such carriers enable the agents of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. A solid carrier may be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the active agents may be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions for oral use may contain active agent(s) with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

Oils or non-aqueous solvents can be required to bring the active agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al, Proc. Natl. Acad. Sci. USA 75: 4194-4198 (1978), incorporated herein by reference, Ligands can also be attached to the liposomes to direct these compositions to particular sites of action.

Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as sodium alginate. The agents can also be formulated as a sustained release preparation.

Dragee cores may be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active agents.

Pharmaceutical preparations that may be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers can be added. All formulations for oral administration may be in dosages suitable for administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or can contain emulsifying agents, for example, such as lecithin, sorbitan monooleate, or acacia. Aqueous solutions may be prepared by dissolving the active component in water and adding suitable colorants, flavors, stabilizers, and thickening agents. Aqueous suspensions may be prepared by dispersing the finely divided active component in water with viscous material, such as natural or synthetic gums, resins, methylcellulose, sodium carboxymethylcellulose, and other well known suspending agents. Suitable fillers or carriers with which the compositions may be administered include agar, alcohol, fats, lactose, starch, cellulose derivatives, polysaccharides, polyvinylpyrrolidone, silica, sterile saline and the like, or mixtures thereof used in suitable, amounts. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

A syrup or suspension may be made by adding the active compound to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric; alcohol, for example, glycerol or sorbitol.

When formulating compounds for oral administration, it may be desirable to utilize gastroretentive formulations to enhance absorption from the gastrointestinal (GI) tract. A formulation which is retained in the stomach for several hours may release compounds of the invention slowly and provide a sustained release that can be used herein. Disclosure of such gastro-retentive formulations are found in Klausner, E. A.; Lavy, M.; Cserepes, E.; Friedman, M.; Hoffman, A. 2003 "Novel gastroretentive dosage forms: evaluation of gastroretentivity and its effect on levodopa in humans," Pharm. Res. 20, 1466-73, Hoffman, Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J; Bodrneier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques can be utilized to maximize absorption of the compounds of the invention.

The solubility of the components of the compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such cosolvents can be employed at a level of from about 0.01% to 2% by weight.

The compositions may be packaged in multidose form. Preservatives may be preferred to prevent microbial contamination during use. Suitable preservatives include: benzalkonium, chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g. from 0.001% to 0.008%, preferably about 0.005% by weight. It has been found that a concentration of benzalkonium chloride of 0.005% can be sufficient to preserve the compositions of the present invention from microbial attack.

In instances relating to topical/local application, the compositions may include one or more penetration enhancers. For example, the formulations may comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars starches, cellulose derivatives, gelatin, and/or other polymers. In another embodiment, the compositions may include one or more such penetration enhancers.

The compositions for local/topical application may include one or more antimicrobial preservatives such as quaternary ammonium compounds, organic mercurials, p-hydroxy benzoates, aromatic alcohols, chlorobutanol, and the like.

The compositions may be formulated into aerosol solutions, suspensions or dry powders. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a transporter, carrier, or ion channel inhibitor can be dissolved, suspended or emulsified in a propellant or a mixture of solvent and propellant, e.g., for administration as a nasal spray or inhalant. Aerosol formulations can contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range may additionally be used. Antimicrobial agents or preservatives may also be included in the formulation.

An aerosol formulation for inhalations and inhalants may be designed so that the agent or combination of agents is carried into the respiratory tree of the subject when administered by the nasal or oral respiratory route. Inhalation solutions may be administered, for example, by a nebulizer. Inhalations or insufflations comprising finely powdered or liquid drugs may be delivered to the respiratory system as a pharmaceutical aerosol of a solution or suspension of the agent or combination of agents in a propellant, e.g., to aid in disbursement. Propellants may be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants may include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons may also be used as a propellant. Ether propellants include, for example, dimethyl ether as well as the ethers. An aerosol formulation of the invention may also comprise more than one propellant. For example, the aerosol formulation may comprise more than one propellant from the same class, such as two or more fluorocarbons; or more than one, more than two, more than three propellants from different classes, such as a fluorohydrocarbon and a hydrocarbon. Pharmaceutical compositions of the present invention may also be dispensed with a compressed gas, e.g., an inert gas such as carbon dioxide, nitrous oxide or nitrogen.

Aerosol formulations may also include, other components, for example, ethanol, isopropanol, propylene glycol, as well as surfactants or other components such as oils and detergents. These components may serve to stabilize the formulation and/or lubricate valve components.

The aerosol formulation may be packaged under pressure and can be formulated as an aerosol using solutions, suspensions, emulsions, powders and semisolid preparations. For example, a solution aerosol formulation may comprise a solution of an agent of the invention such as a transporter, carrier, or ion channel inhibitor in (substantially) pure propellant or as a mixture of propellant and solvent. The solvent may be used to dissolve the agent and/or retard the evaporation of the propellant. Solvents may include, for example, water, ethanol and glycols. Any combination of suitable solvents may be use, optionally combined with preservatives, antioxidants, and/or other aerosol components.

An aerosol formulation may be a dispersion or suspension. A suspension aerosol formulation may comprise a suspension of an agent or combination of agents of the instant invention, e.g., a transporter, carrier, or ion channel inhibitor, and a dispersing agent, Dispersing agents may include, for example, sorbitan trioleate, oleyl alcohol, oleic acid, lecithin and corn oil. A suspension aerosol formulation may also include lubricants, preservatives, antioxidant, and/or other aerosol components.

An aerosol formulation may similarly be formulated as an emulsion. An emulsion aerosol formulation may include, for example, an alcohol such as ethanol, a surfactant, water anal a propellant, as well as an agent or combination of agents of the invention, e.g., a transporter, carrier, or ion channel. The surfactant used may be nonionic, anionic or cationic, One example of an emulsion aerosol formulation comprises, for example, ethanol, surfactant, water and propellant. Another example of an emulsion aerosol formulation comprises, for example, vegetable oil, glyceryl monostearate and propane.

The compounds may be formulated for administration as suppositories. A low melting wax, such as a mixture of triglycerides, fatty acid glycerides, Witepsol S55 (trademark of Dynamite Nobel Chemical, Germany), or cocoa butter is first melted and the active component is dispersed homogeneously, for example, by stirring. The molten homogeneous mixture is then poured into convenient sized molds, allowed to cool, and to solidify.

The compounds may be formulated for vaginal administration. Pessaries, tampons, creams, gels, pastes, foams or sprays containing in addition to the active ingredient such carriers as are known in the art to be appropriate.

The compounds may be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, may be utilized in a formulation suitable for intra ocular implantation or injection for sustained release administration, as well. Any suitable biodegradable and biocompatible polymer may be used.

Administration of Pharmaceutical Compositions

In some aspects, the compositions and methods described herein elicit an immune response to an epitope of an antigenic peptide in a subject. In some cases, the compositions are colorectal cancer vaccines, NSCLC cancer vaccines, or ovarian cancer vaccines. In some cases, the colorectal cancer vaccine is a multiantigen colorectal cancer vaccine, multiantigen NSCLC cancer vaccine, or multiantigen ovarian cancer vaccine.

In some cases, the subject is tumor bearing prior to administration of the vaccine. In other cases, the subject is not tumor bearing prior to administration of the vaccine. In other cases, the subject is not tumor bearing prior to administration of the vaccine but becomes tumor bearing after administration of the vaccine. In other cases, the subject is not tumor bearing prior to administration of the vaccine and does not become tumor bearing after administration of the vaccine. In an aspect, the tumors are colorectal cancer tumors, NSCLC cancer tumors, or ovarian cancer tumors. In some aspects, the subject is a rodent and the colorectal cancer tumors in rodents are AOM-induced tumors.

The vaccine described herein may be delivered via a variety of routes. Delivery routes may include oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott & Wilkins, Baltimore Md. (1999). The vaccine described herein can be administered to muscle, or can be administered via intradermal or subcutaneous injections, or transdermally, such as by iontophoresis. Epidermal administration of the vaccine can be employed.

In some instances, the vaccine may also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine may be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine may include material for a single immunization, or may include material for multiple immunizations (i.e. a 'multidose' kit). The inclusion of a preservative is preferred in multidose arrangements. As an alternative (or in addition) to including a preservative in multidose compositions, the compositions can be contained in a container having an aseptic adaptor for removal of material.

The vaccine may be administered in a dosage volume of about 0.1, 0.2, 0.3, 0.4, 0.5, 0.6, 0.7, 0.8, 0.9, or 1.0 mL. Sometimes the vaccine can be administered in a higher dose e.g. of more than 1 ml.

In some aspects, the compositions described herein are administered to a subject in need thereof as a vaccine. In some cases, the subject is immunized with a multiantigen colorectal cancer vaccine, multiantigen NSCLC cancer vaccine, or multiantigen ovarian cancer vaccine. In some cases, the subject is immunized with one dose of the vaccine. In other cases, the subject is immunized with more than one dose of the vaccine. In an aspect, the subject is immunized with more than one, more than two, more than three, more than four, more than five, more than six, more than seven, more than eight, more than nine, more than ten, more than 11, more than 12, more than 13, more than 14, more than 15, more than 16, more than 17, more than 18, more than 19 or more than 20 doses of the vaccine. In an aspect, the subject is immunized with three doses of the vaccine.

In some aspects, in the cases that a subject receives more than one dose of the vaccine, time elapses between the first dose and each subsequent dose of the vaccine. In some cases, the time that elapses between the first dose an each subsequent dose of the vaccine is seconds, minutes, hours, days, weeks, months or years. In an aspect, more than one dose is administered to the subject by intervals. In some cases, the intervals occur over seconds, minutes, hours, days, weeks, months or years. In some cases, subjects receive a booster dose. In an aspect, the booster is administered to the subject more than one, more than two, more than three, more than four, more than five, more than six, more than seven, more than eight, more than nine, more than ten, more than 11, more than 12, more than 13, more than 14, more than 15, more than 16, more than 17, more than 18, more than 19 or more than 20 booster doses of the vaccine. In an aspect, the subject receives up to three boosters of the vaccine.

In some cases, intervals are the same between each dose of the vaccine. In some cases, intervals are the same between each booster of the vaccine. In some cases, intervals are different between each dose of the vaccine. In some cases, intervals are different between each booster of the vaccine.

In an aspect, more than one dose is administered to the subject over an interval of at least one day. In some cases, the interval is one day, two day, three day, four day, five day, six day, seven day, eight day, nine day, ten day, 11 day, 12 day, 13 day, 14 day, 15 day, 16 day, 17 day, 18 day, 19 day, 20 day, 21 day, 22 day, 23 day, 24 day, 25 day, 26 day, 27 day, 28 day, 29 day or 30 day interval. In other cases, the interval is a range of days, and in some aspects, the range of days is 1-5 days, 1-7 days, 1-10 days, 3-15 days, 5-10 days, 5-15 days, 5-20 days, 7-10 days, 7-15 days, 7-20 days, 7-25 days, 10-15 days, 10-20 days, 10-25 days, 15-20 days, 15-25 days, 15-30 days, 20-30 days, 20-35 days, 20-40 days, 20-50 days, 25-50 days, 30-50 days, 35-50 days, or 40-50 days.

In some aspects, subjects are evaluated after administration of the vaccine. In some cases, the subject is evaluated within one month (e.g., short term) of the final administration of the vaccine. In an aspect, short term is one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the final administration of the vaccine. In some cases, the subject is evaluated within four months (e.g., long term) of the final administration of the vaccine. In an aspect, long term is one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or 31 weeks after the final administration of the vaccine.

In some cases, the subject receives at least one booster dose of the vaccine after the final administration of the vaccine doses. In an aspect, at least one booster dose is administered to the subject one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or 31 weeks after the final administration of the vaccine doses. In some cases, the subject receives one booster, two boosters, three boosters, four boosters, five boosters, six boosters, seven boosters, eight boosters, nine boosters, ten boosters, 11 boosters, 12 boosters, 13 boosters, 14 boosters, 15 boosters, 16 boosters, 17 boosters, 18 boosters, 19 boosters, 20 boosters, 21 boosters, 22 boosters, 23 boosters, 24 boosters, 25 boosters, 26 boosters, 27 boosters, 28 boosters, 29 boosters or 30 booster doses.

The disclosure provides in a further aspect a pharmaceutical kit comprising an intradermal administration device and a vaccine formulation as described herein. In some aspects, the device is preferably supplied already filled with the vaccine. In some aspects, preferably the vaccine is in a liquid volume smaller than for conventional intramuscular vaccines as described herein, particularly a volume of between about 0.05 ml and 0.2 nil. In some aspects, preferably the device is a short needle delivery device for administering the vaccine to the dermis.

Suitable devices for use with the intradermal vaccines described herein include short needle devices such as those described in U.S. Pat. Nos. 4,886,499, 5,190,521, 5,328,483, 5,527,288, 4,270,537, 5,015,235, 5,141,496, 5,417,662. In some aspects, intradermal vaccines are also administered by devices which limit the effective penetration length of a needle into the skin, such as those described in WO99/34850, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556 U.S. Pat. Nos. 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, in some aspects, conventional syringes are used in the classical mantoux method of intradermal administration. However, the use of conventional syringes requires highly skilled operators and thus devices which are capable of accurate delivery without a highly skilled user are preferred.

Another case of the disclosure relates to a method to immunize a subject or population of subjects against a disease in order to prevent a disease, and/or reduce the severity of disease in the subject or population of subjects. The method includes the step of administering to a subject or population of subjects that has the disease (or believed not have the disease), a composition of the disclosure.

The composition of one case of the disclosure may be administered using techniques well known to those in the art. In some aspects, preferably, compounds are formulated and administered by genetic immunization. Techniques for formulation and administration are found in "Remington's Pharmaceutical Sciences", 18th ed., 1990, Mack Publishing Co., Easton, Pa. In some aspects, suitable routes include parenteral delivery, such as intramuscular, intradermal, subcutaneous, intramedullary injections, as well as, intrathecal, direct intraventricular, intravenous, intraperitoneal, intranasal, or intraocular injections, just to name a few. Other routes include oral or transdermal delivery. For injection, in some aspects, the composition of one case of the disclosure is formulated in aqueous solutions, preferably in physiologically compatible buffers such as Hanks' solution, Ringer's solution, or physiological saline buffer.

For parenteral application, which includes intramuscular, intradermal, subcutaneous, intranasal, intracapsular, intraspinal, intrasternal, and intravenous injection, in some aspects particularly suitable are injectable, sterile solutions, preferably oily or aqueous solutions, as well as suspensions, emulsions, or implants, including suppositories. In some aspects, formulations for injection may be presented in unit dosage form, e.g., in ampoules or in multi-dose containers, with an added preservative. In some aspects, the compositions take such forms as suspensions, solutions or emulsions in oily or aqueous vehicles, and contain formulator agents such as suspending, stabilizing and/or dispersing agents. Alternatively, in other aspects, the active ingredient is in powder form for constitution with a suitable vehicle, e.g., sterile pyrogen-free water, before use.

In some aspects, for enteral application, particularly suitable are tablets, dragees, liquids, drops, suppositories, or capsules. In some aspects, the pharmaceutical compositions are prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). In some aspects, the tablets are coated by methods well known in the art. In some aspects, liquid preparations for oral administration take the form of, for example, solutions, syrups or suspensions, or are presented as a dry product for constitution with water or other suitable vehicle before use. In some aspects, such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). In some aspects, the preparations also contain buffer salts, flavoring, coloring and sweetening agents as appropriate. In some aspects, a syrup, elixir, or the like is used wherein a sweetened vehicle is employed.

In some aspects, sustained or directed release compositions are formulated, e.g., liposomes or those wherein the active compound is protected with differentially degradable coatings, e.g., by microencapsulation, multiple coatings, etc. In some aspects, it is also possible to freeze dry the new compounds and use the lyophilizates obtained, for example, for the preparation of products for injection.

For administration by inhalation, the compounds for use according to one case of the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, in some aspects, the dosage unit is determined by providing a valve to deliver a metered amount. In some aspects, capsules and cartridges of e.g., gelatin for use in an inhaler or insufflator are formulated containing a powder mix of the compound and a suitable powder base such as lactose or starch. Topical or transdermal application may include non-sprayable forms, viscous to semi-solid forms, or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient; preferably in combination with a solid or liquid inert carrier material, is packaged in a squeeze bottle or in admixture with a pressurized volatile, normally gaseous propellant, e.g., a freon. In some aspects, the compositions may be presented in a pack or dispenser device which contains one or more unit dosage forms containing the active ingredient. In some aspects, the pack comprises metal or plastic foil, such as a blister pack. In some aspects, the pack or dispenser device is accompanied by instructions for administration.

In accordance with one case of the present disclosure, the compositions comprise a pharmaceutically acceptable excipient, carrier, buffer, stabilizer or other materials well known to those skilled in the art. Such materials should be non-toxic and should not interfere with the efficacy of the active ingredient. In some aspects, the precise nature of the carrier or other material depends on the route of administration, e.g., intravenous, cutaneous or subcutaneous, intramucosal (e.g., gut), intranasal, intramuscular, or intraperitoneal routes.

"Subject" refers to any member without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The disclosure is intended for use involving any of the above vertebrate species, since the immune systems of all of these vertebrates operate similarly.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

Immunogenicity of Compositions

In some aspects, the immunogenicity of the compositions described herein are evaluated in a subject. In some cases, the epitope encoded by the composition (e.g., plasmid-based vaccines) is evaluated in a recipient subject. In an aspect, the recipient subject is a rodent, a non-human primate or a human. In some cases, the rodent is a mouse.

In some aspects, the compositions and methods described herein elicit an immune response to an epitope of an antigenic peptide in a subject. In some cases, the compositions are colorectal cancer, NSCLC, or ovarian cancer vaccines. In some cases, the colorectal cancer vaccine is a multiantigen colorectal cancer vaccine. In some cases, the NSCLC vaccine is a multiantigen NSCLC vaccine. In some cases, the ovarian cancer vaccine is a multiantigen ovarian cancer vaccine.

In some aspects, the immune response is a Type I immune response, a Type II immune response or both a Type I and a Type II immune response. In some cases, a Type I immune response results in the secretion of inflammatory cytokines (e.g., IFN-γ, TNF-α) by antigen specific T cells. In some aspects, the inflammatory cytokines (e.g., Type I cytokines) activate cytotoxic T cells which kill cells which express at least one epitope encoded for (e.g., nucleic acids, plasmids) or delivered (e.g., peptide, protein) by the vaccine. In some cases, the ThI cytokines activate additional immune cells. In some cases, a Type II immune response results in the secretion of immunosuppressive cytokines (e.g., IL-10, IL-4 and IL-5) by regulatory T cells. In some aspects, the immunosuppressive cytokines (e.g., Type II cytokines) activate regulatory T cells which do not kill cells which express at least one antigenic epitope encoded for (e.g., nucleic acids, plasmids) or delivered (e.g., peptide, protein) by the vaccine but rather suppress the Th1 immune response.

In some aspects, whether a Th1 or a Th2 immune response, or both, occurs in a subject is the result of the affinity between the epitope and the MHC-T cell receptor interaction. In some cases, the affinity of the binding peptides for MHC molecules is high. In other cases, the affinity of the binding peptides for MHC molecules is low. In some cases, low affinity binding peptides induce a Th1 response. In other cases, high affinity binding peptides induce a Th2 response. In some aspects, the affinity of candidate binding peptides for MHC molecules is screened. In an aspect, IFN-γ and IL-10 secretion induced by a candidate binding peptide is determined as described herein or using techniques known to one of ordinary skill in the art.

In some aspects, the immunogenicity of the vaccine is analyzed in the subject using any of the plurality of methods known to one of ordinary skill in the art. In some cases, immunogenicity is analyzed by detecting expression of peptides in the subject encoded by the vaccine administered to the subject. In an aspect, detection methods include ELISPOT, ELISA, Western blotting, flow cytometry, histology, chromatography, mass spectrometry and the like. In some aspects, immunogenicity to isolated peptides produced in the subject in response to the vaccine is analyzed. In some cases, a sample of tumor cells, cancer cells, spleen cells or normal cells taken from the subject is analyzed.

In some cases, lymphocytes are isolated from the subject for analysis of immunogenicity. In an aspect, lymphocytes are isolated from the spleen, from the lymph nodes and/or from the draining lymph nodes. In some cases, the lymphocytes are isolated after administration of the single dose of the vaccine. In other cases, the lymphocytes are isolated after administration of the last dose of a plurality of doses of the vaccine. In an aspect, lymphocytes are isolated one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days or 30 days after administration of either the single dose of the vaccine.

In some cases, the lymphocytes are isolated after administration of the last dose of a plurality of doses of the vaccine. In an aspect, lymphocytes are isolated one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days or 30 days after administration of the last dose of a plurality of doses of the vaccine.

In some cases, a protein detection method is used to determine the amount of each peptide encoded for by the nucleic acids of the composition (e.g., the plasmid-based vaccine) produced by the subject. In an aspect, an ELISPOT is performed and the ELISPOT detects IFN-γ. In another aspect, a different ELISPOT is performed and the ELISPOT detects Granzyme B. In some cases, a protein detection method is used to determine the presence of protein specific T cells in response to the composition (e.g., plasmid-based vaccine) produced by the subject. In an aspect, an ELISPOT is performed and the ELISPOT detects IFN-γ. In another aspect, a different ELISPOT is performed and the ELISPOT detects Granzyme B.

In some aspects, immunogenicity of the peptides encoded by the vaccine is determined by comparing the results from subjects after administration of the composition (e.g., vaccine) to the results of the methods described herein from subjects after administration of a control composition (e.g., nothing encoded by the plasmids or no peptides). In some cases, the control is the adjuvant alone. In other cases, the control is a negative control (e.g., blank plasmids lacking antigenic peptide epitopes). In some aspects, immunogenicity is determined by an increase in the amount of IFN-g produced (e.g., IFN-γ positive spots on an ELISPOT) or increase in the amount of tumor specific Granzyme B produced (Granzyme B positive spots on an ELISPOT). In some aspects, the increase is observed in subjects after administration of the composition (e.g., vaccine) compared to subjects administered a control composition. In some cases, the increase is statistically different from the control as indicated by a P value (e.g., p<0.05). In some aspects, statistically different at p<0.05 is statistically significant.

In an aspect, the statistical significance of immunogenicity is determined by comparing two groups (n=10 subjects per group) for a 98% power where at least the two-sided level may be 0.05 and the true effect size may be 2.0. In some cases, the effect size is defined as the difference in mean specific T cell response level divided by the common standard deviation. In some aspects, a true effect size of about 1.5 or less would not be significant.

In some aspects, additional parameters are analyzed after administration of at least one dose of the vaccine. In some cases, blood is isolated from a subject and a plurality of tests performed on the blood known to one of ordinary skill in the art. In an aspect, a basic metabolic panel and/or a complete blood count is performed. In some cases, additional tissues are examined. In an aspect, the colon, rectum, small intestine, cecum, appendix, anal canal, peritoneum, spleen, skin, skeletal muscle, lymph node, bone, bone marrow, ovary, oviduct, uterus, peripheral nerve, brain, heart, thymus, lung, kidney, liver and/or pancreas are examined after administration of at least one dose of the vaccine.

Efficacy of the Compositions using Model Systems

In some aspects, the compositions described herein are utilized with a plurality of mouse model systems. In some cases, the mouse models include genetically diverse mouse models. In an aspect, the mice used in the mouse model systems include, APCmin mutant mice. In another aspect, the mice used in the model mouse systems include mice injected with Azoxymethane (AOM).

In some cases, the mouse model is a tumor implant model. In an aspect, a tumor implant model is used to analyze the therapeutic efficacy of the compositions described herein. In an aspect the tumor implant model is a MC-38 tumor implant model. In an aspect, the composition is a colorectal cancer vaccine. In some cases, tumor cells are implanted subcutaneously in the mouse. In an aspect, at least 1,000, 2,500, 5,000, 7,500, 10,000, 12,500, 15,000, 17,500, 20,000, 22,500, 25,000, 27,500, 30,000, 35,000, 40,000, 45,000, 50,000, 75,000, 100,000, 125,000, 150,000, 175,000, 200,000, 225,000, 250,000, 275,000, 300,000, 350,000, 400,000, 450,000, 500,000, 750,000, 1,000,000, 1,250,000, 1,500,000, 1,750,000, 2,000,000, 2,500,000, 3,000,000, 3,500,000, 4,000,000, 4,500,000, 5,000,000, 5,500,000, 6,000,000, 6,500,000, 7,000,000, 7,500,000, 8,000,000, 8,500,000, 9,000,000, 9,500,000 or at least 1,000,000,000 tumor cells are implanted subcutaneously in the mouse.

In some aspects, tumor growth is measured using methods known to one of ordinary skill in the art. In an aspect, methods of measurement include tumor diameter, tumor volume, tumor mass and the like. In some cases, imaging, extraction or histologic techniques are used. In an aspect, any of the techniques include use of a contrast agent.

In some cases, the efficacy of the vaccine is determined by the size of tumor growth relative to a control (e.g., unvaccinated mouse or a mouse treated with a control vaccine). In an aspect, in the absence of vaccination, greater than 90% of the mice develop tumors and in the presence of vaccination, a 60% inhibition of tumor growth is observed. In some cases, vaccination inhibits at least 2%, 5%, 7%, 10%, 15%, 20%, 25%, 30%, 35%, 40%, 45%, 50%, 55%, 60%, 65%, 70%, 75%, 80%, 85%, 90%, 95% or at least 99% of tumor growth.

In some aspects, after administration of the vaccine, the subject is 100% tumor free. In other cases, the subject is less than 100% tumor free after administration of the vaccine. In an aspect, the subject is less than 99%, 95%, 90%, 85%, 80%, 75%, 70%, 65%, 60%, 55%, 50%, 45%, 40%, 35%, 30%, 25%, 20%, 15% or less than 10% tumor free after administration of the vaccine. In some cases, the subject becomes tumor free hours after administration of the vaccine. In an aspect, the subject becomes tumor free one hour, two hours, three hours, four hours, five hours, six hours, seven hours, eight hours, nine hours, ten hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours or more after administration of the vaccine. In other cases, the subject becomes tumor free days after administration of the vaccine. In an aspect, the subject becomes tumor free one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days or more after administration of the vaccine. In other cases, the subject becomes tumor free weeks after administration of the vaccine. In an aspect, the subject becomes tumor free one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks or more after administration of the vaccine. In other cases, the subject becomes tumor free months after administration of the vaccine. In an aspect, the subject becomes tumor free one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months or more after administration of the vaccine. In other cases, the subject becomes tumor free years after administration of the vaccine. In an aspect, the subject becomes tumor free one year, two years, three years, four years, five years, six years, seven years, eight years, nine years, ten years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years or more after administration of the vaccine.

In some cases, the efficacy of the vaccine is determined by the amount of IFN-γ produced in a vaccinated subject (e.g., mouse) relative to a control (e.g., unvaccinated mouse). In some cases, the efficacy of the vaccine is determined by the amount of IL-10 produced in a vaccinated subject (e.g., mouse) relative to a control (e.g., unvaccinated mouse).

In some aspects, polyclonality of the epitope-specific immune response is evaluated. In some cases, an evaluation of polyclonality is performed by assessing the production of IgG antibodies in response to epitopes of the administered vaccine. In some cases, IgGs are elicited to one antigen. In other cases, IgGs are elicited to multiple antigens. In some cases, a lysate is prepared from a sample taken from a subject and evaluated from the pre-immunization and post-immunization serum of the subject. In an aspect, a subject is a mouse of the APCmin mouse model and IgGs detected using a method of peptide detection, such as ELISA or ELISPOT.

In some cases, the response to each antigen between pre-vaccination subjects (e.g., mice) and post-vaccination subjects (e.g., mice) is analyzed using statistical methods. In an aspect, statistical methods include analysis using single factor ANOVA. In some cases, an analysis of the number of antigens to which subjects (e.g., mice) developed immunity during the course of vaccination is performed.

Toxicity and Safety Profile of Compositions

In some aspects, the compositions described herein are assessed for toxicity and safety. Methods to assess toxicity and safety known to one of ordinary skill in the art may be used with the compositions as described herein. In some cases, a dose escalation study is performed. In some cases, toxicity and safety studies screen for the development of diseases in the subject, damage to organs in the subject, damage to tissues in the subject, damage to cells in the subject, blood disorders and the like. In an aspect, diseases include autoimmune diseases.

Manufacture and Quality Control of Compositions

In some aspects, manufacture and testing of the compositions described herein (e.g., plasmid-based vaccines) are performed in compliance with current standards of cGMP Biologics Production Facilities (BPF). In some aspects, process development includes the transfer of the candidate cells (e.g., cell line(s)) each containing the appropriate plasmid constructs with the kanamycin selection marker to the cGMP BPF. In some cases, a research bank is generated from the bacterial stock. In an aspect, a scaled pilot production that may match a later cGMP manufacture is utilized to assess plasmid yield and purity. In some cases, the preliminary manufacturing batch records and quality control testing schedules are established. In an aspect, the master cell bank(s) are generated from each bacterial stock. In some cases, quality control testing is performed inclusive of; plasmid and host cell identity, plasmid copy number, purity, viability, and retention of antibiotic resistance (plasmid retention).

In some cases, finalized and approved manufacturing batch records and standard operating procedures are followed for cGMP production and purification of the vaccine plasmid(s) and lot release criteria may be developed. In some cases, the final bulk/pooled purified product is quality control tested in accordance with current regulatory guidelines and then may be vialed as single dose units following validated fill and finish standard operating procedures. In some aspects, in compliance with cGMP regulations, the vialed product undergoes quality control testing prior to final product release.

Immunogenicity

In some aspects, the vaccine elicits an immunogenic response in the subject. In some cases, the type of immune response elicited after immunization is determined. In an aspect, the compositions described herein elicit a Th1 immune response when administered to a subject. In some cases, the Th1 immune response includes formation of and persistence of antigen specific T cells that recognize at least one peptide of the vaccine. In an aspect, a peptide is a stem cell and/or an EMT antigen.

In some aspects, the type of immune response is determined through an assessment of the types of cytokine secreted by antigen specific T cells. In some cases, the types of cytokines are identified using an ELISPOT assay. In an aspect, an ELISPOT method includes analysis of sample supernatants after antigen stimulation (e.g., 72 hours). In some cases, the sample supernatants are evaluated for a panel of cytokines. In some cases, the evaluation is a multiplex analysis. In an aspect, the multiplex analysis of cytokines includes the cytokines for Th1 (e.g., IFN-g, IL-2, TNF-α, IL-1b, GM-CSF), Th17 (IL-17), and Th2 (e.g., IL-6, IL-4, IL-10, IL-13). In some cases, the presence of TGF-β in sample supernatants is analyzed. In an aspect, TGF-β is analyzed using an ELISA method. In some cases, the magnitude of or pattern of secretion serves as a biomarker of clinical outcome after vaccination.

In some aspects, heat maps are generated from multiplexed cytokine data. In some cases, the heat maps are color coded as to the magnitude of antigen specific cytokine increase (e.g., red) or decrease (e.g., blue) with vaccination. In an aspect, the intensity of the colors symbolizes the lowest (e.g., pale) to highest (e.g., vivid) quartile of response. In some cases, the heat maps depict specific patterns of the type of and magnitude of the immune response to the at least one immunizing antigen. In an aspect, the heat maps depict the magnitude of cytokine secretion.

In some cases, a subject is classified as immunized by development of protein specific precursor frequencies that are more robust than 1:20,000 PBMC to the majority of the immunizing antigens. In some cases, if subjects have pre-existent immunity to any of the antigens, then the responses augment more than twice the baseline response.

In some cases, the analysis of immunogenicity determines the magnitude of the Th1 antigen specific immune response. In an aspect, the Th1 response is determined by performing an IFN-g ELISPOT, which is linear and precise between 2.0 and $3.5 \times 10^5$ PBMC/well, has a detection limit of 1:60,000, and has a detection efficiency of 93%. In some cases, pre-vaccine and post-vaccine samples are analyzed simultaneously to correct for variability. In an aspect, a cryopreservation method that preserves antigen specific T cell responses in frozen cells when compared to freshly isolated PBMC is used. In some cases, the samples include 1 ug/ml protein antigens (e.g., recombinant proteins are available on all of the proposed candidate antigens, human myoglobin (negative control)) or 1 ug/ml CMV lysate and 0.5 U/ml tt (positive controls) and peptide antigens encompassed within the vaccine at 10 ug/ml).

In some aspects, the colorectal cancer vaccine exhibits immunologic success that is analyzed using statistical methods. Often immunologic success of the vaccine is the occurrence of an immune response (e.g., Th1) to greater than 50% of the antigens expressed by the plasmids within the vaccine. In some cases, the vaccine is administered to a group of 22 subjects such that the probability of an observed success rate in excess of 50% may be less than 0.1 if the true success rate is 40%. In an aspect, the observed success rate is 0.06. In some cases, the vaccine is administered to a group of 22 subjects such that the probability of an observed success rate in excess of 50% is greater than 0.7 if the true success rate is 70%.

In an aspect, use of a group of 22 patients demonstrates, with at least 80% confidence, that an estimated immunologic response rate may be within at least 0.14 of the true response rate. In some cases, if half of the subjects elicit an immunogenic response, then the power is at least 91% for statistical significance (at the two-sided level of 0.05) and the difference in continuous measures if the true effect size is 1.5. In an aspect, Spearman's correlation coefficient is used to estimate the correlation between two continuous measures. In some cases, the data estimates an expected response rate in a larger population.

In another aspect, 25% of subjects elicit an immunogenic response to the vaccine. In some cases, 25% of subjects with an immunogenic response are the baseline to evaluate the effectiveness of a vaccine. In some cases, the true response rate is 60%, where use of a group of 22 subjects provides a power of 97% for a statistically significant response rate compared to the fixed rate of 25% (one-sided level of significance of 0.05).

Applications

In some aspects, the compositions described herein are administered to a subject in need of a vaccine for preventing cancer, such as colorectal cancer, non-small cell lung cancer, or ovarian cancer. In some aspects, the methods described herein are combined with the compositions described herein for administration to a subject in need of a vaccine for preventing cancer. In some cases, administration of the vaccine initiates the elimination of cells as the cells begin to express increased levels proteins that are components of the vaccine. In some cases, the proteins are stem cell/EMT associated. In an aspect, increased levels of proteins are expressed during the malignant transformation of normal cells into cancer cells, such as for example colorectal cancer cells, NSCLC cells, or ovarian cancer cells. In some cases, elimination of the colorectal cancer cells, NSCLC cells, or ovarian cancer cells before the disease becomes clinically evident prevents the occurrence of colorectal cancer, NSCLC, or ovarian cancer in a subject.

In some aspects, the vaccine for preventing colorectal cancer, NSCLC, or ovarian cancer is administered in a single dose administered to the subject, the dose of at least 10 ug, 15 ug, 20 ug, 25 ug, 30 ug, 35 ug, 40 ug, 45 ug, 50 ug, 55 ug, 60 ug, 65 ug, 70 ug, 75 ug, 80 ug, 85 ug, 86 ug, 87 ug, 88 ug, 89 ug, 90 ug, 91 ug, 92 ug, 93 ug, 4 ug, 95 ug, 96 ug, 97 ug, 98 ug, 99 ug, 100 ug, 101 ug, 102 ug, 103 ug, 104 ug, 105 ug, 106 ug, 107 ug, 108 ug, 109 ug, 110 ug, 111 ug, 112 ug, 113 ug, 114 ug, 115 ug, 116 ug, 117 ug, 118 ug, 119 ug, 120 ug, 125 ug, 130 ug, 135 ug, 140 ug, 145 ug, 150 ug, 155 ug, 160 ug, 165 ug, 170 ug, 175 ug, 180 ug, 185 ug, 190 ug, 195 ug, or at least 200 ug/plasmid. In an aspect, the single dose administered to the subject is 100 ug/plasmid.

In some aspects, the vaccine for preventing colorectal cancer, NSCLC, or ovarian cancer is administered in more than one dose administered to the subject, each dose of at least 10 ug, 15 ug, 20 ug, 25 ug, 30 ug, 35 ug, 40 ug, 45 ug, 50 ug, 55 ug, 60 ug, 65 ug, 70 ug, 75 ug, 80 ug, 85 ug, 86 ug, 87 ug, 88 ug, 89 ug, 90 ug, 91 ug, 92 ug, 93 ug, 4 ug, 95 ug, 96 ug, 97 ug, 98 ug, 99 ug, 100 ug, 101 ug, 102 ug, 103 ug, 104 ug, 105 ug, 106 ug, 107 ug, 108 ug, 109 ug, 110 ug, 111 ug, 112 ug, 113 ug, 114 ug, 115 ug, 116 ug, 117 ug, 118 ug, 119 ug, 120 ug, 125 ug, 130 ug, 135 ug, 140 ug, 145 ug, 150 ug, 155 ug, 160 ug, 165 ug, 170 ug, 175 ug, 180 ug, 185 ug, 190 ug, 195 ug, or at least 200 ug/plasmid. In some cases, each dose administered to the subject is greater than or less than the previous dose administered to the subject.

In some aspects, the compositions described herein are administered to a subject in need of a vaccine for treating cancer, such as colorectal cancer, NSCLC, or ovarian cancer. In some aspects, the methods described herein are combined with the compositions described herein for administration to a subject in need of a vaccine for treating cancer. In some cases, administration of the vaccine initiates the elimination of cells that express increased levels proteins that are components of the vaccine. In some cases, the proteins are stem cell/EMT associated. In an aspect, increased levels of proteins are expressed by cancer cells, such as for example colorectal cancer cells, NSCLC cells, or ovarian cancer cells. In some cases, elimination of the colorectal cancer cells, NSCLC cells, or ovarian cancer cells after the disease becomes clinically evident prevents the persistence and propagation of colorectal cancer, NSCLC, or ovarian cancer in a subject.

In some aspects, the vaccine for treating colorectal cancer, NSCLC, or ovarian cancer is administered in a single dose administered to the subject, the dose of at least 10 ug, 15 ug, 20 ug, 25 ug, 30 ug, 35 ug, 40 ug, 45 ug, 50 ug, 55 ug, 60 ug, 65 ug, 70 ug, 75 ug, 80 ug, 85 ug, 86 ug, 87 ug, 88 ug, 89 ug, 90 ug, 91 ug, 92 ug, 93 ug, 4 ug, 95 ug, 96 ug, 97 ug, 98 ug, 99 ug, 100 ug, 101 ug, 102 ug, 103 ug, 104 ug, 105 ug, 106 ug, 107 ug, 108 ug, 109 ug, 110 ug, 111 ug, 112 ug, 113 ug, 114 ug, 115 ug, 116 ug, 117 ug, 118 ug, 119 ug, 120 ug, 125 ug, 130 ug, 135 ug, 140 ug, 145 ug, 150 ug, 155 ug, 160 ug, 165 ug, 170 ug, 175 ug, 180 ug, 185 ug, 190 ug, 195 ug, or at least 200 ug/plasmid. In an aspect, the single dose administered to the subject is 100 ug/plasmid.

In some aspects, the vaccine for treating colorectal cancer, NSCLC, or ovarian cancer is administered in more than one dose administered to the subject, each dose of at least 10 ug, 15 ug, 20 ug, 25 ug, 30 ug, 35 ug, 40 ug, 45 ug, 50 ug, 55 ug, 60 ug, 65 ug, 70 ug, 75 ug, 80 ug, 85 ug, 86 ug, 87 ug, 88 ug, 89 ug, 90 ug, 91 ug, 92 ug, 93 ug, 4 ug, 95 ug, 96 ug, 97 ug, 98 ug, 99 ug, 100 ug, 101 ug, 102 ug, 103 ug, 104 ug, 105 ug, 106 ug, 107 ug, 108 ug, 109 ug, 110 ug, Mug, 112 ug, 113 ug, 114 ug, 115 ug, 116 ug, 117 ug, 118 ug, 119 ug, 120 ug, 125 ug, 130 ug, 135 ug, 140 ug, 145 ug, 150 ug, 155 ug, 160 ug, 165 ug, 170 ug, 175 ug. 180 ug, 185 ug, 190 ug, 195 ug, or at least 200 ug/plasmid. In some cases, each dose administered to the subject is greater than or less than the previous dose administered to the subject.

Subjects

In some aspects, the compositions described herein are administered to a subject in need of a vaccine for cancer, such as for example colorectal cancer, NSCLC, or ovarian cancer. In some aspects, the methods described herein are combined with the compositions described herein for administration to a subject in need of a vaccine for cancer. In some cases, the vaccine is administered to a subject who does not have cancer. In other cases, the vaccine is administered to a subject who has had cancer, such as for example colorectal cancer, NSCLC, or ovarian cancer. In yet other cases, the vaccine is administered to a subject who has cancer, such as for example colorectal cancer, NSCLC, or ovarian cancer.

In some cases, the subject is a healthy individual. In some cases, the subject is an individual with cancer, such as for example colorectal cancer, NSCLC, or ovarian cancer. In an aspect, the individual is a patient. In some cases, the subject is a human individual. In other cases, the subject is a non-human individual. In an aspect, non-human individuals include a non-human primate, monkey, macaque, baboon, chimpanzee, orangutan, mouse, rat, guinea pig, rabbit, horse, cow, pig, dog, cat or any individual that may develop or has colorectal cancer, NSCLC, or ovarian cancer.

Types of Colorectal Cancer

In some aspects, the compositions described herein are administered to a subject in need of a vaccine for colorectal cancer. In some aspects, the methods described herein are combined with the compositions described herein for administration to a subject in need of a vaccine for colorectal cancer. Often, the colorectal cancer is any type of colorectal cancer, for example, the colorectal cancer is adenocarcinoma, mucinous adenocarcinoma, signet ring cell adenocarcinoma, gastrointestinal carcinoid tumors, primary colorectal lymphomas, gastrointestinal stromal tumors, leiomyosarcomas, melanomas, or squamous cell carcinomas. Sometimes, the colorectal cancer is a relapsed, refractory, or metastasized colorectal cancer. The compositions described herein can be administered for the treatment of a relapsed, refractory, or metastasized colorectal cancer.

In some cases, the subject is classified with a particular grade of colorectal cancer. In an aspect, the grades of colorectal cancer are Grade X, Grade 1, Grade 2, Grade 3 or Grade 4. In another aspect, colorectal cancers are indicated by a category of tubule formation, nuclear grade and/or the mitotic rate. In yet another aspect, each category is assigned a specific score between one and three. In some cases, the subject has a particular stage of colorectal cancer. In some cases, the stages are assigned based on the tumor, the regional lymph nodes and/or distant metastasis. In an aspect, the stages assigned to the tumor are TX, T0, T is, T1, T2, T3 or T4. In an aspect, the stages assigned to the regional lymph nodes are NX, N0, N1, N2 or N3. In an aspect, the stages assigned to the distant metastasis are MX, M0 or M1. In some cases, the stages are stage 0, stage I, stage II, stage III or stage IV. Often the colorectal cancer is classified as more than one grade, or stage of cancer.

Non-Small Cell Lung Cancer

In some aspects, the compositions described herein are administered to a subject in need of a vaccine for non-small cell lung cancer (NSCLC). In some aspects, the methods described herein are combined with the compositions described herein for administration to a subject in need of a vaccine for NSCLC cancer. Sometimes, the NSCLC cancer is a relapsed, refractory, or metastasized NSCLC cancer. The compositions described herein can be administered for the treatment of a relapsed, refractory, or metastasized NSCLC cancer.

Non-small cell lung cancer (NSCLC) can be the most common type of lung cancer. NSCLC can be a slower growing cancer relative to other types of lung cancer such as SCLC. There can be about four subtypes of NSCLC, comprising adenocarcinoma, squamous cell carcinoma, large cell carcinoma, and large cell neuroendocrine tumors. Adenocarcinoma has glad-like properties and can begin in the cells that form the lining of the lungs. Adenocarcinoma can further be subdivided into adenocarcinoma in situ (AIS) which can begin in the alveoli and minimally invasive adenocarcinoma (MIA) which can encompass smaller adenocarcinoma lung tumors. Squamous cell carcinoma can originate in the thin, flat cells that line the passage of the respiratory tract. Large cell carcinoma comprises a fast growing form of NSCLC. Large cell neurodendocrine tumors comprise the fastest growing form of NSCLC relative to large cell carcinoma.

In some cases, the subject is classified with a particular grade or staging of NSCLC cancer. In an aspect, the grades or stagings of NSCLC comprise stages I, II, III, and IV. Stage I encompasses when the cancer is located only in the lungs and has not spread to any lympho nodes. Stage II encompasses when the cancer is in the lung and nearby lymph nodes. Stage III encompasses when cancer is located in the lung and in the lymph nodes in the middle of the chest. Further Stage III can be subdivided into Stage IIIA and Stage IIIB. Stage IIIA indicates when the cancer has spread to the lymph nodes on the same side of the chest as the cancer origin. Stage IIIB indicates when the cancer has spread to the lymph nodes on the opposite side of the chest as the cancer origin. Stage IV encompasses when the cancer has spread to both lungs, to fluid in the area around the lungs, or to another part of the body.

Ovarian Cancer

In some aspects, the compositions described herein are administered to a subject in need of a vaccine for ovarian cancer. In some aspects, the methods described herein are combined with the compositions described herein for administration to a subject in need of a vaccine for ovarian cancer. Sometimes, the ovarian cancer is a relapsed, refractory, or metastasized ovarian cancer. The compositions described herein can be administered for the treatment of a relapsed, refractory, or metastasized ovarian cancer. Sometimes, the composition comprises EGFR epitopes. The EGFR epitope comprises an epitope with an amino acid sequence of at least 90% sequence identity to the amino acid sequence of SEQ ID NOs: 11-13. Sometimes, the composition comprises EGFR epitopes and one or more additional epitopes selected from CDC25B, COX2, FASCIN1, IGF1R, PRL3, RCAS1, or VCP.

Additional Therapeutic Agents

In some instances, the cancer vaccine (e.g., colorectal cancer, non-small cell lung cancer, or ovarian cancer vaccine) described herein is administered to a patient in combination with an additional therapeutic agent. In some instances, the additional therapeutic agent is a chemotherapeutic agent, a steroid, an immunotherapeutic agent, a targeted therapy, or a combination thereof.

In some embodiments, the additional therapeutic agent is selected from: Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In some embodiments, the additional therapeutic agent is selected from: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the additional therapeutic agent is selected from: agents which act by arresting cells in the G2-M phases due to stabilized microtubules, e.g., Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In some embodiments, the additional therapeutic agent is selected from: agents that affect the tumor micro-environment such as cellular signaling network (e.g. phosphatidylinositol 3-kinase (PI3K) signaling pathway, signaling from the B-cell receptor and the IgE receptor). Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TKI258, TLN-232, TTP607, XL147, XL228, XL281RO5126766, XL418, XL765.

In some embodiments, the additional therapeutic agent is selected from: inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In some embodiments, the additional therapeutic agent is selected from: interferons, interleukins, Tumor Necrosis Factors, Growth Factors, or the like.

In some embodiments, the additional therapeutic agent is selected from: ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

In some embodiments, the additional therapeutic agent is selected from: Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

In some embodiments, the additional therapeutic agent is selected from: Monoclonal Antibodies such as for example alemtuzumab, bevacizumab, catumaxomab, cetuximab, edrecolomab, gemtuzumab, panitumumab, rituximab, trastuzumab; Immunosuppressants, eculizumab, efalizumab, muromab-CD3, natalizumab; TNF alpha Inhibitors such as for example adalimumab, afelimomab, certolizumab pegol, golimumab, infliximab; Interleukin Inhibitors, basiliximab, canakinumab, daclizumab, mepolizumab, tocilizumab, ustekinumab; Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

In some embodiments, the additional therapeutic agent is selected from: Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

In some embodiments, the additional therapeutic agent is selected from a checkpoint inhibitor. Exemplary checkpoint inhibitors include:

PD-L1 inhibitors such as Genentech's MPDL3280A (RG7446), Anti-mouse PD-L1 antibody Clone 10F.9G2 (Cat # BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, and AstraZeneca's MEDI4736;

PD-L2 inhibitors such as GlaxoSmithKline's AMP-224 (Amplimmune), and rHIgM12B7;

PD-1 inhibitors such as anti-mouse PD-1 antibody Clone J43 (Cat # BE0033-2) from BioXcell, anti-mouse PD-1 antibody Clone RMP1-14 (Cat # BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG4 monoclonal antibody nivolumab (Opdivo®, BMS-936558, MDX1106), AstraZeneca's AMP-514 and AMP-224, and Pidilizumab (CT-011) from Cure-Tech Ltd;

CTLA-4 inhibitors such as Bristol Meyers Squibb's anti-CTLA-4 antibody ipilimumab (also known as Yervoy®, MDX-010, BMS-734016 and MDX-101), anti-CTLA4 Antibody, clone 9H10 from Millipore, Pfizer's tremelimumab (CP-675,206, ticilimumab), and anti-CTLA4 antibody clone BNI3 from Abcam;

LAGS inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12;

B7-H3 inhibitors such as MGA271;

KIR inhibitors such as Lirilumab (IPH2101);

CD137 (41BB) inhibitors such as urelumab (BMS-663513, Bristol-Myers Squibb), PF-05082566 (anti-4-1BB, PF-2566, Pfizer), or XmAb-5592 (Xencor);

PS inhibitors such as Bavituximab;

and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40 (CD134), GITR, ICOS, BTLA (CD272), CD160, 2B4, LAIR1, TIGHT, LIGHT, DR3, CD226, CD2, or SLAM.

In some embodiments, the additional therapeutic agent is a CD40 agonist. The CD40 agonist can be an antibody or fragments thereof or small molecule. Exemplary CD40 agonist include: dacetuzmumab (SGN-40 or huS2C6 from Seattle Genetics), SEA-CD40 (Seattle Genetics), CP-870, 893 (Pfizer), Chi Lob 7/4 (University of Southampton), or ADC-1013. Additional CD40 agonist can include those such as FGK-45 described in Medina-Echeverz et al., "Agonistic CD40 antibody induces immune-mediated liver damage and modulates tumor-induced myeloid suppressive cells" *J. for ImmunoTherapy of Cancer* 2(3):P174 (2014).

Samples

A sample for analysis of the immunogenicity, safety and/or toxicity may be isolated from an individual. In some cases, the sample may be selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and genitourinary tracts. In some cases, the sample may be tissue, often a biopsy sample. For example, the biopsy may contain skin tissue, colon tissue, rectal tissue, glandular tissue, skeletal muscle tissue and/or adipose tissue.

Kits

Kits and articles of manufacture are also provided herein for use with one or more methods described herein. The kits can contain one or more of the polypeptides and/or one or more of the nucleic acid molecules described herein, such as the polypeptides and nucleic acid molecules identified as SEQ ID NOs: 1-45, or polypeptides and/or nucleic acid molecules having a sequence at least 40%, 50%, 60%, 70%, 80%, 90%, 95%, or more sequence homology with a polypeptide or nucleic acid molecule selected from the group consisting of SEQ ID NOs: 1-45. The kits can also contain nucleic acids that encode one or more of the polypeptides described herein. The kits can further contain adjuvants, reagents, and buffers necessary for the makeup and delivery of the vaccines.

The kits can also include a carrier, package, or container that is compartmentalized to receive one or more containers such as vials, tubes, and the like, each of the container(s)

comprising one of the separate elements, such as the polypeptides and adjuvants, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Identification of Colorectal Cancer Antigens and Determination of MHC Class II Binding Epitopes with High Homology Between Human and Mouse A literature search in PubMed was performed using terms "protein expression" and "poor prognosis" and "colorectal cancer." The search produced 125 papers, from which 8 proteins were selected for further evaluation using the following criteria: (1) incidence of expression; (2) independent predictor of poor prognosis, (3) independent predictor of early disease recurrence, and (4) known biologic function in colon cancer pathogenesis. Table 1 shows the eight proteins: CDC25B, COX2, EGFR, FASCIN1, IGF1R, PRL3, RCAS1, and VCP.

TABLE 1

| | CRC Antigens. | |
|---|---|---|
| Protein | Incidence of over-expression (n) | % Murine Whole Protein Homology |
| CDC25B | 45% (181) | 82% |
| COX2 | 81% (284) | 93% |
| EGFR | 54% (99) | 95% |
| FASCIN1 | 71% (221) | 99% |
| IGF1R | 51% (144) | 98% |
| PRL3 | 56% (46) | 77% |
| RCAS1 | 45% (106) | 99% |
| VCP | 68% (88) | 100% |

Human Subjects.

Figure 2:
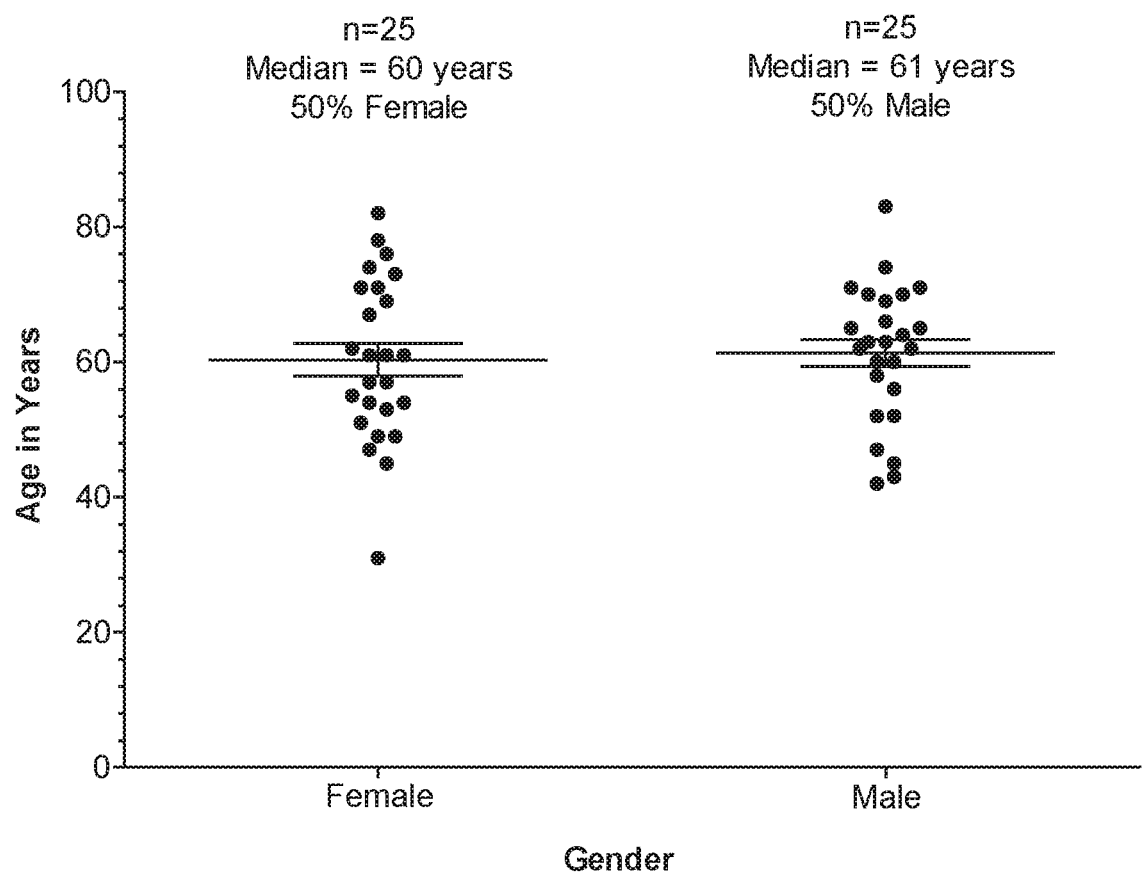
FIG. 2 shows colorectal cancer patient stage distribution.
Figure 3:
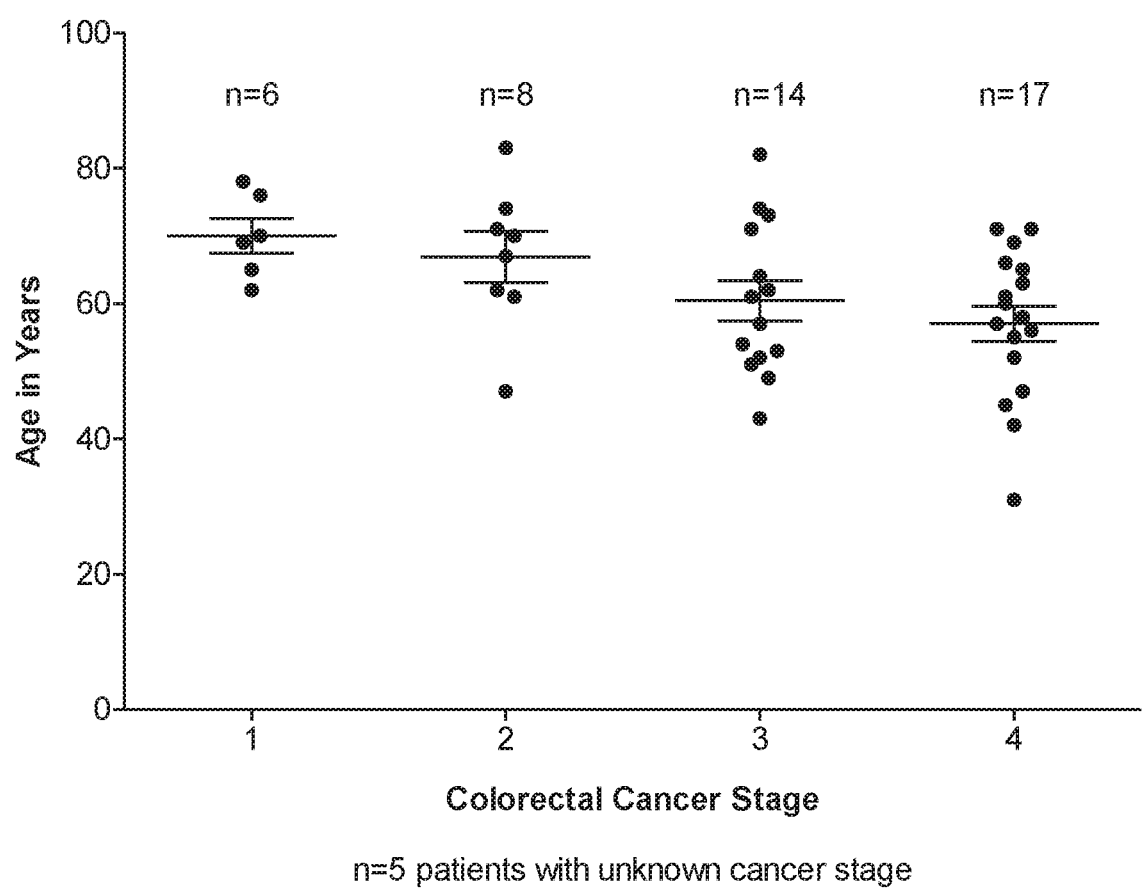
FIG. 3 shows normal donor age and gender statistics.

FIG. 1 shows fifty colorectal cancer patients were evaluated for antibody responses against each candidate protein. The colorectal cancer patients ranged in age from 31-83 (median age 61.5), and 50% were female. FIG. 2 shows stage 1 (12%), stage 2 (16%), stage 3 (28%), and stage 4 (34%) colorectal cancer patient sera were included. All sera were aliquoted and stored at −80 degrees Celsius. FIG. 3 shows fifty normal donors ranged in age from 23-84 (median age 51.5), and 32% were female. All sera were aliquoted and stored at −80 degrees Celsius. Peripheral blood mononuclear cells (PBMC) from 10 volunteer controls and 10 colorectal cancer patients were collected and cryopreserved.

Indirect ELISA Assays Using Recombinant Proteins.

Proteins were synthesized for all proposed candidate antigens. The IgG antibody response to candidate antigens were assessed by indirect ELISA as previously described in Park (2008), with the adjustment that Immulux HB flat bottom microplates were coated overnight with 100 ng/ml human full length recombinant protein in carbonate buffer. Developed plates were read at 450 nm. The results were calculated as the OD of the protein-coated wells subtracted from the OD of the buffer-coated wells as previously described in Cecil (2013).

Evaluation of Indirect ELISA Assays and Validation by Western Blot.

Figure 4:
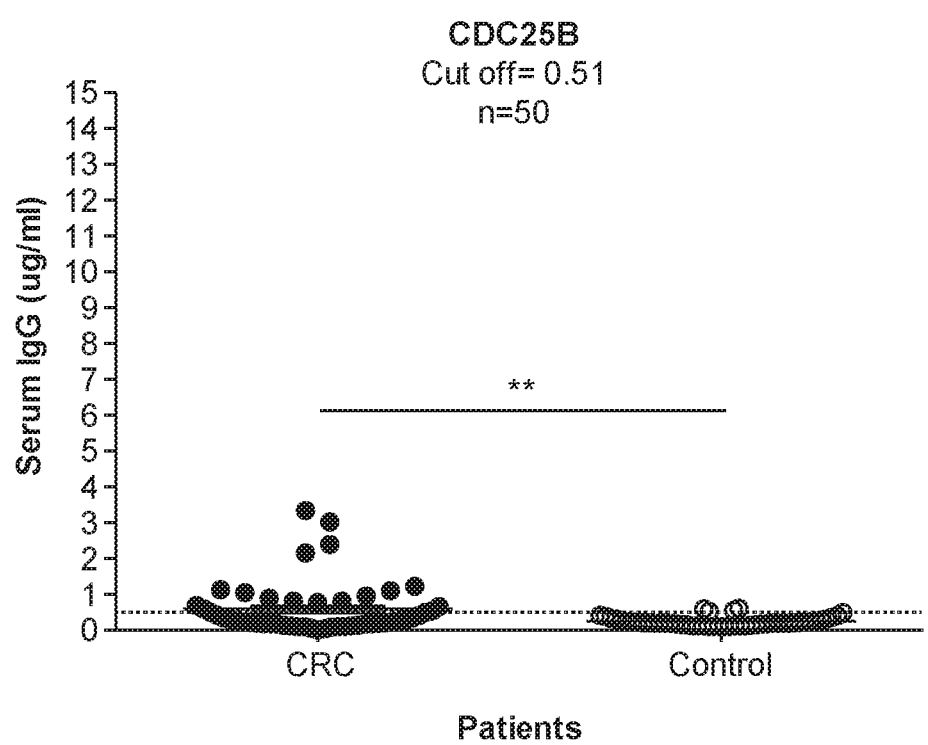
FIG. 4 depicts indirect human ELISA results for CDC25B.
Figure 5:
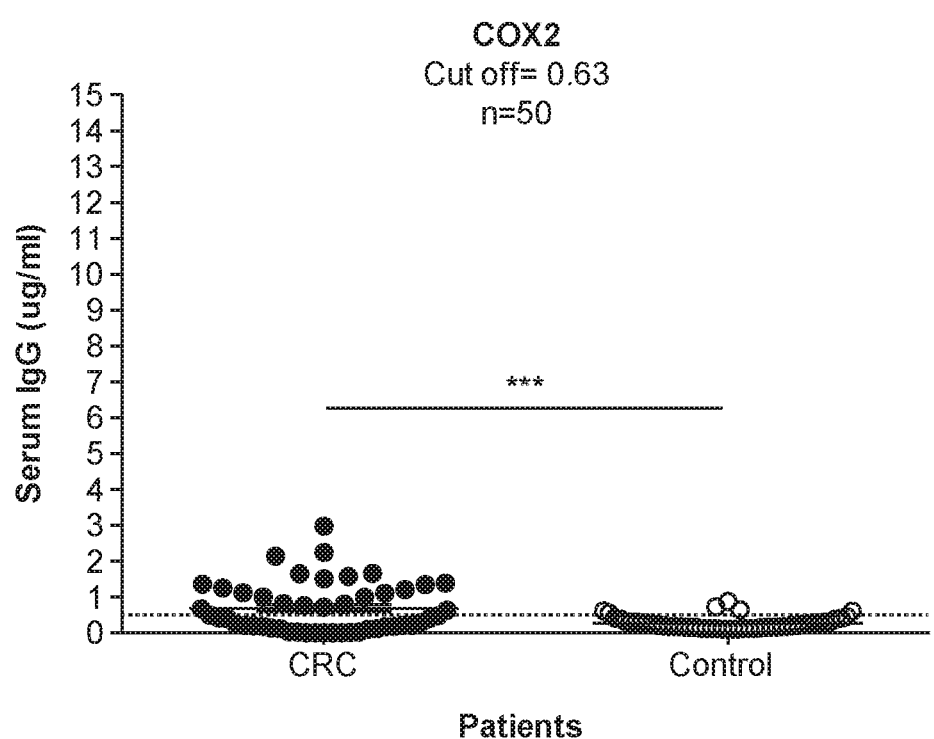
FIG. 5 depicts indirect human ELISA results for COX2.
Figure 6:
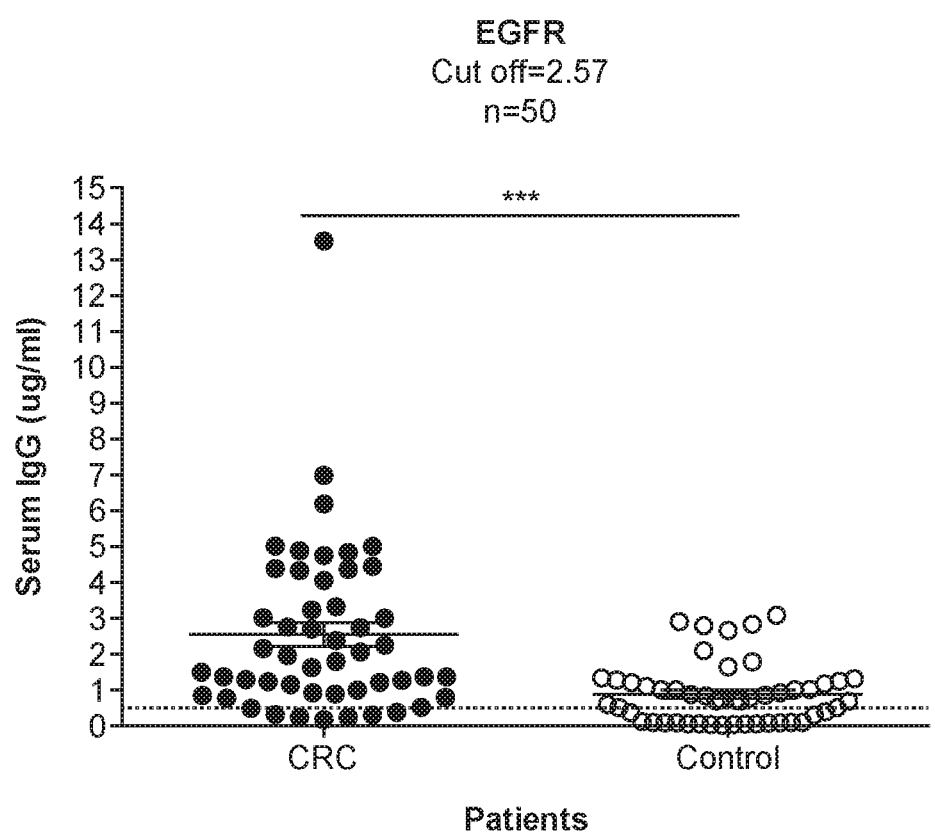
FIG. 6 depicts indirect human ELISA results for EGFR.
Figure 7:
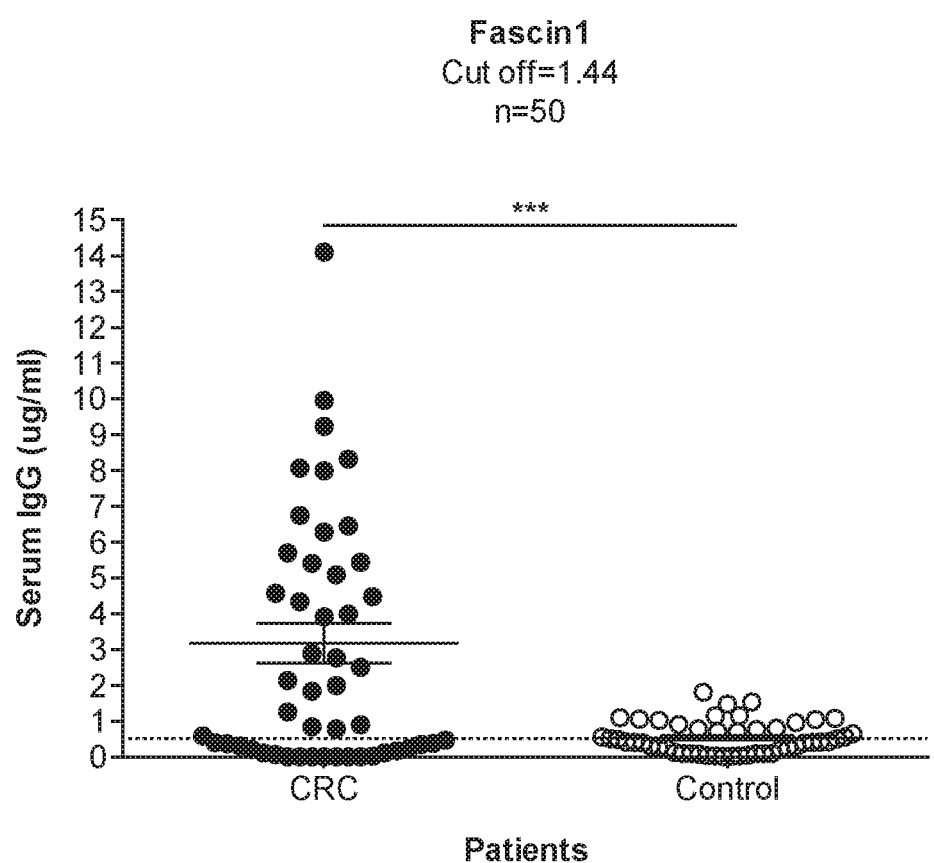
FIG. 7 depicts indirect human ELISA results for FASCIN1.
Figure 8:
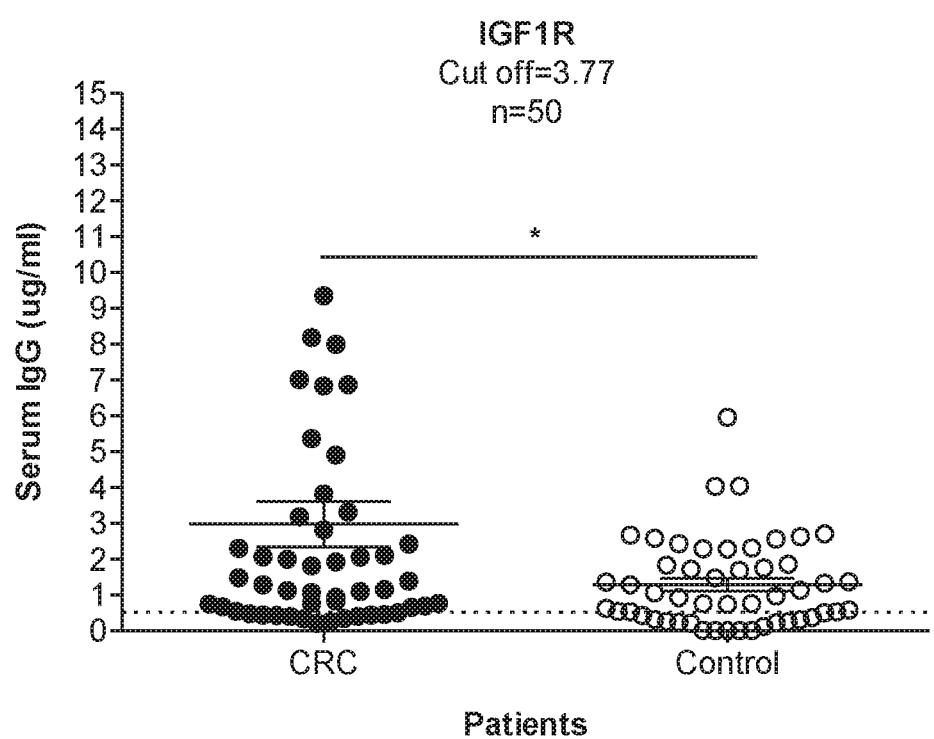
FIG. 8 depicts indirect human ELISA results for IGF1R.
Figure 9:
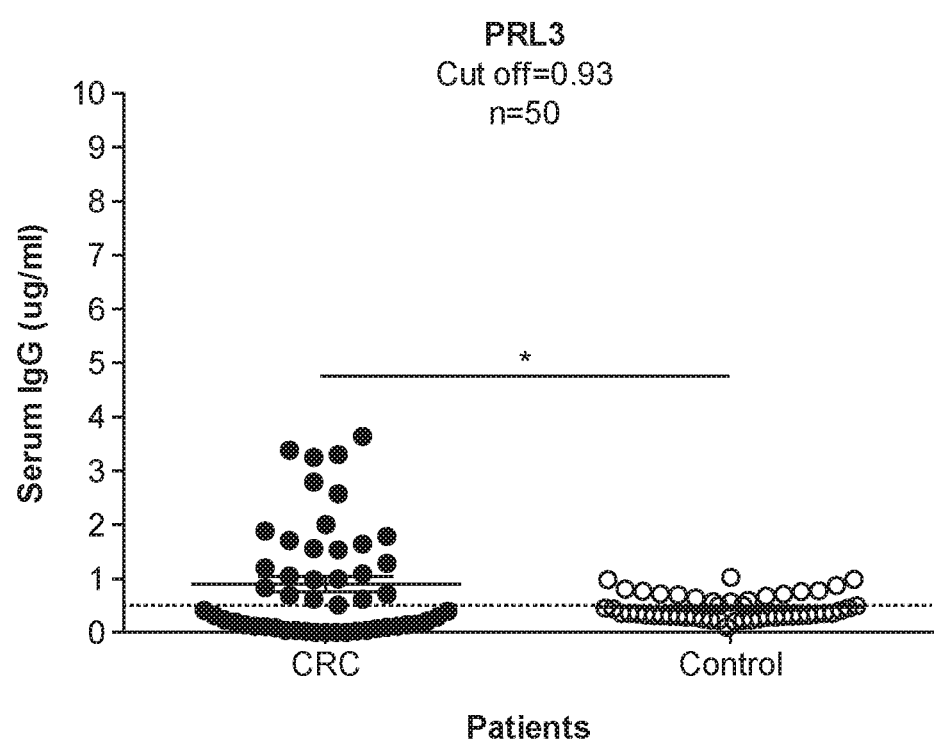
FIG. 9 depicts indirect human ELISA results for PRL3.
Figure 10:
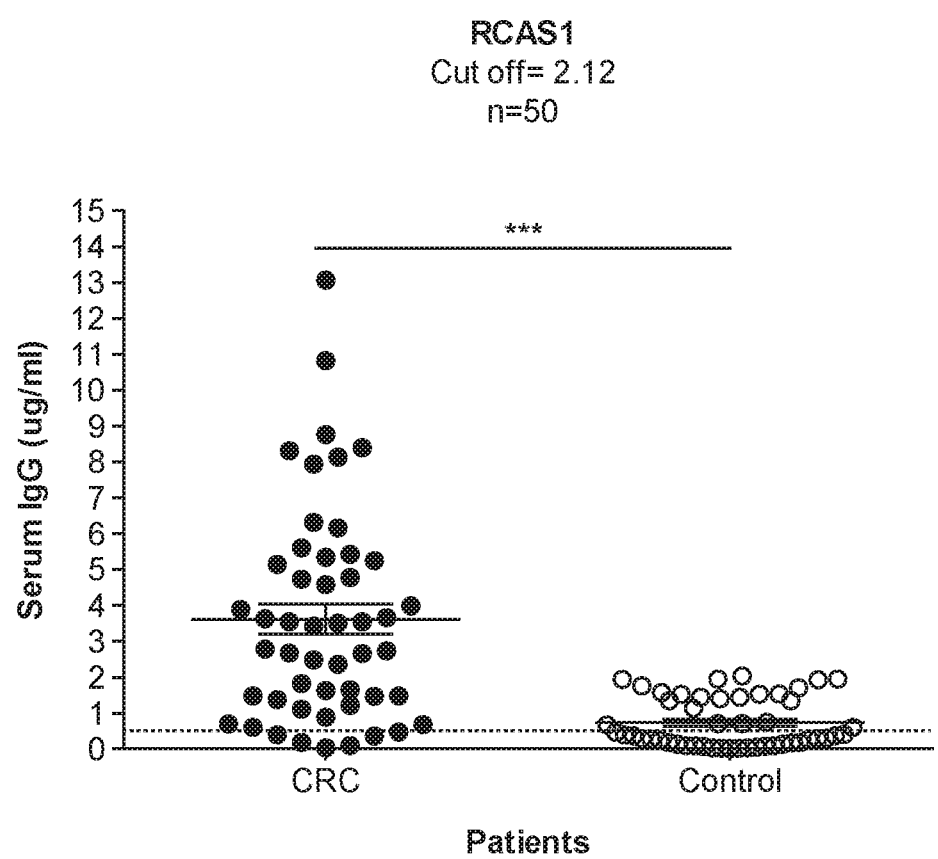
FIG. 10 depicts indirect human ELISA results for RCAS1.
Figure 11:
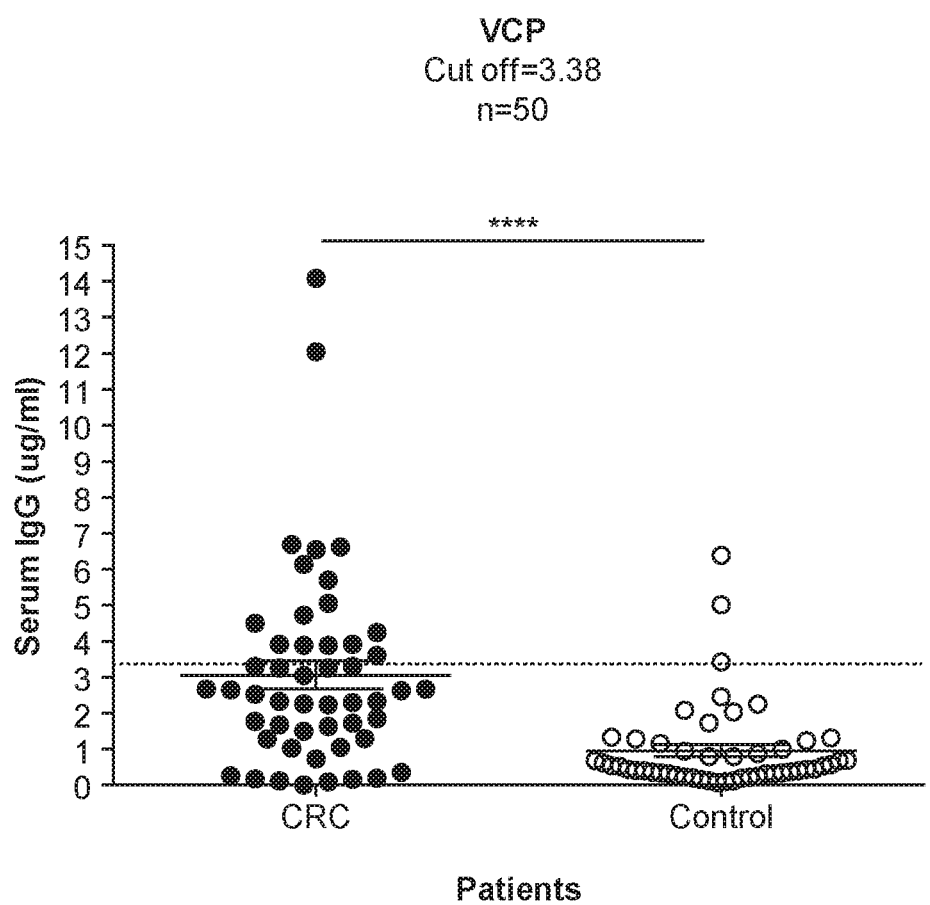
FIG. 11 depicts indirect human ELISA results for VCP.

All proteins tested were immunogenic, i.e., there was at least one individual analyzed who demonstrated detectable IgG antibody immunity directed against the specific antigen that could be documented by Indirect ELISA with appropriate specificity controls. Antibody responses could be identified in both volunteer controls as well as cancer patients. To describe the incidence of immunity to a particular antigen, the mean ug/ml and two standard deviations of the control population was used to determine a cutoff value above which a response was considered positive with 95% confidence. The human serum IgG responses were assessed using the unpaired two-tailed student's t test and significance was set at p<0.05 using GraphPad Prism version 5.0. FIG. 4 shows the cutoff value for CDC25B was determined at 0.51 ug/ml. FIG. 5 shows the cutoff value for COX2 was determined at 0.63 ug/ml. FIG. 6 shows the cutoff value for EGFR was determined at 2.57 ug/ml. FIG. 7 shows the cutoff value for FASCINI was determined at 1.44 ug/ml. FIG. 8 shows the cutoff value for IGF1R was determined at 3.77 ug/ml. FIG. 9 shows the cutoff value for PRL3 was determined at 0.93 ug/ml. FIG. 10 shows the cutoff value for RCAS1 was determined at 2.12 ug/ml. FIG. 11 shows the cutoff value for VCP was determined at 3.38 ug/ml. FIGS. 4-11 show the protein specific serum IgG (ug/ml) on the y-axis and the experimental groups on the x-axis. The mean and two standard deviations of normal controls is represented by the dotted line and shows the cutoff with p<0.05 between cancer and normal control groups. Antibodies to all tested antigens were significantly elevated in colorectal cancer patients compared to volunteer normal donor controls.

Positive and negative samples for CDC25B, COX2, FASCIN1, and RCAS1 were validated by Western blotting as previously described in Park (2008). 300 ng of recombinant CDC25B, COX2, FASCIN1, and RCAS1 were separated on Mini-PROTEAN TGX gels probed with anti-CDC25B, anti-COX2, anti-FASCIN1, anti-RCAS1 polyclonal antibodies or experimental sera.

Identification of Candidate Antigens for Epitope Mapping.

All eight immunogenic proteins associated with colorectal cancer were selected to move forward with epitope mapping.

Example 2

Identification of Promiscuous High Affinity Binding Class II Epitopes Derived from Colorectal Cancer Antigens Constructed Peptides Per in Silico Mapping.

Peptide sequences were predicted and screened as described in Park (2008). Heat maps and binding affinity scores were generated for the eight proteins and epitopes were ranked by the highest predicted binding affinity. Final peptides were selected that shared ≥90% homology between human and mouse. Peptides with the highest predicted binding affinity were selected and synthesized. The peptides were synthesized and purified by high-performance liquid chromatography and then lyophilized. Table 2 lists the 45 peptides for the eight antigens that were selected and synthesized. Table 3 shows that the median peptide coverage for the candidate proteins was 21% of the total sequence (range 4-54%).

TABLE 2

CRC Peptides.

| Peptide | Peptide sequence | Amino Acid Sequence | % Murine Peptide Homology |
|---|---|---|---|
| CDC25B #38 | p130-150 | QAIQAASRIIRNEQFAIRRFQ (SEQ ID NO: 1) | 78% |
| CDC25B #39 | p405-427 | VDGKHQDLKYISPETMVALLTGK (SEQ ID NO: 2) | 100% |
| COX-2 #32 | p81-96 | FKGFWNVVNNIPFLRN (SEQ ID NO: 3) | 87% |
| COX-2 #33 | p279-295 | GLVPGLMMYATIWLREH (SEQ ID NO: 4) | 100% |
| COX-2 #34 | p538-553 | GEVGFQIINTASIQLSIC (SEQ ID NO: 5) | 94% |
| COX-2 #35 | p96-111 | NAIMSYVLTSRSHLID (SEQ ID NO: 6) | |
| COX-2 #36 | p218-235 | HIYGETLARQRKLRLFKD (SEQ ID NO: 7) | |
| COX-2 #37 | p314-331 | LFQTSRLILIGETIKIVI (SEQ ID NO: 8) | |
| COX-2 #38 | p356-371 | QFQYQNRIAAEFNTLY (SEQ ID NO: 9) | |
| COX-2 #39 | p391-409 | QQFIYNNSILLEHGITQFV (SEQ ID NO: 10) | |
| EGFR #40 | p306-325 | SCVRACGADSYEMEEDGVRK (SEQ ID NO: 11) | 80% |
| EGFR #41 | p603-619 | NNTLVWKYADAGHVCHL (SEQ ID NO: 12) | 88% |
| EGFR #42 | p897-915 | VWSYGVTVWELMTFGSKPY (SEQ ID NO: 13) | 100% |
| Fascin1 #5 | p136-154 | IAMHPQVNIYSVTRKRYAH (SEQ ID NO: 14) | 100% |
| Fascin1 #6 | p190-209 | TADHRFLRHDGRLVARPEPA (SEQ ID NO: 15) | 95% |
| Fascin1 #24 | p21-40 | NKYLTAEAFGFKVNASASSL (SEQ ID NO: 16) | 100% |
| Fascin1 #25 | p274-398 | ELFLMKLINRPIIVFRGEHGFIGCR (SEQ ID NO: 17) | 100% |
| Fascin1 #26 | p10-25 | VQIQFGLINCGNKYLT (SEQ ID NO: 18) | |
| Fascin1 #27 | p59-75 | AVCLRSHLGRYLAADKD (SEQ ID NO: 19) | |
| Fascin1 #28 | p311-326 | TGKYWTLTATGGVQST (SEQ ID NO: 20) | |
| Fascin1 #29 | p253-272 | LFALEQSCAQVVLQAANERN (SEQ ID NO: 21) | |

TABLE 2-continued

CRC Peptides.

| Peptide | Peptide sequence | Amino Acid Sequence | % Murine Peptide Homology |
|---|---|---|---|
| Fascin1 #30 | p426-443 | KDSTGKYWTVGSDSAVTS (SEQ ID NO: 22) | |
| IGF1R #1 | p384-398 | VVTGYVKIRHSHALV (SEQ ID NO: 23) | 100% |
| IGF1R #2 | p575-588 | TQYAVYVKAVTLTMV (SEQ ID NO: 24) | 100% |
| IGF1R #3 | p951-965 | LVIMLYVFHRKRNNS (SEQ ID NO: 25) | 100% |
| IGF1R #4 | p1122-1136 | GMAYLNANKFVHRDL (SEQ ID NO: 26) | 100% |
| PRL-3 #1 | p12-30 | VSYKHMRFLITHNPTNATL (SEQ ID NO: 27) | 89% |
| PRL-3 #2 | p33-53 | FIEDLKKYGATTVVRVCEVTY (SEQ ID NO: 28) | 100% |
| PRL-3 #3 | p104-122 | PCVAGLGRAPVLVALALIES (SEQ ID NO: 29) | 100% |
| PRL-3 #4 | p124-142 | MKYEDAIQFIRQKRRGAIN (SEQ ID NO: 30) | 100% |
| PRL-3 #29 | p81-95 | VEDWLSLVKAKFCEA (SEQ ID NO: 31) | 92% |
| RCAS1 #13 | p91-110 | EPDYFKDMTPTIRKTQKIVI (SEQ ID NO: 32) | 100% |
| RCAS1 #14 | p93-113 | DYFKDMTPTIRKTQKIVIKKR (SEQ ID NO: 33) | 100% |
| RCAS1 #21 | p8-27 | LFKFCTCLATVFSFLKRLIC (SEQ ID NO: 34) | 95% |
| RCAS1 #30 | p126-148 | GFSSRLAATQDLPFIHQSSELGD (SEQ ID NO: 35) | 96% |
| RCAS1 #31 | p161-181 | EEEDAAWQAEEVLRQQKLADR (SEQ ID NO: 36) | 95% |
| VCP #18 | p82-102 | IRMNRVVRNNLRVRLGDVISI (SEQ ID NO: 37) | 100% |
| VCP #19 | p49-65 | LQLFRGDTVLLKGKKRR (SEQ ID NO: 38) | 100% |
| VCP #20 | p138-156 | YFLEAYRPIRKGDIFLVRG (SEQ ID NO: 39) | 100% |
| VCP #23 | p161-180 | VEFKVVETDPSPYCIVAPDT (SEQ ID NO: 40) | 100% |
| VCP #24 | p224-242 | LRHPALFKAIGVKPPRGIL (SEQ ID NO: 41) | |
| VCP #25 | p261-277 | ETGAFFFLINGPEIMSK (SEQ ID NO: 42) | |
| VCP #26 | p446-462 | AVTMDDFRWALSQSNPS (SEQ ID NO: 43) | |
| VCP #27 | p337-352 | QRAHVIVMAATNRPNS (SEQ ID NO: 44) | |
| VCP #28 | p615-629 | KNVFIIGATNRPDII (SEQ ID NO: 45) | |

TABLE 3

Peptide coverage for candidate proteins.

| Peptide | Protein length | Peptide no. | Peptide sequence | AA length | % coverage |
|---|---|---|---|---|---|
| CDC25B | 566 aa | 38 | p130-150 | 21 | 7.77 |
|  |  | 39 | p405-427 | 23 |  |
| COX2 | 604 aa | 32 | p81-96 | 16 | 22.52 |
|  |  | 33 | p279-295 | 17 |  |
|  |  | 34 | p538-553 | 16 |  |
|  |  | 35 | p96-111 | 16 |  |
|  |  | 36 | p218-235 | 18 |  |
|  |  | 37 | p314-331 | 18 |  |
|  |  | 38 | p356-371 | 16 |  |
|  |  | 39 | p391-409 | 19 |  |
| EGFR | 1210 aa | 40 | p306-325 | 20 | 4.63 |
|  |  | 41 | p603-619 | 17 |  |
|  |  | 42 | p897-915 | 19 |  |
| FASCIN1 | 493 aa | 5 | p136-154 | 19 | 34.69 |
|  |  | 6 | p190-209 | 20 |  |
|  |  | 24 | p21-40 | 20 |  |
|  |  | 25 | p374-398 | 25 |  |
|  |  | 26 | p10-25 | 16 |  |
|  |  | 27 | p59-75 | 17 |  |
|  |  | 28 | p311-326 | 16 |  |
|  |  | 29 | p253-272 | 20 |  |
|  |  | 30 | p426-443 | 18 |  |
| IGF1R | 1367 aa | 1 | p384-398 | 15 | 4.32 |
|  |  | 2 | p575-588 | 14 |  |
|  |  | 3 | p951-965 | 15 |  |
|  |  | 4 | p1122-1136 | 15 |  |
| PRL3 | 173 aa | 1 | p12-30 | 19 | 53.76 |
|  |  | 2 | p33-53 | 21 |  |
|  |  | 3 | p104-122 | 19 |  |
|  |  | 4 | p124-142 | 19 |  |
|  |  | 29 | p81-95 | 15 |  |
| RCAS1 | 213 aa | 13 | p91-110 | 20 | 49.30 |
|  |  | 14 | p93-113 | 21 |  |
|  |  | 21 | p8-27 | 20 |  |
|  |  | 30 | p126-181 | 23 |  |
|  |  | 31 | p161-181 | 21 |  |
| VCP | 806 aa | 18 | p82-201 | 21 | 19.98 |
|  |  | 19 | p49-65 | 17 |  |
|  |  | 20 | p138-156 | 19 |  |
|  |  | 23 | p161-180 | 20 |  |
|  |  | 24 | p224-242 | 19 |  |
|  |  | 25 | p261-277 | 17 |  |
|  |  | 26 | p446-462 | 17 |  |
|  |  | 27 | p337-352 | 16 |  |
|  |  | 28 | p615-629 | 15 |  |

IFN-γ ELISpot Assays.

Figure 12:
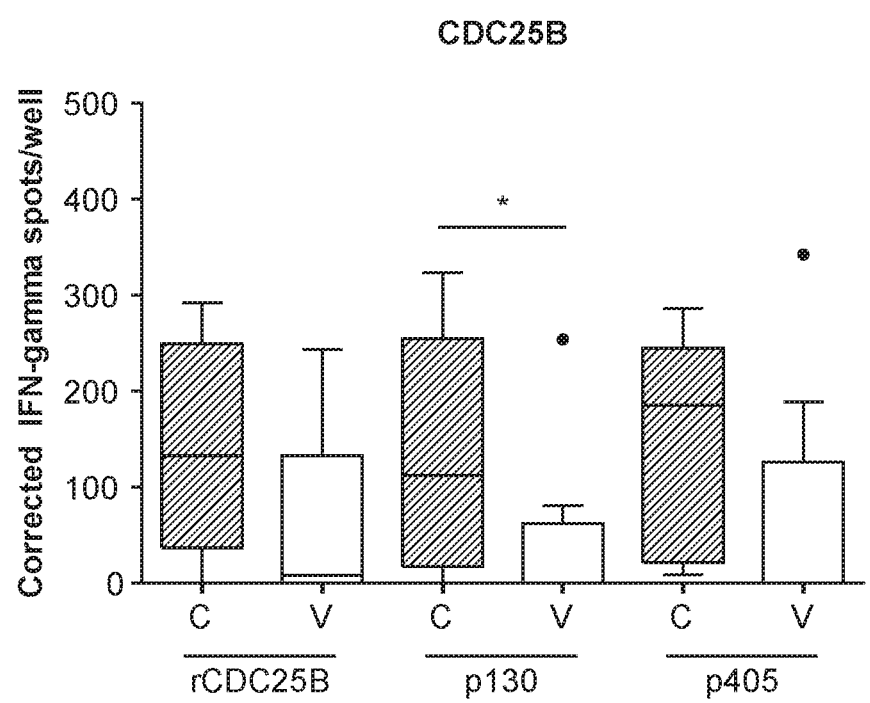
FIG. 12 shows corrected IFN-γ spots per well for CDC25B.
Figure 13:
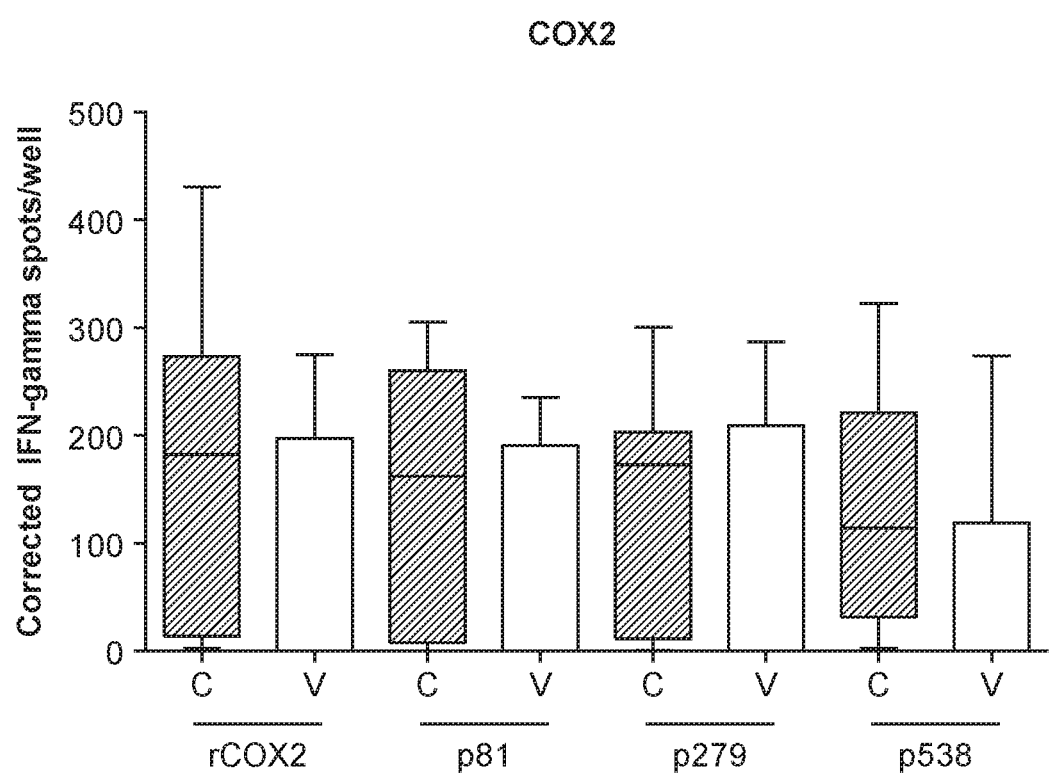
FIG. 13 shows corrected IFN-γ spots per well for COX2.
Figure 14:
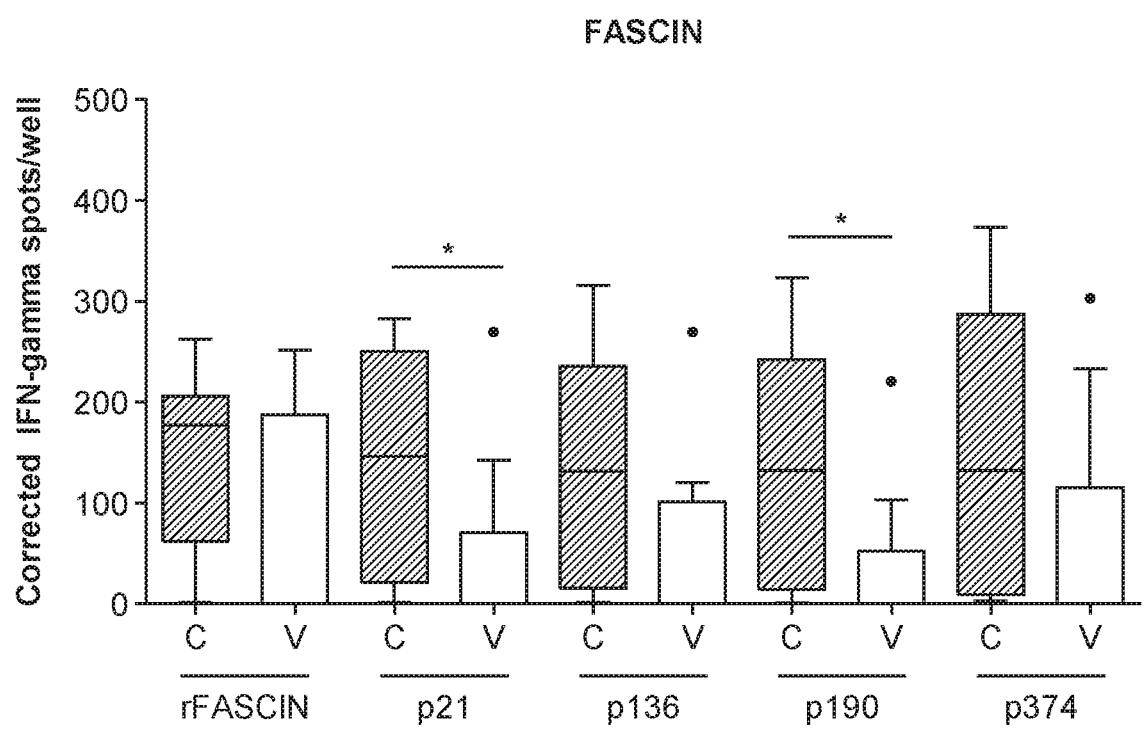
FIG. 14 shows corrected IFN-γ spots per well for FASCIN1.
Figure 15:
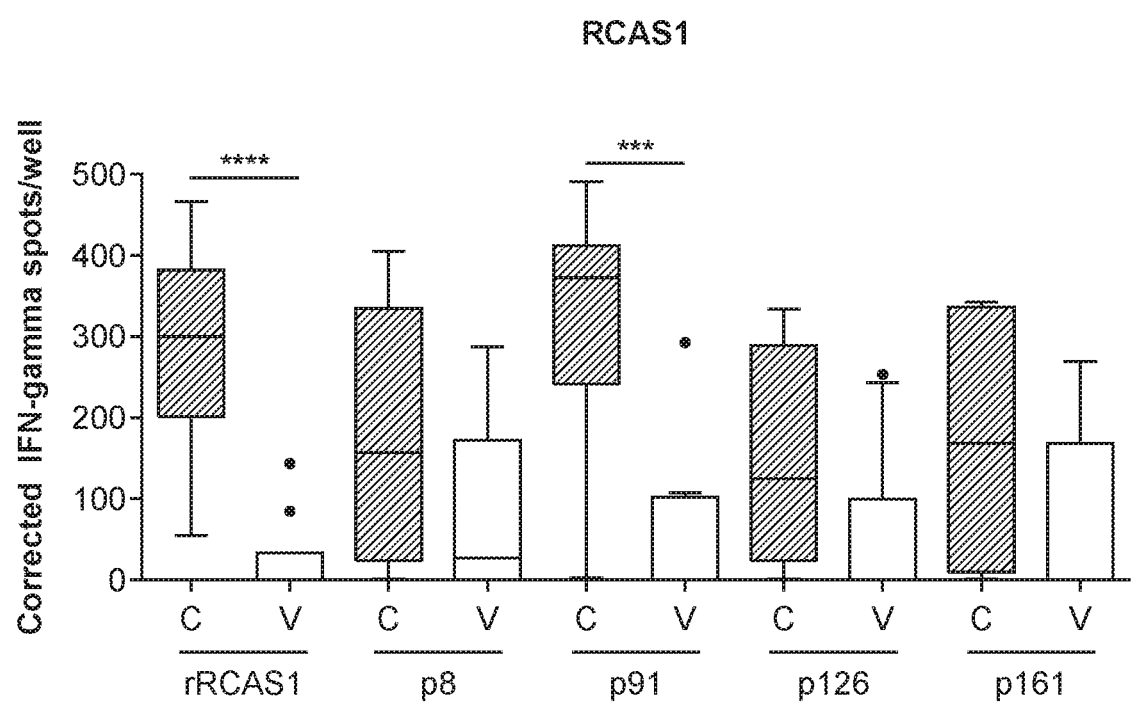
FIG. 15 shows corrected IFN-γ spots per well for RCAS1.
Figure 16:
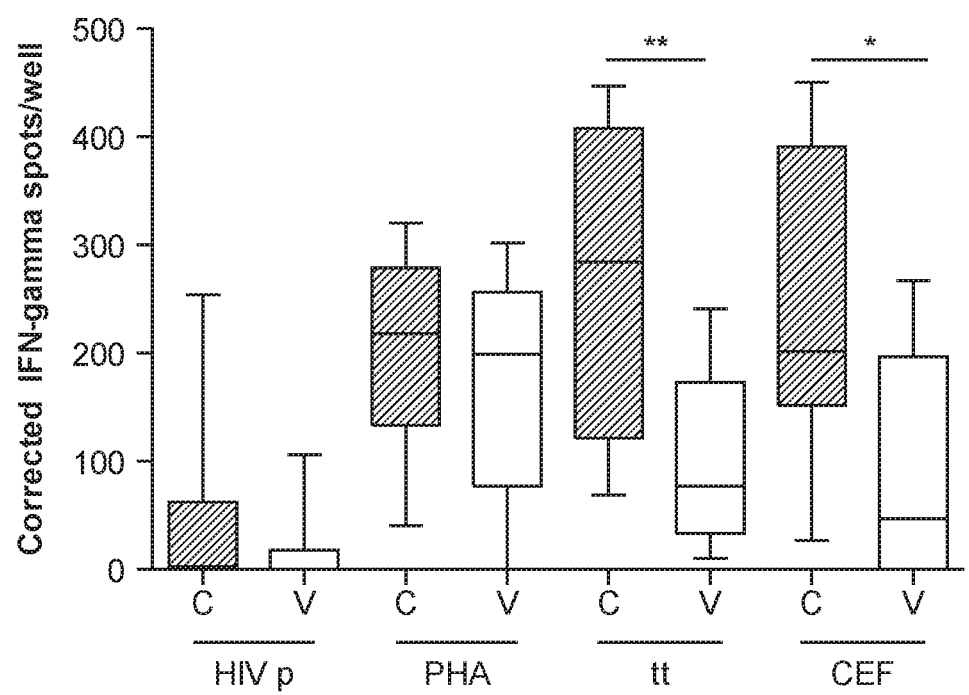
FIG. 16 shows corrected IFN-γ spots per well for HIVp17, PHA, tt, and CEF.

CDC25B, COX2, FASCIN1, and RCAS1 proteins, and CDC25B, COX2, FASCIN1, and RCAS1 peptides derived from web-based algorithms predicted to bind human MHCII epitopes, induce Th1 immunity at a greater magnitude of response in cancer patients compared to volunteer normal donor controls. PBMC's were evaluated by antigen specific IFN-γ ELISpot. Cells were plated at $2 \times 10^5$ per well in medium with 10 ug/ml of the selected CDC25B, COX2, FASCIN1, and RCAS1 peptides, HIVp17 (Genemed Synthesis Inc.), PHA (1 ug/ml Sigma, St. Louis, Mo.), CEF (2.5 ug/ml, AnaSpec, Fremont, Calif.), or X-Vivo 15 with Gentamicin, L-Glutamine, and Phenol Red (Lonza, Walkersville, Md.) media alone for 7 days at 37 degrees Celsius in 5% $CO_2$ incubator. On day 5, recombinant human IL-2 (10 Um') was added. A second in vitro stimulation was performed on day 8 by adding $2 \times 10^5$ peptide loaded (same concentrations as above) autologous irradiated (30000 rads) human PBMC's to the original culture and incubating for 24 hours Millipore MultiScreen 96-well Assay Plates (Millipore, Houston, Tex.) were coated with 2% bovine serum albumin in PBS followed by 24 hour incubation with the PBMC culture. After multiple washes, 0.1 ug/ml biotinylated anti-human IFN-γ (clone 1-D1K, Mabtech, Mariemont, Ohio) was added for two hours. The ELISpot assays were developed and statistical significance were calculated on corrected spots per well as previously described in Park 2008 and Cecil 2013. Corrected spots per well (CSPW) for colorectal cancer and volunteer control for each peptide is present as interquartile box plots with Tukey whiskers. Median CSPW are shown by the horizontal bar, *$p<0.05$ or ***$p<0.001$ compared to volunteer normal donor controls. FIG. 12 shows CSPW for IFN-γ on the y-axis and CDC25B antigens (rCDC25B, p130, and p405) tested in colorectal cancer and volunteer normal donor control on the x-axis. FIG. 13 shows CSPW for IFN-γ on the y-axis and COX2 antigens (rCOX2, p81, p279, and p538) tested in colorectal cancer and volunteer normal donor control on the x-axis. FIG. 14 shows CSPW for IFN-γ on the y-axis and FASCIN1 antigens (rFASCIN1, p21, p138, p190, and p374) tested in colorectal cancer and volunteer normal donor control on the x-axis. FIG. 15 shows CSPW for IFN-γ on the y-axis and RCAS1 antigens (rRCAS1, p8, p91, p126, and p161) tested in colorectal cancer and volunteer normal donor control on the x-axis. FIG. 16 shows CSPW for IFN-γ on the y-axis and antigens (HIVp17, PHA, tt, and CEF) tested in colorectal cancer and volunteer normal donor control on the x-axis.

Example 3

Construction of a Peptide Vaccine Targeting Colorectal Cancer Antigens and Determination of Safety and Immunogenicity Using 3 Mouse Models Determination of immunogenicity and effectiveness of peptide based vaccine constructs containing peptides from CDC25B, COX2, EGFR, FASCIN1, IGF1R, PRL3, RCAS1, and VCP using three mouse models: APCmin mouse model, AOM mouse model, and MC-38 mouse model. Table 4 shows a summary of peptide efficacy in the three mouse models.

TABLE 4

Summary of peptide efficacy in the three mouse models.

| Protein | APCmin Small Bowel (Spontaneous) | APCmin Colon (Spontaneous) | Azoxymethane + FVB (Induced) | MC-38 + B6 (Tumor Implant) |
|---|---|---|---|---|
| CDC25B | Yes | No | Yes | Yes |
| COX2 | Yes | No | Yes | Yes |
| EGFR | Yes | No | Yes | No |
| FASCIN1 | Yes | No | No | Yes |
| IGF1R | Yes | No | No | No |
| PRL3 | Yes | No | No | Yes |
| RCAS1 | Yes | No | No | Yes |
| VCP | Yes | Yes | No | No |
| MIX (CDC25B, COX2, PRL3) | Yes | Yes | Yes | Yes |

APCmin Mouse Model.

Offspring from APCmin were genotyped by PCR for the presence of the Min mutation using primers as follows: Wild-Type: 5'-GCCATCCCTTCACGTTAG-3' (SEQ ID NO: 46), Common 5'-TTCCACTTTGGCATAAGGC-3' (SEQ ID NO: 47), Mutant: 5'-TCCTGAGAAAGACA-GAAGTTA-3' (SEQ ID NO: 48). Both male and female mice testing positive for the Min mutation were included in the study and randomized into groups.

APCmin In-Vivo Experiments.

At 4-6 weeks of age, mice were immunized in CFA/IFA, PBS, and vaccine groups. Each group received subcutaneous injections (100 ul PBS, 50 ul CFA with 50 ul PBS, 50 ug per peptide with 50 ul CFA) once every 7-10 days for a total of three doses and one booster was given 4-5 weeks after the third vaccine. See Table 5 for peptides included in vaccine compositions. CFA was replaced with IFA after the first vaccine. All mice were sacrificed at 14 to 17 weeks of age, the gastrointestinal tracts were collected and tumors counted.

TABLE 5

APCmin in-vivo experiments: peptides included in vaccine compositions.

| Vaccine | Peptide | Peptide sequence | Amino Acid Sequence |
|---|---|---|---|
| CDC25B | CDC25B #38 | p130-150 | QAIQAASRIIRNEQFAIRRFQ (SEQ ID NO: 1) |
|  | CDC25B #39 | p405-427 | VDGKHQDLKYISPETMVALLTGK (SEQ ID NO: 2) |
| COX2 | COX-2 #32 | p81-96 | FKGFWNVVNNIPFLRN (SEQ ID NO: 3) |
|  | COX-2 #33 | p279-295 | GLVPGLMMYATIWLREH (SEQ ID NO: 4) |
|  | COX-2 #34 | p538-553 | GEVGFQIINTASIQSLIC (SEQ ID NO: 5) |
| EGFR | EGFR #40 | p306-325 | SCVRACGADSYEMEEDGVRK (SEQ ID NO: 11) |
|  | EGFR #41 | p603-619 | NNTLVWKYADAGHVCHL (SEQ ID NO: 12) |
|  | EGFR #42 | p897-915 | VWSYGVTVWELMTFGSKPY (SEQ ID NO: 13) |
| FASCIN1 | Fascin1 #5 | p136-154 | IAMHPQVNIYSVTRKRYAH (SEQ ID NO: 14) |
|  | Fascin1 #6 | p190-209 | TADHRFLRHDGRLVARPEPA (SEQ ID NO: 15) |
|  | Fascin1 #24 | p21-40 | NKYLTAEAFGFKVNASASSL (SEQ ID NO: 16) |
|  | Fascin1 #25 | p274-398 | ELFLMKLINRPIIVFRGEHGFIGCR (SEQ ID NO: 17) |
| IGF1R | IGF1R #1 | p384-398 | VVTGYVKIRHSHALV (SEQ ID NO: 23) |
|  | IGF1R #2 | p575-588 | TQYAVYVKAVTLTMV (SEQ ID NO: 24) |
|  | IGF1R #3 | p951-965 | LVIMLYVFHRKRNNS (SEQ ID NO: 25) |
|  | IGF1R #4 | p1122-1136 | GMAYLNANKFVHRDL (SEQ ID NO: 26) |
| PRL3 | PRL-3 #1 | p12-30 | VSYKHMRFLITHNPTNATL (SEQ ID NO: 27) |
|  | PRL-3 #2 | p33-53 | FIEDLKKYGATTVVRVCEVTY (SEQ ID NO: 28) |
|  | PRL-3 #3 | p104-122 | PCVAGLGRAPVLVALALIES (SEQ ID NO: 29) |
|  | PRL-3 #4 | p124-142 | MKYEDAIQFIRQKRRGAIN (SEQ ID NO: 30) |
|  | PRL-3 #29 | p81-95 | VEDWLSLVKAKFCEA (SEQ ID NO: 31) |
| RCAS1 | RCAS1 #13 | p91-110 | EPDYFKDMTPTIRKTQKIVI (SEQ ID NO: 32) |
|  | RCAS1 #14 | p93-113 | DYFKDMTPTIRKTQKIVIKKR (SEQ ID NO: 33) |
|  | RCAS1 #21 | p8-27 | LFKFCTCLATVFSFLKRLIC (SEQ ID NO: 34) |
|  | RCAS1 #30 | p126-148 | GFSSRLAATQDLPFIHQSSELGD (SEQ ID NO: 35) |
|  | RCAS1 #31 | p161-181 | EEEDAAWQAEEVLRQQKLADR (SEQ ID NO: 36) |
| VCP | VCP #18 | p82-102 | IRMNRVVRNNLRVRLGDVISI (SEQ ID NO: 37) |
|  | VCP #19 | p49-65 | LQLFRGDTVLLKGKKRR (SEQ ID NO: 38) |
|  | VCP #20 | p138-156 | YFLEAYRPIRKGDIFLVRG (SEQ ID NO: 39) |
|  | VCP #23 | p161-180 | VEFKVVETDPSPYCIVAPDT (SEQ ID NO: 40) |

Figure 17:
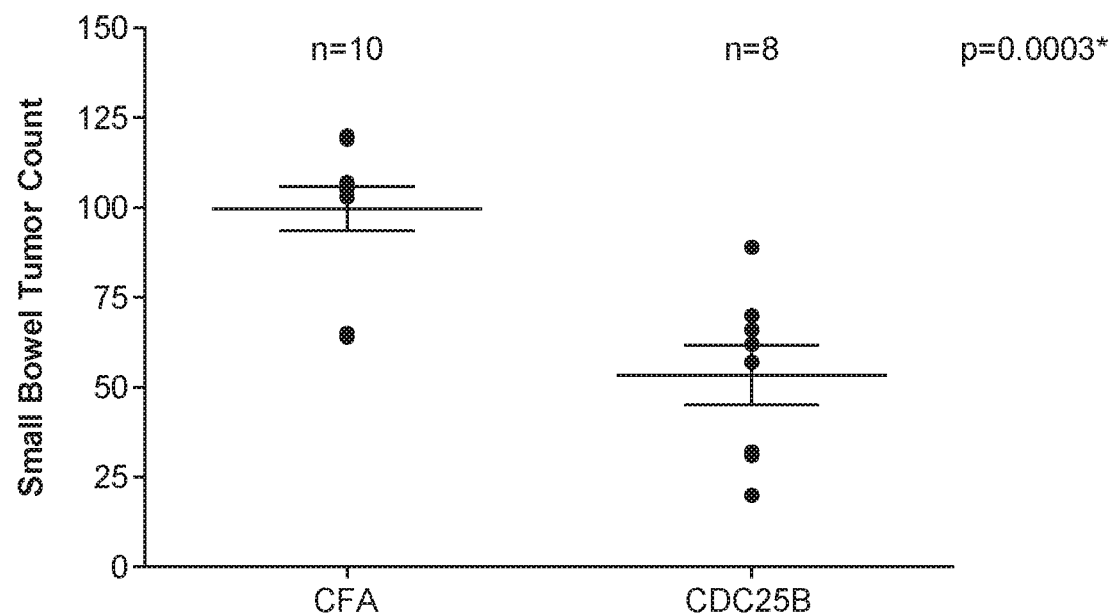
FIG. 17 demonstrates CDC25B vaccine efficacy on small bowel tumor count in APCmin mice.
Figure 18:
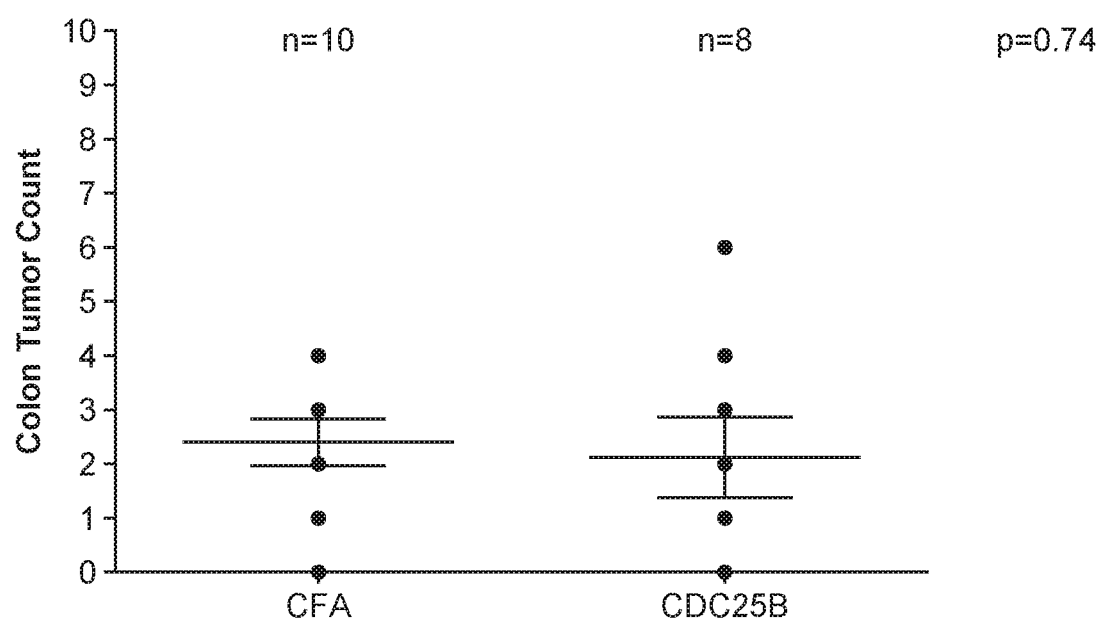
FIG. 18 demonstrates lack of CDC25B vaccine efficacy colon tumor count in APCmin mice.

FIG. 17 shows immunization with the peptides derived from CDC25B significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and CDC25B (group n=8), p=0.0003. FIG. 18 shows immunization with peptides derived from CDC25B does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and CDC25B (group n=8), p=0.74.

Figure 19:
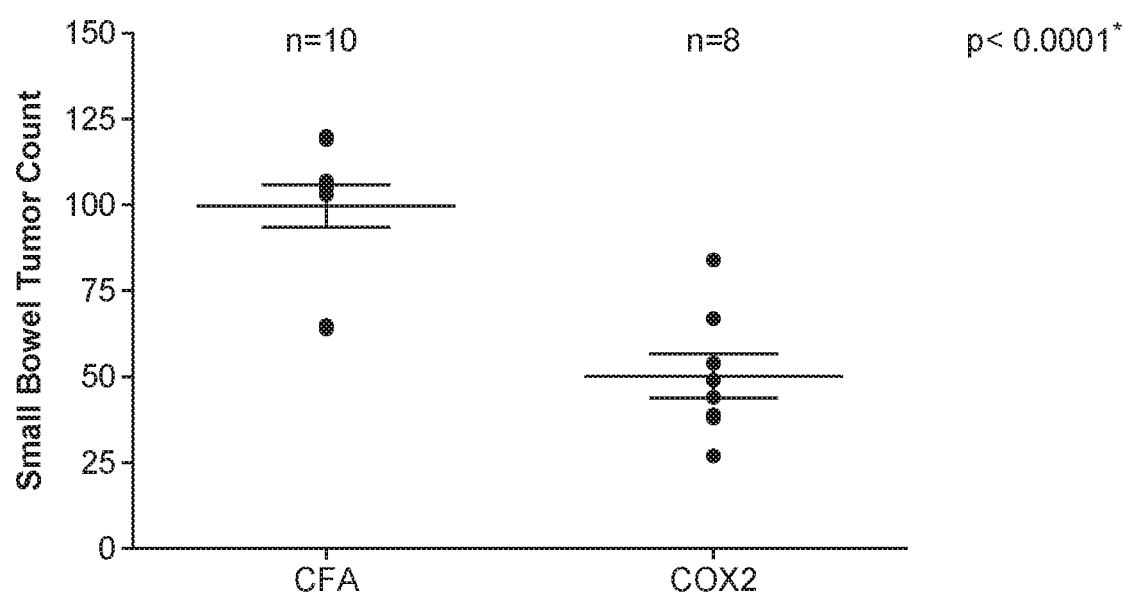
FIG. 19 demonstrates COX2 vaccine efficacy on small bowel tumor count in APCmin mice.
Figure 20:
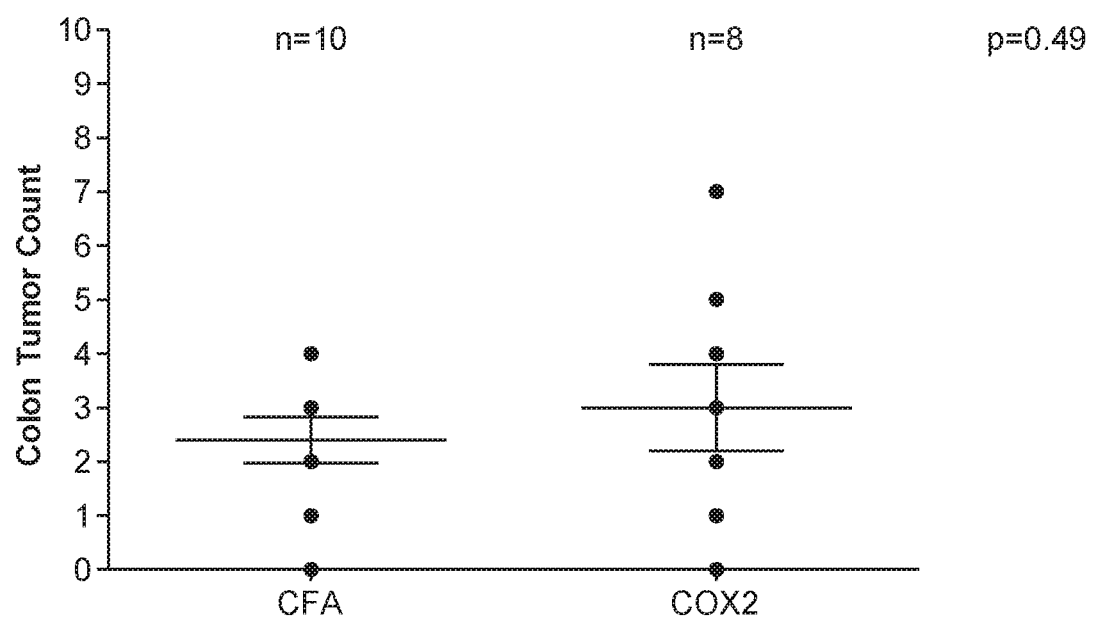
FIG. 20 demonstrates lack of COX2 vaccine efficacy colon tumor count in APCmin mice.

FIG. 19 shows immunization with the peptides derived from COX2 significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and COX2 (group n=8), p<0.0001. FIG. 20 shows immunization with peptides derived from COX2 does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and COX2 (group n=8), p=0.84.

Figure 21:
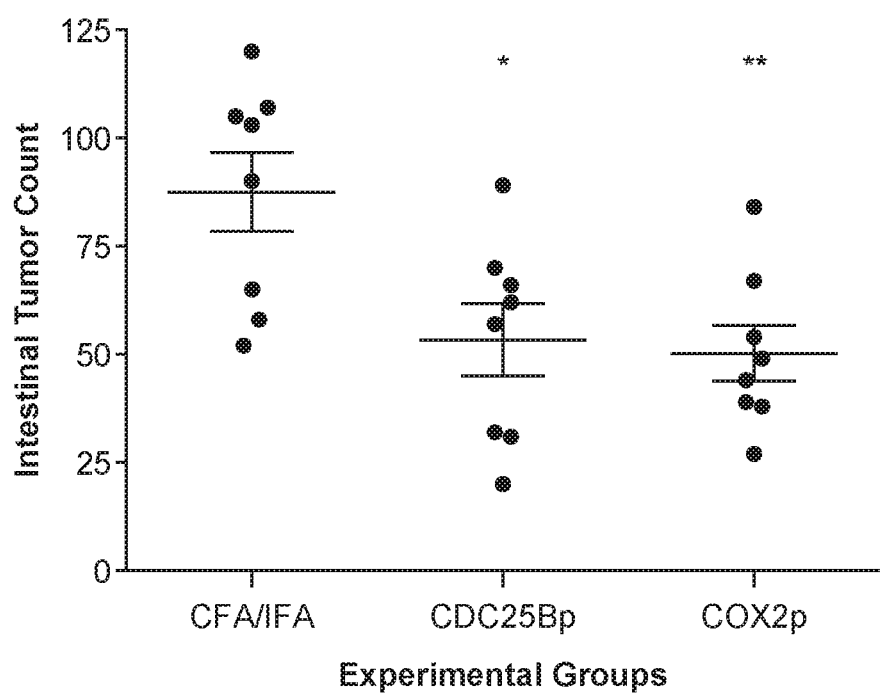
FIG. 21 demonstrates CDC25B and COX2 vaccine efficacy on small bowel tumor count in APCmin mice.

FIG. 21 shows immunization with peptides derived from CDC25B and COX2 significantly inhibits tumor burden in APCmin mice (n=8 mice/group). The small bowel tumor count is shown on the y-axis and the experimental groups are shown on the x-axis. Each value point represents the number of tumors in the small bowel of one mouse. Calculated p-values using the unaired, two-tailed student t test were statistically significant *p<0.05 or **p<0.005 compared to CFA control group.

Figure 22:
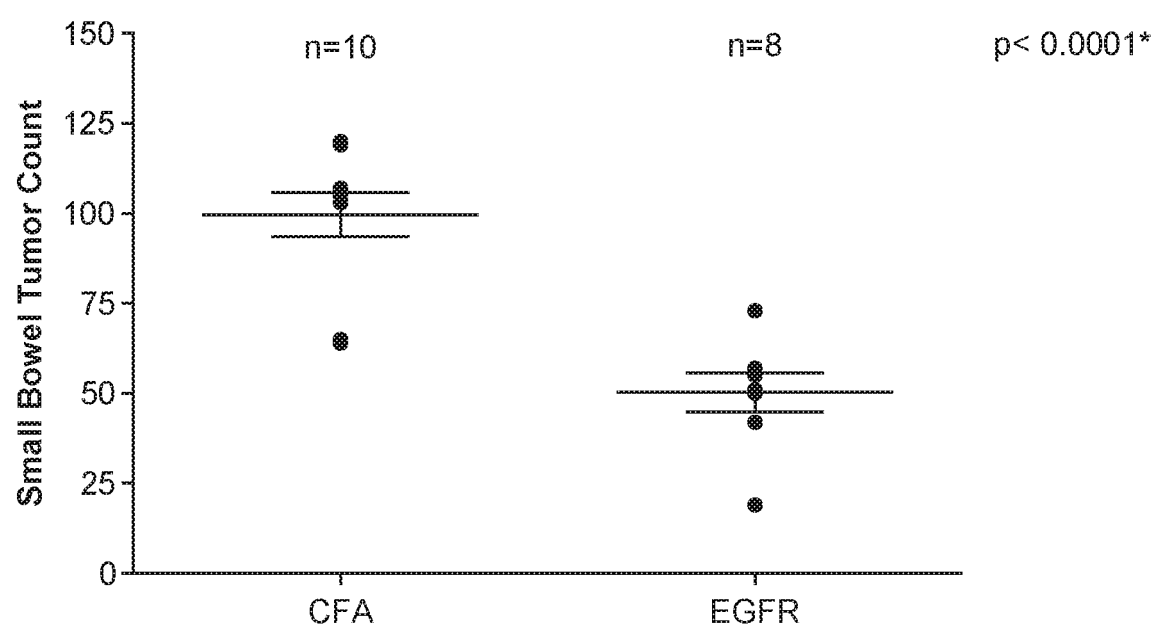
FIG. 22 demonstrates EGFR vaccine efficacy on small bowel tumor count in APCmin mice.
Figure 23:
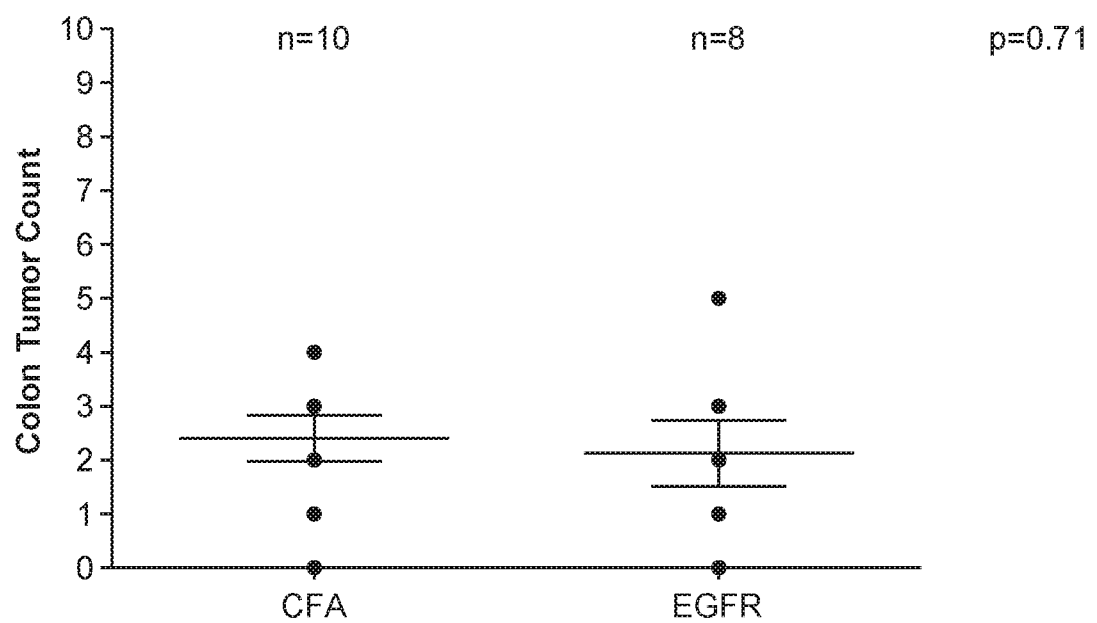
FIG. 23 demonstrates lack of EGFR vaccine efficacy colon tumor count in APCmin mice.

FIG. 22 shows immunization with the peptides derived from EGFR significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and EGFR (group n=8), p<0.0001. FIG. 23 shows immunization with peptides derived from EGFR does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and EGFR (group n=8), p=0.71.

Figure 24:
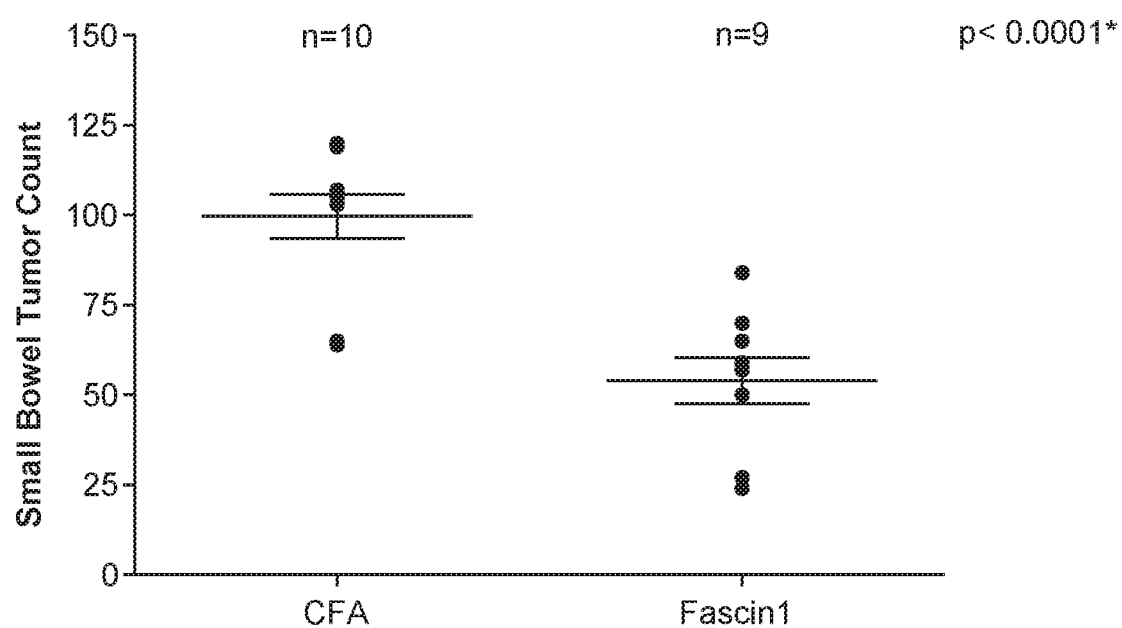
FIG. 24 demonstrates FASCIN1 vaccine efficacy on small bowel tumor count in APCmin mice.
Figure 25:
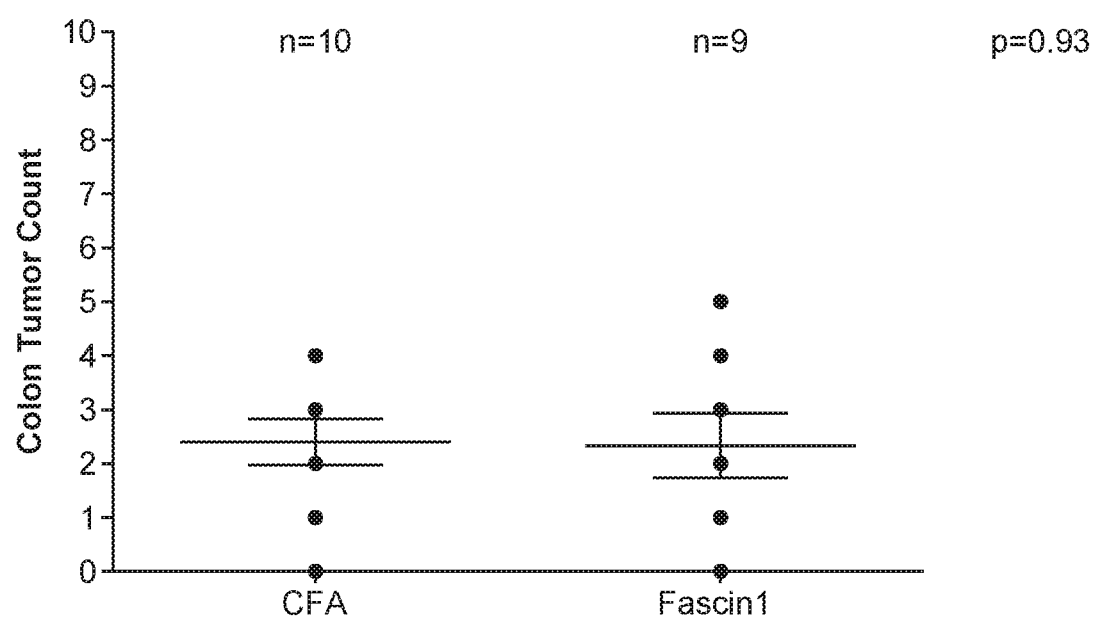
FIG. 25 demonstrates lack of FASCIN1 vaccine efficacy colon tumor count in APCmin mice.

FIG. 24 shows immunization with the peptides derived from FASCIN1 significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and FASCIN1 (group n=9), p<0.0001. FIG. 25 shows immunization with peptides derived from FASCIN1 does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and FASCIN1 (group n=9), p=0.93.

Figure 26:
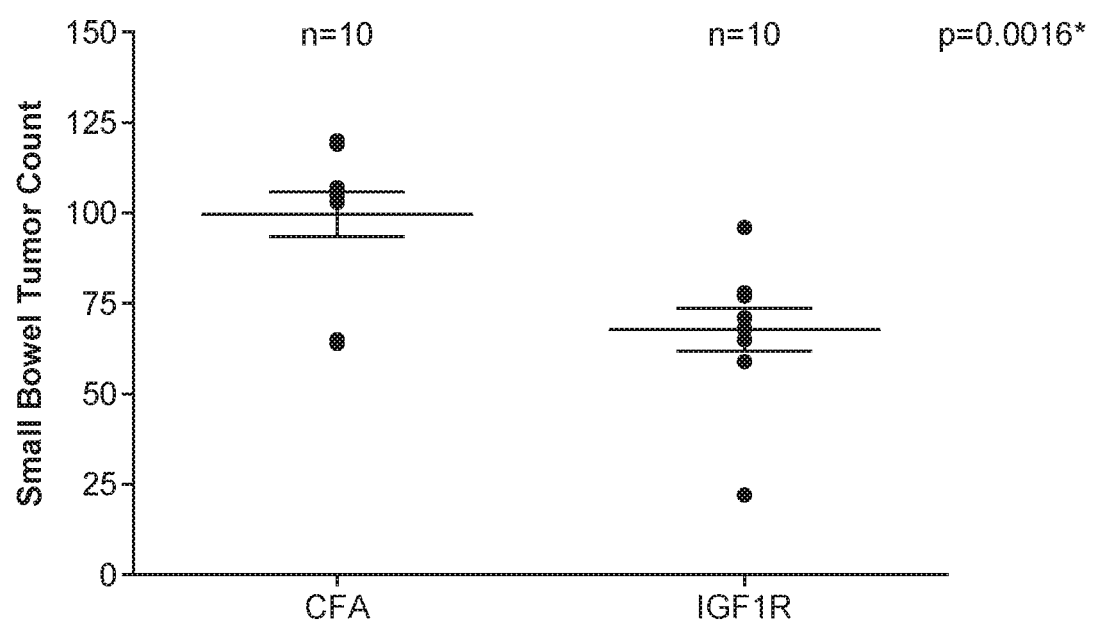
FIG. 26 demonstrates IGF1R vaccine efficacy on small bowel tumor count in APCmin mice.
Figure 27:
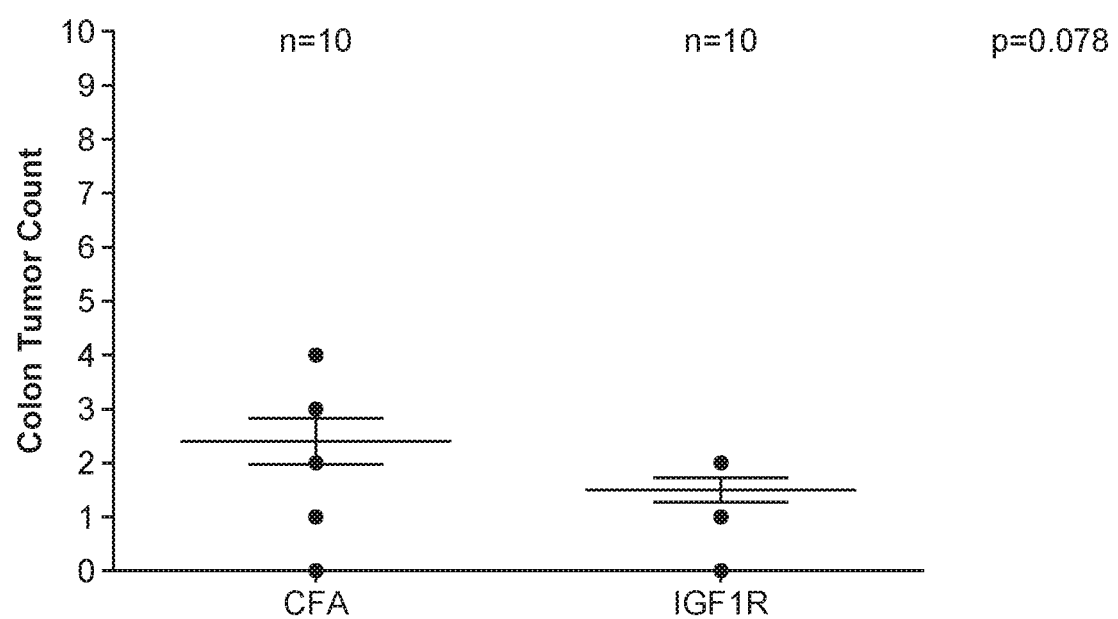
FIG. 27 demonstrates lack of IGF1R vaccine efficacy colon tumor count in APCmin mice.

FIG. 26 shows immunization with the peptides derived from IGF1R significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and IGF1R (group n=10), p=0.0016. FIG. 27 shows immunization with peptides derived from IGF1R does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and IGF1R (group n=10), p=0.078.

Figure 28:
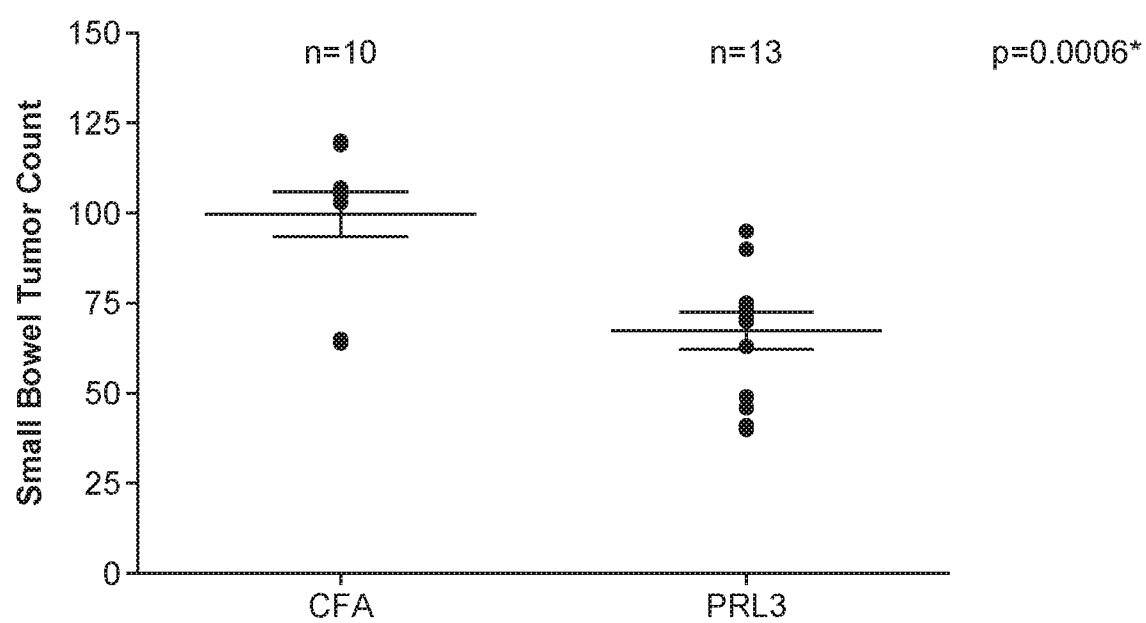
FIG. 28 demonstrates PRL3 vaccine efficacy on small bowel tumor count in APCmin mice.
Figure 29:
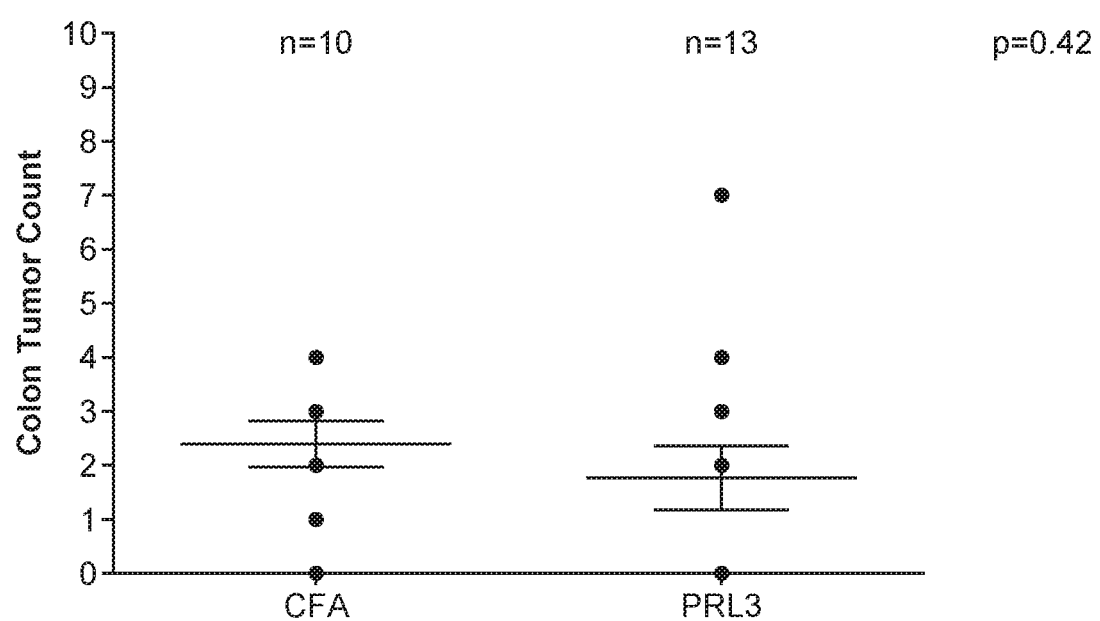
FIG. 29 demonstrates lack of PRL3 vaccine efficacy colon tumor count in APCmin mice.

FIG. 28 shows immunization with the peptides derived from PRL3 significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and PRL3 (group n=13), p=0.0006. FIG. 29 shows immunization with peptides derived from PRL3 does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and PRL3 (group n=13), p=0.42.

Figure 30:
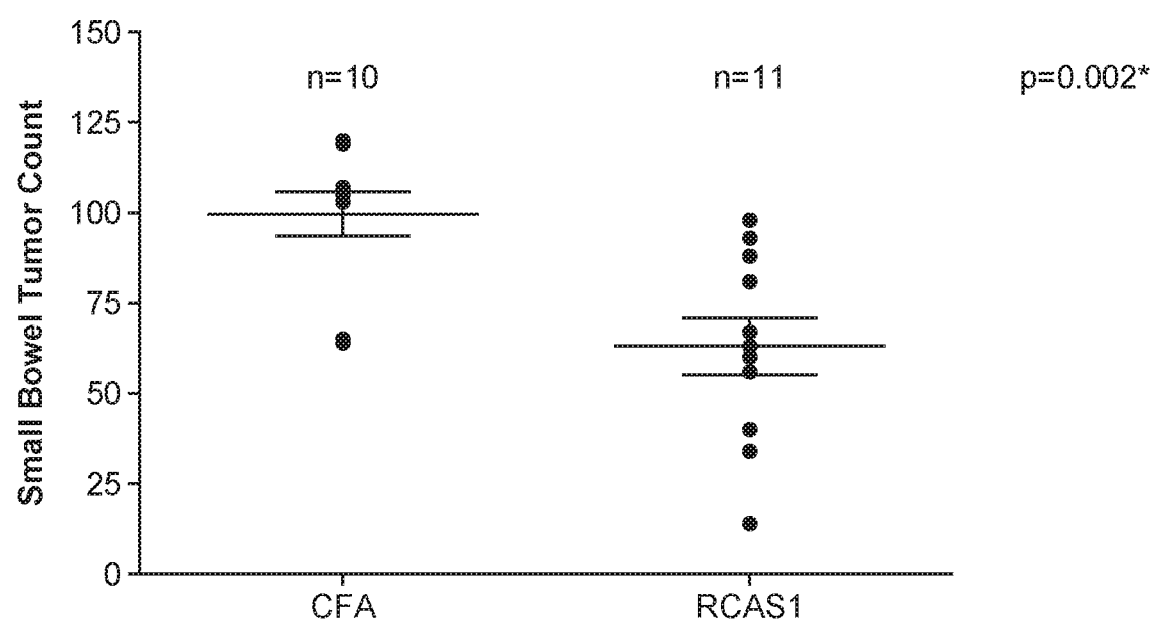
FIG. 30 demonstrates RCAS1 vaccine efficacy on small bowel tumor count in APCmin mice.
Figure 31:
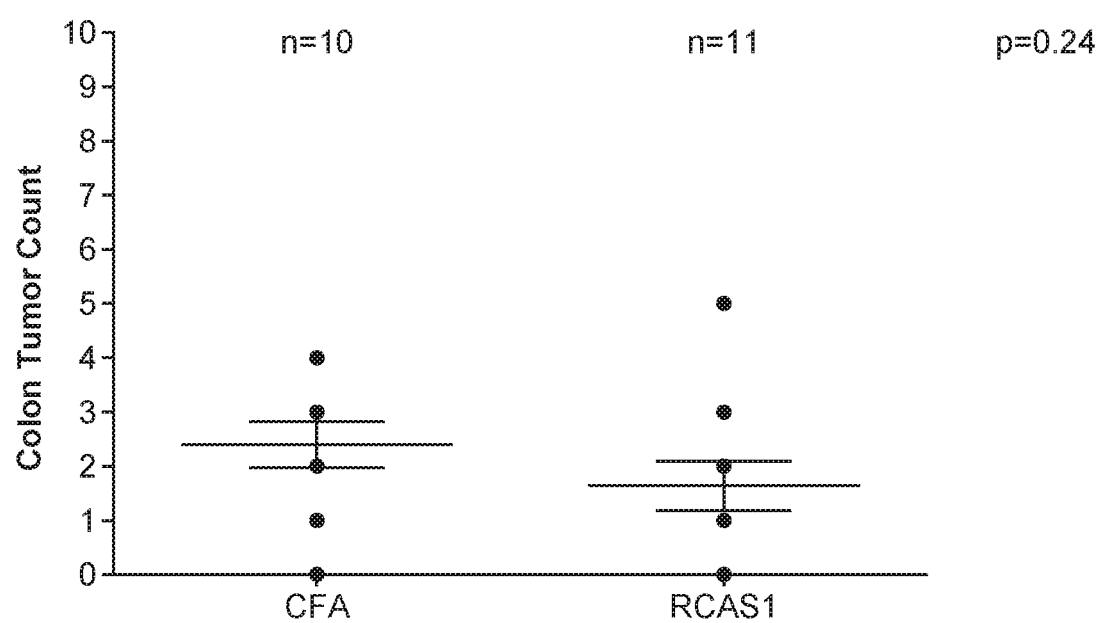
FIG. 31 demonstrates lack of RCAS1 vaccine efficacy colon tumor count in APCmin mice.

FIG. 30 shows immunization with the peptides derived from RCAS1 significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and RCAS1 (group n=11), p=0.002. FIG. 31 shows immunization with peptides derived from RCAS1 does not significantly inhibit colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and RCAS1 (group n=11), p=0.24.

Figure 32:
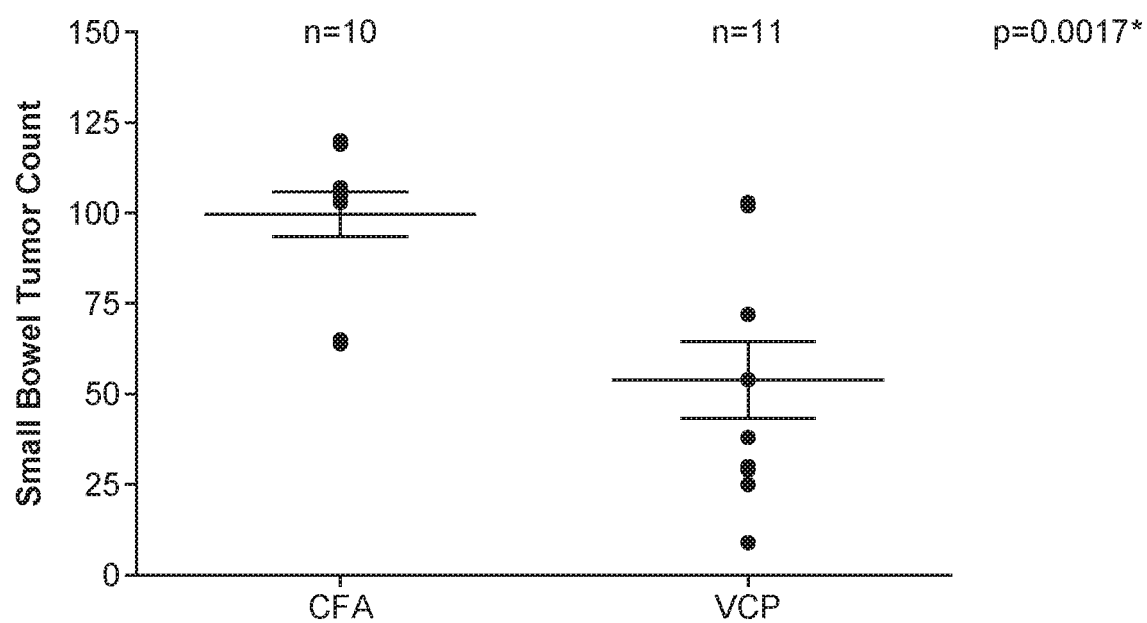
FIG. 32 demonstrates VCP vaccine efficacy on small bowel tumor count in APCmin mice.
Figure 33:
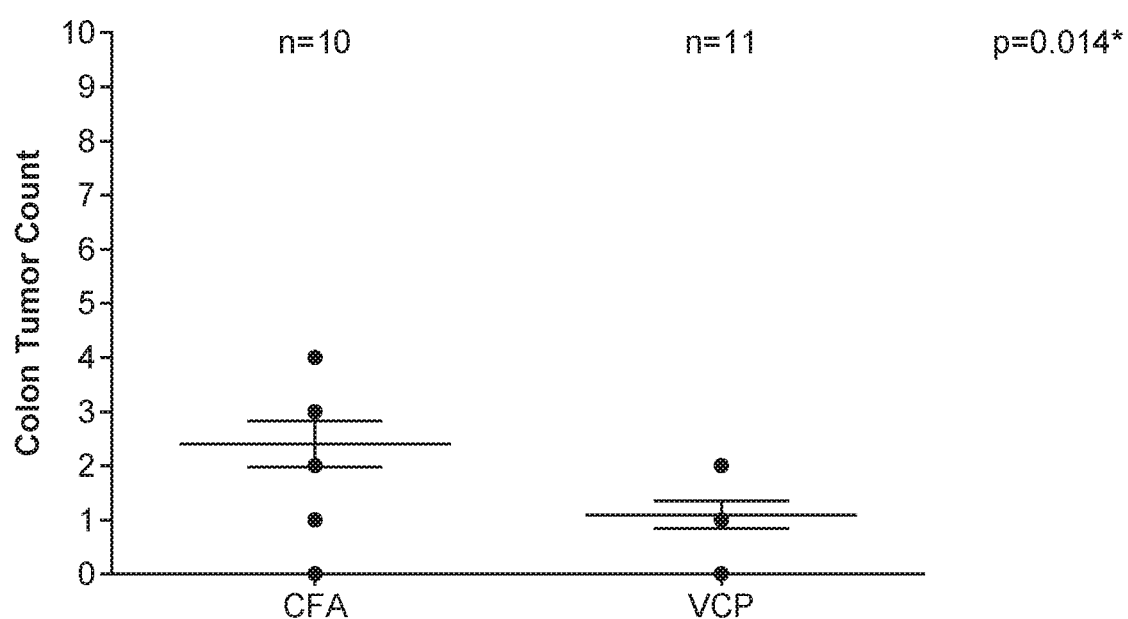
FIG. 33 demonstrates VCP vaccine efficacy on colon tumor count in APCmin mice.

FIG. 32 shows immunization with the peptides derived from VCP significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and VCP (group n=11), p=0.0017. FIG. 33 shows immunization with peptides derived from VCP significantly inhibits colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and VCP (group n=11), p=0.014.

Figure 34:
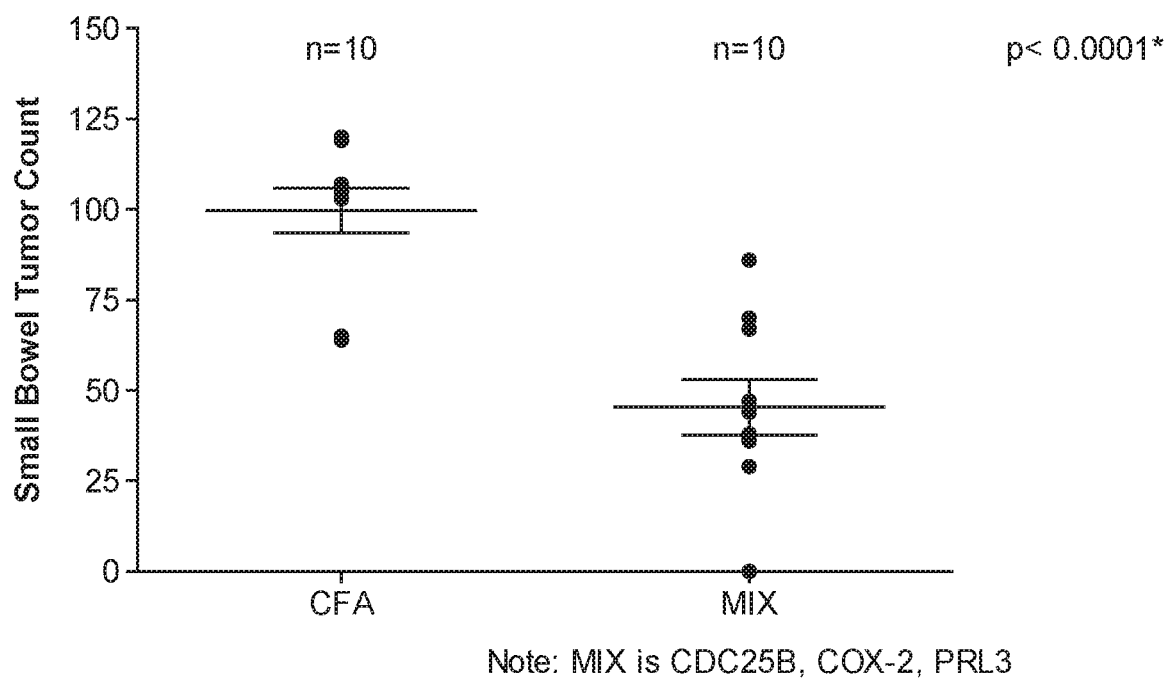
FIG. 34 demonstrates MIX vaccine efficacy on small bowel tumor count in APCmin mice.
Figure 35:
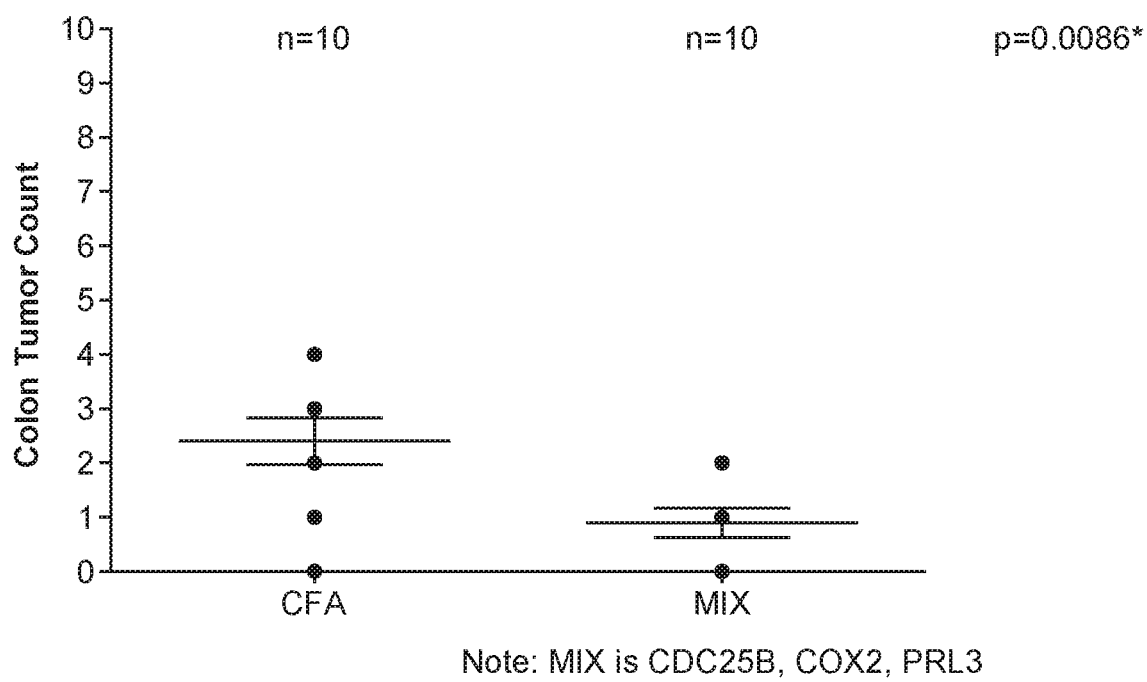
FIG. 35 demonstrates MIX vaccine efficacy on colon tumor count in APCmin mice.

FIG. 34 shows immunization with the peptides derived from MIX, a combination of CDC25B, COX2, and PRL3, significantly inhibits small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were statistically significant between APCmin mice immunized with CFA/IFA (n=10) and MIX (group n=10), p<0.0001. FIG. 35 shows immunization with peptides derived from MIX significantly inhibits colon tumor burden in APCmin mice. The colon tumor count is shown on the y-axis and the APCmin immunized groups are on the x-axis. Each value point represents the number of tumors in the colon of one mouse. Calculated p-values using the unpaired, two-tailed student t test were not statistically significant between APCmin mice immunized with CFA/IFA (n=10) and MIX (group n=10), p=0.0086.

APCmin Survival Study In-Vivo Experiments.

At 4-6 weeks of age, mice were immunized with CFA/IFA, PBS, and vaccine groups. Each group received subcutaneous injections (100 ul PBS, 50 ul CFA with 50 ul PBS, 50 ug per peptide with 50 ul CFA) once every 7-10 days for a total of three doses and a booster vaccine was given every 4-5 weeks after the third vaccine. See Table 6 for peptides included in vaccine compositions. CFA was replaced with IFA after the first vaccine. Mice were observed for health and wellbeing twice weekly and were sacrificed if moribund. At sacrifice, small intestines were collected and small bowel tumors counted.

TABLE 6

APCmin survival study in-vivo experiments: peptides included in vaccine compositions

| Vaccine | Peptide | Peptide sequence | Amino Acid Sequence |
|---|---|---|---|
| CDC25B | CDC25B #38 | p130-150 | QAIQAASRIIRNEQFAIRRFQ (SEQ ID NO: 1) |
|  | CDC25B #39 | p405-427 | VDGKHQDLKYISPETMVALLTGK (SEQ ID NO: 2) |
| COX2 | COX-2 #32 | p81-96 | FKGFWNVVNNIPFLRN (SEQ ID NO: 3) |
|  | COX-2 #33 | p279-295 | GLVPGLMMYATIWLREH (SEQ ID NO: 4) |
|  | COX-2 #34 | p538-553 | GEVGFQIINTASIQSLIC (SEQ ID NO: 5) |
| EGFR | EGFR #40 | p306-325 | SCVRACGADSYEMEEDGVRK (SEQ ID NO: 11) |
|  | EGFR #41 | p603-619 | NNTLVWKYADAGHVCHL (SEQ ID NO: 12) |
|  | EGFR #42 | p897-915 | VWSYGVTVWELMTFGSKPY (SEQ ID NO: 13) |
| FASCIN1 | Fascin1 #5 | p136-154 | IAMHPQVNIYSVTRKRYAH (SEQ ID NO: 14) |
|  | Fascin1 #6 | p190-209 | TADHRFLRHDGRLVARPEPA (SEQ ID NO: 15) |
|  | Fascin1 #24 | p21-40 | NKYLTAEAFGFKVNASASSL (SEQ ID NO: 16) |
|  | Fascin1 #25 | p274-398 | ELFLMKLINRPIIVFRGEHGFIGCR (SEQ ID NO: 17) |
| IGF1R | IGF1R #1 | p384-398 | VVTGYVKIRHSHALV (SEQ ID NO: 23) |
|  | IGF1R #2 | p575-588 | TQYAVYVKAVTLTMV (SEQ ID NO: 24) |
|  | IGF1R #3 | p951-965 | LVIMLYVFHRKRNNS (SEQ ID NO: 25) |
|  | IGF1R #4 | p1122-1136 | GMAYLNANKFVHRDL (SEQ ID NO: 26) |
| PRL3 | PRL-3 #1 | p12-30 | VSYKHMRFLITHNPTNATL (SEQ ID NO: 27) |
|  | PRL-3 #2 | p33-53 | FIEDLKKYGATTVVRVCEVTY (SEQ ID NO: 28) |
|  | PRL-3 #3 | p104-122 | PCVAGLGRAPVLVALALIES (SEQ ID NO: 29) |

TABLE 6-continued

APCmin survival study in-vivo experiments:
peptides included in vaccine compositions

| Vaccine | Peptide | Peptide sequence | Amino Acid Sequence |
|---|---|---|---|
| | PRL-3 #4 | p124-142 | MKYEDAIQFIRQKRRGAIN (SEQ ID NO: 30) |
| | PRL-3 #29 | p81-95 | VEDWLSLVKAKFCEA (SEQ ID NO: 31) |
| RCAS1 | RCAS1 #13 | p91-110 | EPDYFKDMTPTIRKTQKIVI (SEQ ID NO: 32) |
| | RCAS1 #14 | p93-113 | DYFKDMTPTIRKTQKIVIKKR (SEQ ID NO: 33) |
| | RCAS1 #21 | p8-27 | LFKFCTCLATVFSFLKRLIC (SEQ ID NO: 34) |
| | RCAS1 #30 | p126-148 | GFSSRLAATQDLPFIHQSSELGD (SEQ ID NO: 35) |
| | RCAS1 #31 | p161-181 | EEEDAAWQAEEVLRQQKLADR (SEQ ID NO: 36) |
| VCP | VCP #18 | p82-102 | IRMNRVVRNNLRVRLGDVISI (SEQ ID NO: 37) |
| | VCP #19 | p49-65 | LQLFRGDTVLLKGKKRR (SEQ ID NO: 38) |
| | VCP #20 | p138-156 | YFLEAYRPIRKGDIFLVRG (SEQ ID NO: 39) |
| | VCP #23 | p161-180 | VEFKVVETDPSPYCIVAPDT (SEQ ID NO: 40) |

Figure 36:
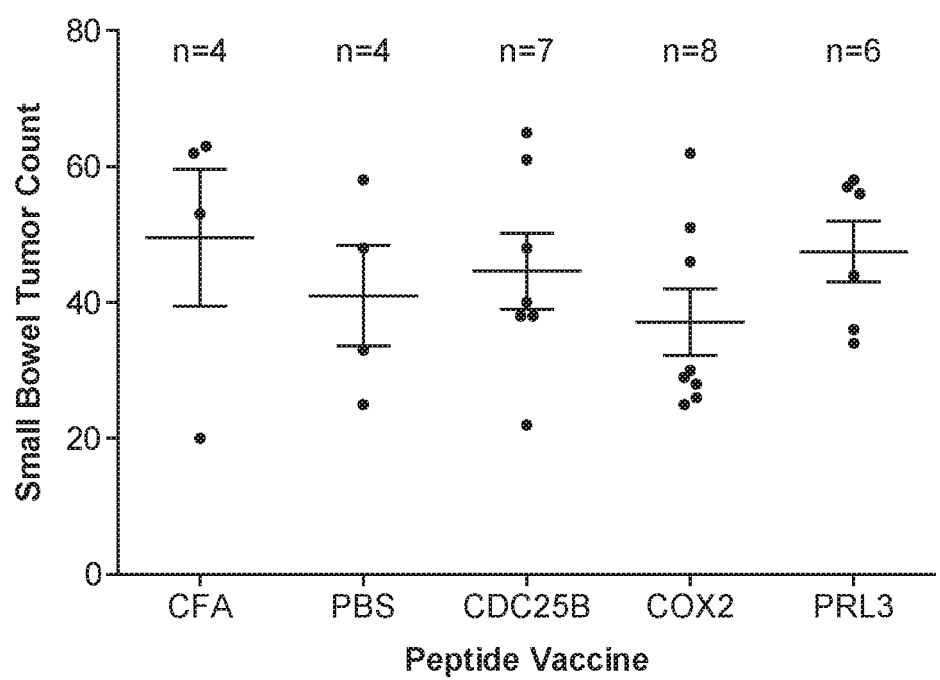
FIG. 36 depicts CDC25B, COX2, and PRL3 vaccine effect on APCmin mice survival.

FIG. 36 shows immunization with the peptides derived from CDC25B, COX2, and PRL3 peptides does not significantly inhibit small bowel tumor burden in APCmin mice. The small bowel tumor count is shown on the y-axis and the APCmin immunized groups are on the x-axis. Each value point represents the number of tumors in the small bowel of one mouse. Calculated p-values using the unpaired, two-tailed student t test were not statistically significant between APCmin mice immunized with CFA/IFA (n=4) and vaccine groups, CDC25B (n=7, p=0.65), COX2 (n=8, p=0.24), PRL3 (n=6, p=0.84).

APCmin toxicology study in-vivo experiments. Blood from APCmin mice immunized with PBS (n=2), CFA (n=3), CDC25B (n=6), COX2 (n=2), and PRL3 (n=2) were transferred to a clot activator tube for serum separation and a lithium heparin tube for plasma. Data from normal C57Bl6/J controls were taken from "The Jackson Laboratory Densitometric survey of 11 inbred strains of mice. MPD:jaxphenol. Mouse Phenome Database web site, The Jackson Laboratory, Bay Harbor, Me. USA. phenome.jax.org, May 2013." P-values were calculated using Tukey's Multiple Comparison Test. *=p<0.05, =p<0.01, *=p<0.001.

Figure 37:
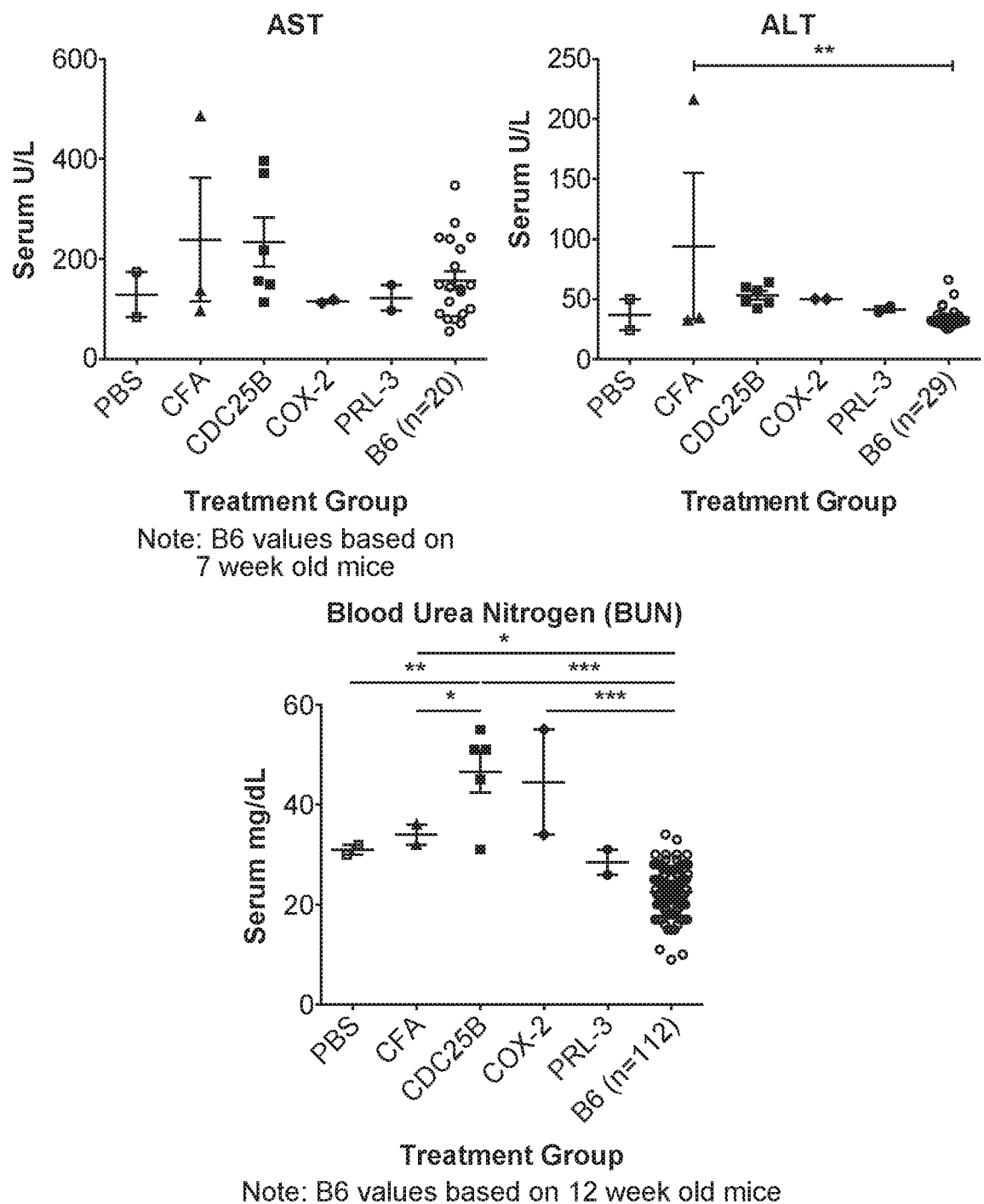
FIG. 37 depicts CDC25B, COX2, and PRL3 vaccine toxicology.
Figure 37:
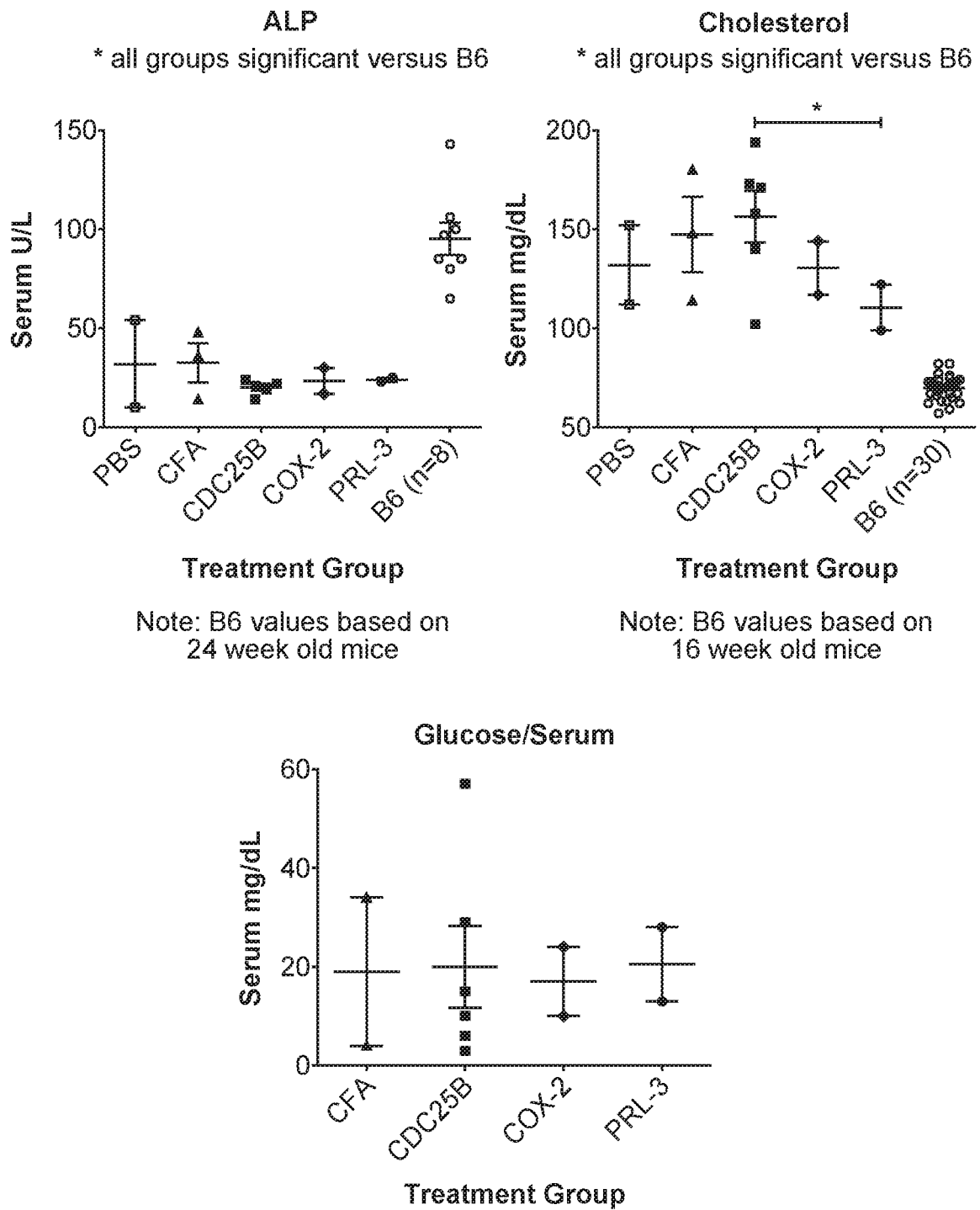

FIG. 37 shows blood from mice immunized with PBS, CFA, CDC25B, COX2, and PRL3 was analyzed for AST, ALT, BUN, ALP, Cholesterol, and Glucose/Serum. The y-axis shows the levels of chemical compounds in serum either in units per liter or milligrams per deciliter. The mouse immunized groups are shown on the x-axis.

APCmin IFN-γ Study In-Vivo Experiments.

96-well MAIPS nitrocellulose plates were pre-soaked in 70% EtOH and incubated overnight with anti-mouse IFN-γ antibody at 10 ug/ml. The next day, the plates were washed three times with PBS and blocked with PBS+2% BSA for 2 hours in a 37 degree Celsius $CO_2$ incubator. The plates were washed three times with PBS and isolated mouse splenocytes plated with $3 \times 10^5$ cells/well (6 replicates/antigen). Antigens were added and the plate was put into a 37 degree Celsius $CO_2$ incubator for 72 hours. Positive controls were PHA (5 ug/ml), PMA/I (2 ug/ml), and CD3 (1:10,000), negative controls were no antigen wells, and all peptides were added at 20 ug/ml. The plates were washed once with 1xPBS, and then washed twice with PBS+0.05% Tween buffer.

Figure 38:
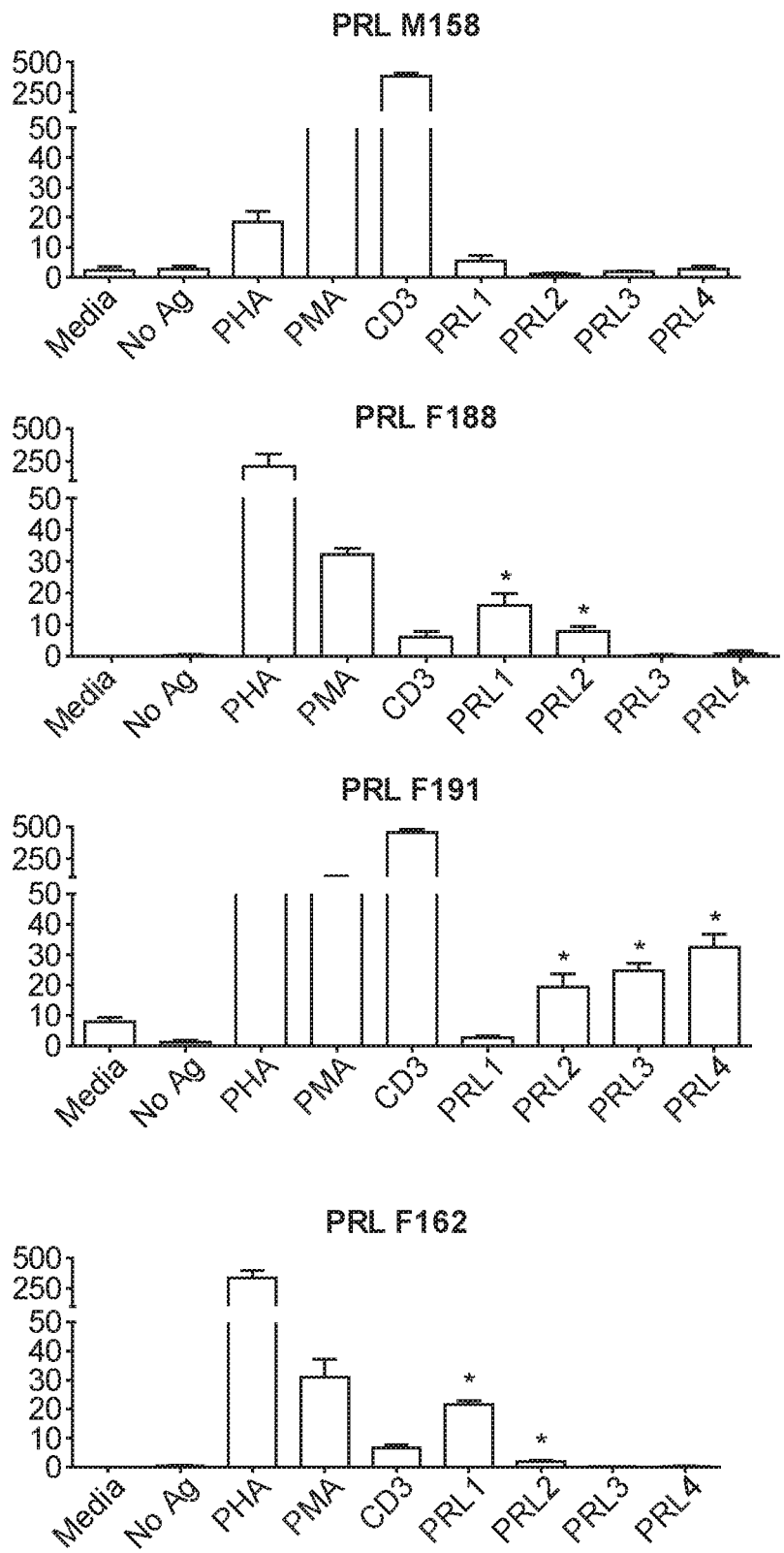
FIG. 38 depicts ELISpot results for APCmin mice immunized with PRL3.
Figure 38:
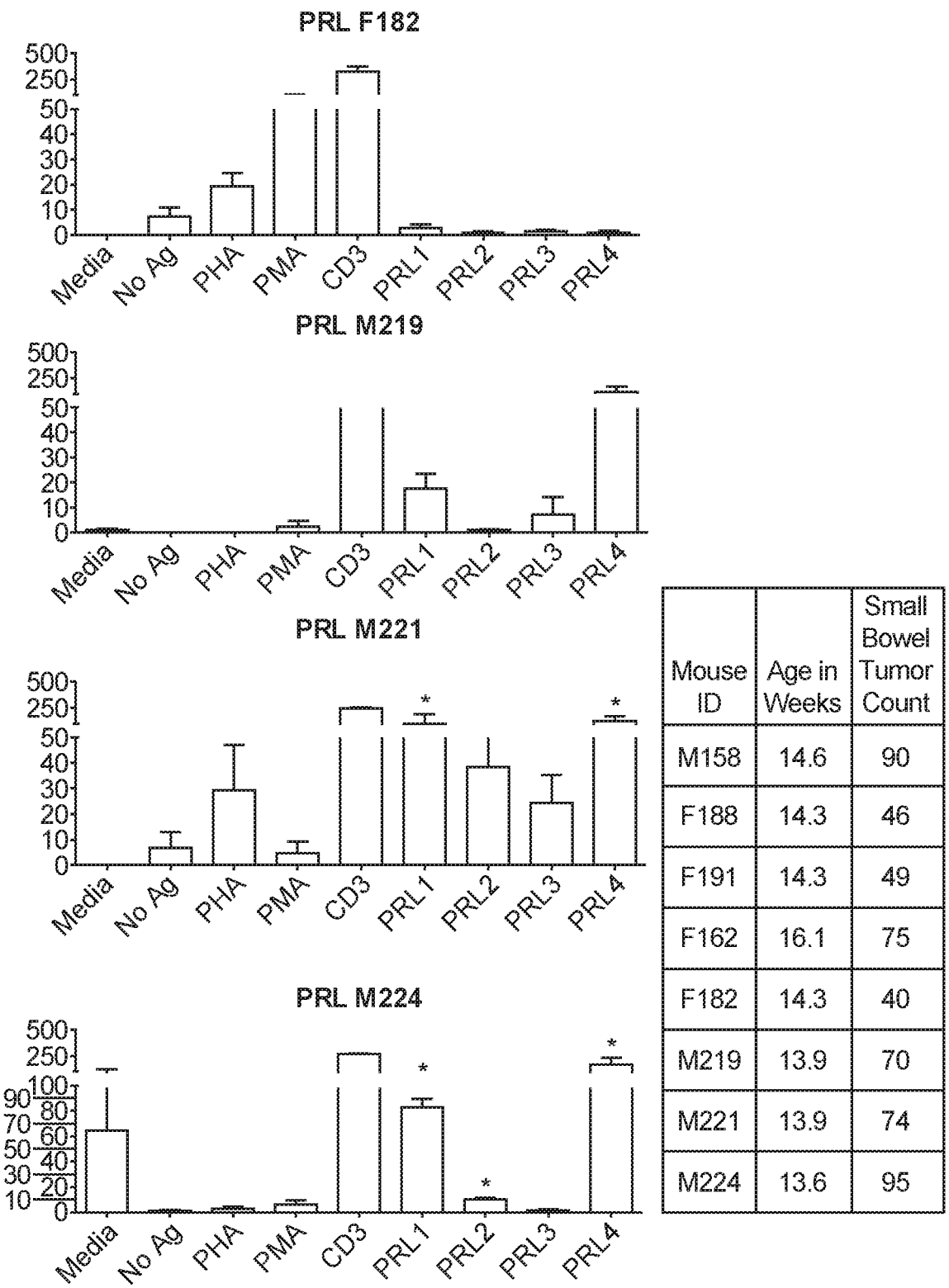
Figure 39:
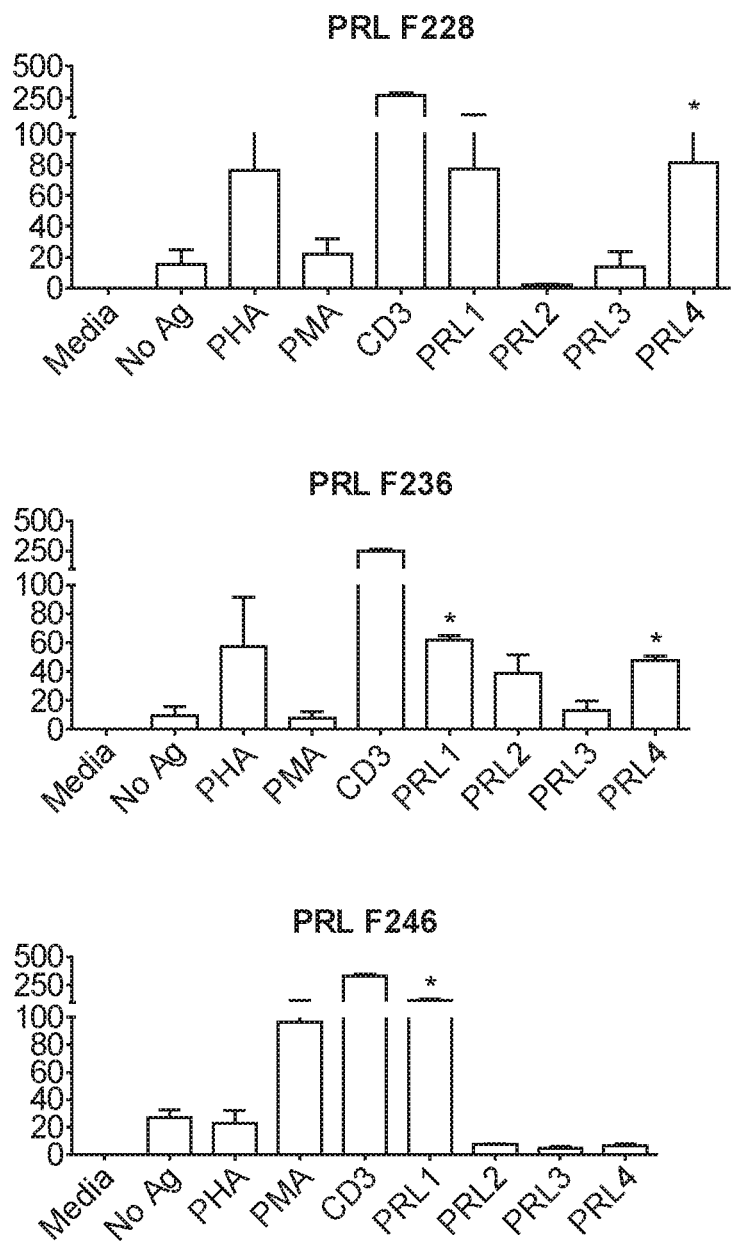
FIG. 39 depicts ELISpot results for APCmin mice immunized with PRL3.
Figure 39:
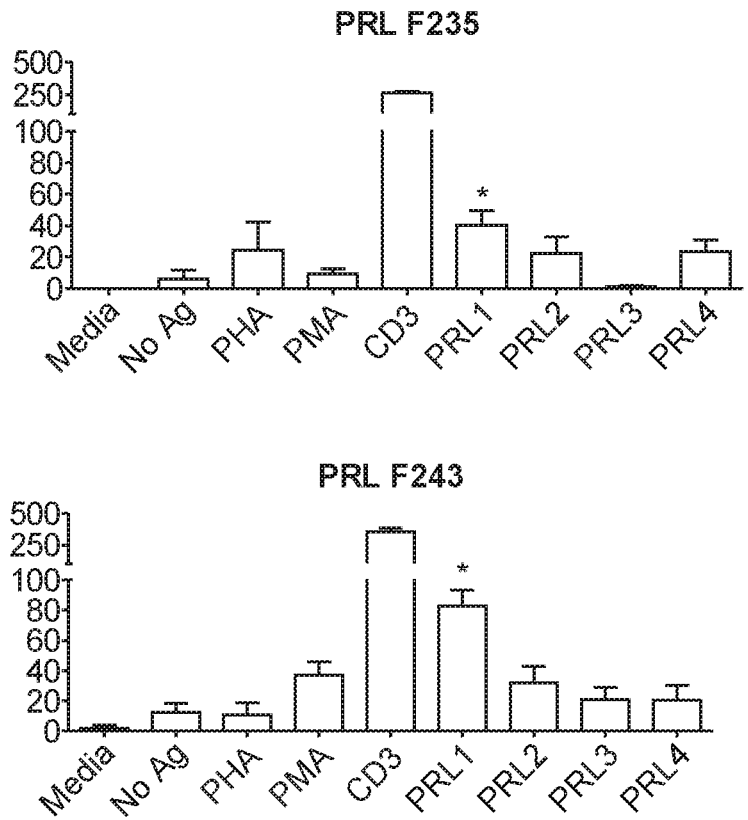

For FIGS. 38-39, IFN-γ responses to immunization of PRL3 peptides are shown with the average spots per well (6 well replicates) on the y-axis and the antigens used to stimulate the t-cells are on the x-axis. The asterisk (*) above columns indicates significance compared to no antigen wells using the unpaired, two-tailed student's t test, p<0.05. The table adjacent to the ELISpot figures shows the age in weeks at sacrifice and small bowel tumor counts of individual immunized mice. FIG. 38 shows IFN-γ responses for 8 mice (M158, F188, F191, F162, F182, M219, M221, and M224) immunized with PRL3 antigens. FIG. 39 shows IFN-γ responses for 5 mice (F228, F236, F246, F235, and F243) immunized with PRL3 antigens.

AOM Mouse Model.

AOM mouse in-vivo experiments. At 6 weeks of age, FVB mice were immunized in CFA/IFA, PBS, and vaccine groups. Each group received subcutaneous injections (100 ul PBS, 50 ul CFA with 50 ul PBS, 50 ug per peptide with 50 ul CFA) once every 10-14 days for a total of three doses and a booster was given every 4-5 weeks after the third vaccine. See Table 7 for peptides included in vaccine compositions. CFA was replaced with IFA after the first vaccine. Seven days after the third vaccine, mice were injected with Azoxymethane (AOM) at 10 mg/kg, twice weekly for 6 weeks. At 26 weeks of age, all mice were sacrificed and tumors in the colon were counted.

TABLE 7

AOM mouse in-vivo experiments:
peptides included in vaccine compositions

| Vaccine | Peptide | Peptide sequence | Amino Acid Sequence |
|---|---|---|---|
| CDC25B | CDC25B #38 | p130-150 | QAIQAASRIIRNEQFAIRRFQ (SEQ ID NO: 1) |
|  | CDC25B #39 | p405-427 | VDGKHQDLKYISPETMVALLTGK (SEQ ID NO: 2) |
| COX2 | COX-2 #32 | p81-96 | FKGFWNVVNNIPFLRN (SEQ ID NO: 3) |
|  | COX-2 #33 | p279-295 | GLVPGLMMYATIWLREH (SEQ ID NO: 4) |
|  | COX-2 #34 | p538-553 | GEVGFQIINTASIQSLIC (SEQ ID NO: 5) |
| EGFR | EGFR #40 | p306-325 | SCVRACGADSYEMEEDGVRK (SEQ ID NO: 11) |
|  | EGFR #41 | p603-619 | NNTLVWKYADAGHVCHL (SEQ ID NO: 12) |
|  | EGFR #42 | p897-915 | VWSYGVTVWELMTFGSKPY (SEQ ID NO: 13) |
| FASCIN1 | Fascin1 #5 | p136-154 | IAMHPQVNIYSVTRKRYAH (SEQ ID NO: 14) |
|  | Fascin1 #6 | p190-209 | TADHRFLRHDGRLVARPEPA (SEQ ID NO: 15) |
|  | Fascin1 #24 | p21-40 | NKYLTAEAFGFKVNASASSL (SEQ ID NO: 16) |
|  | Fascin1 #25 | p274-398 | ELFLMKLINRPIIVFRGEHGFIGCR (SEQ ID NO: 17) |
| IGF1R | IGF1R #1 | p384-398 | VVTGYVKIRHSHALV (SEQ ID NO: 23) |
|  | IGF1R #2 | p575-588 | TQYAVYVKAVTLTMV (SEQ ID NO: 24) |
|  | IGF1R #3 | p951-965 | LVIMLYVFHRKRNNS (SEQ ID NO: 25) |
|  | IGF1R #4 | p1122-1136 | GMAYLNANKFVHRDL (SEQ ID NO: 26) |
| PRL3 | PRL-3 #1 | p12-30 | VSYKHMRFLITHNPTNATL (SEQ ID NO: 27) |
|  | PRL-3 #2 | p33-53 | FIEDLKKYGATTVVRVCEVTY (SEQ ID NO: 28) |
|  | PRL-3 #3 | p104-122 | PCVAGLGRAPVLVALALIES (SEQ ID NO: 29) |
|  | PRL-3 #4 | p124-142 | MKYEDAIQFIRQKRRGAIN (SEQ ID NO: 30) |
|  | PRL-3 #29 | p81-95 | VEDWLSLVKAKFCEA (SEQ ID NO: 31) |
| RCAS1 | RCAS1 #13 | p91-110 | EPDYFKDMTPTIRKTQKIVI (SEQ ID NO: 32) |
|  | RCAS1 #14 | p93-113 | DYFKDMTPTIRKTQKIVIKKR (SEQ ID NO: 33) |
|  | RCAS1 #21 | p8-27 | LFKFCTCLATVFSFLKRLIC (SEQ ID NO: 34) |
|  | RCAS1 #30 | p126-148 | GFSSRLAATQDLPFIHQSSELGD (SEQ ID NO: 35) |
|  | RCAS1 #31 | p161-181 | EEEDAAWQAEEVLRQQKLADR (SEQ ID NO: 36) |
| VCP | VCP #18 | p82-102 | IRMNRVVRNNLRVRLGDVISI (SEQ ID NO: 37) |
|  | VCP #19 | p49-65 | LQLFRGDTVLLKGKKRR (SEQ ID NO: 38) |
|  | VCP #20 | p138-156 | YFLEAYRPIRKGDIFLVRG (SEQ ID NO: 39) |
|  | VCP #23 | p161-180 | VEFKVVETDPSPYCIVAPDT (SEQ ID NO: 40) |

Figure 40:
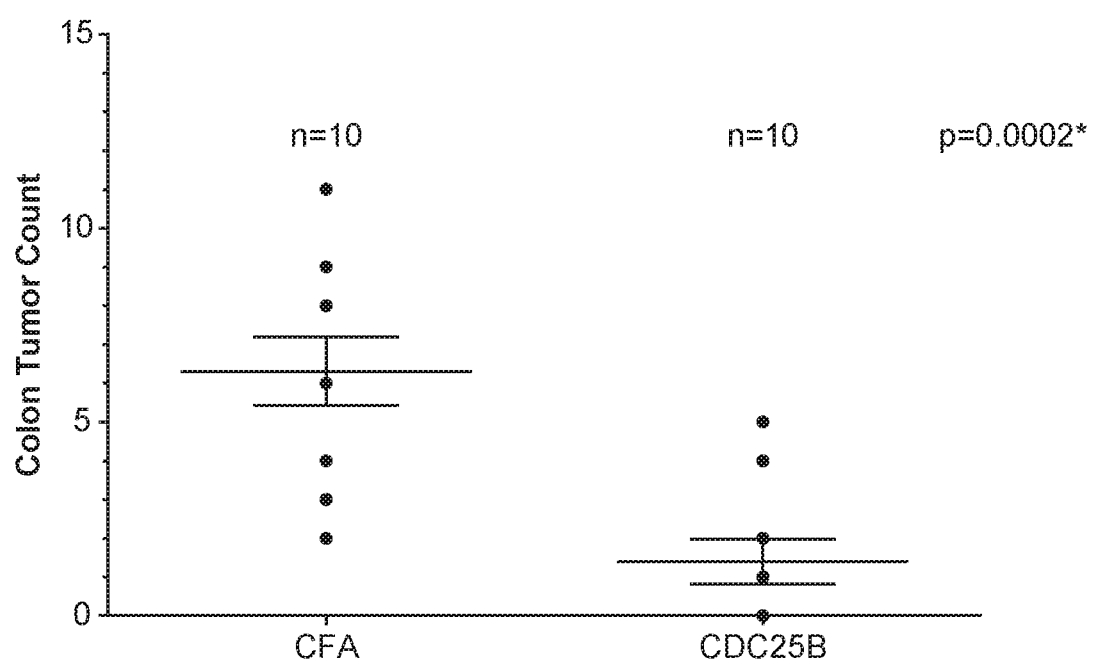
FIG. 40 shows CDC25B vaccine efficacy on colon tumor count in AOM mice.

FIG. 40 shows immunization with the peptides derived from CDC25B significantly inhibits colon tumor burden in AOM mice. The colon tumor count is shown in the y-axis and the AOM immunized groups are on the x-axis. Calculated p-values using the unpaired, two-tailed student t test were statistically significant between AOM mice immunized with CFA/IFA (n=10) and CDC25B (group n=10), p=0.002.

Figure 41:
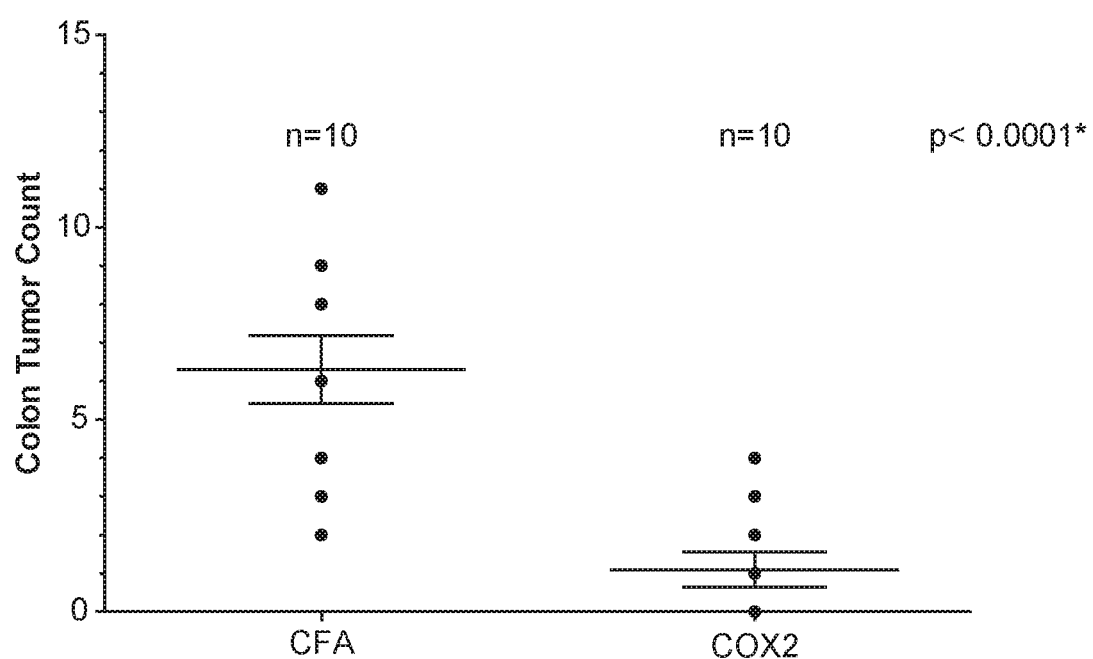
FIG. 41 shows COX2 vaccine efficacy on colon tumor count in AOM mice.

FIG. 41 shows immunization with the peptides derived from COX2 significantly inhibits colon tumor burden in AOM mice. The colon tumor count is shown in the y-axis and the AOM immunized groups are on the x-axis. Calculated p-values using the unpaired, two-tailed student t test were statistically significant between AOM mice immunized with CFA/IFA (n=10) and COX2 (group n=10), p<0.0001.

Figure 42:
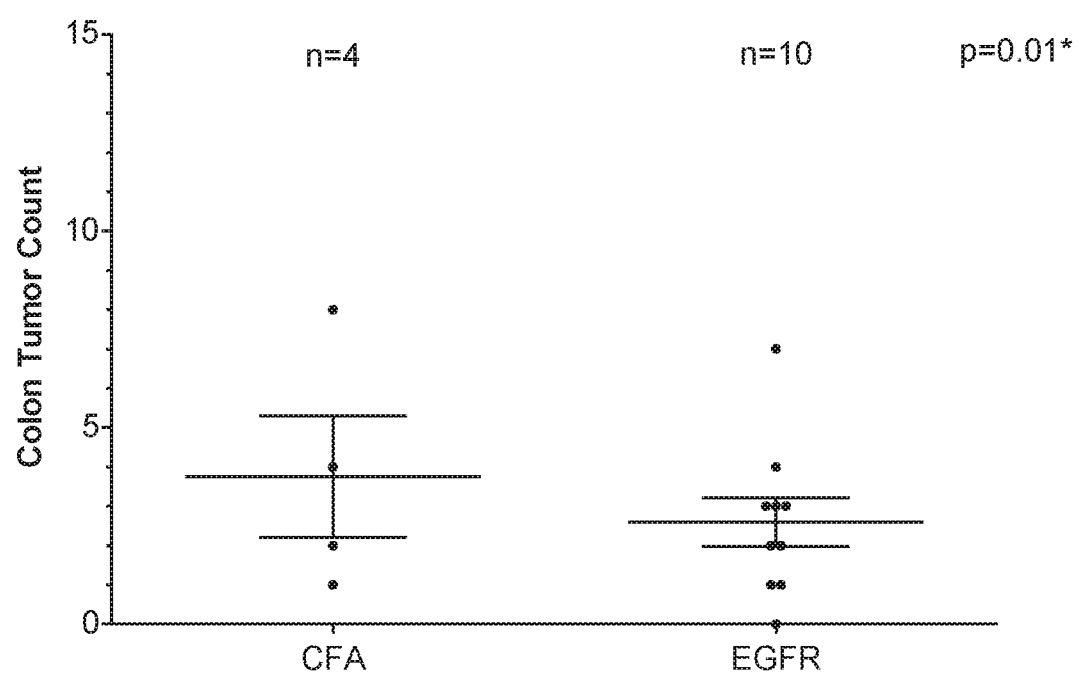
FIG. 42 shows EGFR vaccine efficacy on colon tumor count in AOM mice.

FIG. 42 shows immunization with the peptides derived from EGFR significantly inhibits colon tumor burden in AOM mice. The colon tumor count is shown in the y-axis and the AOM immunized groups are on the x-axis. Calculated p-values using the unpaired, two-tailed student t test were statistically significant between AOM mice immunized with CFA/IFA (n=4) and EGFR (group n=10), p=0.01.

Figure 43:
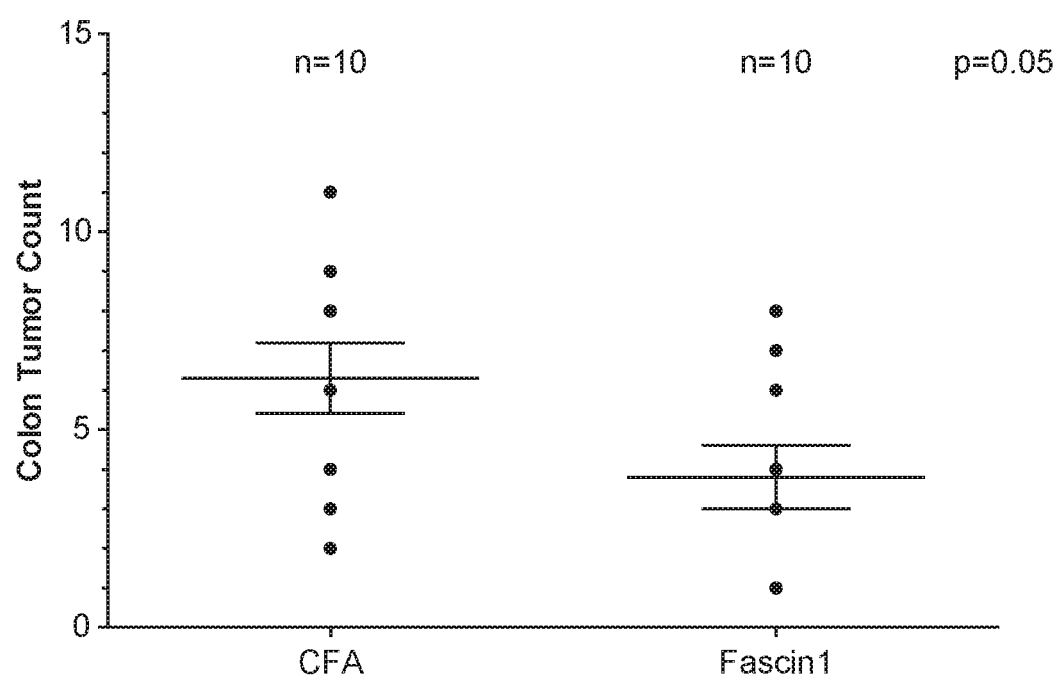
FIG. 43 shows lack of FASCIN1 vaccine efficacy on colon tumor count in AOM mice.

FIG. 43 shows immunization with the peptides derived from FASCIN1 does not significantly inhibit colon tumor burden in AOM mice. The colon tumor count is shown in the y-axis and the AOM immunized groups are on the x-axis. Calculated p-values using the unpaired, two-tailed student t test were statistically significant between AOM mice immunized with CFA/IFA (n=10) and FASCIN1 (group n=10), p=0.05.

Figure 44:
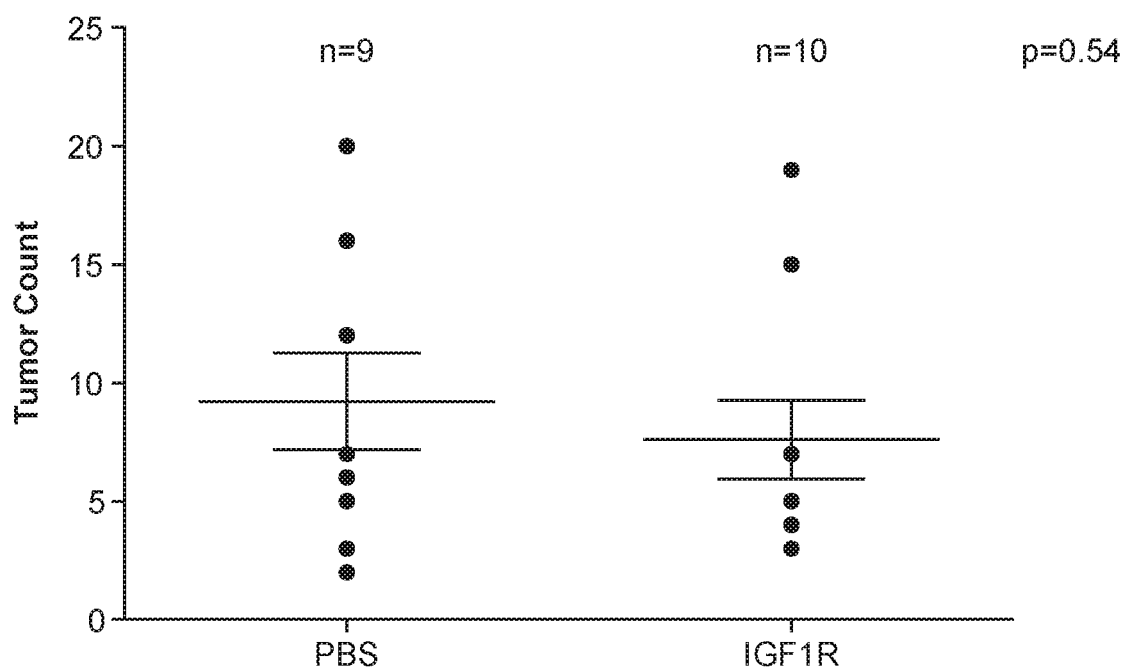
FIG. 44 shows lack of IGF1R vaccine efficacy on colon tumor count in AOM mice.

FIG. 44 shows immunization with the peptides derived from IGF1R does not significantly inhibit colon tumor burden in AOM mice. The colon tumor count is shown in the y-axis and the AOM immunized groups are on the x-axis. Calculated p-values using the unpaired, two-tailed student t test were statistically significant between AOM mice immunized with PBS (n=9) and IGF1R (group n=10), p=0.54. P-values are compared to PBS control group, CFA control group died due to AOM overdose.

Figure 45:
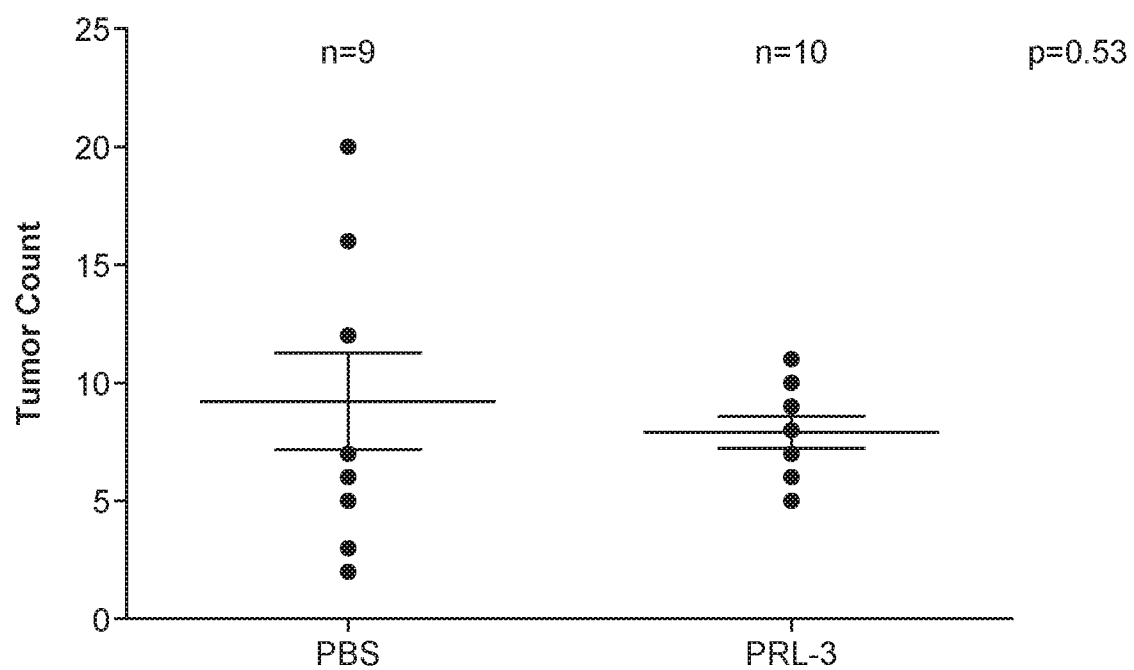
FIG. 45 shows lack of PRL3 vaccine efficacy on colon tumor count in AOM mice.

FIG. 45 shows immunization with the peptides derived from PRL3 does not significantly inhibit colon tumor burden in AOM mice. The colon tumor count is shown in the y-axis and the AOM immunized groups are on the x-axis. Calculated p-values using the unpaired, two-tailed student t test were statistically significant between AOM mice immunized with PBS (n=9) and PRL3 (group n=10), p=0.53. P-values are compared to PBS control group, CFA control group died due to AOM overdose.

Figure 46:
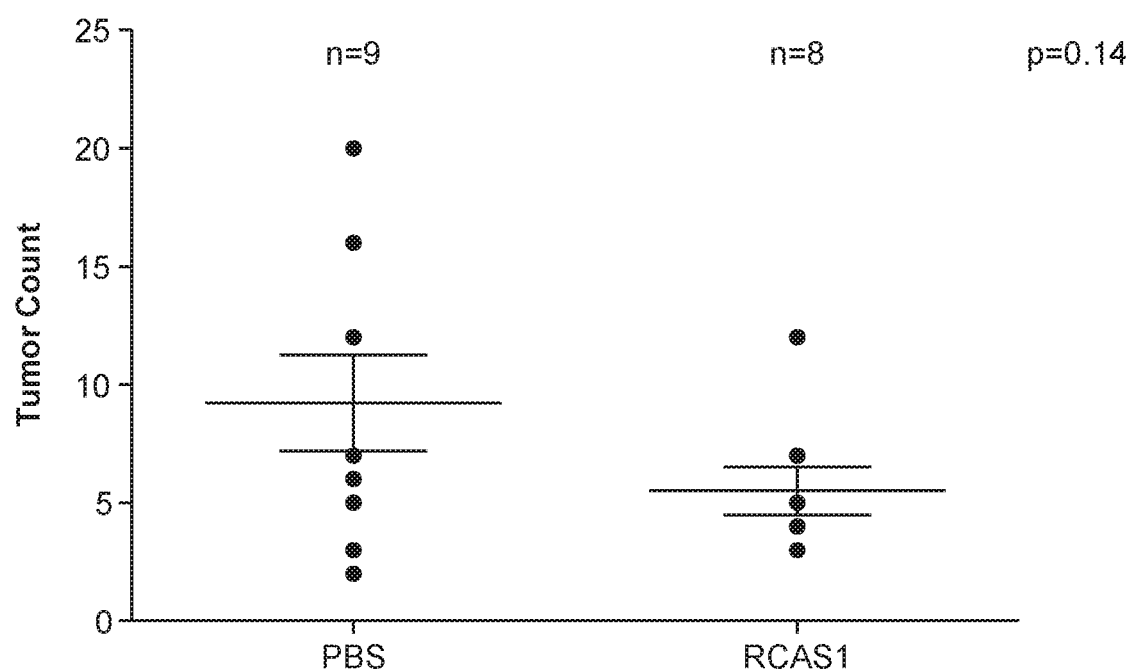
FIG. 46 shows lack of RCAS1 vaccine efficacy on colon tumor count in AOM mice.

FIG. 46 shows immunization with the peptides derived from RCAS1 do not significantly inhibit colon tumor burden in AOM mice. The colon tumor count is shown in the y-axis and the AOM immunized groups are on the x-axis. Calculated p-values using the unpaired, two-tailed student t test were statistically significant between AOM mice immunized with PBS (n=9) and RCAS1 (group n=8), p=0.14. P-values are compared to PBS control group, CFA control group died due to AOM overdose.

Figure 47:
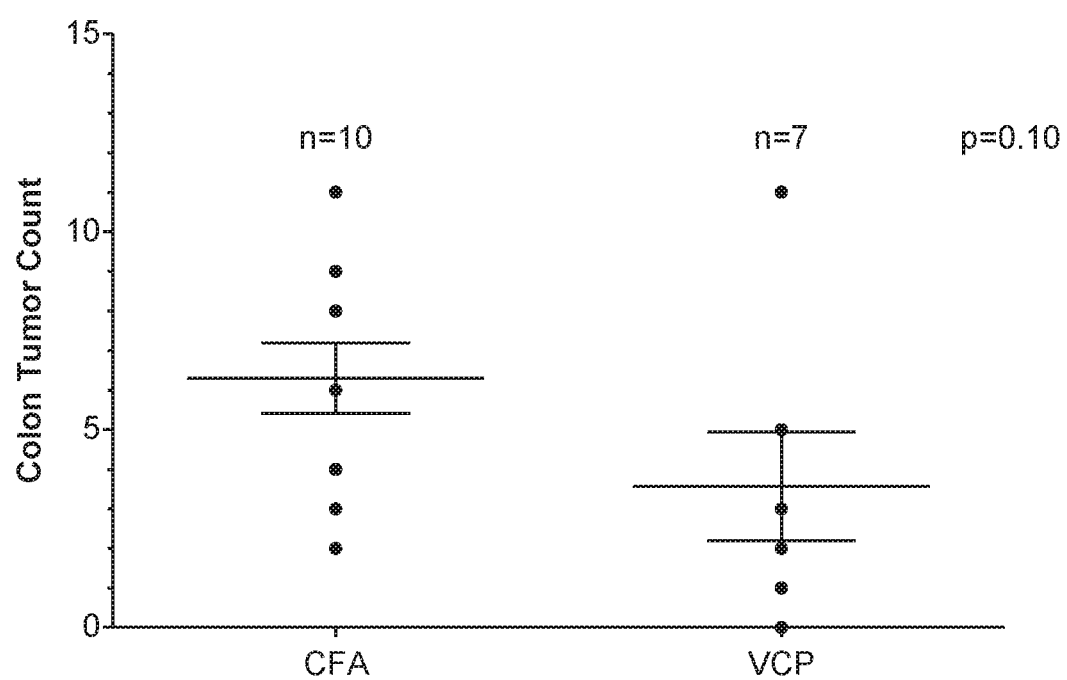
FIG. 47 shows lack of VCP vaccine efficacy on colon tumor count in AOM mice.

FIG. 47 shows immunization with the peptides derived from VCP does not significantly inhibit colon tumor burden in AOM mice. The colon tumor count is shown in the y-axis and the AOM immunized groups are on the x-axis. Calculated p-values using the unpaired, two-tailed student t test were statistically significant between AOM mice immunized with CFA/IFA (n=10) and VCP (group n=7), p=0.1.

Figure 48:
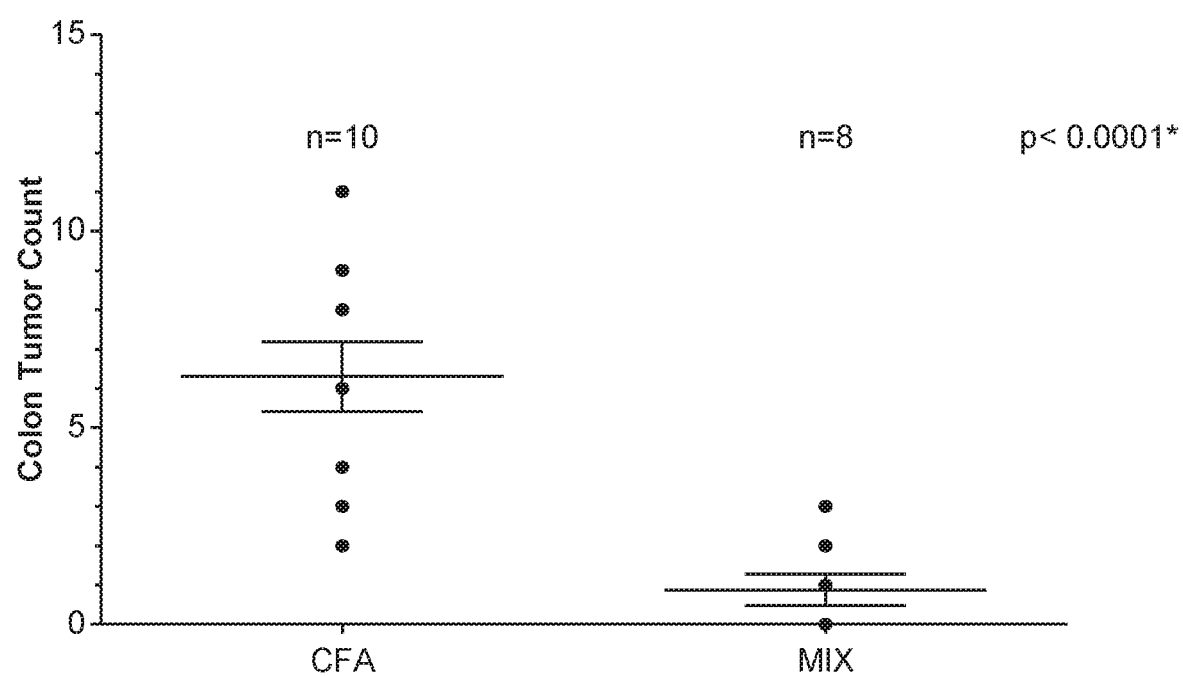
FIG. 48 shows MIX vaccine efficacy on colon tumor count in AOM mice.

FIG. 48 shows immunization with the peptides derived from MIX, a combination of CDC25B, COX2, and PRL3, significantly inhibits colon tumor burden in AOM mice. The colon tumor count is shown in the y-axis and the AOM immunized groups are on the x-axis. Calculated p-values using the unpaired, two-tailed student t test were statistically significant between AOM mice immunized with CFA/IFA (n=10) and MIX (group n=8), p<0.0001.

AOM IFN-γ Study In-Vivo Experiments.

96-well MAIPS nitrocellulose plates were pre-soaked in 70% EtOH and incubated overnight with anti-mouse IFN-γ antibody at 10 ug/ml. The next day, the plates were washed three times with PBS and blocked with PBS+2% BSA for 2 hours in a 37 degree Celsius $CO_2$ incubator. The plates were washed three times with PBS and isolated mouse splenocytes plated with $3 \times 10^5$ cells/well (6 replicates/antigen). Antigens were added and the plate was put in a 37 degree Celsius $CO_2$ incubator for 72 hours. Positive controls were PHA (5 ug/ml), PMA/I (2 ug/ml), and CD3 (1:10,000), negative controls were no antigen wells, and all peptides were added at 20 ug/ml. The plates were washed once with 1×PBS, and then washed twice with PBS+0.05% Tween buffer. Anti-mouse IFN-γ antibody at 5 ug/ml in PBS+0.05% Tween was added to each well and the plate incubated overnight at 4 degrees Celsius. The plates were washed twice with PBS+0.05% Tween then once with PBS. Diluted streptavidin-HRP was added to the plates and incubated at RT for 45 minutes. The plates were developed using AEC ELISPOT Substrate kit. An increase in the number of protein specific IFN-γ producing spots that was statistically different compared to no antigen control wells and/or controls (p<0.05) was taken as an indication of immune response.

Figure 49:
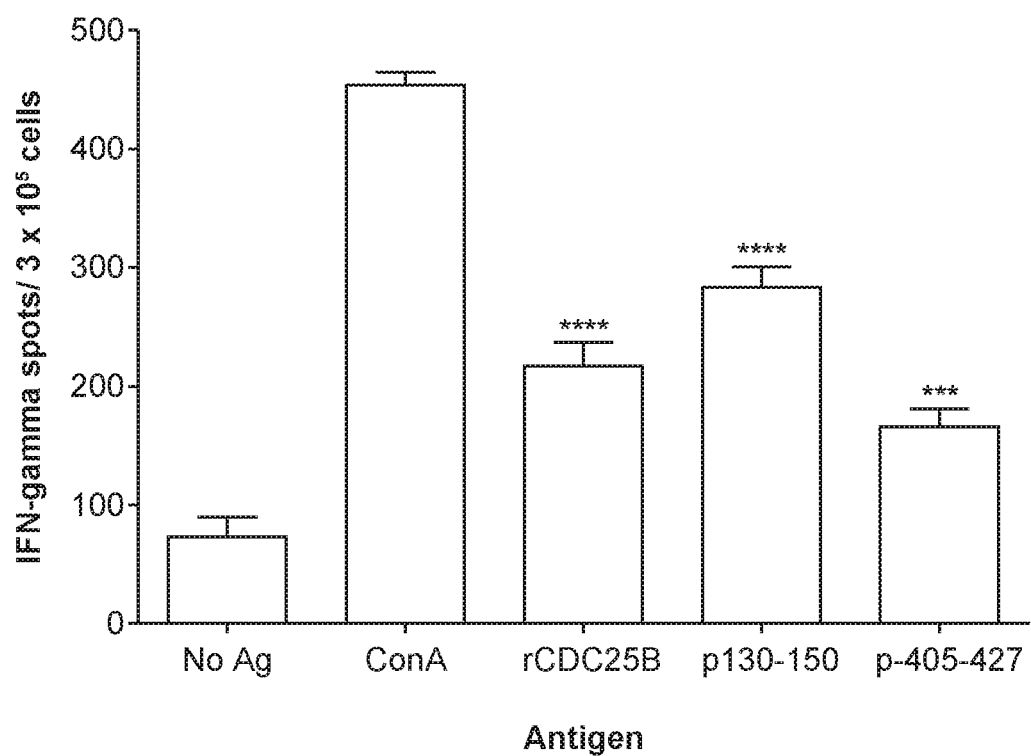
FIG. 49 demonstrates ELISpot results for AOM mice immunized with CDC25B.
Figure 50:
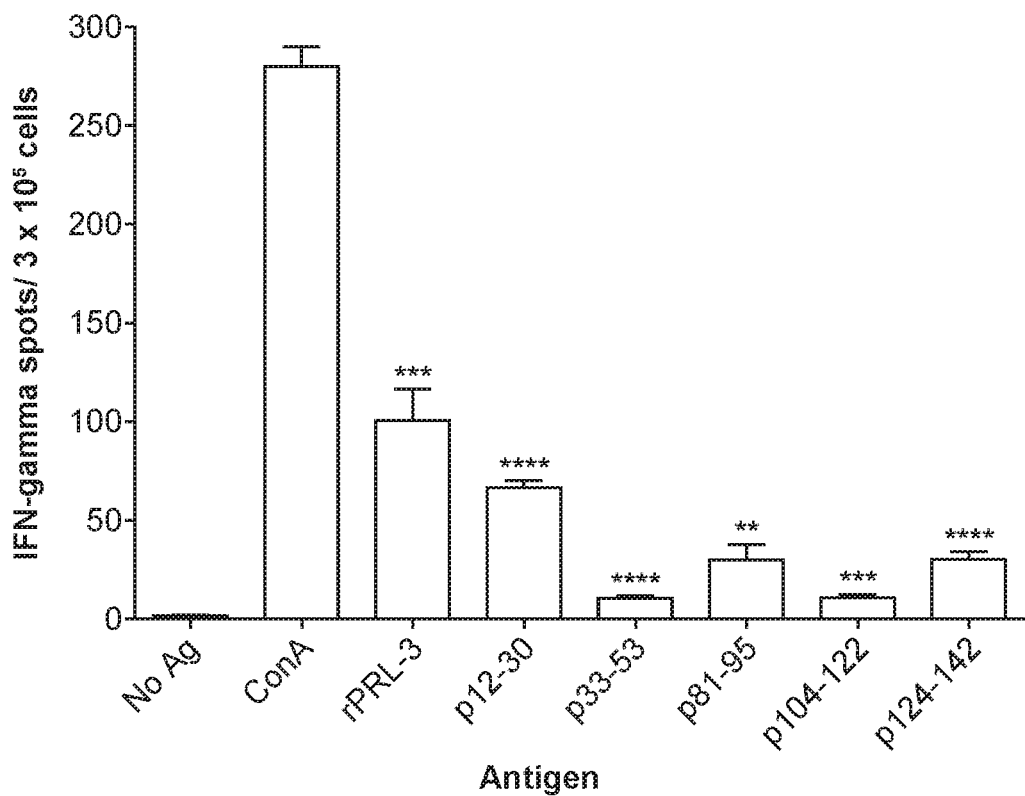
FIG. 50 demonstrates ELISpot results for AOM mice immunized with PRL3.
Figure 51:
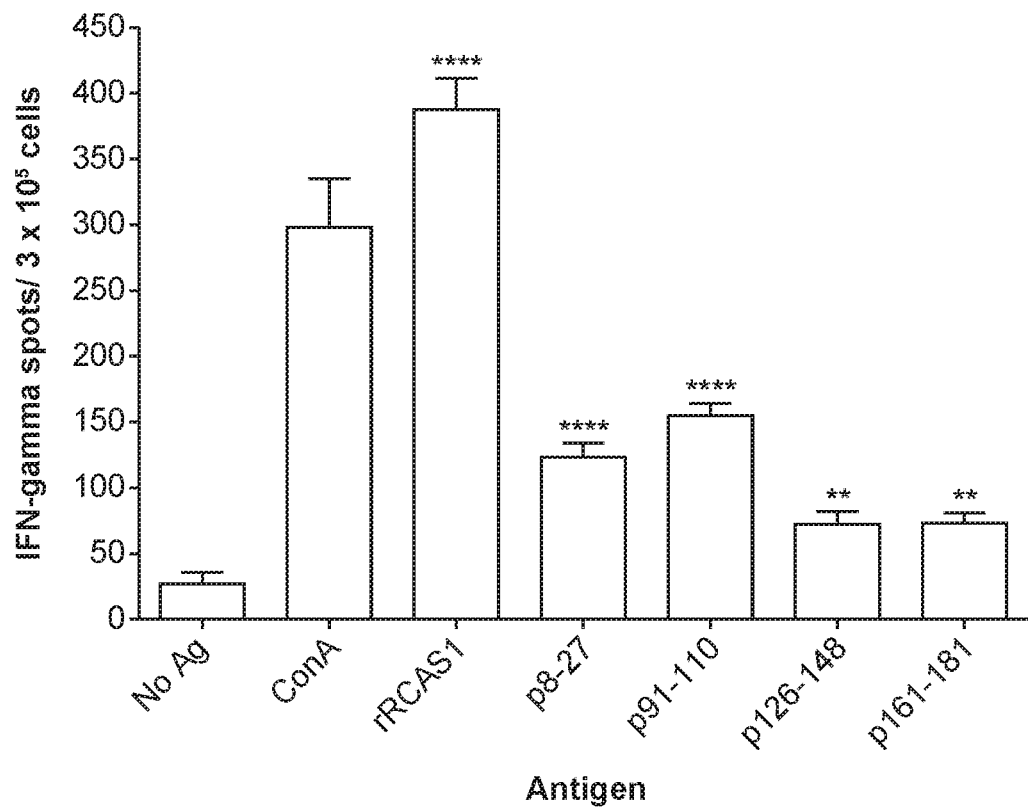
FIG. 51 demonstrates ELISpot results for AOM mice immunized with RCAS1.

For FIGS. 49-51, IFN-γ responses to immunization of peptides are shown with the pool of n=3 mice and average spots per well (6 well replicates) on the y-axis and the antigens used to stimulate the t-cells are on the x-axis. The asterisk (*) above columns indicates the significance compared to no antigen wells using the unpaired, two-tailed student's t test, p<0.05. The table adjacent to the ELISpot figures shows the age in weeks at sacrifice and colon tumor counts of individual immunized mice. FIG. 49 shows IFN-γ responses for three mice (F31, F32, and F38) immunized with CDC25B antigens: CDC25B, p130-150, and p405-427. FIG. 50 shows IFN-γ responses for three mice (F91, F93, F95) immunized with PRL3 antigens: PRL-3, p12-30, p33-53, p81-95, p104-122, and p124-142. FIG. 51 shows IFN-γ responses for three mice (F121, F124, and F126) immunized with RCAS1 antigens: RCAS1, p8-27, p91-110, p126-148, and p161-181.

Figure 52:
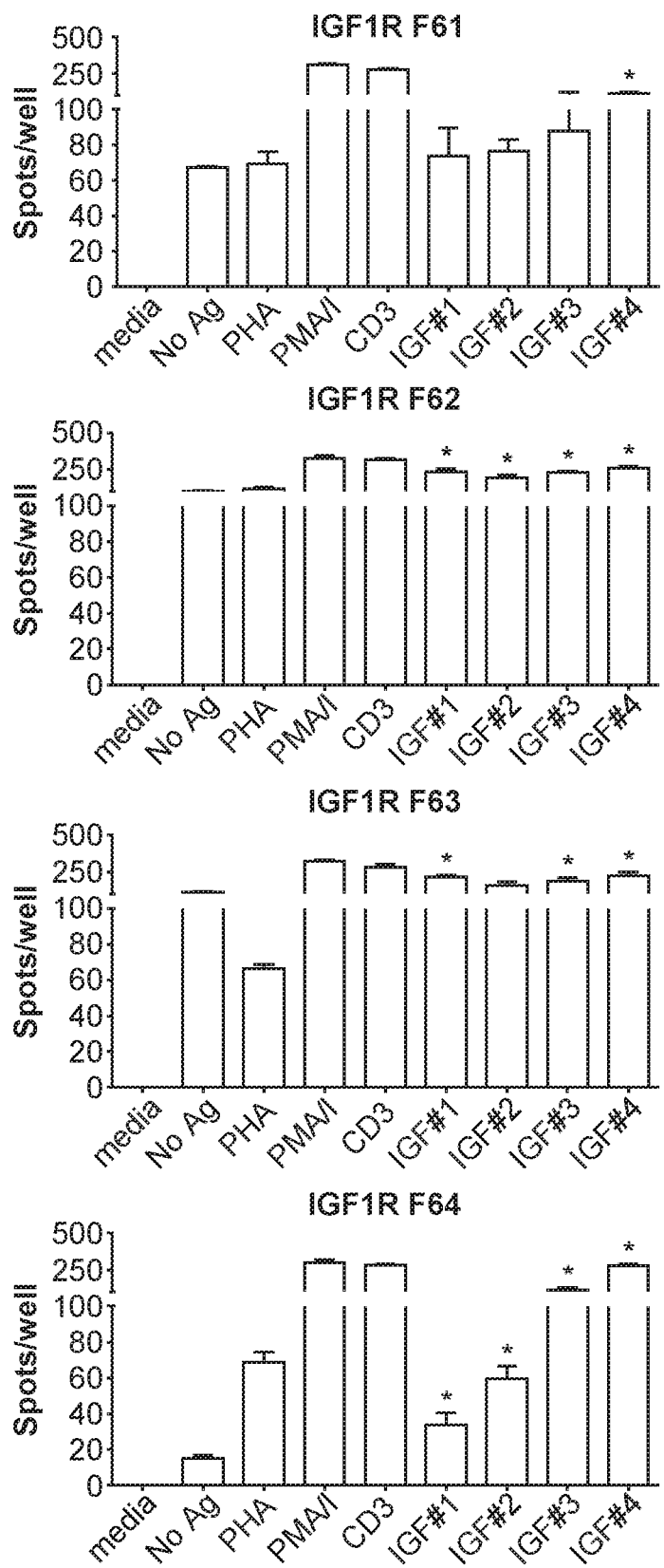
FIG. 52 demonstrates ELISpot results for AOM mice immunized with IGF1R.
Figure 53:
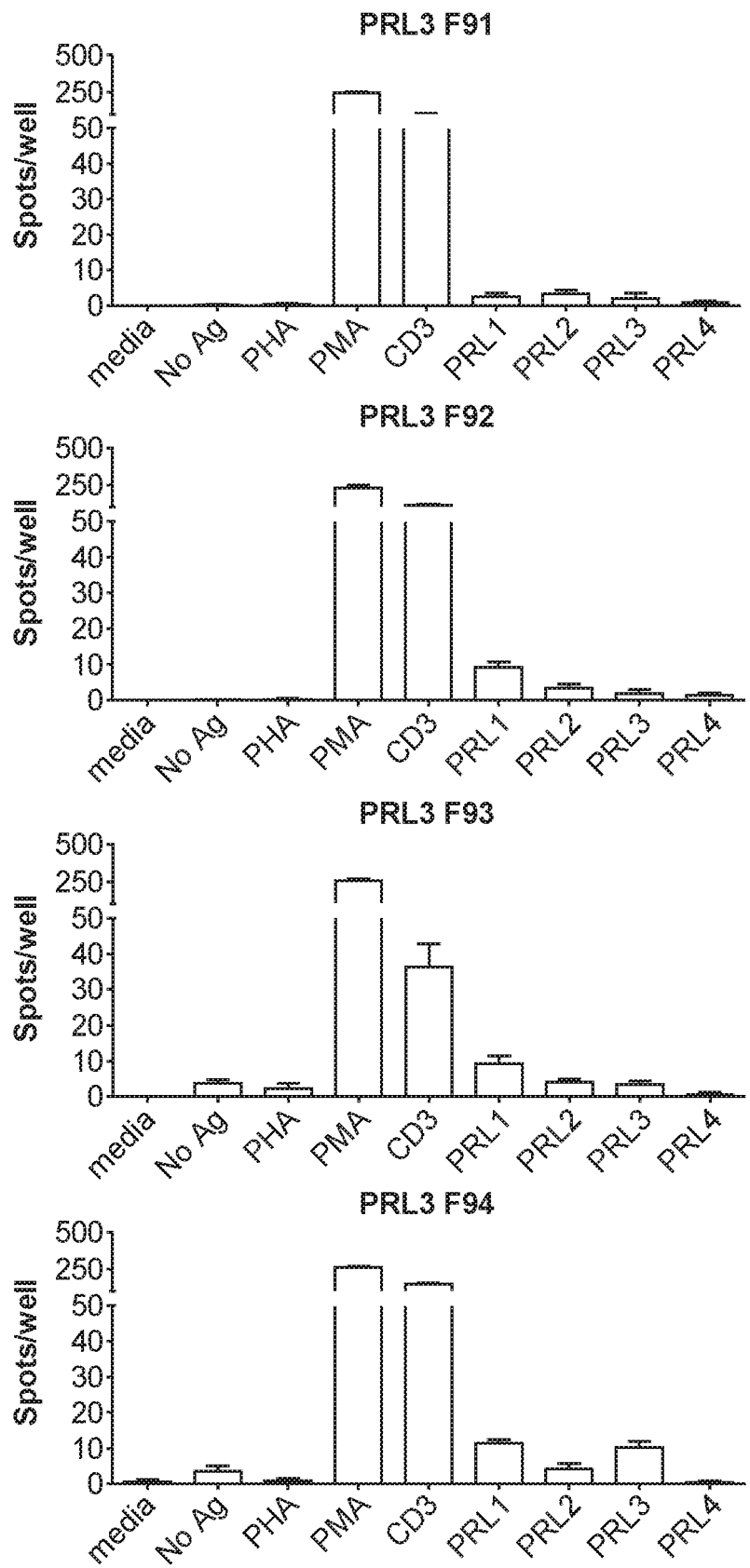
FIG. 53 demonstrates ELISpot results for AOM mice immunized with PRL3.
Figure 54:
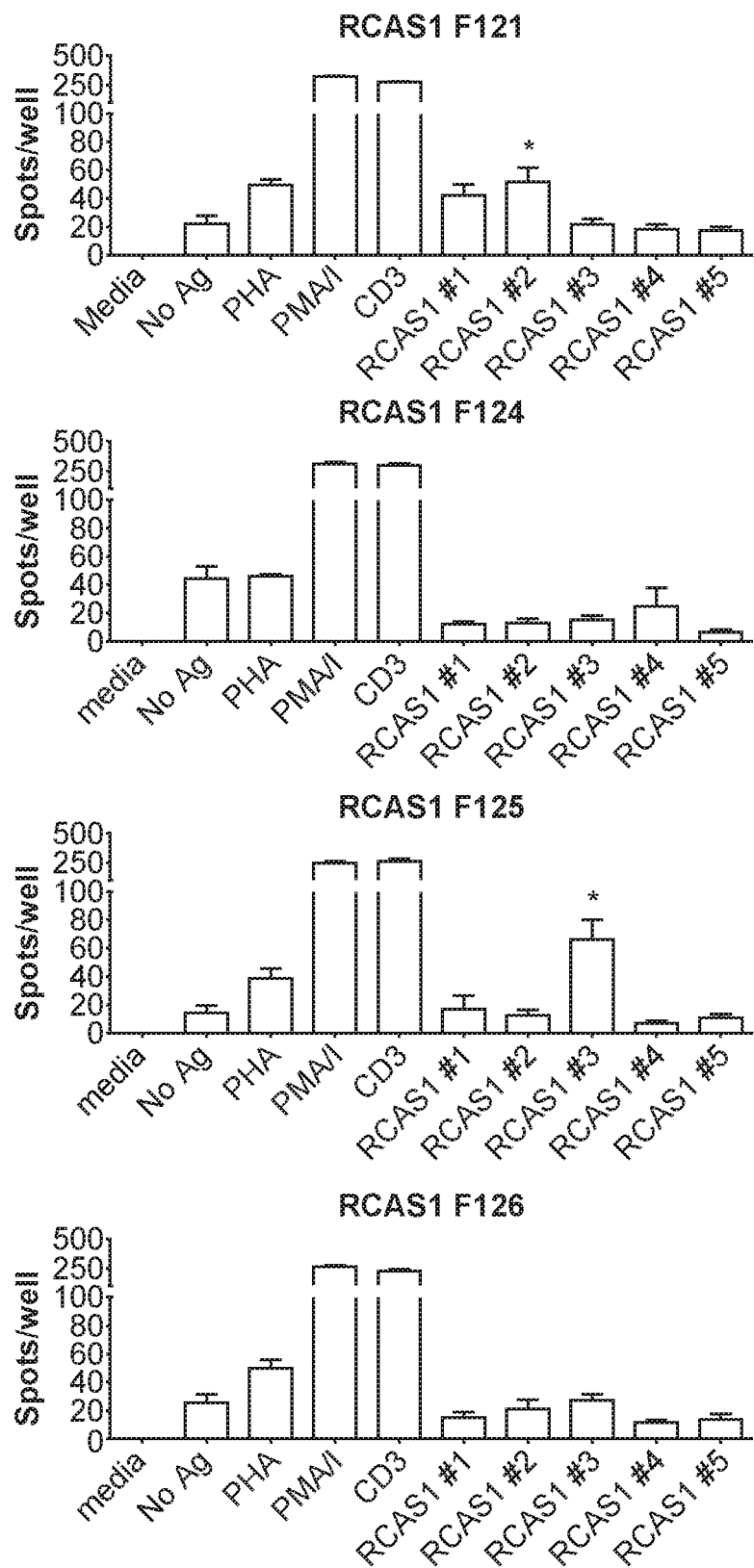
FIG. 54 demonstrates ELISpot results for AOM mice immunized with RCAS1.
Figure 54:
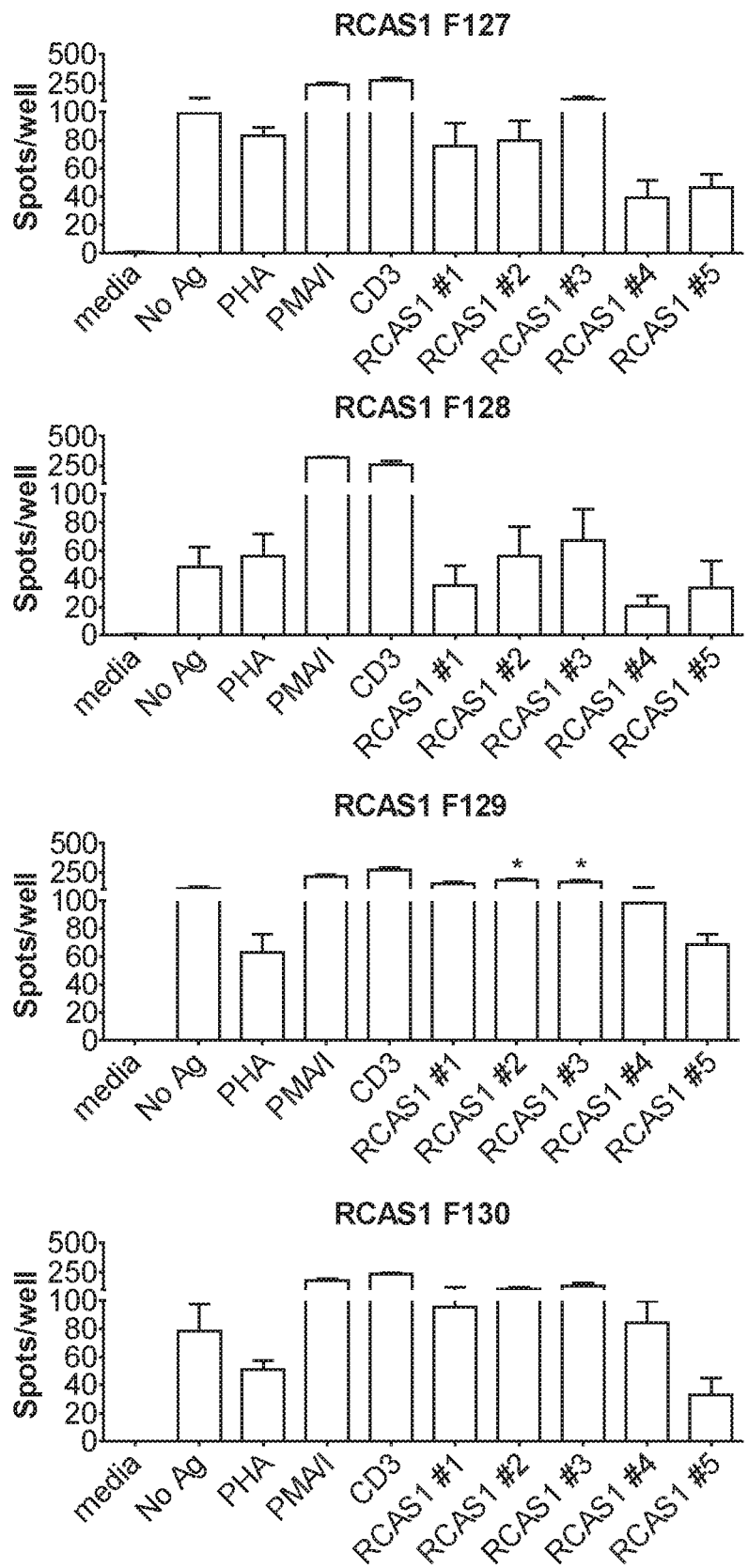

For FIGS. 52-54, IFN-γ responses to immunization of IGF1R peptides are shown with the average spots per well (6 well replicates) on the y-axis and the antigens used to stimulate the t-cells are on the x-axis. The asterisk (*) above columns indicates significance compared to no antigen wells using the unpaired, two-tailed student's t test, p<0.05. The table adjacent to the ELISpot figures shows the age in weeks at sacrifice and colon tumor counts of individual immunized mice. FIG. 52 shows IFN-γ responses for 10 mice (F61, F62, F63, F64, F65, F66, F67, F68, F69, and F70) immunized with IGF1R. FIG. 53 shows IFN-γ responses for 10 mice (F91, F92, F93, F94, F95, F96, F97, F98, F99, and F100) immunized with PRL3. FIG. 54 shows IFN-γ responses for 8 mice (F121, F124, F125, F127, F128, F129, and F130) immunized with RCAS1.

AOM mRNA Study In-Vivo Experiments.

Total RNA was isolated from immunized mice and gene expression quantitated as previously described (Broussard, 2013). Table 8 shows the specific mRNA primers used.

TABLE 8

AOM mRNA study: mRNA Primers

| Primer | Species | Assay ID | Lot # | Sequence |
|---|---|---|---|---|
| Gapdh | Mouse | Mm99999915_g1 | 872515 | TGAACGGATTTGGCCGTATTGGGCG (SEQ ID NO: 49) |
| beta-actin | Mouse | Mm00607939_s1 | 1149103 | ACTGAGCTGCGTTTTACACCCTTTC (SEQ ID NO: 50) |
| CDC25B | Mouse | Mm00499136_m1 | 625264 | GCAGAGCGCACGTTTGAACAGGCCA (SEQ ID NO: 51) |
| COX2 | Mouse | Mm00478374_m1 | 873050 | GACTGGGCCATGGAGTGGACTTAAA (SEQ ID NO: 52) |
| EGFR | Mouse | Mm00433023_m1 | 894365 | GCAGTTGCCCCAAATGTGATCCAAG (SEQ ID NO: 53) |
| IGF1R | Mouse | Mm00802831_m1 | 927741 | GAAGTGGAGCAGAATAATCTAGTCC (SEQ ID NO: 54) |
| Fascin1 | Mouse | Mm00456046_m1 | 801010 | CATCAAAGACTCCACGGGCAAGTAC (SEQ ID NO: 55) |
| PRL3 | Mouse | Mm00477233_m1 | 740942 | GTTCATCCGACAGAAGCGCCGTGGG (SEQ ID NO: 56) |
| RCAS1 | Mouse | Mm00834632_g1 | 604308 | AAACTCAGAAAATTGTCATTAAGAA (SEQ ID NO: 57) |
| VCP | Mouse | Mm00726245_s1 | 578786 | CTGTCGTAGTTTGGGGTGGTGCAGG (SEQ ID NO: 58) |

Figure 55:
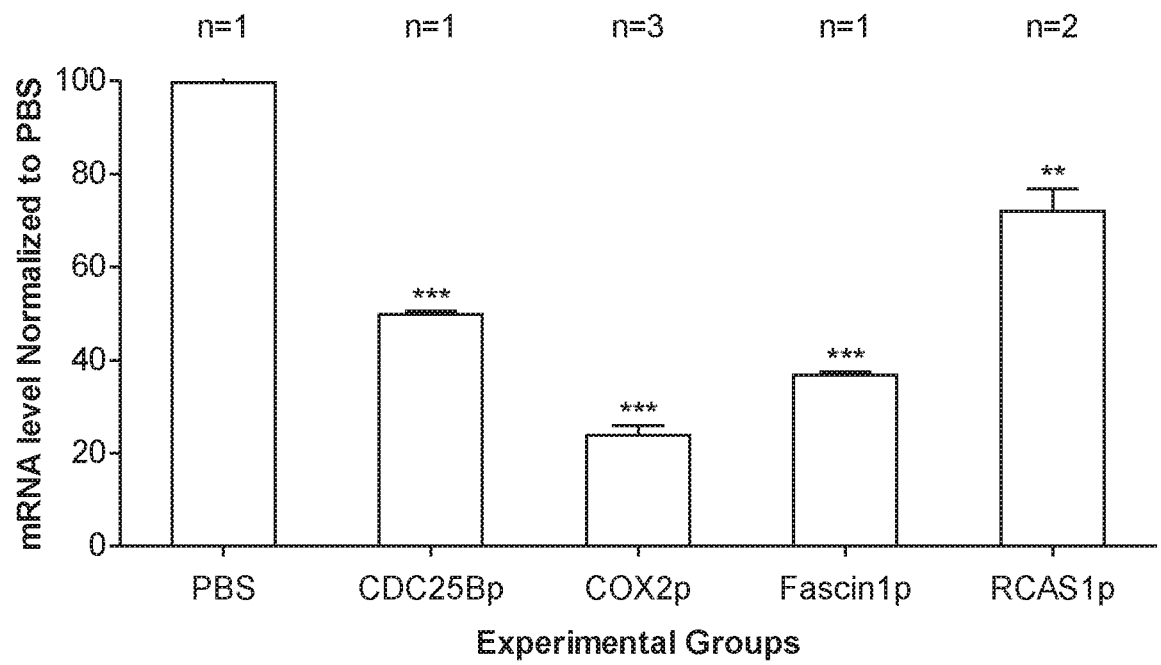
FIG. 55 depicts mRNA expression in AOM mice immunized with CDC25B, COX2, FASCIN1, and RCAS1.

FIG. 55 shows mRNA levels for AOM mice immunized with CDC25B, COX2, FASCIN1, and RCAS1. The y-axis shows the relative mRNA expression normalized to PBS. The x-axis shows the experimental groups in AOM treated FVB mice colon tumors. Calculated p-values are the difference between expression in PBS-treated mice and peptide immunized mice, *p<0.05, p<0.01, *p<0.001.

AOM Protein Expression In-Vivo Study Experiments.

Western blots were performed using protein isolated from colon tumors of mice immunized with peptides derived from CDC25B, COX2, EGFR, FASCIN1, IGF1R, PRL3, RCAS1, and VCP as previously described (Broussard, 2013). Specific reagents used included: CDC25B (goat polyclonal AF1649, R&D Systems, Minneapolis, Minn.), COX2 (rabbit polyclonal ab15191, Abcam Inc., Cambridge, Mass.), EGFR (goat polyclonal, AF1280, R&D Systems), FASCIN1 (mouse monoclonal D-10, sc-46675, Santa Cruz Biotechnology, Santa Cruz, Calif.), IGF1R (rabbit polyclonal N-20, sc-712, Santa Cruz Biotechnology), PRL3 (mouse monoclonal 318, sc-130355, Santa Cruz Biotechnology), RCAS1 (goat polyclonal, ab52032, Abcam Inc.), VCP (rabbit polyclonal H-120, sc-20799, Santa Cruz Biotechnology), and recombinant human proteins (all from Abnova, Jhongli, Taiwan): CDC25B (ab158074, Abcam), COX2 (ptgs2) (ab159279, Abcam), EGFR, FASCIN1 (TP303031, Origene Technologies), PRL3 (ptp4a3), RCAS1 (ebag9) (TP315667, Origene Technologies), VCP and 20 ug of IGF1R transfected COS7 cell lysate (Cecil et al, 2012).

Figure 56:
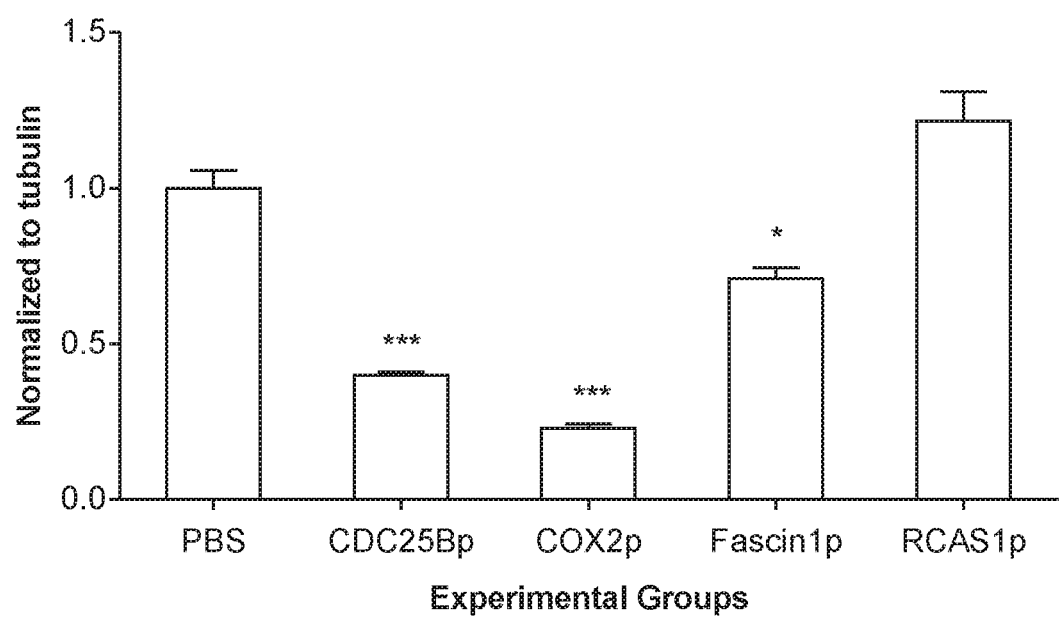
FIG. 56 depicts protein expression in AOM mice immunized with CDC25B, COX2, FASCIN1, and RCAS1.

FIG. 56 shows protein expression for AOM mice immunized with CDC25B, COX2, FASCIN1, and RCAS1. The y-axis shows the relative protein expression normalized to tubulin. The x-axis shows the experimental groups in AOM treated FVB mice colon tumors (n=1). Calculated p-values are the differences between expression in PBS-treated mice and peptide immunized mice, *p<0.05, p<0.01, *p<0.001.

MC-38 Mouse Model.

MC-38 tumor implant in-vivo experiments. At 6 weeks of age, mice were immunized in CFA/IFA, PBS, and vaccine groups. Each group received subcutaneous injections (100 ul PBS, 50 ul CFA with 50 ul PBS, 50 ug per peptide with 50 ul CFA) once every 10-14 days for a total of three doses. See Table 9 for peptides included in vaccine compositions. CFA was replaced with IFA for the second and third vaccines. Two weeks after the final vaccine, we subcutaneously implanted $4 \times 10^4$ MC-38 cells (murine adenocarcinoma), and measured tumor growth with Vernier calipers 2-3 times per week. Tumor volume was calculated as length×width× height×π/6, which is the standard volume calculation of an ellipsoid. Mice were sacrificed when tumor size in control mice reached greater than 1000 mm$^3$.

TABLE 9

MC-38 tumor implant in-vivo experiments: peptides included in vaccine compositions

| Vaccine | Peptide | Peptide sequence | Amino Acid Sequence |
|---|---|---|---|
| CDC25B | CDC25B #38 | p130-150 | QAIQAASRIIRNEQFAIRRFQ (SEQ ID NO: 1) |
|  | CDC25B #39 | p405-427 | VDGKHQDLKYISPETMVALLTGK (SEQ ID NO: 2) |

TABLE 9-continued

MC-38 tumor implant in-vivo experiments:
peptides included in vaccine compositions

| Vaccine | Peptide | Peptide sequence | Amino Acid Sequence |
|---|---|---|---|
| COX2 | COX-2 #32 | p81-96 | FKGFWNVVNNIPFLRN (SEQ ID NO: 3) |
|  | COX-2 #33 | p279-295 | GLVPGLMMYATIWLREH (SEQ ID NO: 4) |
|  | COX-2 #34 | p538-553 | GEVGFQIINTASIQSLIC (SEQ ID NO: 5) |
| EGFR | EGFR #40 | p306-325 | SCVRACGADSYEMEEDGVRK (SEQ ID NO: 11) |
|  | EGFR #41 | p603-619 | NNTLVWKYADAGHVCHL (SEQ ID NO: 12) |
|  | EGFR #42 | p897-915 | VWSYGVTVWELMTFGSKPY (SEQ ID NO: 13) |
| FASCIN1 | Fascin1 #5 | p136-154 | IAMHPQVNIYSVTRKRYAH (SEQ ID NO: 14) |
|  | Fascin1 #6 | p190-209 | TADHRFLRHDGRLVARPEPA (SEQ ID NO: 15) |
|  | Fascin1 #24 | p21-40 | NKYLTAEAFGFKVNASASSL (SEQ ID NO: 16) |
|  | Fascin1 #25 | p274-398 | ELFLMKLINRPIIVFRGEHGFIGCR (SEQ ID NO: 17) |
| IGF1R | IGF1R #1 | p384-398 | VVTGYVKIRHSHALV (SEQ ID NO: 23) |
|  | IGF1R #2 | p575-588 | TQYAVYVKAVTLTMV (SEQ ID NO: 24) |
|  | IGF1R #3 | p951-965 | LVIMLYVFHRKRNNS (SEQ ID NO: 25) |
|  | IGF1R #4 | p1122-1136 | GMAYLNANKFVHRDL (SEQ ID NO: 26) |
| PRL3 | PRL-3 #1 | p12-30 | VSYKHMRFLITHNPTNATL (SEQ ID NO: 27) |
|  | PRL-3 #2 | p33-53 | FIEDLKKYGATTVVRVCEVTY (SEQ ID NO: 28) |
|  | PRL-3 #3 | p104-122 | PCVAGLGRAPVLVALALIES (SEQ ID NO: 29) |
|  | PRL-3 #4 | p124-142 | MKYEDAIQFIRQKRRGAIN (SEQ ID NO: 30) |
|  | PRL-3 #29 | p81-95 | VEDWLSLVKAKFCEA (SEQ ID NO: 31) |
| RCAS1 | RCAS1 #13 | p91-110 | EPDYFKDMTPTIRKTQKIVI (SEQ ID NO: 32) |
|  | RCAS1 #14 | p93-113 | DYFKDMTPTIRKTQKIVIKKR (SEQ ID NO: 33) |
|  | RCAS1 #21 | p8-27 | LFKFCTCALTVFSFLKRLIC (SEQ ID NO: 34) |
|  | RCAS1 #30 | p126-148 | GFSSRLAATQDLPFIHQSSELGD (SEQ ID NO: 35) |
|  | RCAS1 #31 | p161-181 | EEEDAAWQAEEVLRQQKLADR (SEQ ID NO: 36) |
| VCP | VCP #18 | p82-102 | IRMNRVVRNNLRVRLGDVISI (SEQ ID NO: 37) |
|  | VCP #19 | p49-65 | LQLFRGDTVLLKGKKRR (SEQ ID NO: 38) |
|  | VCP #20 | p138-156 | YFLEAYRPIRKGDIFLVRG (SEQ ID NO: 39) |
|  | VCP #23 | p161-180 | VEFKVVETDPSPYCIVAPDT (SEQ ID NO: 40) |

Figure 57:
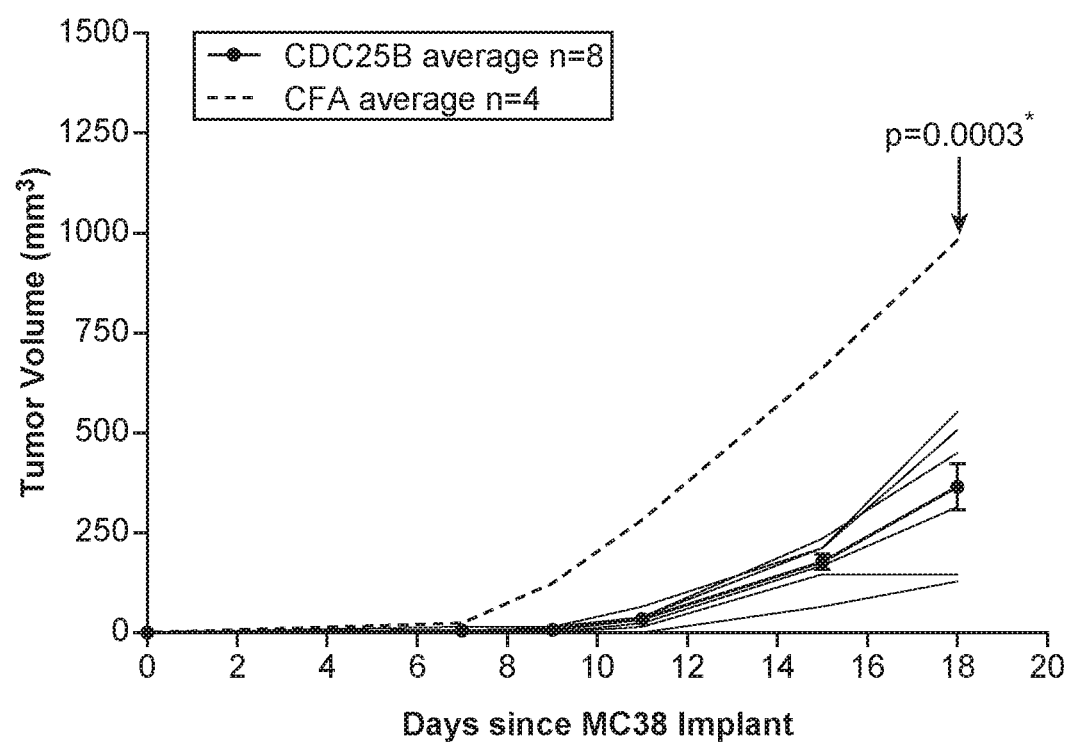
FIG. 57 shows tumor volume for MC-38 mice immunized with CDC25B.

FIG. 57 shows immunization with peptides derived from CDC25B significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=4) and CDC25B (n=8) at day 18, p=0.0003. Mice were sacrificed 18 days after MC-38 tumor was implanted.

Figure 58:
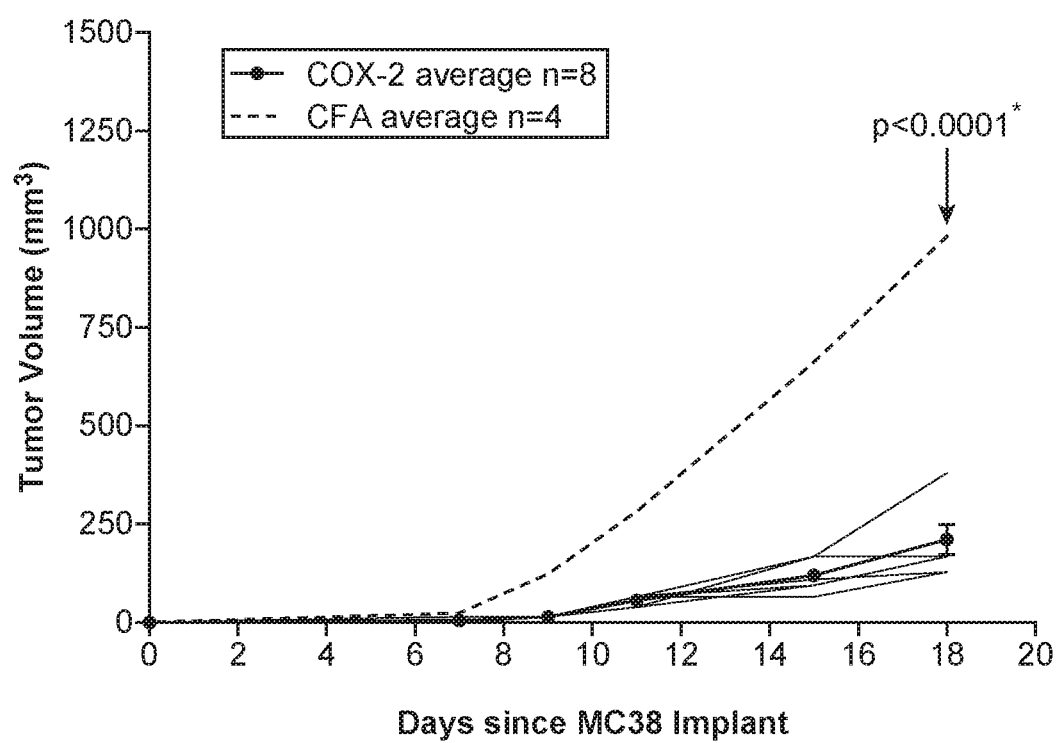
FIG. 58 shows tumor volume for MC-38 mice immunized with COX2.

FIG. 58 shows immunization with peptides derived from COX2 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=4) and COX2 (n=8) at day 18, p<0.0001. Mice were sacrificed 18 days after MC-38 tumor was implanted.

Figure 59:
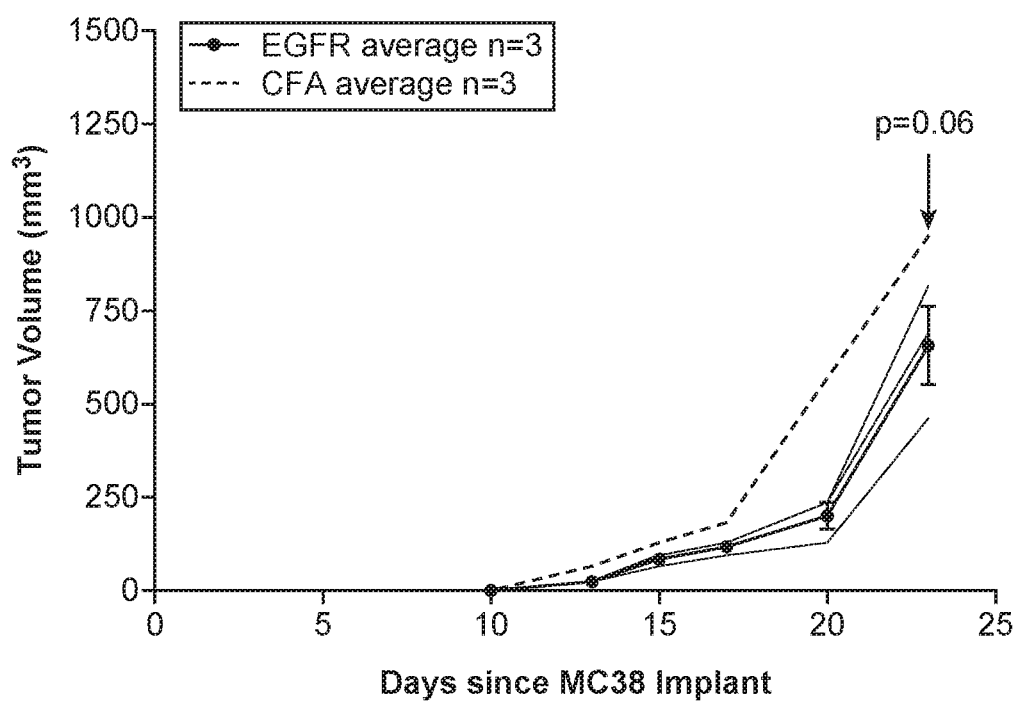
FIG. 59 shows tumor volume for MC-38 mice immunized with EGFR.

FIG. 59 shows immunization with peptides derived from EGFR does not significantly inhibit tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were not statistically significant between C57Bl/6 mice immunized with CFA/IFA (n=3) and EGFR (n=3) at day 23, p=0.06. Mice were sacrificed 23 days after MC-38 tumor was implanted.

Figure 60:
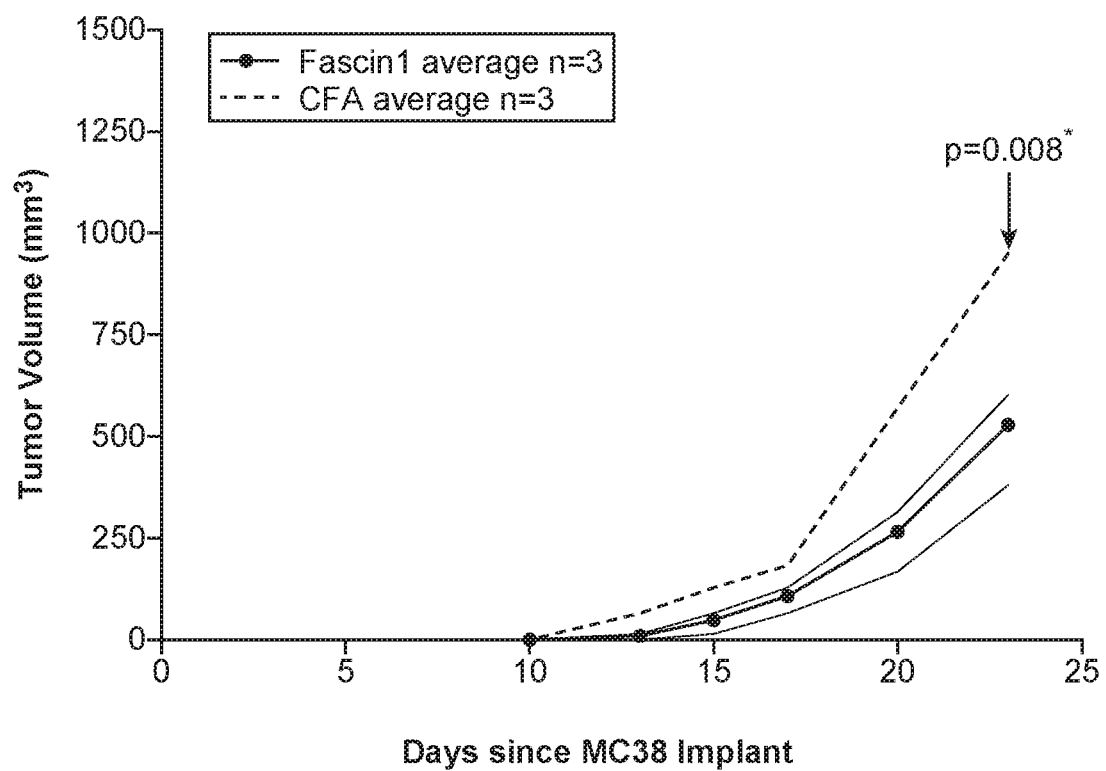
FIG. 60 shows tumor volume for MC-38 mice immunized with FASCIN1.

FIG. 60 shows immunization with peptides derived from FASCIN1 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=3) and FASCIN1 (n=3) at day 23, p=0.008. Mice were sacrificed 23 days after MC-38 tumor was implanted.

Figure 61:
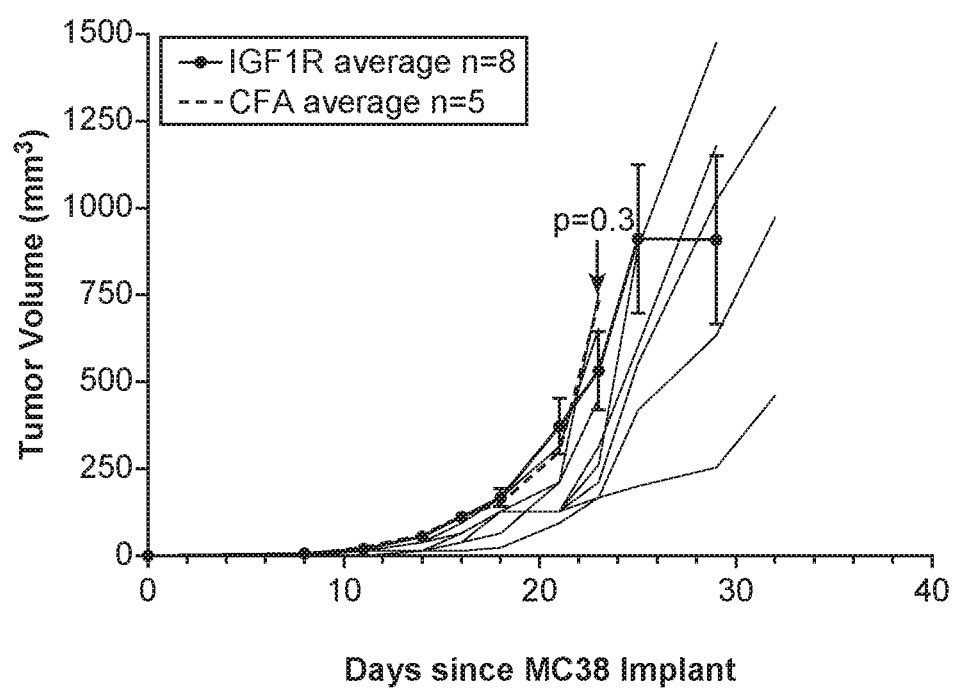
FIG. 61 shows tumor volume for MC-38 mice immunized with IGF1R.

FIG. 61 shows immunization with peptides derived from IGF1R does not significantly inhibit tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were not statistically significant between C57Bl/6 mice immunized with CFA/IFA (n=5) and IGF1R (n=8) at day 23, p=0.3. CFA/IFA immunized mice were sacrificed 23 days after MC-38 tumor implant and IGF1R immunized mice were sacrificed 28-32 days after tumor implant.

Figure 62:
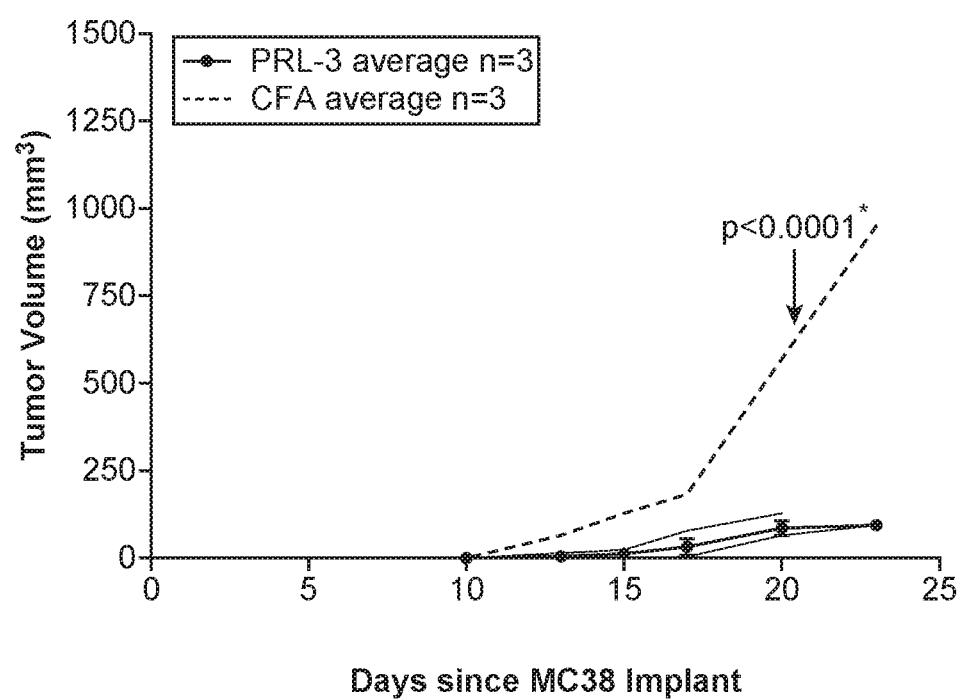
FIG. 62 shows tumor volume for MC-38 mice immunized with PRL3.

FIG. 62 shows immunization with peptides derived from PRL3 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=3) and PRL3 (n=3) at day 20, p<0.0001. Mice were sacrificed 23 days after MC-38 tumor was implanted.

Figure 63:
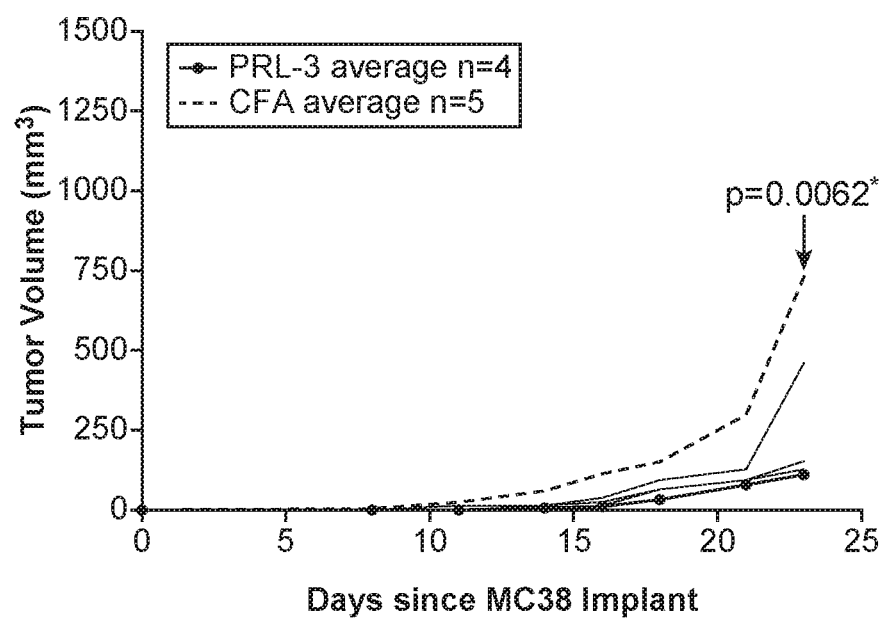
FIG. 63 shows tumor volume for MC-38 mice immunized with PRL3.

FIG. 63 shows immunization with peptides derived from PRL3 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=5) and PRL3 (n=4) at day 23, p=0.0062. Mice were sacrificed 23 days after MC-38 tumor was implanted.

Figure 64:
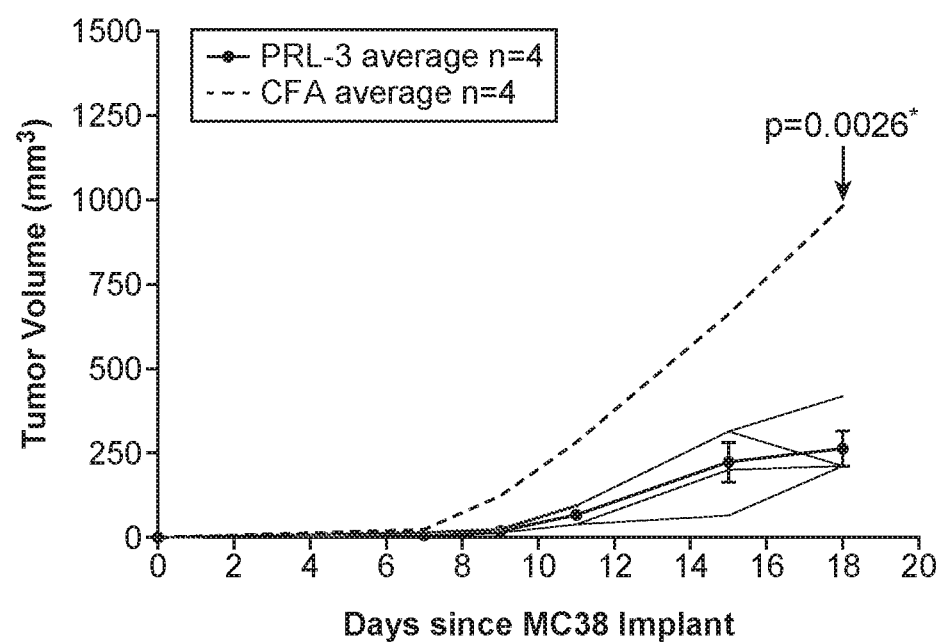
FIG. 64 shows tumor volume for MC-38 mice immunized with PRL3.

FIG. 64 shows immunization with peptides derived from PRL3 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=4) and PRL3 (n=4) at day 18, p=0.0026. Mice were sacrificed 18 days after MC-38 tumor was implanted.

Figure 65:
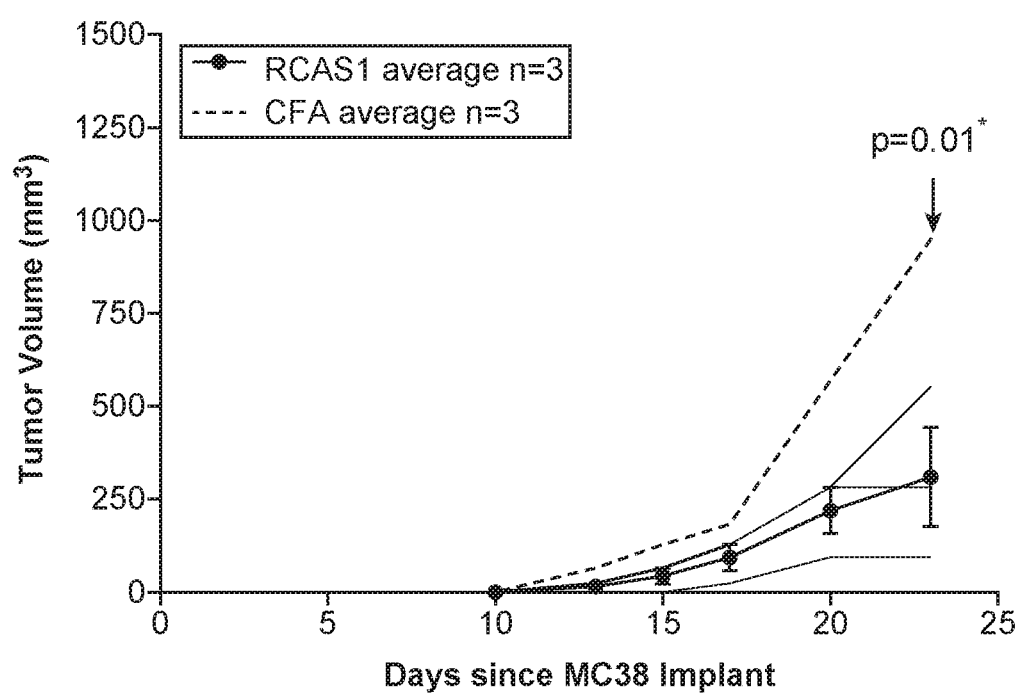
FIG. 65 shows tumor volume for MC-38 mice immunized with RCAS1.

FIG. 65 shows immunization with peptides derived from RCAS1 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=3) and RCAS1 (n=3) at day 23, p=0.01. Mice were sacrificed 23 days after MC-38 tumor was implanted.

Figure 66:
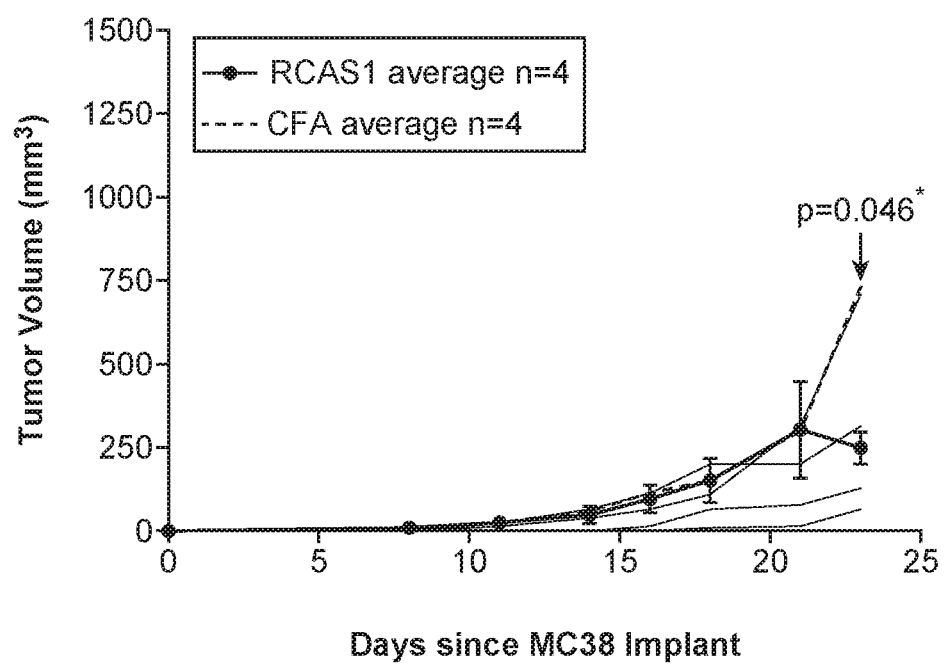
FIG. 66 shows tumor volume for MC-38 mice immunized with RCAS1.

FIG. 66 shows immunization with peptides derived from RCAS1 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=4) and RCAS1 (n=4) at day 23, p=0.046. Mice were sacrificed 23 days after MC-38 tumor was implanted.

Figure 67:
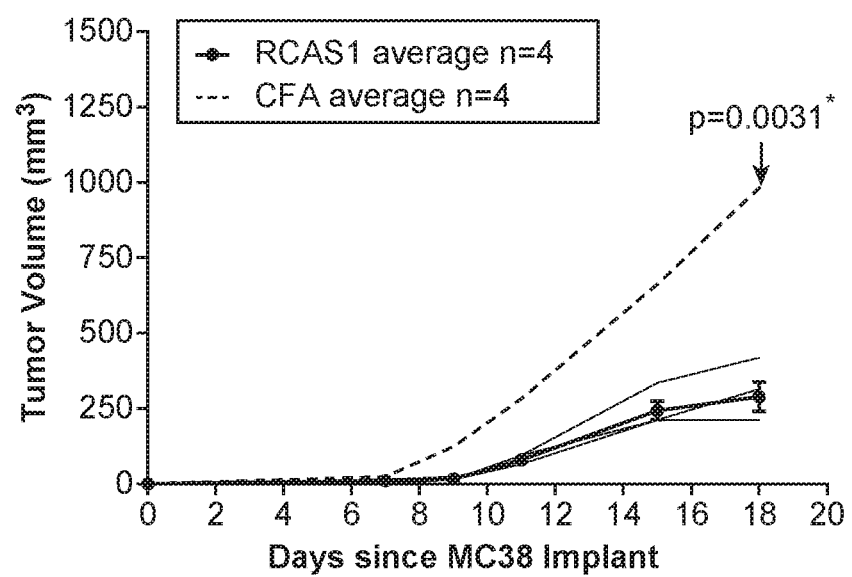
FIG. 67 shows tumor volume for MC-38 mice immunized with RCAS1.

FIG. 67 shows immunization with peptides derived from RCAS1 significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=4) and RCAS1 (n=4) at day 18, p=0.0031. Mice were sacrificed 18 days after MC-38 tumor was implanted.

Figure 68:
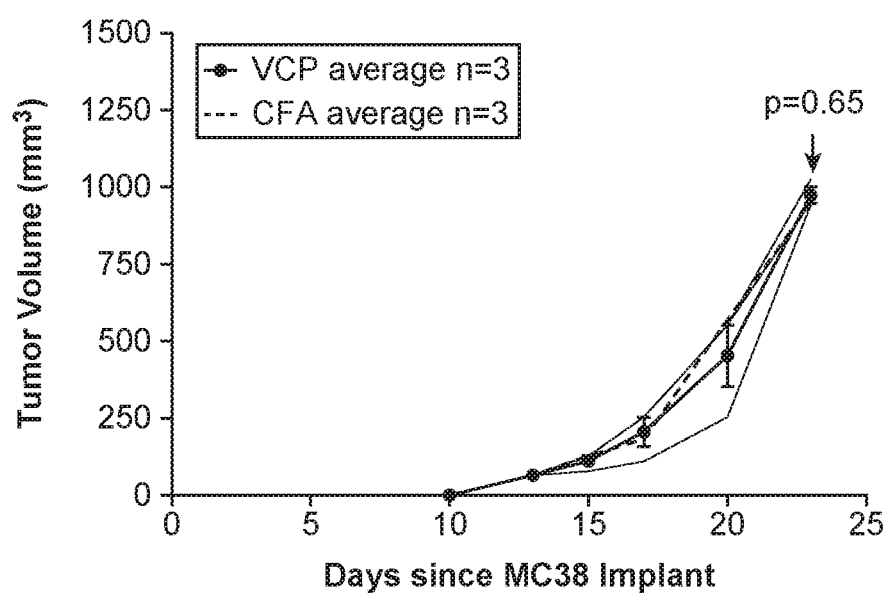
FIG. 68 shows tumor volume for MC-38 mice immunized with VCP.

FIG. 68 shows immunization with peptides derived from VCP does not significantly inhibit tumor volume in MC-38 tumor implant mice. the tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=3) and VCP (n=3) at day 23, p=0.65. Mice were sacrificed 23 days after MC-38 tumor was implanted.

Figure 69:
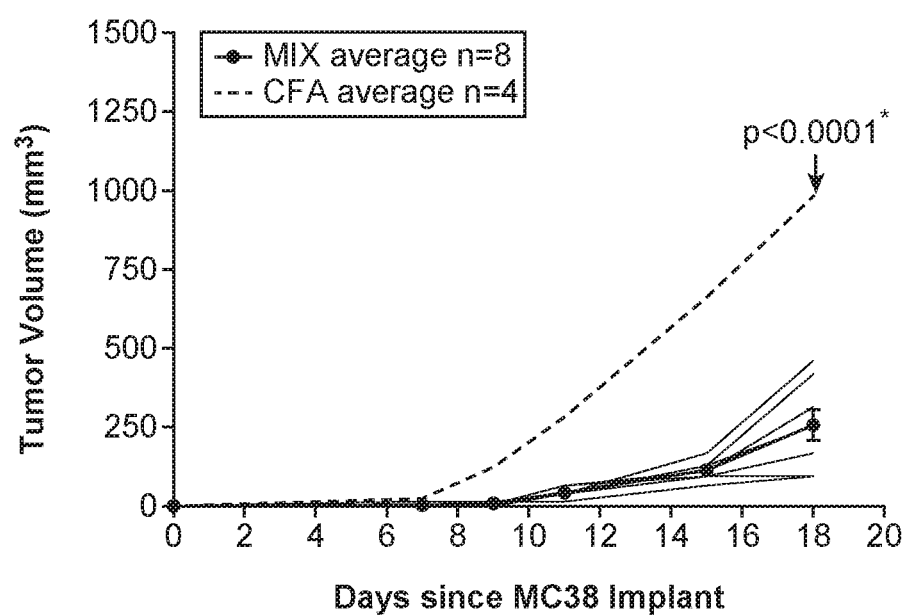
FIG. 69 shows tumor volume for MC-38 mice immunized with MIX.

FIG. 69 shows immunization with peptides derived from MIX, a combination of CDC25B, COX2, and PRL3, significantly inhibits tumor volume in MC-38 tumor implant mice. The tumor volume in mm$^3$ is shown on the y-axis and the days since MC-38 tumor implant in C57Bl/6 mice immunized groups are on the x-axis. Calculated p-values using the unpaired, two-tailed student t test were statistically significant between C57Bl/6 mice immunized with CFA/IFA (n=4) and MIX (n=8) at day 18, p<0.0001. Mice were sacrificed 18 days after MC-38 tumor was implanted.

MC-38 IFN-γ Study In-Vivo Experiments.

96-well MAIPS nitrocellulose plates (Millipore) were pre-soaked in 70% EtOH and incubated overnight with anti-mouse IFN-g antibody (Mabtech) at 10 ug/ml. The next day, the plates were washed three times with PBS and blocked with PBS+2% BSA for 2 hours in a 37° C. $CO_2$ incubator. The plates were washed three times with PBS and isolated mouse splenocytes plated with 3×10$^5$ cells/well (6 replicates/antigen). Antigens were added and the plate was put into a 37° C. $CO_2$ incubator for 72 hours. Positive controls were PHA (5 ug/mL), PMA/I (2 ug/mL), and CD3 (1:10,000), negative controls were no antigen wells, and all peptides were added at 20 ug/mL. The plates were washed once with 1×PBS, and then washed twice with PBS+0.05% Tween buffer. Anti-mouse IFN-γ antibody (Mabtech) at 5 ug/ml in PBS+0.05% Tween was added to each well and the plate incubated overnight at 4° C. The plates were washed twice with PBS+0.05% Tween then once with PBS. Diluted streptavidin-HRP (Mabtech) was added to the plates and incubated at RT for 45 minutes. The plates were developed using AEC ELISPOT Substrate kit (BD Biosciences). An increase in the number of protein specific IFN-g producing spots that was statistically different than no antigen control wells and/or controls (p<0.05) was taken as an indication of immune response.

Figure 70:
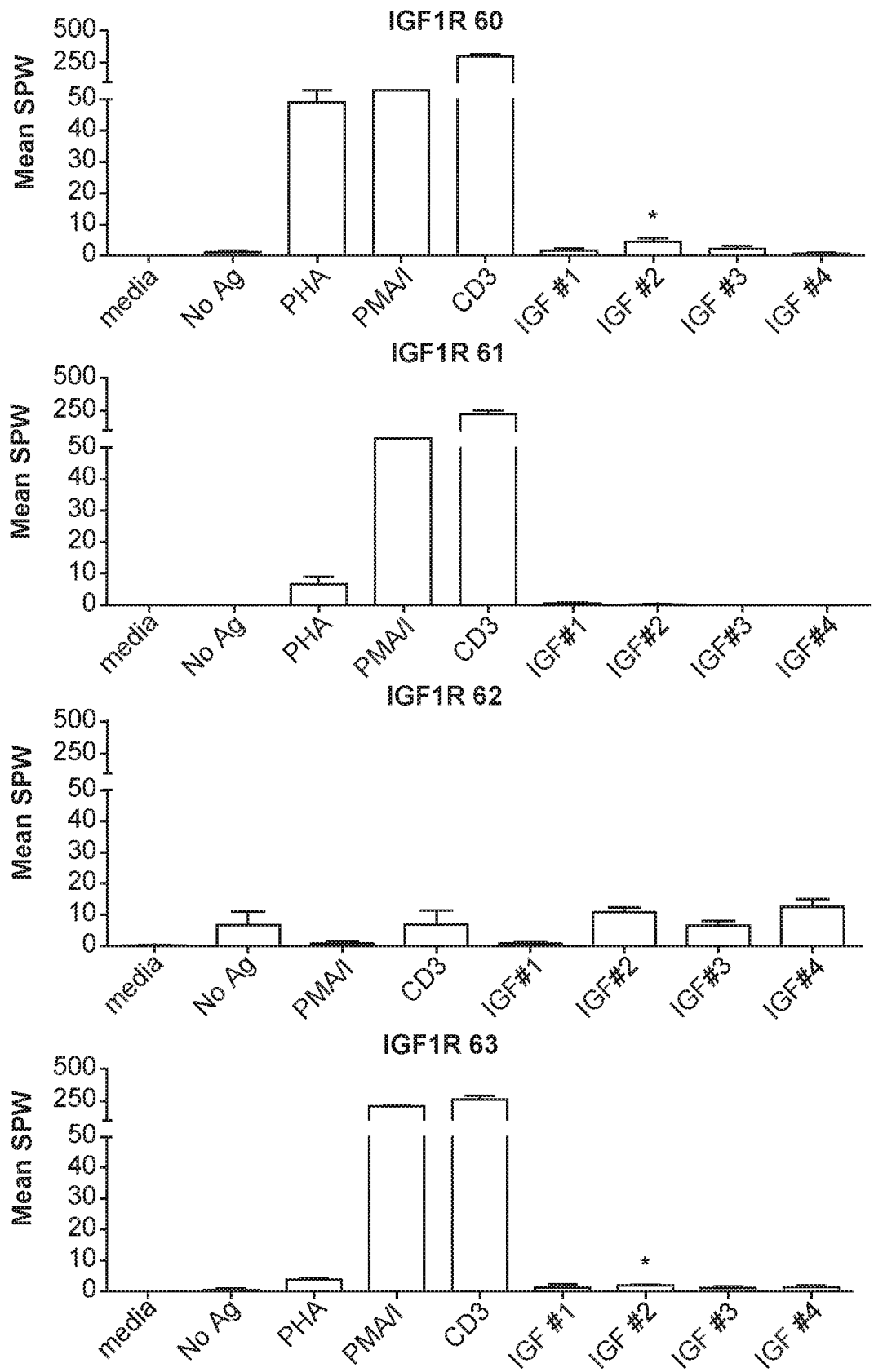
FIG. 70 demonstrates ELISpot results for MC-38 mice immunized with IGF1R.
Figure 70:
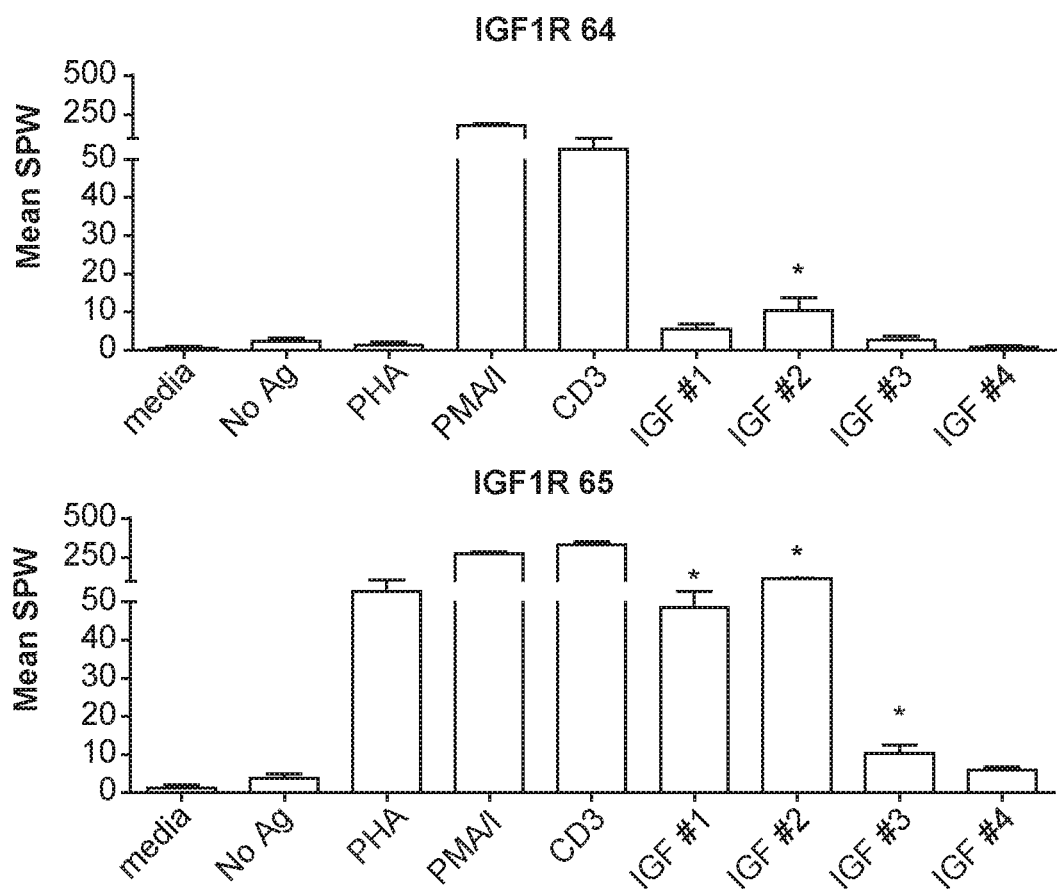

For FIG. 70, IFN-γ responses to immunization of IGF1R peptides are shown with the average spots per well (6 well replicates) on the y-axis and the antigens used to stimulate the t-cells are on the x-axis. The asterisk (*) above columns indicates significance compared to no antigen wells using the unpaired, two-tailed student's t test, p<0.05. The table adjacent to the ELISpot figures shows the days since MC-38 tumor implant, tumor volume in $mm^3$, and age in weeks at sacrifice of individual immunized mice.

Figure 71:
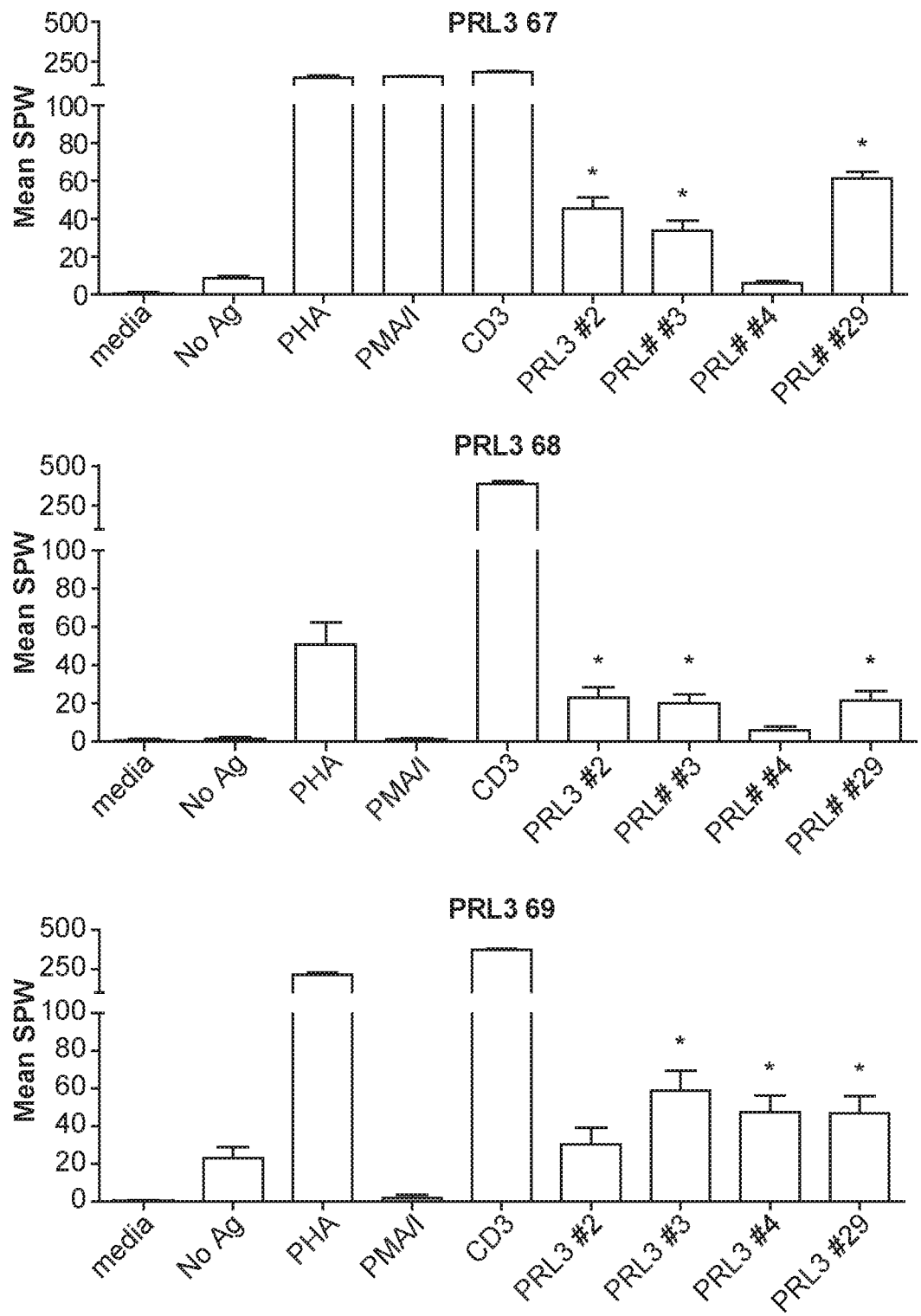
FIG. 71 demonstrates ELISpot results for MC-38 mice immunized with PRL3.
Figure 71:
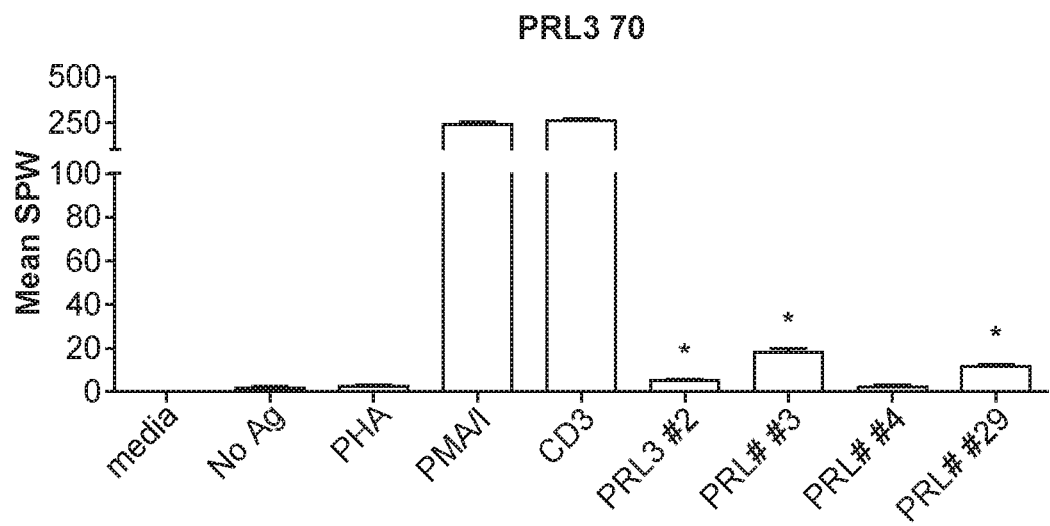

For FIG. 71, IFN-γ responses to immunization of PRL3 peptides are shown with the average spots per well (6 well replicates) on the y-axis and the antigens used to stimulate the t-cells are on the x-axis. The asterisk (*) above columns indicates significance compared to no antigen wells using the unpaired, two-tailed student's t test, p<0.05. The table adjacent to the ELISpot figures shows the days since MC-38 tumor implant, tumor volume in $mm^3$, and age in weeks at sacrifice of individual immunized mice.

Figure 72:
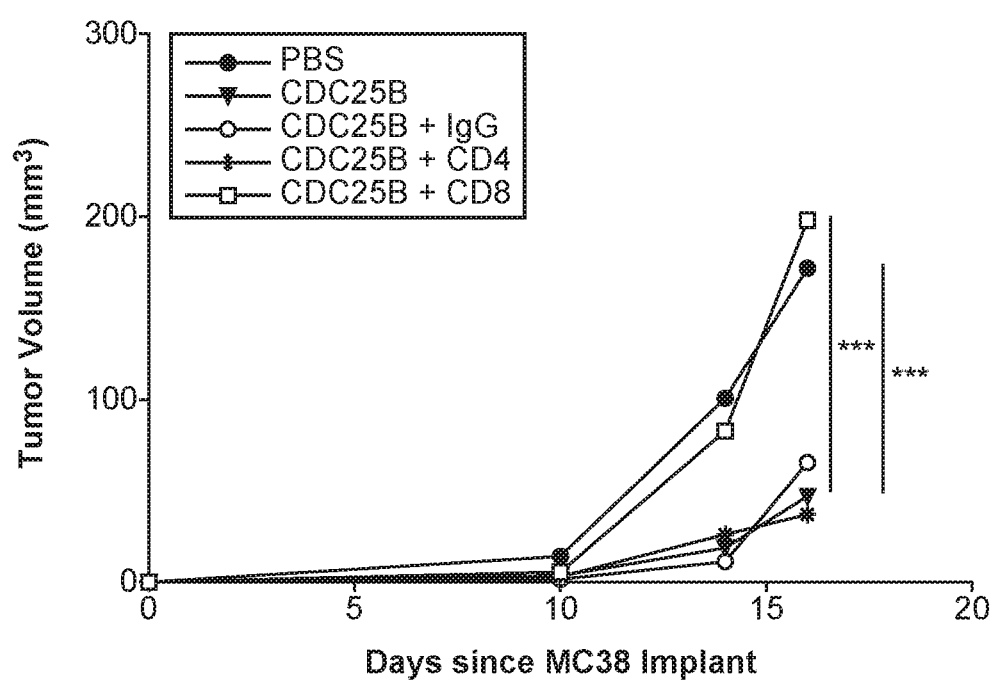
FIG. 72 shows tumor volume for CDC25B immunized MC-38 mice with IgG, CD8, and CD4 depletion.
Figure 73:
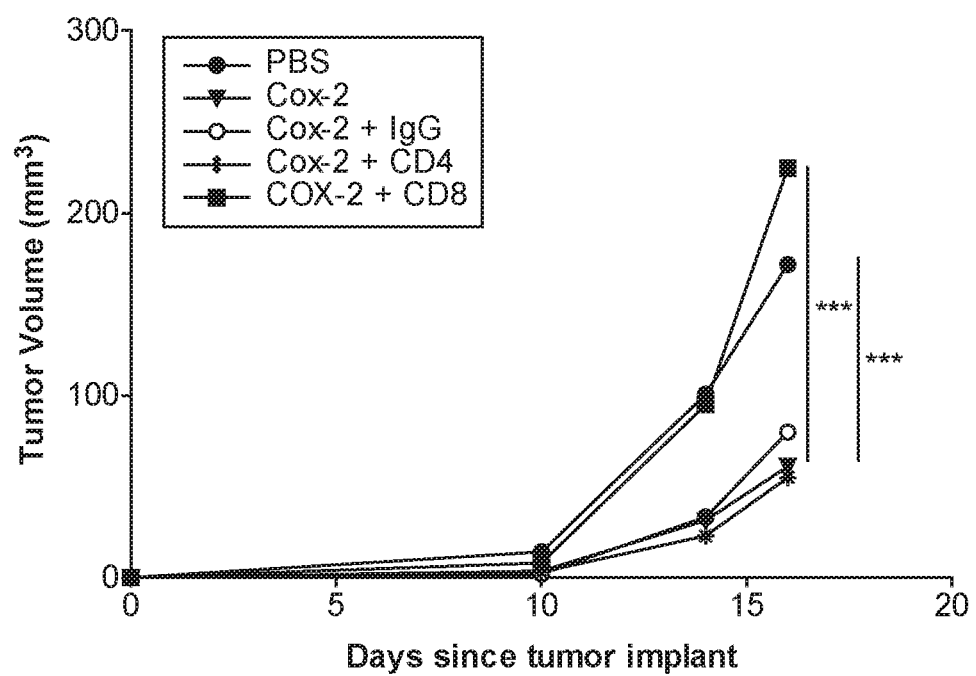
FIG. 73 shows tumor volume for COX2 immunized MC-38 mice with IgG, CD8, and CD4 depletion.
Figure 74:
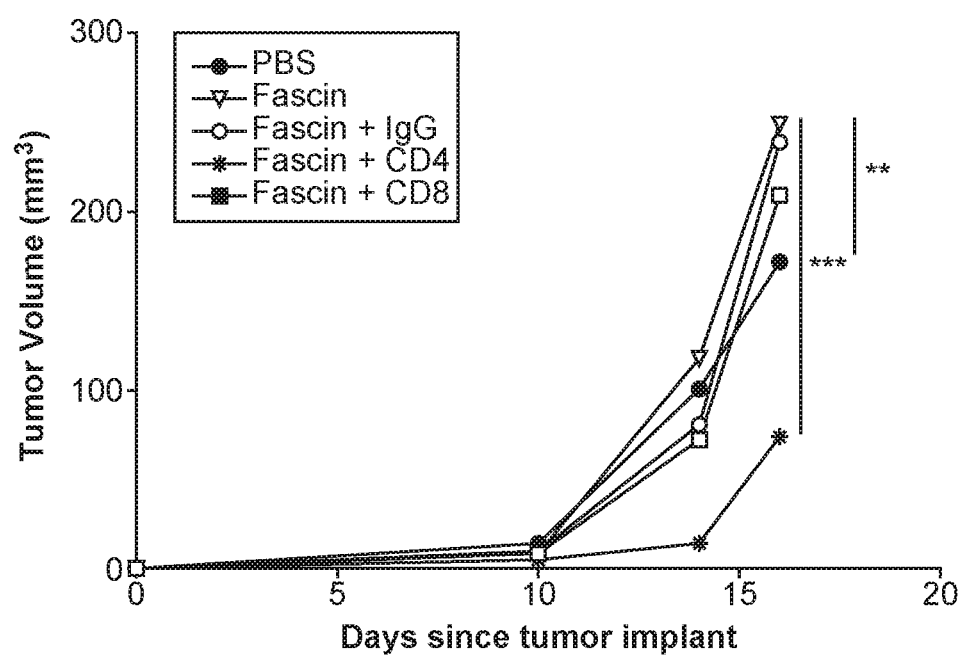
FIG. 74 shows tumor volume for FASCIN1 immunized MC-38 mice with IgG, CD8, and CD4 depletion.

MC-38 tumor implant with CD4 and CD8 depletion study in-vivo experiments. C57Bl6/J Female mice were purchased from The Jackson Laboratory (San Diego, Calif.) at five weeks of age. After one week of acclimatization, mice were vaccinated subcutaneously with either PBS alone (n=5) or Vaccine+Adjuvant (n=20) three times, two weeks apart. Complete Freund's Adjuvant was used in the first vaccine, followed with Incomplete Freund's Adjuvant (Sigma-Aldrich, St. Louis, Mo.) for subsequent vaccines. Two weeks after the final vaccine, mice were challenged with 40,000 MC38 cells subcutaneously. Upon palpable tumor development, n=5 mice per vaccination group were injected intraperitoneally with either 100 ug anti Rat IgG2b, 100 ug anti-CD8, or 250 ug anti-CD4 (UCSF Monoclonal Antibody Core, San Francisco, Calif.) for three consecutive days. Antibodies were continued twice per week until the study was concluded. Mice were monitored for tumor growth every 2-3 days using Vernier calipers. Tumor volumes were calculated as length×width×height×0.5236. FIG. 72 shows tumor volume for CDC25B immunized MC-38 mice with IgG, CD8, and CD4 depletion. FIG. 73 shows tumor volume for COX2 immunized MC-38 mice with IgG, CD8, and CD4 depletion. FIG. 74 shows tumor volume for FASCIN1 immunized MC-38 mice with IgG, CD8, and CD4 depletion.

Example 4—Method of Identifying Promiscuous MHC Class II Epitopes for Development of Human Vaccines Predicted MHCII epitopes to 14 of the most frequent HLA-DR proteins were identified using compiled results from three different publicly available algorithms. The algorithm-generated epitope binding scores were used to map epitopes within protein sequences predicted to contain epitopes that interact with multiple HLA-DR proteins, referred to as "promiscuous epitopes". The 14 HLA-DR proteins screened by the algorithms were: HLA-DRB1*0101, HLA-DRB1*0301, HLA-DRB1*0401, HLA-DRB1*0404, HLA-DRB1*0405, HLA-DRB1*0701, HLA-DRB1*0802, HLA-DRB1*0901, HLA-DRB1*1101, HLA-DRB1*1201, HLA-DRB1*1302, HLA-DRB1*1501, HLA-DRB4*0101, and HLA-DRB5*0101. The web-based algorithms employed were SYFPEITHI (www.syfpeithi.de/Scripts/MHCServer.dll/EpitopePrediction.htm), PROPRED (www.imtech.res.in/raghava/propred/), and RANKPEP (imed.med.ucm.es/Tools/rankpep.html). The number of HLA-DR proteins available for screening varied for each website (6, 11, or 13 of the 14 listed above). Query protein sequences were obtained from the NCBI database and copied in the FASTA format for entry into the algorithm search engines and the top twenty scoring epitopes for each HLA-DR protein were used to create the "MHCII heatmap" of the query protein. For compiling and analyzing the epitope prediction data a MS Excel-based workbook was developed, referred to as the "MHCII Heatmap Template". Because each of the three algorithms has a different numerical scoring system for identified epitopes, the epitope scores were first normalized before compiling results from the different search methods. To normalize epitope scores, all scores were divided by the top score obtained by each algorithm, such that the epitope with the highest predicted affinity would have a normalized score of 1.0. The normalized scores were then pasted in to the MHCII Heatmap Template, which, with several embedded equations and functions, performed the following tasks: (i) each amino acid of a particular epitope was assigned the normalized score of the epitope, (ii) the number of different HLA-DR proteins/alleles that had epitopes at each amino acid position was calculated and graphed, (iii) the sum of the normalized scores from every epitope was calculated and graphed at every amino acid position, and (iv) a "Multiple Score" was calculated and graphed, which was the product of the normalized score sum and the number of HLA-DR alleles. The Multiple Score represents both the epitope binding strength and the epitope promiscuity, and this value was used to create the MHCII heatmap of the query protein. The graph of amino acid position (x axis) versus Multiple Score (y axis) allows easy visualization of protein regions predicted to contain promiscuous epitopes. Additionally, an MS Access application was created to simplify the input of FASTA protein sequences into vertical columns of the MHCII Heatmap Template. Once protein sequence has been entered, MHCII heatmap figures can be created by color-coding the amino acids based on Multiple Score values to aid in peptide selection for immunological assays. Generally, color-coding indicates Multiple Scores of 75-100%, 50-75%, 25-50%, and 10-25%.

Figure 75:
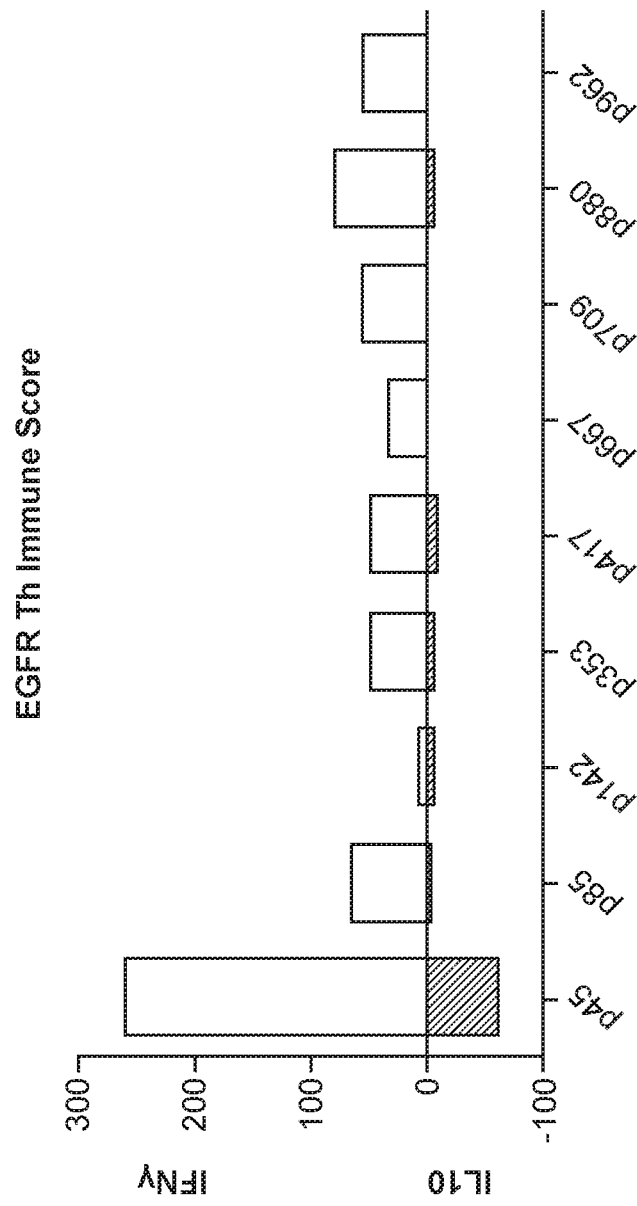
FIG. 75 illustrates an immune score result for peptides disclosed herein.

Peptides were constructed based on composite scores. Peripheral blood mononuclear cells (PBMC) from 40 human donors were evaluated by ELISPOT for antigen-specific IFN-gamma (g) and IL-10 production induced by the predicted epitopes covering a minimum of 25% of the protein. For the IFN-g ELISPOT, cells were plated at 2×105 per well (96-well plate) in medium with 10 ug/mL of the various peptides or HIVp17, PHA (1 ug/ml), CEF (2.5 ug/mL) or medium alone for 7 days at 37° C. in 5% CO2. On day 5, recombinant human IL-2 (10 U/ml) was added. A second in vitro stimulation (IVS) was performed on day 8 by adding 2×105 peptide-loaded (same concentrations as listed above) autologous irradiated (3000 rads) human PBMC to the original culture, and incubated for 24 h. 96-well nitrocellulose plates were coated with 10 ug/ml anti-human IFN-g. The washed nitrocellulose plates were blocked with 2% bovine serum albumin in DPBS followed by a 24 h incubation with the PBMC culture. After extensive washing, biotinylated anti-human IFN-g was added for 2 h. For the IL-10 ELISPOT, an anti-human IL-10-coated (2 ug/ml) nitrocellulose 96-well plate was blocked as described above. PBMC concentration and peptide stimulations were as described above, except that PHA was used at 20 ug/ml. After extensive washing, biotinylated anti-human IL-10 was added for 2 h. After extensive washing, 1 ug/mL Streptavidin-AP was added for 45 minutes. Spots were visualized by incubating the plate with BCIP and NBT solutions spots were counted on the C.T.L. ELISPOT plate reader. The raw data was imported into the TVG database ELISPOT tool and positive responses were defined by a statistically significant difference (p<0.05) between the mean number of spots from five replicates in the experimental wells and the mean number from no antigen control wells. A TH1/TH2 ratio was created that analyzed both the magnitude and frequency of ELISPOT responses for each of the predicted class II-specific peptides using the following algorithm: (corrected mean spots per well)×(percent of responding donors). TH1/TH2 activity ratios were also derived from ELISA assays for the Type I and II cytokines using antigen specific T-cell stimulated media as well as by multi-plex assay for complex Th1/Th2 phenotypes. Incidence and magnitude were incorporated into those analyses in a similar fashion. FIG. 75 shows the Th1 (IFNgamma) in comparison with Th2 (IL10) stimulating activity of each of the EGFR peptides tested.

REFERENCES

Park K H, Gad E, Goodell V, Dang Y, Wild T, Higgins D, Fintak P, Childs J, Dela Rosa C, Disis M L (2008) Insulin-like growth factor-binding protein-2 is a target for the immunomodulation of breast cancer. Cancer Research 68:8400-8409

Cecil D, Park K H, Gad E, Childs J S, Higgins D M, Plymate S R, Disis M L (2013) T-helper I immunity, specific for the breast cancer antigen insulin-like growth factor-I receptor (IGF-IR), is associated with increased adiposity. Breast Cancer Research Treatment 139:657-665

Broussard E K, Kim R, Wiley J C, Marquez J P, Annis J E, Pritchard D, and Disis M L. (2013) "Identification of Putative Immunologic Targets for Colon Cancer Prevention Based on Conserved Gene Upregulation from Pre-invasive to Malignant Lesions." *Cancer Prevention Research* (2013): 666-74.

Ramduth D, Day C L, Thobak gale C F, Mkhwanazi N P, de Pierres C, Reddy S, van der Stok M, Mncube X, Nair K, Moodley E S, Kaufmann D E, Streeck H, Coovadia H M, Kiepiela P, Goulder P J, Walker B D (2009) Immunodominant HIV-1 infections. PLoS ONE 4:e5013

What is claimed is:

1. A composition comprising an isolated and purified plasmid comprising a nucleotide sequence encoding a polypeptide, wherein the polypeptide comprises a plurality of sequences, wherein the plurality of sequences comprises a first sequence selected from the sequences consisting of at least 90% sequence identity to SEQ ID NOs: 1-2, a second sequence selected from the sequences consisting of at least 90% sequence identity to SEQ ID NOs: 3-10, and a third sequence selected from the sequences consisting of at least 90% sequence identity to SEQ ID NOs: 27-31.

2. The composition of claim 1, wherein the plurality of sequences further comprises a sequence comprising at least 90% sequence identity to an amino acid sequence selected from SEQ ID NOs: 23-26.

3. The composition of claim 1, wherein the plurality of sequences each comprise at least 95% sequence identity to at least 8 contiguous amino acids from a sequence selected from SEQ ID NOs: 1-10 and 27-31.

4. The composition of claim 2, wherein the plurality of sequences further comprises an additional sequence comprising at least 90% sequence identity to at least 8 contiguous amino acids from a sequence selected from SEQ ID NOs: 1-45.

5. The composition of claim 1, wherein the plurality of sequences are contiguous.

6. The composition of claim 2, wherein the plurality of sequences are contiguous.

7. The composition of claim 5, wherein the contiguous sequence further comprises a linker between two or more sequences of the plurality of sequences.

8. The composition of claim 6, wherein the contiguous sequence further comprises a linker between two or more sequences of the plurality of sequences.

9. The composition of claim 1 further comprising an excipient.

10. A method of treating a subject in need thereof, the method comprising administering to the subject in need thereof the composition of claim 1.

11. The method of claim 10, wherein the polypeptide further comprises a sequence comprising at least 90% sequence identity to an amino acid sequence selected from SEQ ID NOs: 23-26.

* * * * *